US008003095B2

(12) United States Patent
Kreij et al.

(10) Patent No.: US 8,003,095 B2
(45) Date of Patent: *Aug. 23, 2011

(54) METHOD OF USING LIPID ACYLTRANSFERASE

(75) Inventors: Arno De Kreij, Papendrecht (NL);
Susan Mampusti Madrid, Vedbaek (DK); Jørn Dalgaard Mikkelsen, Hvidovre (DK); Jørn Borch Søe, Tilst (DK)

(73) Assignee: Danisco A/S, Copenhagen (DK)

( * ) Notice: Subject to any disclaimer, the term of this patent is extended or adjusted under 35 U.S.C. 154(b) by 938 days.

This patent is subject to a terminal disclaimer.

(21) Appl. No.: 11/483,331

(22) Filed: Jul. 7, 2006

(65) Prior Publication Data

US 2007/0122525 A1   May 31, 2007

Related U.S. Application Data

(63) Continuation of application No. 11/182,408, filed on Jul. 15, 2005, now Pat. No. 7,807,398, which is a continuation-in-part of application No. PCT/IB2004/000655, filed on Jan. 15, 2004.

(60) Provisional application No. 60/489,441, filed on Jul. 23, 2003.

(30) Foreign Application Priority Data

| Jan. 17, 2003 | (GB) | 0201121.0 |
| Jan. 17, 2003 | (GB) | 0301117.8 |
| Jan. 17, 2003 | (GB) | 0301118.6 |
| Jan. 17, 2003 | (GB) | 0301119.4 |
| Jan. 17, 2003 | (GB) | 0301120.2 |
| Jan. 17, 2003 | (GB) | 0301122.8 |
| Dec. 24, 2003 | (GB) | 0330016.7 |

(51) Int. Cl.
*A61K 38/45* (2006.01)
*C12Q 1/48* (2006.01)

(52) U.S. Cl. ......................... 424/94.5; 435/15; 435/193
(58) Field of Classification Search ................ 424/94.5; 435/15, 193
See application file for complete search history.

(56) References Cited

U.S. PATENT DOCUMENTS

| 2,888,385 | A | 5/1959 | Grandel |
| 3,260,606 | A | 7/1966 | Azuma |
| 3,368,903 | A | 2/1968 | Johnson |
| 3,520,702 | A | 7/1970 | Menzi |
| 3,634,195 | A | 1/1972 | Melachouris |
| 3,652,397 | A | 3/1972 | Pardun |
| 3,677,902 | A | 7/1972 | Aunstrup |
| 3,817,837 | A | 6/1974 | Rubenstein et al. |
| 3,850,752 | A | 11/1974 | Wilhelmus et al. |
| 3,852,260 | A | 12/1974 | Knutsen |
| 3,939,350 | A | 2/1976 | Kronick et al. |
| 3,973,042 | A | 8/1976 | Kosikowski |
| 3,996,345 | A | 12/1976 | Ullman et al. |
| 4,034,124 | A | 7/1977 | Van Dam |
| 4,065,580 | A | 12/1977 | Feldman |
| 4,160,848 | A | 7/1979 | Vidal |
| 4,202,941 | A | 5/1980 | Terada |
| 4,275,149 | A | 6/1981 | Litman et al. |
| 4,277,437 | A | 7/1981 | Maggio |
| 4,366,241 | A | 12/1982 | Tom et al. |
| 4,399,218 | A | 8/1983 | Gauhl |
| 4,567,046 | A | 1/1986 | Inoue |
| 4,683,202 | A | 7/1987 | Mullis |
| 4,689,297 | A | 8/1987 | Good |
| 4,707,291 | A | 11/1987 | Thom |
| 4,707,364 | A | 11/1987 | Barach |
| 4,708,876 | A | 11/1987 | Yokoyama |
| 4,798,793 | A | 1/1989 | Eigtved |
| 4,808,417 | A | 2/1989 | Masuda |
| 4,810,414 | A | 3/1989 | Huge-Jensen |
| 4,814,331 | A | 3/1989 | Kerkenaar |
| 4,816,567 | A | 3/1989 | Cabilly et al. |
| 4,818,695 | A | 4/1989 | Eigtved |
| 4,826,767 | A | 5/1989 | Hansen |
| 4,865,866 | A | 9/1989 | Moore |
| 4,904,483 | A | 2/1990 | Christensen |
| 4,916,064 | A | 4/1990 | Derez |

(Continued)

FOREIGN PATENT DOCUMENTS

AR    331094    2/1995

(Continued)

OTHER PUBLICATIONS

Delphine Briand et al., "Substrate Specificity of the Lipase from *Candida parapsilosis*", Lipids, 1995, vol. 30, No. 8. "Definition of Recombined Milk", International Dairy Federation, 1979, doc. 116, p. 5.
Stryer, L., Biochemistry, 1981, $2^{nd}$ Edition, W H Freeman and Co., San Francisco, p. 16.
Jennifer L. Seffernick et al., "Melamine Deaminase and Atrazine Chlorohydrolase: 98 Percent Identical but Functionally Different", Journal of Bacteriology, Apr. 2001, vol. 183, No. 8, pp. 2405-2410.
Andrzej Witkowski et al., "Conversion of β-Ketoacyl Synthase to a Malonyl Decarboxylase by Replacement of the Active-Site Cysteine with Glutamine", Biochemistry, 1999, vol. 38, No. 6, pp. 11643-11650.
"AOCS Introduction to the Processing of Fats and Oils", American Oil Chemists Society, 2003, pp. III 16-19.

(Continued)

*Primary Examiner* — Tekchand Saidha
(74) *Attorney, Agent, or Firm* — Vedder Price P.C.; Thomas J. Kowalski; Heidi Lunasin

(57) ABSTRACT

A method for the in situ production of an emulsifier in a foodstuff, wherein a lipid acyltransferase is added to the foodstuff. Preferably the emulsifier is produced without an increase or without a substantial increase in the free fatty acid content of the foodstuff. Preferably, the lipid acyltransferase is one which is capable of transferring an acyl group from a lipid to one or more of the following acyl acceptors: a sterol, a stanol, a carbohydrate, a protein or a sub-unit thereof, glycerol. Preferably, in addition to an emulsifier one or more of a stanol ester or a stanol ester or a protein ester or a carbohydrate ester or a diglyceride or a monoglyceride may be produced. One or more of these may function as an additional emulsifier.

26 Claims, 67 Drawing Sheets

U.S. PATENT DOCUMENTS

| | | | |
|---|---|---|---|
| 5,112,624 A | 5/1992 | Johna | |
| 5,213,968 A | 5/1993 | Castle | |
| 5,219,733 A | 6/1993 | Myojo | |
| 5,219,744 A | 6/1993 | Kurashige | |
| 5,232,846 A | 8/1993 | Takeda | |
| 5,264,367 A | 11/1993 | Aalrust | |
| 5,273,898 A | 12/1993 | Ishii | |
| 5,288,619 A | 2/1994 | Brown | |
| 5,290,694 A | 3/1994 | Nakanishi | |
| 5,310,679 A | 5/1994 | Artiss et al. | |
| 5,378,623 A | 1/1995 | Hattori | |
| 5,523,237 A | 6/1996 | Budtz | |
| 5,536,661 A | 7/1996 | Boel | |
| 5,558,781 A | 9/1996 | Buchold | |
| 5,650,188 A | 7/1997 | Gaubert | |
| 5,674,707 A | 10/1997 | Hintz et al. | |
| 5,677,160 A | 10/1997 | Oester | |
| 5,695,802 A | 12/1997 | Van Den Ouweland | |
| 5,716,654 A | 2/1998 | Groenendaal | |
| 5,741,665 A | 4/1998 | Kato et al. | |
| 5,763,383 A | 6/1998 | Hashida | |
| 5,766,912 A | 6/1998 | Boel | |
| 5,776,741 A | 7/1998 | Pedersen | |
| 5,814,501 A | 9/1998 | Becker | |
| 5,821,102 A | 10/1998 | Berka | |
| 5,824,354 A | 10/1998 | Ritter et al. | |
| 5,827,719 A | 10/1998 | Sandal | |
| 5,830,736 A | 11/1998 | Oxenboll | |
| 5,834,280 A | 11/1998 | Oxenboll | |
| 5,856,163 A | 1/1999 | Hashida | |
| 5,863,759 A | 1/1999 | Boel | |
| 5,869,438 A | 2/1999 | Svendsen | |
| 5,874,558 A | 2/1999 | Boel | |
| 5,879,920 A | 3/1999 | Dale | |
| 5,892,013 A | 4/1999 | Svendsen | |
| 5,914,306 A | 6/1999 | Svendsen | |
| 5,916,619 A | 6/1999 | Miyazaki | |
| 5,919,746 A | 7/1999 | Hirayama | |
| 5,929,017 A | 7/1999 | Gormsen | |
| 5,965,384 A | 10/1999 | Boel | |
| 5,965,422 A | 10/1999 | Loffler | |
| 5,976,855 A | 11/1999 | Svendsen | |
| 5,989,599 A | 11/1999 | Chmiel | |
| 5,990,069 A | 11/1999 | Andre | |
| 6,001,586 A | 12/1999 | Schellenberger | |
| 6,001,640 A | 12/1999 | Loeffler | |
| 6,020,180 A | 2/2000 | Svendsen | |
| 6,066,482 A | 5/2000 | Steffens | |
| 6,074,863 A | 6/2000 | Svendsen | |
| 6,103,505 A | 8/2000 | Clausen | |
| 6,110,508 A | 8/2000 | Olesen | |
| 6,140,094 A | 10/2000 | Loffler | |
| 6,143,543 A | 11/2000 | Michelsen | |
| 6,143,545 A | 11/2000 | Clausen | |
| 6,146,869 A | 11/2000 | Harris | |
| 6,156,548 A | 12/2000 | Christensen | |
| 6,180,406 B1 | 1/2001 | Stemmer | |
| 6,254,645 B1 | 7/2001 | Kellis | |
| 6,254,903 B1 | 7/2001 | Schuster et al. | |
| 6,344,328 B1 | 2/2002 | Short | |
| 6,350,604 B1 | 2/2002 | Hirayama | |
| 6,358,543 B1 | 3/2002 | Soe | |
| 6,361,974 B1 | 3/2002 | Short | |
| 6,365,204 B1 | 4/2002 | Spendler | |
| 6,432,898 B1 | 8/2002 | Rey | |
| 6,495,357 B1 | 12/2002 | Fuglsang | |
| 6,506,588 B2 | 1/2003 | Tsutsumi | |
| 6,509,182 B2 | 1/2003 | Tsutsumi | |
| 6,511,837 B2 | 1/2003 | Tsutsumi | |
| 6,514,739 B1 | 2/2003 | Udagawa | |
| 6,558,715 B1 | 5/2003 | Rey | |
| 6,582,942 B1 | 6/2003 | Christensen | |
| 6,624,129 B1 | 9/2003 | Borch | |
| 6,645,749 B2 | 11/2003 | Vind | |
| 6,682,922 B2 | 1/2004 | Berka | |
| 6,686,189 B2 | 2/2004 | Rey | |
| 6,726,942 B2 | 4/2004 | Soe et al. | |
| 6,730,346 B2 | 5/2004 | Rey | |
| 6,815,190 B1 | 11/2004 | Abo | |
| 6,852,346 B2 | 2/2005 | Soe | |
| 6,866,837 B2 | 3/2005 | Reubi et al. | |
| 6,936,289 B2 | 8/2005 | Olsen et al. | |
| 6,964,944 B1 | 11/2005 | Callisen et al. | |
| 6,967,035 B2 | 11/2005 | Bojsen et al. | |
| 7,226,771 B2 | 6/2007 | Gramatikova et al. | |
| 7,718,204 B2 | 5/2010 | Soe et al. | |
| 2002/0098536 A1 | 7/2002 | Norinobu | |
| 2002/0110854 A1 | 8/2002 | Tsutsumi | |
| 2002/0142434 A1 | 10/2002 | Tsutsumi | |
| 2002/0168746 A1 | 11/2002 | Tsutsumi | |
| 2002/0182734 A1 | 12/2002 | Diaz-Torres | |
| 2003/0003561 A1 | 1/2003 | Vind | |
| 2003/0028923 A1 | 2/2003 | Lardizabal | |
| 2003/0040450 A1 | 2/2003 | Rey | |
| 2003/0074695 A1 | 4/2003 | Farese | |
| 2003/0100092 A1 | 5/2003 | Berka | |
| 2003/0119164 A1 | 6/2003 | Udagawa | |
| 2003/0148495 A1 | 8/2003 | Hastrup | |
| 2003/0180418 A1 | 9/2003 | Rey | |
| 2003/0185939 A1 | 10/2003 | Nielsen | |
| 2003/0215544 A1 | 11/2003 | Nielsen | |
| 2004/0005399 A1 | 1/2004 | Chakrabarti | |
| 2004/0142441 A1 | 7/2004 | Weiss et al. | |
| 2004/0235106 A1 | 11/2004 | Kapeller-Libermann | |
| 2004/0235119 A1 | 11/2004 | Hoppe et al. | |
| 2005/0059130 A1 | 3/2005 | Bojsen | |
| 2005/0059131 A1 | 3/2005 | Bisgard-Frantzen | |
| 2005/0118697 A1 | 6/2005 | Budolfsen | |
| 2005/0142647 A1 | 6/2005 | Wassell | |
| 2006/0040357 A1 | 2/2006 | Bardaru et al. | |
| 2006/0075518 A1 | 4/2006 | Yaver et al. | |
| 2006/0141457 A1 | 6/2006 | Lindqvist et al. | |
| 2007/0026106 A1 | 2/2007 | Kreij et al. | |
| 2007/0122525 A1 | 5/2007 | Kreij | |
| 2007/0207247 A1* | 9/2007 | Budolfsen et al. | 426/549 |
| 2008/0063783 A1 | 3/2008 | Kreij et al. | |
| 2008/0070287 A1 | 3/2008 | Soe | |
| 2008/0131936 A1 | 6/2008 | Miasnikov et al. | |
| 2008/0187643 A1 | 8/2008 | Horlacher et al. | |

FOREIGN PATENT DOCUMENTS

| | | |
|---|---|---|
| AR | 249546 | 12/1996 |
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| CN | 036151 | 2/2002 |
| CN | 172509 | 6/2003 |
| CN | 97181706.5 | 10/2003 |
| CN | 101200754 | 12/2007 |
| DE | 2817087 | 11/1978 |
| DE | 19620649 | 11/1997 |
| DE | 69129988 | 3/1999 |
| DE | 69330066 | 10/2001 |
| DE | 69527835 | 4/2003 |
| DE | 69528070 | 6/2003 |
| DE | 69333065 | 7/2003 |
| DE | 69904161 | 7/2003 |
| DE | 69716711 | 9/2003 |
| DE | 69333065 | 4/2004 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |

| | | | | | | |
|---|---|---|---|---|---|---|
| DK | PA0543/98 | 4/1998 | | EP | 1193314 | 4/2002 |
| DK | PA199801572 | 11/1998 | | EP | 0746618 | 8/2002 |
| DK | PA5677000 | 12/1998 | | EP | 1233676 | 8/2002 |
| DK | PA199801604 | 12/1998 | | EP | 0648263 | 9/2002 |
| DK | PA199901736 | 12/1999 | | EP | 0784674 | 9/2002 |
| DK | PA200000989 | 6/2000 | | EP | 1073339 | 11/2002 |
| DK | PA200000991 | 6/2000 | | EP | 1275711 | 1/2003 |
| DK | PA200100285 | 2/2001 | | EP | 1285969 | 2/2003 |
| DK | PA200100843 | 5/2001 | | EP | 1298205 | 4/2003 |
| DK | EP659049 | 6/2001 | | EP | 0635053 | 6/2003 |
| DK | EP0784674 | 11/2002 | | EP | 0675944 | 6/2003 |
| DK | EP0869167 | 1/2003 | | EP | 0817838 | 6/2003 |
| DK | EP1073339 | 1/2003 | | EP | 1280919 | 6/2003 |
| DK | PA200300634 | 4/2003 | | EP | 0746608 | 8/2003 |
| DK | 5559215 | 7/2003 | | EP | 0851913 | 5/2004 |
| DK | EP0746608 | 10/2003 | | EP | 1262562 | 6/2004 |
| DK | EP1042458 | 3/2004 | | EP | 1433852 | 6/2004 |
| EP | 0064855 | 11/1982 | | EP | 0977869 | 7/2004 |
| EP | 0010296 | 12/1982 | | EP | 0743017 | 9/2004 |
| EP | 0109244 | 5/1984 | | EP | 0675949 | 10/2004 |
| EP | 0130064 | 1/1985 | | EP | 0880590 | 10/2004 |
| EP | 0140542 | 5/1985 | | EP | 0897423 | 10/2004 |
| EP | 0167309 | 1/1986 | | EP | 1466980 | 10/2004 |
| EP | 0171995 | 2/1986 | | EP | 0839186 | 11/2004 |
| EP | 0205208 | 12/1986 | | EP | 1162889 | 2/2005 |
| EP | 0206390 | 12/1986 | | EP | 1532863 | 5/2005 |
| EP | 0257388 | 3/1988 | | EP | 1559788 | 8/2005 |
| EP | 0260573 | 3/1988 | | EP | 1363506 | 11/2005 |
| EP | 0334462 | 9/1989 | | EP | 1 624 047 A1 | 2/2006 |
| EP | 0195311 | 6/1990 | | EP | 1 624 047 B1 | 10/2006 |
| EP | 0375102 | 6/1990 | | EP | 1762622 | 3/2007 |
| EP | 0426211 | 5/1991 | | EP | 1 788 080 | 5/2007 |
| EP | 0445692 | 9/1991 | | ES | 535608 | 9/1984 |
| EP | 0449375 | 10/1991 | | ES | 535602 | 10/1984 |
| EP | 0468731 | 1/1992 | | ES | 535609 | 3/1985 |
| EP | 0493045 | 7/1992 | | GB | 1086550 | 10/1967 |
| EP | 0583265 | 10/1992 | | GB | 1442418 | 7/1976 |
| EP | 0513709 | 11/1992 | | GB | 1577933 | 10/1980 |
| EP | 0542351 | 5/1993 | | GB | 0028701.1 | 11/2000 |
| EP | 0558112 | 9/1993 | | GB | 2358784 | 8/2001 |
| EP | 0258068 | 11/1993 | | GB | 0301117.8 | 1/2003 |
| EP | 0238023 | 12/1993 | | GB | 0301118.6 | 1/2003 |
| EP | 0575133 | 12/1993 | | GB | 0301119.4 | 1/2003 |
| EP | 0580252 | 1/1994 | | GB | 0301120.2 | 1/2003 |
| EP | 0258068 | 8/1994 | | GB | 0301121.0 | 1/2003 |
| EP | 0622446 | 11/1994 | | GB | 0301122.8 | 1/2003 |
| EP | 0652289 | 5/1995 | | GB | 2379165 | 3/2003 |
| EP | 0654527 | 5/1995 | | GB | 2267033 | 11/2003 |
| EP | 0396162 | 9/1995 | | GB | 0330016.7 | 12/2003 |
| EP | 0687414 | 12/1995 | | JP | 59183881 | 4/1960 |
| EP | 0585988 | 3/1996 | | JP | 54-076892 | 6/1979 |
| EP | 0721981 | 7/1996 | | JP | 54-76892 | 6/1979 |
| EP | 0752008 | 1/1997 | | JP | 5476892 | 6/1979 |
| EP | 0776604 | 6/1997 | | JP | 55131340 | 10/1980 |
| EP | 0531104 | 8/1997 | | JP | 57-189638 | 11/1982 |
| EP | 0808903 | 11/1997 | | JP | 57-189637 | 12/1982 |
| EP | 0682116 | 12/1997 | | JP | 60078529 | 5/1985 |
| EP | 0812910 | 12/1997 | | JP | 62118883 | 11/1985 |
| EP | 0305216 | 3/1998 | | JP | 63042691 | 8/1986 |
| EP | 0847701 | 6/1998 | | JP | 62061590 | 3/1987 |
| EP | 0548228 | 8/1998 | | JP | 62285749 | 12/1987 |
| EP | 0866796 | 9/1998 | | JP | 10203974 | 8/1988 |
| EP | 0702712 | 12/1998 | | JP | 1252294 | 10/1989 |
| EP | 0882797 | 12/1998 | | JP | 2-49593 | 2/1990 |
| EP | 0897667 | 2/1999 | | JP | 2-153997 | 6/1990 |
| EP | 0913092 | 5/1999 | | JP | 04075592 | 3/1992 |
| EP | 0913468 | 5/1999 | | JP | 6014773 | 3/1992 |
| EP | 0321811 | 12/1999 | | JP | 4121186 | 4/1992 |
| EP | 1131416 | 6/2000 | | JP | 15626492 | 6/1992 |
| EP | 0739985 | 11/2000 | | JP | 04200339 | 7/1992 |
| EP | 1057415 | 12/2000 | | JP | 4300839 | 10/1992 |
| EP | 1071734 | 1/2001 | | JP | 4327536 | 11/1992 |
| EP | 0659049 | 3/2001 | | JP | 5211852 | 8/1993 |
| EP | 1103606 | 5/2001 | | JP | 6345800 | 12/1994 |
| EP | 1108360 | 6/2001 | | JP | 8268882 | 4/1995 |
| EP | 1138763 | 10/2001 | | JP | 7231788 | 9/1995 |
| EP | 1145637 | 10/2001 | | JP | 7330794 | 12/1995 |
| EP | 0191217 | 2/2002 | | JP | 8143457 | 6/1996 |
| EP | 0869167 | 2/2002 | | JP | 8266213 | 10/1996 |

| | | | | | |
|---|---|---|---|---|---|
| JP | 9040689 | 2/1997 | WO | 98/41623 | 9/1998 |
| JP | 10155493 | 6/1998 | WO | 98/44804 | 10/1998 |
| JP | 10155493 A | 6/1998 | WO | 98/45453 | 10/1998 |
| JP | 11 228986 | 8/1999 | WO | 98/50532 | 11/1998 |
| JP | 11290078 | 10/1999 | WO | 98/51163 | 11/1998 |
| JP | 2000226335 | 8/2000 | WO | 98/59028 | 12/1998 |
| JP | 03/024096 | 7/2001 | WO | 99/33964 | 7/1999 |
| JP | 3553958 | 5/2004 | WO | 99/34011 | 7/1999 |
| KR | 93-700773 | 3/1993 | WO | 99/37782 | 7/1999 |
| KR | 94-10252 | 10/1994 | WO | 99/42566 | 8/1999 |
| KR | 95-700043 | 1/1995 | WO | 99/50399 | 10/1999 |
| KR | 95-702583 | 6/1995 | WO | 99/53001 | 10/1999 |
| KR | 96-704602 | 8/1996 | WO | 99/53769 | 10/1999 |
| KR | 2001-7012115 | 9/2001 | WO | 99/55883 | 11/1999 |
| KR | 2003/7008997 | 10/2003 | WO | 00/05396 | 2/2000 |
| NL | 0784674 | 12/2002 | WO | 00/28044 | 5/2000 |
| NL | 0869167 | 1/2003 | WO | 00/32758 | 6/2000 |
| NL | 1073339 | 2/2003 | WO | 00/34450 | 6/2000 |
| NL | 0746608 | 11/2003 | WO | 00/36114 | 6/2000 |
| RU | 2140751 | 6/1997 | WO | 00/43036 | 7/2000 |
| RU | 2235775 | 11/1999 | WO | 00/49164 | 8/2000 |
| RU | 2001117497 | 6/2001 | WO | 00/58517 | 10/2000 |
| SE | 9802548 | 7/1998 | WO | 00/59307 | 10/2000 |
| TR | 200101551 | 12/1999 | WO | 00/60063 | 10/2000 |
| WO | 88/02775 | 4/1988 | WO | 00/61771 | 10/2000 |
| WO | 88/03365 | 5/1988 | WO | 00/71808 | 11/2000 |
| WO | 89/01969 | 3/1989 | WO | 00/75295 | 12/2000 |
| WO | 89/06803 | 7/1989 | WO | 01/16308 | 3/2001 |
| WO | 91/00920 | 1/1991 | WO | 01/27251 | 4/2001 |
| WO | 91/06661 | 5/1991 | WO | 01/29222 | 4/2001 |
| WO | 91/14772 | 10/1991 | WO | WO 00/23461 | 4/2001 |
| WO | WO 91/17243 | 11/1991 | WO | 01/34835 | 5/2001 |
| WO | 92/05249 | 4/1992 | WO | WO 01/39544 | 5/2001 |
| WO | 92/14830 | 9/1992 | WO | 01/39602 | 6/2001 |
| WO | 92/18645 | 10/1992 | WO | 01/42433 | 6/2001 |
| WO | 93/01285 | 1/1993 | WO | 01/47363 | 7/2001 |
| WO | 93/11249 | 6/1993 | WO | 01/66711 | 9/2001 |
| WO | 93/12812 | 7/1993 | WO | 01/78524 | 10/2001 |
| WO | 94/01541 | 1/1994 | WO | WO 01/75083 | 10/2001 |
| WO | 94/04035 | 3/1994 | WO | 01/83559 | 11/2001 |
| WO | 94/14940 | 7/1994 | WO | 01/83770 | 11/2001 |
| WO | 94/14951 | 7/1994 | WO | 01/92502 | 12/2001 |
| WO | 94/26883 | 11/1994 | WO | 02/00852 | 1/2002 |
| WO | 95/06720 | 3/1995 | WO | 02/03805 | 1/2002 |
| WO | 95/09909 | 4/1995 | WO | 02/06457 | 1/2002 |
| WO | 95/22606 | 8/1995 | WO | WO 02/06508 | 1/2002 |
| WO | 95/22615 | 8/1995 | WO | 02/14490 | 2/2002 |
| WO | 95/22625 | 8/1995 | WO | 02/24881 | 3/2002 |
| WO | 95/29996 | 11/1995 | WO | 02/30207 | 4/2002 |
| WO | 95/30744 | 11/1995 | WO | WO 02/39828 | 5/2002 |
| WO | 96/09772 | 4/1996 | WO | 02/055679 | 7/2002 |
| WO | 96/13578 | 5/1996 | WO | 02/062973 | 8/2002 |
| WO | 96/13579 | 5/1996 | WO | 02/065854 | 8/2002 |
| WO | 96/13580 | 5/1996 | WO | 02/066622 | 8/2002 |
| WO | 96/27002 | 9/1996 | WO | 02/094123 | 11/2002 |
| WO | 96/28542 | 9/1996 | WO | WO 03006644 | 1/2003 |
| WO | 96/30502 | 10/1996 | WO | WO 2003006644 | 1/2003 |
| WO | 96/32472 | 10/1996 | WO | 03/020923 | 3/2003 |
| WO | 96/39851 | 12/1996 | WO | 03/040091 | 5/2003 |
| WO | 97/04079 | 2/1997 | WO | 03/060112 | 7/2003 |
| WO | 97/05219 | 2/1997 | WO | 03/070013 | 8/2003 |
| WO | 97/07202 | 2/1997 | WO | 03/089260 | 10/2003 |
| WO | 97/11083 | 3/1997 | WO | 03/089620 | 10/2003 |
| WO | 97/14713 | 4/1997 | WO | WO 03/089620 | 10/2003 |
| WO | 97/27237 | 7/1997 | WO | 03/097825 | 11/2003 |
| WO | 97/27276 | 7/1997 | WO | WO 03/097835 | 11/2003 |
| WO | 97/41212 | 11/1997 | WO | 03/099016 | 12/2003 |
| WO | 97/41735 | 11/1997 | WO | 03/100044 | 12/2003 |
| WO | 97/41736 | 11/1997 | WO | 03/102118 | 12/2003 |
| WO | WO 98/00029 | 1/1998 | WO | 2004/004467 | 1/2004 |
| WO | 98/08939 | 3/1998 | WO | 2004/018660 | 3/2004 |
| WO | 98/14594 | 4/1998 | WO | 2004/053039 | 6/2004 |
| WO | WO 98/13479 | 4/1998 | WO | 2004/053152 | 6/2004 |
| WO | WO 98/16112 | 4/1998 | WO | 2004/059075 | 7/2004 |
| WO | 98/18912 | 5/1998 | WO | 2004/064537 | 8/2004 |
| WO | 98/26057 | 6/1998 | WO | 2004/064987 | 8/2004 |
| WO | WO 98/23162 | 6/1998 | WO | WO 2004/084638 | 10/2004 |
| WO | 98/31790 | 7/1998 | WO | 2004/097012 | 11/2004 |
| WO | WO 98/31790 | 7/1998 | WO | 2004/111216 | 12/2004 |

| | | |
|---|---|---|
| WO | 2005/003339 | 1/2005 |
| WO | 2005/005977 | 1/2005 |
| WO | 97/07205 | 2/2005 |
| WO | 2005/056782 | 6/2005 |
| WO | 2005/066347 | 7/2005 |
| WO | 2005/066351 | 7/2005 |
| WO | 2005066351 | 7/2005 |
| WO | WO 2005069762 | 8/2005 |
| WO | 2005/080540 | 9/2005 |
| WO | 2005/087918 | 9/2005 |
| WO | WO 20045/111203 | 11/2005 |
| WO | 2006/008508 | 1/2006 |
| WO | 2006/008653 | 1/2006 |
| WO | WO 2006018205 | 2/2006 |
| WO | 2006/032279 | 3/2006 |
| WO | WO 2006/045354 | 5/2006 |
| WO | WO 2006/031699 | 6/2006 |
| WO | WO 2006/066590 | 6/2006 |
| WO | WO 2008/003420 | 1/2008 |
| WO | WO 2008/036863 | 3/2008 |
| WO | WO 2008/090395 | 7/2008 |
| WO | WO 2008/094847 | 8/2008 |
| WO | WO 2009/002480 | 12/2008 |
| WO | WO 2009/024736 | 2/2009 |
| WO | WO 2009/024862 | 2/2009 |
| WO | WO 2009/081094 | 7/2009 |

OTHER PUBLICATIONS

Hajime Seino et al., "Enzymatic Synthesis of Carbohydrate Esters of Fatty Acid (10 Esterification of Sucrose, Glucose, Fructose and Sorbitol", JAOCS, Nov. 1984, vol. 61, No. 11.
Roberto A. Chica et al., "Semi-rational approaches to engineering enzyme activity: combining the benefits of directed evolution and rational design", Biotechnology, 2005, vol. 16, pp. 378-384.
Anna Maria V. Garzillo et al., "Production, purification and characterization of glucose oxidase from Penicillium variabile P16[1]", Biotechnol. Appln. Biochem., 1995, vol. 22, pp. 169-178.
Patent Abstracts of Japan; Publication No. 04-370055; Publication Date Dec. 12, 1992.
Patent Abstracts of Japan; Publication No. 07-079687; Publication Date Mar. 28, 1995.
Patent Abstracts of Japan; Publication No. 48-16612; Publication Date May 23, 1973.
"Purifine Enzyme", Verenium Corporation leaftlet, Jan. 2008.
Sequence alignment of database accession No. Q44268 with Seq. ID No. 16.
Sequence alignment of database accession No. Q44268 with Seq. ID No. 70.
S. Sen et al., "Developments in Directed Evolution for Improving Enzyme Functions", Appl. Biotechnol., 2007, vol. 143, No. 3, pp. 212-223.
Buckley J. Thomas, "Substrate specificity of bacterial glycerophospholipid: Cholesterol Acyltransferase", Biochemistry, 1982, vol. 21, pp. 6699-6703.
An-I Yeh et al., "Effects of Oxido-reductants on rheological properties of wheat flour dough and comparison with some characteristics of extruded noodles", Cereal Chemistry, 1999, vol. 76, No. 5, pp. 614-620.
Archer, David B., et al., "Proteolytic degradation of heterologous proteins expressed in Aspergillus Niger", Biotechnology Letter, vol. 14, No. 5, May 1992, pp. 357-362.
Arcos J.A. et al, "Quantative Enzymatic Production of 6.O-Acylglucose Esters", Biotechnology and Bioengineering 1998 57(5).
Arpigny Jean Louis et al, "Bacterial lipolytic enzymes: Classification and properties", Biochemical Journal, vol. 343, No. 1, Oct. 1, 1999, pp. 177-183, XP002375631.
August C.A.P.A. et al. "The use of genetic engineering to obtain efficient production of porcine pancreatic phospholipase A2", Biochimica et Biophysica Acta, vol. 1089, 1991, pp. 345-351.
Ausubel, Frederick M., et al., "Short Protocols in Molecular Biology-A Compendium of Methods from Current Protocols in Molecular Biology", 1995, John Wiley & Sons, Inc.
Bachmatova, I., et al., "Lipase of Pseudomonas mendocina 3121-1 and its Substrate Specificty", Biologija, 1995.

Balcao V.M., Pavia A.L. Malcata F.X., Enzyme Microb Technhol, May 1, 1996; 18(6):392-416.
Balcao, Victor M and Malcata F. Xavier (1998), Biotechnology Advances, vol. 16, No. 2, pp. 309-341.
Ballance, D.J., et al., "Transformation of Aspergillus Nidulans by the orotidine-5'-phosphate decarboxylase gene of neurospora crassa", Biochemical and biophysical Research Communications, vol. 112, No. 1, 1983, pp. 284-289.
Ballance, Molecular Industrial Mycology, Systems and Applications for Filamentous Fungi, Leong and Berka (eds.), Marcel Dekker Inc, New York 1991, pp. 1-29.
Barbesgaard, Peder et al Applied Microbiology and Biotechnology (1992) 36: 569-572.
Barnes, P.J., "Lipids in Cereal Technology", Food and Science Technology, Academic Press, 1983.
Basrl, M., et al., "Amidination of Lipase with Hyrdophobic Imidoesters", JAOCS, vol. 69, No. 6, Jun. 1992.
Bateman A and Haft DH (2002) Brief Bioinform 3, 236-245.
Bateman A et al, (2002) Nucleic Acids Res. 30, 276-280.
Bekkers et al, The use of genetic engineering to obtain efficient production of porcine pancreatic phospholipase A2 by *Saccharomyces cerevisiae*, (1991) Biochim Biophys Acta 1089(3), 345-51.
Bengtsson Olivecrona Gunilla et al. Phospholipase activity of milk lipoprotein lipase, Methods in Enzymology, vol. 197, 1991.
Bentley S D et al, Complete genome sequence of the model actinomycete Streptomyces coelicolor A3(2), Nature vol. 417, 2002, pp. 141-147.
Berger K.G. (1990) Recent developments in palm oil. In Oleagineux 45:437-443.
Berks, Ben C., "A common export pathway for proteins binding complex redox cofactors?" Molecular Microbiology, 1996, vol. 22, pp. 393-404.
Beucage S.L. et al, (1981) Tetrahedron Letters 22, p. 1859-1869.
Bilyk, Alexander, et al., "Lipase-catalyzed triglyceride Hydrolysis in Organic Solvent", pp. 320-323, JAOCS, vol. 68, No. 5, May 1991.
Birch et al., "Evidence of Multiple Extracellular Phospholipase Activities of Aspergillus fumigatus", Infection and Immunity, Mar. 1996, vol. 64, No. 3, 1996.
Birgitte Hugh-Jensen et al., "Rhizomucor miehei Triglyceride Lipase is Processed and Secreted from Transformed Aspergillus oryzae", Lipids, vol. 24, No. 9, 1989.
Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.
Bjorkling, F., et al., "Lipase Catalyzed Organic Synthesis", S. Servie (ed.), Microbial Reagents in Organic Synthesis, pp. 249-260, 1992.
Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.
Bjorkling, Frederik, et al., "Lipase -mediated Formation of Peroxycarboxylic acids used in Catalytic Epoxidation of Alkenes", J. Chem. Soc., Chemical Communications, Issue 19, 1990.
Bjurlin et al. Identification of carboxylesterase activities of commercial triacylglycerol hydrolase (lipase) preparations, Eur. J. Lipid Sci. Technol. 104 (2002) 143-155.
Blain JA et al, the Nature of Mycelial Lipolytic enzymes in filamentous fungi, Fems Microbiol. Lett., 1978, vol. 3, 85-87.
Blecker et al, Improved emulsifying and foaming of whey proteins after enzymic fat hydrolysis, (1997) J Food Science, vol. 62, No. 1.
Blumenthal, Cynthia Z., "Production of toxic metabolites in Aspergillus niger, Aspergillus oryzae, and Trichoderma reesei: justification of mycotoxin testing in food grade enzyme preparations derived from the three fungi", Regulatory Toxicology and Pharmacology, vol. 39, 2004, p. 214-228.
Boel, Esper, et al.; "Rhizomucor miehei Triglyceride Lipase is Synthesized as a Precursor"; Novo Research Institute; vol. 23; No. 7; Jul. 1988.
Bornscheuer U T et al, Trends in Biotechnology, Elsevier Publications, Cambridge GB, vol. 20, No. 10, Oct. 1, 2002, pp. 433-437.

Bornscheuer, Uwe T., Lipase-catalyzed syntheses of monoacylglycerols, Enzyme and Microbiol Technology, vol. 17, pp. 578-586, 1995.

Brady, Leo, et al., "A serine protease triad forms the catalytic centre of a triacylglycerol lipase", Nature, vol. 343, 1990.

Brockerhoff, Hans, et al., "Lipolytic Enzymes", Academic Press, 1974.

Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.

Brzozowski, A.M., et al., "A model for interfacial activation in lipases from the structure of a fungal lipase-inhibitor comples", Nature, vol. 351, 1991.

Buckley J. Thomas et al, Journal of Biological Chemistry, vol. 257, No. 6, pp. 3320-3325, 1982.

Buckley, Biochemistry 1983, 22, 5490-5493.

Bulkacz J et al, Biochim. Biophys. Acta (1981) vol. 664, pp. 148-155. Bulletin of the IDF 294: 1994.

Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.

Butcher, Bronwyn G., et al., Microbiology, 2002, vol. 148, pp. 3983-3992.

Buxton et al, Gene, 1985, 37:207-214.

Carriere et al, "Pancreatic Lipase Structure- Function Relationships by Domain Exchange", American Chemical Society-Biochemistry (1997), 36, pp. 239-248.

Carriére, Frédéric, et al., "Structural basis for the substrate selectivity of pancreatic lipases and some related proteins", Biochemica et Biophysica Acta, vol. 1376, pp. 417-432, 1998.

Caruthers MH et al (1980) Nuc Acids Res Symp Ser 215-23.

Casimir C A et al Progress in Lipid Research, 2004, pp. 534-552.

Castello, Phillippe, et al., "Effect of exogenous lipase on dough lipids during mixing of wheat flours", Cereal Chemistry, 1998, vol. 75, No. 5, pp. 595-601.

Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.

Chakravarti DN et al, Biol. Abstracts, 1981, vol. 72, abstract No. 012592.

Cheng Cheng et al., "Transformation of Trichoderma viride using the Neurospora crassa pyr4 gene and its use in the expression of a Taka-amylase A gene from Aspergillus oryzae", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from Arabidopsis", Phytochemical Analysis, vol. 9, pp. 53-57, 1998.

Christophersen, Claus, et al., "Enzymatic Characterisation of Novamyl a Thermostable α-Amylase", Starch/Sturke, vol. 50, 1998.

Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.

Chung OK et al, "Recent Research on Wheat Lipids" Bakers Digest Oct. 1981.

Ciuffreda, Pierangela, et al., "Spectrophotometric Assay of Lipase Activity: A New 40nitrophenyl Ester of a Dialkylglycerol Suitable as a Chromogenic Substrate of Pseudomonas cepacia Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science and Technology, vol. 103, 2001, pp. 333-340.

Clausen, Kim, "New enzyme for degumming", Oils and Fats International, vol. 17, No. 4, Jun. 2001, pp. 24-25.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.

Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.

Conference May 6-8, 1999 in Santorini, Greece—Lipases & Lipids Structure, Function and Biotechnological Applications—Slides presented by Charlotte Poulsen.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998.

Council Directive of Dec. 21, 1988.

Council Regulation (EC) No. 2991/94 May 21, 1994 Official Journal of the European Communities, Sep. 12 1994, No. L316/2-7.

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cromie, Susan. Psychrotrophs and their Enzyme residues in cheese milk, The Australian Journal of Dairy Technology, vol. 47, Nov. 1992.

Cui et al., "Purification and characterization of an intracellular carboxylesterase from Arthrobacter viscosus NRRL B-1973", Enzyme and Microbial Technology, vol. 24, pp. 200-208, 1999.

Daboussi et al, Heterologous expression of the Aspergillus nidulans regulatory gene nirA in Fusarium oxysporum, (1991) Gene 109(1), 155-60.

Daboussi et al., "Transformation of seven species of filamentous fungi using the nitrate reductase gene of Aspergillus nidulans", Curr. Genet., 15:453-456, 1989.

Daftary, R.D., et al., "Functional Bread-Making Properties of Wheat Flour Lipids", Food Technology, vol. 22, No. 237, Mar. 1968-1979.

Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.

Dalrymple, Brian D., et al., "Three Neocallimastic patriciarum esterases associated with the degradation of complex polysaccharides are members of a new family of hydrolases", Microbiology, vol. 142, pp. 2605-2614, 1997.

Danisco, "Unique Chance for Better Bread" *Direct, A Newsletter from Danisco Ingredients* (1996).

Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.

Database accession No. P10480-& Database UniProt 'Online!, Jul. 1, 1989.

Database accession No. Q44268-& Database UniProt 'Online! Nov. 1, 1996.

Database accession No. Q9F7Y6 Database UniProt 'Online!, Mar. 1, 2001.

Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 19976, pp. 81-84.

Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.

Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.

Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.

Database Uniprotkb Jun. 1, 2003, S. Omura et al: "putative secreted hydrolase from streptomyces avermitilis" XP002376340 retrieved from EBI, Hinxton, UK Database accession No. Q828T4 abstract.

Database Uniprotkb May 1, 2000, S.D. Bentley et al: "Putative Secreted Hydrolase from Streptomyces coelicolor" XP002376339 retrieved from EBI, Hinxton, UK Database accession No. Q9S2A5 abstract.

Davies, Progress in Industrial Microbiology, Martinelli and Kinghorn (eds.), Elsevier, Amsterdam 1994, 29:525-560.

De Haas GH et al, "Purification and Properties of Phospholipase A from Porcine Pancreas" Biochim. Biophys. ACTA, 1968, vol. 139, pp. 103-117.

Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.

Dellaporta, et al.; "A Plant DNA Minipreparation Version II"; Plant Molecular Biology Reporter(1983); vol. 1(4); pp. 19-21.

Derewenda et al, "The crystal and molecular structure of the Rhizomuxor miehei Triacylglyceride Lipase at 1.9 Å Resolution", J. Mol. Biol. 1992, 227:818-839.

Derewenda, Urszula, et al., "Catalysis at the Interface: The Anatomy of a Conformational Change in a Triglyceride Lipase", Biochemistry, vol. 31, pp. 1532-1541, 1992.

Direct, A Newsletter from Danisco Ingredients, Sep. 1996.

Directive 2000/36/EC. Http://europa.eu.int/scadplus/leg/en/lvb/121122b.htm. Dato: Jun. 16, 2004.

Drost-Lustenberger, Cornelia, et al., "Lipopan F BG-application and mechanism of a new lipase for bread baking", Cereal Food, 2003.

Drost-Lustenberger, Cornelia, et al., "Lipopan F BG-unlocking the natural strengthening potential in dough", Cereal Food, 2004.

Duan, Rui Dong, Fat Digestion and Absorption (2000), p. 25-46, publisher AOCS Press, Champaign III CODEN 69ACBA Conference; general review written in English.

Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.

Ducancel, Frederic, et al., "Complete amino acid sequence of a PLA2 from the tiger snake Notechis scutatus scutatus as deduced from a complementary DNA", Nucleic Acids Research, vol. 16, No. 18, 1988.

Dugi KA et al, "Human hepatic and lipoprotein lipase: the loop covering the catalytic site mediates lipase substrate specificity", Journal of Biological Chemistry (1995), vol. 270, pp. 25, 396-pp. 25, 401.

Dutilh & Groger, "Improvement of Product Attributes of Mayonnaise by Enzymic Hydrolysis of Egg Yolk with Phospholipase A2", 1981 J. Sci. Food Agric. 32, 451-458.

Eddine et al, "Cloning and expression analysis of NhL1, a gene encoding an extracellular lipase from the fungal pea pathogen Nextria haematococca MP VI (*Fusarium solani* f. sp. pisi) that is expressed in planta", Mol. Genet. Genomics (2001) 265: 215-224.

EFEMA Index of Food Emulsifiers Jan. 2004, 4th Edition.

Ellaiah et al., "Production of lipase by immobilized cells of Aspergillus niger", Process Biochemistry, vol. 39, 2004, pp. 525-528.

Elyk, Alexander, et al., "Lipase-Catalyzed . . . ", JACOS, vol. 08, No. 5, May 1991, pp. 320-323.

Engelhorn and Raab, "Rapid Electroblotting of Small DNA Fragments from Polyacrylamide Gels", Biotechniques (1991) 11(5):594-6.

Engelhorn et al., "Rapid Electroblotting of Small DNA Fragments from Polyacrylamide Gels"; Biotechniques(1991); vol. 11(5); pp. 594-596.

Enzymes in food processing (3rd Ed.), Academic press 1993.

EPO, Mobay Chemical Corporation—Decision of the Technical Board of Appeal 3.3.1 dated Jul. 1, 1982, *Official Journal EPO*, Oct. 1982, pp. 394-402.

Ettinger, William F. et al., "Structure of Cutinase Gene, cDNA, and the Derived Amino Acid Sequence from Phytopathogenic Fungi", Biochemistry, vol. 26, pp. 7883-7892, 1987.

Euromonitor International, "The World Market for Dairy Products—Introduction, Executive Summary, Operating Environment, World Market Overview, Key Trends and Developments" in *Euromonitor, Strategy 2000*, Feb. 2001.

European Parliament and Council Directive No. 95/2/EC of Feb. 20, 1995 on food additives other than colours and sweeteners.

European Parliament and Council Directive No. 98/72/EC of Oct. 15, 1998 amending Directive 95/2/EC on food additives other than colours and sweeteners.

Eurpean Journal of Biochemistry, vol. 166, 1987, Published by Springer International on behalf of the Federation of European Biochemical Societies.

Ezra, David, et al., "Coronamycins, peptide antibiotics produced by a verticillate *Streptomyces* sp. (MSU-2110) endophytic on *Monstera* sp.", Microbiology, 2004, vol. 150, p. 785-793.

Fauvel, et al.; "Purification of Two Lipases With High Phospholipase A, Activity from Guinea-Pig Pancreas"; Biochimica et Biophysica Acta(1981); vol. 663; pp. 446-456.

Fernandez-Garcia et al., "The use of lipolytic and proteolytic enzymees in the manufacture of manchego type cheese from ovine and bovine milk", 1994 J. Dairy Sci. 77: 2139-2149.

Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.

Ferrer et al, 2000, J. Chem. Technol. Biotechnol. 75, 569-576.

Finizym Technical Information, Novo Enzymes, 1981.

Fødevarenubusteriet (2003). Bekendtgørelse om indhold af transfedtsyrer I olier og fedtstoffer. Bekendtgørelse nr. 160 af Nov. 3, 2003.

Forman, Todd, "Enzymes Used in Bread Baking: an Application Update", Technical Bulletin, Vol. XXVI, Issue 10, Oct. 2004.

Fox, et al.; "Isolation and some Properties of Extracellular Heat-Stable Lipases: from *Pseudomonas fluorescens* Strain AFT 36"; Journal of Dairy Research (1988); vol. 50; pp. 77-89.

Frenken N. et al (1992) Appl. Envir. Microbiol. 58 3787-3791.

Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.

Fugman, Douglas A et al Biochemica et Biophysica acia 795 (1984) 191-195.

Galliard T and Dennis S (1974) Phytochemistry vol. 13, pp. 1731-1735.

Galliard, "The Enzymic Breakdown of Lipids in Potato Tuber by Phospholipid- and Galactolipid- Acyl Hydrolase Activities and by Lipoxygenase", Phytochemistry, 1970, vol. 9, pp. 1725-1734.

Gan, Z. et al., "Rapid Communication- Antisera agains: Wheat Diacylgalactosylglycerol (MGDG) and Diacyldigalactosylglycerol (DGDG)", Journal of Cereal Science, vol. 18, pp. 207-210, 1993.

Ganghro AB & Dahot MU, Sci Int. (Lahore), 1992, vol. 4, pp. 169-172.

Gemel, Joanna et al., "Comparison of galactolipase activity and free fatty acid levels in chloroplasts of chill-sensitive and chill resistant plants", European Journal of Biochemistry, vol. 166, 1987.

Geus et al (1987) Nucleic Acids Research 15(9) p. 3743-3759.

Gilbert, E. Jane, et al., "Purification and properties of extracellular lipase from Pseudomonal aeruginosa EF2", Journal of General Microbiology, 1991, vol. 137, pp. 2223-2229.

Gillian, B., Turgeon et al., "Cochliobolus heterostrophus using the Aspergillus nidulans amdS gene", Mol Gen Genet, 201: 450-453, 1985.

Goodey et al, Yeast Biotechnology, Berry et al (eds.), Allen and Unwin, London 1987, pp. 401-429.

Graille J, Lipid Technology, vol. 5, No. 1, 1993, pp. 11-16.

GRAS Notification dated Apr. 11, 2001 by Novozymes for Lecitase$^R$ and Lipopan™ F.

Greenough et al (1996) Food Chem Toxicology 34:161-166 and PubMed abstract in respect thereof.

Greenough R J et al, Food and Chemical Toxicology, vol. 34(2), 1996, pp. 161-166.

Haas and Berka, 1991, Gene, 109:107-113.

Haas, et al., "Enzymatic Phosphatidylcholine Hydrolysis in Organic Solvents: An Examination of Selected Commercially Available Lipases", JAOCS, vol. 71, No. 5, May 1994, pp. 483-490.

Haas, et al.; "Lipases of the Genera *Rhizopus* and *Rhizomucor*: Versatile Catalysts in Nature and the Laboratory"; Food Biotechnology Micro-organisims (1995); pp. 549-588.

Haggag H F et al. Egypt J Food Sci vol. 22, No. 1 pp. 99-107 (1994).

Hansen, Chr., Danisco and Novozymes, Apr. 3, 2002, Food Ingredients day, R&D—the main ingredients for growth.

Hara, et al.; "Comparative Study of Comercially Available Lipases in Hydrolysis Reaction of Phosphatidylcholine"; JAOCS (1997); vol. 74; No. 9, pp. 1129-1132.

Hawker, Kim L., et al., "Heterologous expression and regulation of the Neurospora crassa nit-4 pathway-specific regulartory gene for nitrate assimilation in Aspergillus nidulans", Gene., vol. 100, pp. 237-240, 1991.

Helmsing, "Purification and Properties of Galactolipase", Biochim., Biophys., Acta, vol. 178, pp. 519-533, 1969.

Henderson, H.E., et al., "Structure-function relationships of lipoprotein lipase: mutation analysis and mutagenesis of the loop region", Journal of Lipid Research, vol. 34, 1993, pp. 1593-1602.

Henke, Erik, et al., "Activity of Lipases and Esterases towards Tertiary Alcohols: Insights into Structure-Function Relationships", Angew. Chem. Int. Ed., 2002, vol. 41, No. 17.

Hernquist L & Anjou K (1993) Diglycerides as a stabilizer of the β'-crystal form in margarines and fats, in Fette Seifen Anstrichmittel 2:64-66.

Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.

Hilton S et al, Biochemistry vol. 29, No. 38, 1990, pp. 9072-9078.

Hilton S, Buckley JT, J Biol Chem. Jan. 15, 1991; 266(2): 997-1000.

Hirayama O et al, Biochim Biophys Acta. 1975, vol. 384(1), p. 127-37.

Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.

Höfelmann et al, J. Food Sci., 1985, 50:1721-1731.

Holmquist et al., "Lipases from Rhizomucor miehei and Humicola lanuginosa: Modification of the Lid covering the active site alters enantioselectivity", Journal of Protein Chemistry, vol. 12, No. 6, 1993.

Holmquist et al., "Probing a Functional Role of Glu87 and Trp89 in the Lid of Humicola lanuginosa Lipase through Transesterification Reactions in Organic Solvent", Journal of Protein Chemistry, 1995, vol. 14, No. 4, pp. 217-224.

Holmquist et al., "Trp89 in the Lid of Humicola lanuginosa Lipase is Important for Efficient Hydrolysis of Tributyrin", Lipids, vol. 29, No. 9, 1994.

Horn T et al, (1980) Nuc Acids Res Symp Ser 225-232.

Hoshino, et al.; "Calcium Ion Regulates the Release of Lipase of *Fusarium oxysporum*"; J. Biochem (1991); vol. 110; pp. 457-461.

Hoshino, et al.; "Purification and Some Characteristics of Extracellular Lipase from *Fusarium oxysporum* f. sp. *lini*"; Biosci. Biotech. Biochem (1992); pp. 660-664.

Hoshino, Tamotsu, et al., "Purfication and Some Characteristics of Extracellular Lipase from Fusarium oxysporum", Biosci. Biotech. Biochem., vol. 56, No. 4, pp. 660-664, 1992.

Hossen, Monjur and Hernandez, Ernesto, Lipids, vol. 39, Aug. 2004, pp. 777-782.

Hou Ching T, Journal of Industrial Microbiology, vol. 13, No. 4, 1994, pp. 242-248.

Hübner et al., "Interactions at the lipid-water interface", Chemistry and physics of Lipids, vol. 96, 1998, pp. 99-123.

Hugh-Jensen, Birgitte, et al., "Rhizomucor miehei Triglyceride Lipase is Processed and Secreted from Transformed Aspergillus oryzae", Lipids, vol. 24, No. 9, pp. 1989.

Icard-Verniere, Christele, et al., "Effects of mixing conditions on pasta dough development on biochemical changes", Cereal Chemistry, 1999, vol. 76, No. 4, pp. 558-565.

Igrejas, Gilberto, et al., "Genetic and Environmental Effects on Puroindoline-a and Puroindoline -b Content and their Relationship to Technological Properties in French Bread Wheats", Journal of Cereal Science, vol. 34, 2001, pp. 37-47.

Ikeda H et al, Nature Biotech, vol. 21, 2003, p. 526-531.

Industrial enzymology (2nd Ed.), The Macmillan press 1996.

Ishihara et al Biochimica et Biophysica Acta 388 (1975) 413-422.

Isobe and Nokihara, Febs. Lett., 1993, 320:101-106.

Isobe K et al, Journal of Molecular Catalysis B: Enzymatic 1 (1995), pp. 37-43.

Iwai and Tsujisaka (in Lipases, Borgström and Brockman (eds.), Elsevier, Amsterdam, 1984, pp. 443-468.

Izco et al. Adv Food Sci vol. 21 N 3/4, (10-116) 1999.

Jacob, Jules S., et al., "The Effects of Galactolipid Depletion on the Structure of a Photosynthetic Membrane", The Journal of Cell Biology, vol. 103, Oct. 1986, pp. 1337-1347.

Jacobsberg B. & Oh C.H. (1976) Studies in Palm Oil Crystallisation, in Journal of the American Oil Chemist Society 53:609-616.

jan-Willem F. A. Simons et al., "Cloning, purification and characterisation of the lipase from Staphylococcus epidermidis", Eur. J. Biochem., vol. 253, pp. 675-683, 1998.

Jeng-yen Lin, Matthew, "Wheat Polar Lipids—A Theseis Submitted to the Graduate Faculty of the North Dakota State University of Agriculture and Applied Science", May 1972.

Joerger et al., "Alteration of Chain Length Selectivity of a Rhizopus delemar Lipase through Site-Directed Mutagenesis", Lipids, vol. 29, No. 6, 1994, pp. 377-384.

Jong et al.; "American Type Culture Collection Catalogue of Filamentous FUNGI"; Eighteenth edition (1991).

Joshi, et al.; "Specificity of Fungal Lipase in Hydrolytic Cleavage of Oil"; Acta Microbiologica Hungarica (1987); vol. 34(2); pp. 111-114.

Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.

Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.

Kaniuga Z, Acta Biochim Pol. (1997), vol. 44(1), p. 21-35.

Kapur J & Sood ML, J. Parasit., 1986, vol. 72, pp. 346-347.

Kasai, Naoya, et al., "Chiral C3 epoxides and halophydrins: Their preparation and synthetic application", Journal of Molecular Catalysis B: Enzymatic, vol. 4, 1998, pp. 237-252.

Kawamura and Doi, J. of Bacteriology Oct. 1984, p. 442-444.

Keller, R.C.A., et al., "Competitive Adsorption Behaviour of Wheat Flour Components and Emulsifiers at an Air-Water Interface", Journal of Cereal Science, vol. 25, 1997, pp. 175-183.

Keum J S et al. Korean J Dairy Sci 15 (2): 103-117 1993.

Kim, Hyung Kwoun, et al., Expression and characterization of Ca2+-independent lipase from Bacillus pumilus B26, Biochimica et Biophysica Acta, vol. 1583, 2002, pp. 205-212.

Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.

Kimura, Yoshiharu, et al., "Application of Immobilized Lipase to Hydrolysis of Triacylglyceride", Eur J. Appl Microbiol Biotechnol, 1983, vol. 17, p. 107-112.

King et al, Molecular and Cell Biology of Yeasts, Walton and Yarronton (eds.), Blackie, Glasgow, 1989, pp. 107-133.

Kirk, Ole, et al., "Fatty Acid Specificity in Lipase-Catalyzed Synthesis of Glucoside Esters" Biocatalysis, 1992, vol. 6, pp. 127-134.

Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.

Klein, Robert R., et al., "Additive Effects of Acyl-Binding Site Mutations on the Fatty Acid Selectivity of Rhizopus delemar Lipase", JAOCS, vol. 74, No. 11, 1997.

Kocak et al, Milchwissenschaft 51(1), 1996.

Kochubei et al Role of lipids in the organization of the closest surroundings of the reaction centers(1976) Institute of Plant Physiology.

Kochubei S M et al, Biophysics (1981), vol. 26(2), p. 299-304.

Kochubei S M et al, Mol Biol (Mosk) (1975), vol. 9(2), (p. 190-3) p. 150-153.
Kochubei S M et al, Mol Biol (Mosk) (1978),(vol. 1, p. 47-54) p. 32-37.
Kolkovski et al (1991) Fish Nutrition in Practice, Biarritz (France), Jun. 24-27.
Kostal, Jan, et al., "Enhanced Arsenic Accumulation in Engineered Bacterial Cells Expressing ArsR", Applied and Environmental Microbiology, Aug. 2004, pp. 4582-4587.
Kouker, et al.; "Specific and Sensitive Plate Assay for Bacterial Lipases"; Applied and Environmental Microbiology (1987); vol. 53(1); pp. 211-213.
Krishna, Sajja Hari, et al., "Enantioselective transesterification of a tertiary alcohol by lipase A from Candida antarctica", Tetrahedron: Asymmetry, vol. 13, 2002, pp. 2693-2696.
Kristensen A.C.J. (2004) Preparation of margarine and spreads by enzyme-generated emulsifiers. Master thesis, The Royal Veterinary and Agricultural University, Frederiksberg, Copenhagen.
Krog, Cereal Foods World, The American Association of Cereal Chemists, p. 10, Jan. 1979, vol. 24, No. 1, pp. 10-11.
Krupa, Zbigniew et al., "Requirement of Galactolipids for Photosystem J Activity in Lyophilized Spinach Chloroplasts", Biochimica et Biophysica Acta, 408, pp. 26-34, 1975.
Kuipers, Oscar P., et al., "Enhanced Activity and Altered Specificity of Phospholipase A2 by Deletion of a Surface Loop", Science, vol. 244, 1989.
U.S. Appl. No. 60/039,791, filed Mar. 4, 1997, Clausen.
U.S. Appl. No. 60/189,780, filed Mar. 16, 2000, Soe.
U.S. Appl. No. 60/489,441, filed Jul. 23, 2003, Kreij.
Richardson, Toby H., et al., "A Novel, High Performance Enzyme for Starch Liquefaction", The Journal of Biological Chemistry, vol. 277, No. 29, Issue of July 19, pp. 25501-26507, 2002.
Roberts et al. (1992) Gene 122(1), 155-61.
Roberts, et al.; "Extracellular Lipase Production by Fungi from Sunflower Seed"; Mycologia(1987); vol. 79(2); pp. 265-273.
Robertson et al, Journal of Biological Chemistry, 1994, 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via Rhizopus arrhizus Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin is a Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in Vigna unguiculata leaves and influence of drought stress", Physiologia Plantarum, vol. 104, pp. 577-586, 1998.
Sahsah, Y., et al., "Purification and characterization of a soluble lipolytic acylhydrolase from Cowpea (Vigna unguiculata L.) leaves", Biochimica et Biophysica Acta, vol. 1215, pp. 66-73, 1994.
Saiki R.K. et al Science (1988) 239, pp. 487-491.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.
Sambrook et al, Chapters 1, 7, 9, 11, 12 and 13—Molecular Cloning a laboratory manual, Cold Spring Harbor Laboratory Press (1989).
Sambrook, J., et al. "A Laboratory Manual, Second Edition", Plasmid Vectors, 1989.

Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.
Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).
Saxena, et al.; "Purification Strategies for Microbial Lipases"; Journal of Microbilogical Methods (2003); pp. 1-18.
Scheib et al.; "Stereoselectivity of Mucorales lipases toward triradylglycerols—A simple solution to a complex problem"; Protein Science (1999); vol. 8; pp. 215-221.
Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.
Scopes, Robert K., "Section 8.4: Ultrafiltration" in Protein Purification Principles and Practice, Third Edition (1994) Springer-Verlag, New York, p. 267-9.
Sequence alignment of the nucleotide sequences of SEQ ID No. 2 of EP'167 and SEQ ID No. 7 of D20 and the amino acid sequences of SEQ ID No. 2 of EP'167 and SEQ ID No. 8 of D20.
Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.
Shimada et al, J. of Bioscience and Bioengineering vol. 91, No. 6, 529-538 (2001).
Shimada et al, J. of Fermentation and Bioengineering vol. 75, No. 5, 349-352 (1993).
Shimada et al, JAOCS vol. 71, No. 9, (Sep. 1994).
Shin, et al.; "Butyl-Toyopearl 650 as a New Hydrophobic Adsorbent for Water-Soluable Enzyme Proteins"; Analytical Biochemistry(1984); vol. 138; pp. 259-261.
Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.
Si, Joan Qi; "New Enzymes for the Baking Industry"; Food Tech Europe (1996) pp. 60-64.
Sias B et al, Biochemistry, (2004), vol. 43(31), p. 10138-48.
Siew W.L. & Ng W.L. (1999) Influence of diglycerides on crystalisation of palm oil, in Journal of Science of Food and Agriculture 79:722-726.
Siew W.L. & Ng W.L. (2000) Differential scanning thermograms of palm oil triglycerides in the presence of diglycerides, in Journal of Oil Palm Research 12:107.
Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.
Skovgaard, et al.;"Comparison of Intra- and extracellualr isozyme banding patterns of Fusarium oxysporum"; Mycol. Res. (1998); vol. 102(9); pp. 1077-1084.
Slotboom et al Chem. Phys. Lipids 4 (1970) 15-29.
Smith, George P.; "The Progeny of sexual PCR"; Nature; vol. 370; No. 18; Aug. 4, 1994.
Smith, Timothy L., et al., "The promoter of the glucoamylase-encoding gene of Aspergillus niger functions in Ustilago maydis"; Gene. 88, 259-262, 1990.
Solares, Laura F., et al., "Enzymatic resolution of new carbonate intermediates for the synthesis of (S)-(+)-zopiclone", Tetrahedron: Asymmetry, vol. 13, 2002, pp. 2577-2582.
Sols and De Le Fuente, "On the substrate specificity of glucose oxidase", Biochem et Biophysica Acta (1957) 24:206-7.
Sonntag N.O.V. (1982a) Glycerolysis of Fats and methyl esters—status, review and critique, in Journal of American Oil Chemist Society 59:795-802A.
Soragni, Elisabetta, et al., "A nutrient-regulated, dual localization phospholipase A2 in the symbiotic fungus" The EMBO Journal, vol. 20, No. 18, pp. 5079-5090, 2001.
Sosland, Josh, "Alive and kicking", Milling & Baking News, Feb. 24, 2004.

Soumanou, Mohamed M., et al., "Two-Step Enzymatic Reaction for the Synthesis of Pure Structured Triacylglycerides", JAOCS, vol. 75, No. 6, 1998.
Spendler, et al., "Functionality and mechanism of a new 2nd generation lipase for baking industry"—Abstract. 2001 AACC Annual Meeting; Symposia at Charlotte, NC. Oct. 14-18, 2001.
Spradlin J E, Biocatalysis in Agric. Technol., ACS Symposium, 389(3), 24-43 (1989).
Sreekrishna K et al (1988) J Basic Microbiol. 28(4), 265-78.
Stadler et al., "Understanding Lipase Action and Selectivity", CCACAA, vol. 68, No. 3, pp. 649-674, 1995.
Steinstraesser, et al., "Activity of Novispirin G10 against Pseudomonas aeruginosa in Vitro and in Infected Burns", Antimicrobial Agents and Chemotherapy, Jun. 2002, vol. 46, No. 6, pp. 1837-1844.
Stemmer, Willem P.C.; "DNA shuffling by random fragmentation and reassembly: in vitro recombination for molecular evolution"; Proc. Natl. Acad. Sci. USA, vol. 91, pp. 10747-10751; Oct. 1994.
Stemmer, Willem P.C.; "Rapid evolution of a protein in vitro by DNA shuffling"; Affymax Research Institute, Nature, vol. 370, Aug. 4, 1994.
Sternberg, M., "Purification of Industrial Enzymes with Polyacrylic Acids", Process Biochemistry, Sep. 1976.
Strickland, James A., et al., "Inhibition of Diabrotica Larval Growth by Patatin, the Lipid Acyl Hydrolase from Potato Tubers", Plant Physiol, vol. 109, pp. 667-674, 1995.
Sudbery et at (1988) Biochem Soc Trans. 16(6), 1081-3.
Sugatani, Junko, et al., "Studies of a Phospholipase B from Penicillium Notatum Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Sugiyama et al., "Molecular cloning of a second phospholipase B gene, caPLB2 from Candida albicans", Medical Mycology, vol. 37, 1999.
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the Pseudomonas family", Biochimica et Biophysica Acta, vol. 1259, 1995, pp. 9-17.
Sweigard, James A., et al., "Cloning and analysis of CUT1, a cutinase gene from Magnaporthe grisea", Mol. Gen. Genet., 232:174-182, 1992.
Swinkels et at (1993) Antonie van Leeuwenhoek 64, 187-201.
Sztajer H et al Acta Biotechnol, vol. 8, 1988, pp. 169-175.
Talker-Huiber, Cynthia Z., et al., "Esterase EstE from Xanthomonas vesicatoria (Xv_EstE) is an outer membrane protein capable of hydrolyzing long-chain polar esters", Appl. Microbiol Biotechnol, 61:479-487, 2003.
Terasaki, Masaru, et al., "Glycerolipid Acyl Hydrolase Activity in the Brown Alga Cladosiphon okamuranus Tokida", Biosci. Biotechnol. Biochem., vol. 67, No. 9, pp. 1986-1989, 2003.
The New Enzyme Operatives, Ingredient Technology, 50, Aug. 1997.
Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et at 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.
Toida J et al, Bioscience, Biotechnology, and Biochemistry, Jul. 1995, vol. 59, No. 7, pp. 1199-1203.
Tombs and Blake, Biochim. Biophys (1982) 700:81-89.
Topakas, E., et al. "Purification and characterization of a feruloyl esterase from Fusarium oxysporum catalyzing esterification of phenolic acids in ternary water—organic solvent mixtures", Journal of Biotechnology, vol. 102, 2003, pp. 33-44.
Torossian and Bell (Biotechnol. Appl. Biochem., 1991, 13:205-211.
Tsao et al. (1973) J Supramol Struct. 1(6), 490-7.
Tsuneo Yamane et al., "Glycerolysis of Fat by Lipase", Laboratory of Bioreaction Engineering, vol. 35, No. 8, 1986.
Tsychiya, Atsushi, et al., "Cloning and nucleotide sequence of the mono- and diacylglycerol lipase gene (mdlB) of Aspergillus oryzae", FEMS Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.
Turner, Progress in Industrial Microbiology, Martinelli and Kinghorn (eds.), Elsevier, Amsterdam, 1994, 29:641-666.
Unknown, *Studies on Lipase* (1964) p. 21.
Uppenberg, Jonas, et al., "Crystallographic and Molecular-Modeling Studies of Lipase B from Candida antarctia Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from Candida antarctica", Structure 1994, vol. 2, No. 4.
Upton C et al TIBS Trends in Biochemical Sciences, Elsevier Publication (1995), vol. 20, pp. 178-179.
Uusitalo et al. (1991) J Biotechnol. 17(1), 35-49.
Uwajima T et al, Agricultural and Biological Chemistry, 43(12), pp. 2633-2634, 1979.
Uwajima T et al, Agricultural and Biological Chemistry, 44(9), pp. 2039-2045, 1980.
Uwajima T et al, Methods in Enzymology, 89(41), pp. 243-248.
Vaidehi, et al.; "Lipase Activity of Some Fungi Isolated from Groundnut"; Current Science (1984); vol. 53(23); p. 1253.
van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.
van Gemeren, I.A., et al., "Expression and Secretion of Defined Cutinase Variants by Aspergillus awamori" Applied and Environmental Microbiology, vol. 64, No. 8, pp. 2794-2799, Aug. 1998.
van Kampen, M.D., et al., "The phospholipase activity of Staphylococcus hyicus lipase strongly depends on a single Ser to Val mutation", Chemistry and Physics of Lipids, vol. 93, 1998, pp. 39-45.
van Oort, Maarten G et al, Biochemistry 1989 9278-9285.
Vaysse et at J. of Biotechnology 53 (1997) 41-46.
Villenueva, Inform, vol. 8, No. 6, Jun. 1997.
Vujaklija, Dušica, et al., "A novel streptomycete lipase: cloning, sequencing and high-level expression of the Streptomyces rimosus GDS (L)-lipase gene", Arch. Microbiol, vol. 178, pp. 124-130, 2002.
Wahnelt S.V., Meusel D, & Tülsner M, (1991) Zur kenntnis des diglyceride influsses auf das kristallisationsverhalten von Fetten, in Fat Science Technology 4:117-121.
Waninge, Rianne, et al., "Milk membrane lipid vesicle structures studied with Cryo-TEM", Colloids and Surfaces B: Biointerfaces 31 (2003), pp. 257-264.
Warmuth et al, 1992, Bio Forum 9, 282-283.
Watanabe et al. Bio sci Biochem 63(5) 820-826, 1999.
Watanabe, Yasuo et al., "Cloning and sequencing of phospholipase B gene from the yeast Torulaspora delbrueckii", FEMS Microbiology Letters, vol. 124, 1994, pp. 29-34.
Webb EC, Enzyme Nomenclature, 1992, p. 310.
Weber et al. J Agric Food Chem 1985, 33, 1093-1096.
Wen-Chen Suen et al., "Improved activity and thermostability of Candida antarctica lipase B by DNA family shuffling", Protein Engineering, Design & Selection, vol. 17, No. 2, pp. 133-140, 2004.
West S.; "Olive and Other Edible Oils"; Industrial Enzymology (1996); pp. 295-299.
Whitehead, Michael, et al., "Transformation of a nitrate reductase deficient mutant of Penicillium chrysogenum with the corresponding Aspergillus niger and A. nidulans niaD genes", Mol Gen Genet, 216: 408-411, 1989.
Wilhelm et al., "A Novel Lipolytic Enzyme Located in the Outer Membrane of Pseudomonas aeruginosa", Journal of Bacteriology, vol. 181, No. 22, Nov. 1999, pp. 6977-6986.
Winnacker, Chapter 11, pp. 424-431 In From genes to clones: introduction to gene technology, VCH (1987).

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.

Witt, Wolfgang et al., "Secretion of Phospholipase B From Saccharomyces Cerevisiae", Biochimica et Biophysica Acta, vol. 795, 1984, pp. 117-124.

Wood et al., Eds., "Biomass, Part B, Lignin, Pectin, and Chitin", Methods in Enzymology (1988) vol. 161, Academic Press, San Diego.

Xu, Jun, et al., "Intron requirement for AFP gene expression in Trichoderma viride", Microbiology, 2003, vol. 149, pp. 3093-3097.

Yamaguchi et al, 1991, Gene 103:61-67.

Yamane et al., "High-Yield Diacylglycerol Formation by Solid-Phase Enzymatic Glycerolysis of Hydrogenated Beef Tallow", JAOCS, vol. 71, No. 3, Mar. 1994.

Yamauchi, Asao et al., "Evolvability of random polypetides through functional selection within a small library", Protein Engineering, vol. 15, No. 7, pp. 619-626, 2002.

Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.

Zaks, Aleksey, et al., "Enzyme-catalyzed processes in organic solvents", Proc. Natl. Acad. Sci. USA, vol. 82, pp. 3192-3196, May 1985.

Zaks, Aleksey, et al., "The Effect of Water on Enzyme Action in Organic Media", The Journal of Biological Chemistry, vol. 263, No. 17, Issue of Jun. 15, pp. 8017-8021, 1988.

Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.

Zangenbert, Niels Honberg, et al., "A dynamic in vitro lipolysis model II. Evaluation of the model", European Journal of Pharmaceutical Sciences, vol. 14, 2001, pp. 237-244.

Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.

Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from Torulaspora delbrueckii", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Kweon et al., "Phospholipid Hydolysate and Antistaling Amylase Effects on Retrogradation of Starch in Bread", Journal of Food Science, vol. 59, No. 5, 1994.

Larsen N. G et al, Journal of Cereal Science (1990), vol. 12(2), p. 155-164.

Lee, Keun Hyeung, et al., "Identification and characterization of the antimicrobial peptide corresponding to C-terminal B-sheet domain of tenecin 1, an antibacterial protein of larvae of Tenebrio molitor", Biochem. J., 1996, vol. 334, pp. 99-105.

Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.

Leidich et al., "Cloning and Disruption of caPLB1, a Phospholipase B Gene Involved in the Pathogenicity of Candida albicans", The Journal of Biological Chemistry, vol. 273, No. 40, oo. 26078-26086, 1998.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, J Agric. Food. Chem. (1993), 41, 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M J Yet al, Cereal Chemistry (1974), vol. 51(1), p34-45.

Lin S et al, Enzyme and Microbial Technology 18 (1996), pp. 383-387.

Lipase A "Amano" 6 Assay Note and Product Specification from Armano Pharmaceutical Co Ltd Nagoya Japan, Dec. 16, 1985.

Lipase A "Amano" 6 Assay Note and Product Specification from Armano Pharmaceutical Co Ltd Nagoya Japan, Aug. 27, 1985.

Lipase A "Amano" 6 product sheet, Apr. 1, 1999.

Lipase SP677 as a Baking Enzyme, from Novo Nordisk, Denmark, Mar. 17, 1994.

Litthauer, Derek, et al., "Pseudomonas luteola lipase: A new member of the 320- residue Pseudomonas lipase family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Longhi, Sonia, et al., "Atomic Resolution (1.0 Å) Crystal Structure of Fusarium solani Cutinase: Stereochemical Analysis" J. Mol. Biol. vol. 268, pp. 779-799, 1997.

Lozano et al., "Over-stabilization of Candida antarctica lipase B by ionic liquids in ester synthesis", Biotechnology Letters, vol. 23, pp. 1529-1533, 2001.

Luzi, Paola et al, Genomics (1995), vol. 26(2), p. 407-9.

Madsen J.S. & Qvist K.B. (1997) J. Food Sci. 62, 579-582.

Mao, Cungui, et al., "Cloning and Characterization of a Saccharomyces cerevisiae Alkaline Ceramidase with Specificity for Dihydroceramide", The Journal of Biological Chemistry, vol. 275, No. 40, 2000, pp. 31369-31378.

Maria Teres Neves Petersen, PhD, "Total Internal Reflection Fluorescence Flow System with Electrochemical Control", TIRF-EC Flow System, Sep. 2002.

Marion D et al—Chapter 6, pp. 131-p. 167 of "Interactions The Keys to Cereal Quality" 1998 ISBN 0 913250-99-6 (ed. Hamer & Hoseney).

Marion D et al pp. 245-260 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelli et al., "The Role of Glu87 and Trp89 in the lid of Humicola lanuginosa lipase", Protein Engineering, vol. 9, No. 6, 1996, pp. 519-524.

Martinez, Chrislaine, et al., "Engineering cysteine mutants to obtain crystallographic phases with a cutinase from Fusarium solani pisi", Protein Engineering, vol. 6, No. 2, pp. 157-165, 1993.

Martinez, Diego, et al., "Genome sequence of the lignocellulose degrading fungus Phanerochaete chrysosporium strain RP78", Nature Biology, May 2, 2004.

Mase et al., "Purification and Characterization of a new Lipase from *Fusarium* sp. TM-30", Biosci. Biotech. Biochem., vol. 59, No. 9, pp. 1771-1772, 1995.

Mason, Research Disclosure, Kenneth Mason Publications, Westbourne GB No. 390, Oct. 1996, pp. 661-662.

Masuda, Naoko, et al., "Primary structure of protein moiety of Penicillium notatum phospholipase B deduced from the Cdna", Eur. J. Biochem., vol. 202, pp. 783-787, 1991.

Matos AR, Lipid Catabolism: Lipid Degradation, 2000, p. 779-781.

Matos, A.R., et al., "A patatin-like protein with galactolipase activity is induced by drought stress in Vigna unguiculata leaves", Biochemical Society Transactions, vol. 28, part 6, 2000.

Matos, AR et al, Febs Letters, 491 (2001) p. 188-192.

Matsuda H et al, Biochim Biophys Acta, (1979), vol. 573(1), p. 155-65.

Matsuoka, et al.; "Purification and properties of a Phospholipase C That has High Activity toward Sphingomyelin from *Aspergillus saitoi*"; Biotiechonology and Applied Biochemistry (1987); vol. 9, pp. 401-409.

Matthes et al, (1984) EMBO J. 3, p. 801-805.

McAuley, Katherine E., et al., "Structure of a feruloyl esterase from Aspergillus niger", Acta Crystallographica, Section D, pp. 878-887, 2004.

McCoy M G et al, Journal of Lipid Research (2002), vol. 43, pp. 921-929.

McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.

McNeill, Gerald P., et al., "High-Yield Enzymatic Glycerolysis of Fats and Oils", JAOCS, vol. 68, No. 1, Jan. 1991.

McNeill, Gerald P., et al., "Selective Distribution of Saturated Fatty Acids into the Monoglyceride Fraction During Enzymatic Glycerolysis", JAOCS, vol. 69, no. 11, Nov. 1992.

Memo: From Charlotte Johanson?, "Short introduction/ status on Ferulic Acid Esterases and Acetyl Xylan Esterases", Jan. 9, 2004.

Meyer, V., et al., "Transcriptional regulation of the Antifungal Protein in Aspergillus giganteus", Mol Genet Genomics, 2002, vol. 266, pp. 747-757.

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from Phanerochaete chrysosporium and *Bjerkandera* sp. BOS55", Enzyme and Microbial Technology, vol. 32, 2003, pp. 769-775.

Miller, Byron S., et al., "A Comparison of Cereal, Fungal, and Bacterial Alpha-Amylases as Supplements for Breadmaking", Food Technology, Jan. 1953.

Mine Y, Food Research International, 29(1), 1996, pp. 81-84.

Ministerio da Ciencia e Tecnologia, *Diario Oficial da Uniao*, Jul. 15, 2003.

Mogensen, Jesper E., et al., "Activation, Inhibition, and Destabilization of Thermomyces lanuginosus Lipase by Detergents", Biochemistry, vol. 44, pp. 1719-1730, 2005.

Mohsen et al., "Specificity of Lipase Produced by Rhyopus Delemar and Its Utilization in Bread Making", Egypt. J Food. Sci. vol. 14, No. 1, pp. 175-182.

Mølgaard, Anne, et al., "Rhamnogalacturonan acetylesterase elucidates the structure and function of a new family of hydrolases", Structure, vol. 9, No. 4, 2000.

Molochnaya Promyshlennost 1980 No. 11 21-25, 47—abstract from Food Sci & Tech Abs.

Monographs for Emulsifiers for Foods, EFEMA Nov. 1985 2nd Edition.

Moore, Charles M., et al., "Metal ion homeostasis in Bacillus subtilis", Current Opinion in Microbiology, 2005, vol. 8, pp. 188-195.

Morgan, Keith R., et al., "Stalling in Starch Breads: The Effect of Antistaling α-Amylase", Starch/Stärke, vol. 49, 1997, pp. 59-66.

Morgan-Jones, Gareth; "Notes on Coelomycetes.II. Concerning the Fusicoccum Anamorph of Botryosphaneria Ribis"; vol. XXX, pp. 117-125; Oct.-Dec. 1987.

Morinaga et al Biotechnology (1984) 2, p. 636-639.

Morten, T. & A., Letter, Rodovre, Jul. 2004.

Mukherjee, Kumar D. et al., "Enrichment of γ-linolenic acid from fungal oil by lipase-catalysed reactions", Appl. Microbiol Biotechnol (1991), vol. 35, pp. 579-584.

Murakami, Nobutoshi, et al., "Enzymatic Transformation of Glyceroglycolipids into sn-1 and sn-2 Lysoglyceroglycolipids by use of Rhizopus arrhizus Lipase", Tetrahedron, vol. 50, No. 7, pp. 1993-2002, 1994.

Mustranta, Annikka, et al., "Comparison of Lipases and Phosphlipases in the Hydrolysis of Phospholipids", Process Biochemistry, vol. 30, No. 5, pp. 393-401, 1995.

Nagano, et al.; "Cloning and Nucleotide Sequence of cDNA Encoding a Lipase from *Fusarium keteroporum*"; J. Biochem (1994); vol. 116; pp. 535-540.

Nagao et al, J. Biochem 124, 1124-1129, 1998.

Nagao et al, J. of Bioscience and Bioengineering vol. 89, No. 5, 446-450, 2000.

Nagao et al, J. of Molecular Catalysis B: Enzymatic 17 (2002) 125-132.

Nagao et al, JAOCS vol. 78, No. 2, 2001.

Nagao, Toshihiro et al., "Cloning and Nucleotide Sequence of CDNA Encoding a Lipase from Fusarium heterosporum", J. Biochem., vol. 116, pp. 535-540, 1994.

Nagao, Toshihiro et al., "Expression of Lipase cDNA from Fusarium heterosporum by Saccharomyces cereviisiae: High-Level Production and Purification", Journal of Fermentation and Bioengineering, 1996, vol. 81, No. 6, pp. 488-492.

Nagodawlthana et al., "Enzymes in Food Processing", Third Edition, 1993, Academic Press, Inc.

National Research Council (U.S.) Committee on Specifications of the Food Chemicals Codex, "Lipase Activity" in *Food Chemicals Codex* (1981) National Academy Press, Washington, D.C. pp. 492-493.

Needleman & Wunsch (1970), J. Of Molecular Biology 48, 443-453.

Nelson and Long, Analytical Biochemistry (1989), 180, p. 147-151.

Nerland A H, Journal of Fish Diseases, vol. 19, No. 2, 1996, pp. 145-150.

Ness, Jon. E., et al., "Dna shuffling of subgenomic sequences of subtilisin" Nature Biotechnology, vol. 17, Sep. 1999.

Nestle Research Center, Brochure for "Food Colloids 2006" in Montreux, Switzerland, Apr. 23-26, 2006.

Neugnot Virginie et al, European Journal of Biochemistry, 2002, vol. 269, pp. 1734-1745.

Newport, G., et al., "KEX2 Influences Candida albicans Proteinase Secretion and Hyphal Formation", The Journal of Biological Chemistry, 1997, vol. 272, No. 46, pp. 28954-28961.

Nicolas, Anne, et al., "Contribution of Cutinase Serine 42 Side Chain to the Stabilization of the Oxyanion Transition State", Biochemistry, vol. 35, pp. 398-410, 1996.

Nierle W et al, Fette Seifen Anstrichmittel (1981), vol. 83(10), p. 391-395.

Nierle, W., et al., "Versuche zur Verlangerung der Haltbarkeit von Dartoffelprodukten", Chem. Mikrobiol. Technol. Lebensm., 1975, vol. 3, pp. 172-175.

Nobutoshi M et al, Tetrahedron Letters (1991), vol. 31(1), p. 1331-4.

Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".

Novozymes Memo—Test of lipases for EP1193314B1, Jul. 6, 2005.

Novozymes Report 2002 Annual Report.

Novozymes, "Biowhitening—a new concept for steamed bread", *BioTimes*, Jan. 2005.

Novozymes, "Breakthrough: Less Fattening Fried Food" *BioTimes*, Jun. 2001, No. 2.

Novozymes, "Enzymes for dough strengthening", 2001.

Novozymes, "Lipopan F BG- application and mechanism of a new lipase for bread baking" (Draft) *Cereal Food* (2003) (Author: Drost-Lustenberger, C. et al.).

Novozymes, "Product Sheet for Lipopan F BG", *Cereal Food*, (2001).

Novozymes, "Product Sheet for Lipopan FS BG", *Cereal Food* (2002).

Novozymes, "Product Sheet for Lipopan S BG", *Cereal Food* (2002).

Novozymes, "Strong sales for lipase that makes dough stronger" *BioTimes*, Dec. 2003.

Novozymes, "The perfect roll every time for steers", *BioTimes*, Sep. 2003.
Novozymes, "The value of innovation", *BioTimes*, Mar. 2004.
Novozymes, "The vital role of technical service in baking", *BioTimes*, Jun. 2004.
Ohm, J.B., et al., "Relationships of Free Lipids with Quality Factors in Hard Winter Wheat Flours", Cereal Chem., vol. 79, No. 2, pp. 274-278, 2002.
Ohta, S. et al., "Application of Enzymatic Modification of Phospholipids on Breadmaking", Abstract from AACC 68th Annual Meeting in Kansas City, MO, Oct. 30-Nov. 3, 1983, published in Cerial Foods World, p. 561.
Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.
Okiy D.A. (1977) Partial glycerides and palm oil Crystallisation, in Journal of Science and Food Agriculture 28:955.
Okiy D.A. (1978) Interaction of triglycerides and diglycerides of palm oil, in Oleagineux 33:625-628.
Okiy D.A., Wright, W.B., Berger, K.G. & Morton I.D. (1978), The physical properties of modified palm oil, in Journal of Science of Food and Agriculture 29:1061-1068.
Oluwatosin, Yemisi E., et al., "Phenotype: a Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.
Orberg, Marie-Louise, "Self-assembly Structures Formed by Wheat Polar Lipids and their Interaction with Lipases", Master of Scient Thesis, Apr. 2005.
Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.
Osman, Mohamed, et al., "Lipolytic activity of Alternaria alternata and Fusarium oxysporum and certain properties of their lipids", Microbios Letters, vol. 39, pp. 131-135, 1988.
Ostrovskaya L K et al, Dokl Akad Nauk SSSR, (vol. 186(4), p. 961-3) p. 59-61.
O'Sullivan et al, J Plant Physiol, vol. 313, (1987) p. 393-404.
Palomo, Jose M., et al., "Enzymatic production of (3S, 4R)-(-)-4-(4'-fluorophenyl)-6-oxo-piperidin-3-carboxylic acid using a commerical preparation of lipase A from Candida antarctica: the role of a contaminant esterase" Tetrahedron: Asymmetry, vol. 13, 2002, pp. 2653-2659.
Palomo, Jose M., et al., "Enzymatic resolution of (±)-glycidyl butyrate in aquenous media. Strong modulation of the properties of the lipase from Rhizopus oryzae via immobilization techniques", Tetrahedron: Asymmetry, vol. 15, 2004, pp. 1157-1161.
Palomo, Jose M., et al., "Modulation of the enantioselectivity of Candida antarctica B lipase via conformational engineering: kinetic resolution of (±)-α-hydroxy-phenylacetic acid derivatives", Tetrahedron: Asymmetry, vol. 13, 2002, pp. 1337-1345.
Patent Abstracts of Japan vol. 016, No. 528 (C-1001), Oct. 29, 1992 & JP 04 200339 A see abstract.
Patent Abstracts of Japan vol. 095, No. 001, 28 Feb. 1995 & JP 06 296467 A see abstract.
Peelman F, et al, Protein Science Mar. 1998; 7(3): 587-99.
Penninga et al, Biochemistry (1995), 3368-3376.
Persson, Mattias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the Humicola lanuginosa Lipase", Biochemistry, 1998, vol. 37, pp. 12375-12383.
Peters, Günther H., et al., "Theoretical Investigation of the Dynamics of the Active Site Lid in Rhizomucor miehei Lipase", Biophysical Journal, vol. 71, 1996, pp. 119-129.
Plijter J and JHGM Mutsaers, The surface rheological properties of dough and the influence of lipase on it, Gist-brocades, Bakery Ingredients Division, Oct. 1994.

Plou et al, J. Biotechnology 92 (2002) 55-66.
Ponte J G, Cereal Chemistry (1969), vol. 46(3), p. 325-29.
Punt and van den Hondel, Meth. Enzym., 1992, 216:447-457.
Pyler, E.J., "Baking Science and Technology Third Edition", vol. 1, 1988.
Pyler, E.J., "Baking Science and Technology Third Edition", vol. II, 1988.
Queener et al. (1994) Ann N. Y Acad Sci. 721, 178-93.
Rambosek and Leach, CRC Crit. Rev. Biotechnol., 1987, 6:357-393.
Rapp, Peter, et al., "Formation of extracellular lipases by filamentous fungi, yeasts, and bacteria", Enzyme Microb. Technol., 1992, vol. 14, November.
Rapp, Peter; "Production, regulation, and some properties of lipase activity from *Fusarium oxysporum* f. sp. *vasinfectum*"; Enzyme and Microbial Technology(1995); vol. 17; pp. 832-838.
Reetz M.T., Jaeger K.E. Chem Phys Lipids. Jun. 1998; 93(1-2): 3-14.
Reetz Manfred T, Current Opinion in Chemical Biology, Apr. 2002, vol. 6, No. 2, pp. 145-150.
Reiser J et al. (1990) Adv Biochem Eng Biotechnol. 43, 75-102.
Richardson & Hyslop, pp. 371-476 in Food Chemistry, 1985, second edition, Owen R. Fennema (ed), Manel Dekker, Inc, New York and Basel.
Richardson and Hyslop, "Enzymes: XI—Enzymes Added to Foods During Processing" in *Food Chemistry*, Marcel Dekker, Inc., New York, NY 1985.
Arskog and Joergensen, "Baking performance of prior art lipases from *Candida cylindracea* and *Aspergillus foeditus* and their actiivty on galactolipids in dough", Novozymes Report 2005.
Arskog and Joergensen, "Baking performance of prior art lipases from *Humicola lanuginosa, Aspergillus tubigensis, Rhizopus delemar and Rhizomucor miehei*, and their actiivty on galactolipids in dough", Novozymes Report 2005.
Nerland A.H., "The Nucleotide Sequence of the Gene Encoding GCAT from Aeromonas salmonicida SSP. Salmonicida", Journal of Fish Diseases, 1996, vol. 19, No. 2, pp. 145-150, XP008049669.
Nerland A.H., "Glycerophospholipid-cholesterol acyltransferase precursor", SwissProt, Feb. 11, 2005, XP002318368.
Brumlik, et al.; "Identification of the Catalytic Triad of the Lipase/Acyltransferase from *Aeromonas lydrophila*"; Journal of Bacteriology (1996); vol. 178(7); pp. 2060-2064.
Hilton, et al.; "Purification and Spectral Study of a Microbial Fatty Acyltransferase: Activation by Limited Proteolysis"; American Chemical Society (1990); vol. 29 (38); pp. 9072-9078.
Mason, et al.; "Use of Lipolytic Enzyme From *Areomonas* in Detergents"; Research Disclosures (1996); No. 390; pp. 661-662.
Nerland, A.H.; "The Nucleotide Sequence of the Gene Encoding GCAT from *Areomonas salmonicida* ssp. *salmonicida*"; Journal of Fish Diseases (1996); vol. 19; pp. 145-150.
Neugnot, et al.; "The lipase/acyltransferase from *Candida parapsilosis*, Molecular cloning and characterization of purified recombinant enzymes"; Eur. J. Biochem(2002); vol. 269; pp. 1734-1745.
Upton, et al.; "A New Family of Lipolytic Enzymes"; Elsevier Science Ltd. (1995); vol. 20(5); pp. 178-179.
Verenium Corporation leaflet Purifine Enzyme, "Convert Gums to Oils Significantly Increase oil Yields no increase in Free Fatty Acids", San Diego, Jan. 2008.
AOCS Introduction to the Processing of Fats and Oils, four modules on CD-ROM American Oil Chemists Society, 2003, pp. 111-16-111-19.
Anguita et al.,Appl. Environ. Microbiol., 1983, vol. 59, No. 8, pp. 2411-2417.
Sutrisno et al., Journal of Bioscience and Bioengineering, 2001vol. 91, No. 6, pp. 599-602.
Kalscheuer et al., Applied and Environmental Microbiology, 2004, vol. 70, No. 12, pp. 7119-7125.
Brunel et al., J. Biotechnology, Jul. 1, 2004, vol. 111, No. 1, pp. 41-50.
AACC Method 54-21 Farinograph Method for Flour Nov. 3, 1999.
Anderson D, "A Primer in Oils Processing Technology" in Bailey's Industrial Oil and Fat Products, Sixth edition, John Wiley, 2005, vol. 5, chapter 1, p. 1-56. ISBN 978047138401.

AOAC Official method 999.10 (Lead, Cadmium, Zinc, Copper, and Iron in Foods Atomic absorption Spectrophotometry after Microwave Digestion, First Action 1999 NMKL-AOAC Method.

AOCS Method 2c-25 1997 Moisture and Volatile Matter Air Oven Method.

Archer D.B. & Peberdy, The Molecular Biology of Secreted Enzyme Production by Fungi, Critical Reviews in Biotechnology, 1997, vol. 17, No. 4, p. 273-306.

Aust K., "Applications of lecithin in bakery foods," AIB Research Technical Bulletin, vol. XV, issue 12, Dec. 1993, p. 1-6.

Banas A. et al., "Cellular sterol ester synthesis in plants is performed by an enzyme (Phospholipid: Sterol Acyltransferase) different from the yeast and mammalian Acyl-CoA: Sterol AcylTransferase", Journal of Biological Chemistry, 2005, vol. 280, No. 41, p. 34626-34634.

Beggs J.D., Transformation of yeast by a replicating hybrid plasmid, Nature (London), 1978, vol. 275, p. 104.

Bessette, "Efficient folding or proteins with multiple disulphide bonds in the *Escherida coli cytoplasm*", Proc. Natl. Acad. Sci. USA, 1999, vol. 96, p. 13703-13708.

Bo Yang et al., "Optimization of Enzymatic Degumming Process for Rapseed Oil," JAOCS, 2006, vol. 83, No. 7, p. 653-658.

Briand et al, "Substrate Specificity of the Lipase from Candida parapsilosis", Lipids, Aug. 1995, vol. 30, No. 8, p. 747-754.

Bru R., López-Nicolás J.M., García-Carmona F., (1995) "Aggregation of polyunsaturated fatty acid in the presence of cyclodextrins", Colloids and Surfaces A: Physiochemical and Engineering Aspects. 97, p. 263-269.

Buchold H. et. al., "Enzymatische Phosphatidentfernung aus Pflanzenolen'" Technologies, 1993, vol. 95, No. 8, p. 300-304, ISSN:0931-5985.

Buckley J. Thomas et al., Substrate specificity of bacterial glycerophospholipid: Cholesterol Acyltransferase, Biochemistry, 1982, vol. 21, p. 6699-6703.

Bylund G. (ed), 1995, Dairy Processing Handbook, Chapter 2, p. 17-42, Lund, Sweden.

Bylund G. (ed), 1995, Dairy Processing Handbook, Chapter 9, p. 227-246, Lund, Sweden.

Ceci L.N. et al, Oil recovery and lecithin production using water degumming sludge of crude soybean oils, Journal of the Science of Food and Agriculture, 2008, vol. 88, No. 14, p. 2460-2466.

Cereghino et al., Heterologous protein expression in the methylotrophic yeast *Pichia pastoris*, FEMS Microbiology Review, 2000, vol. 24, No. 1, p. 45-66.

Chica et al, "Semi-rational approaches to engineering enzyme activity: combining the benefits of directed evolution and rational design" Current Opinion in Biotechnology, 2005, vol. 16, p. 378-384.

Christou P., Genetic engineering of crop legumes and cereals: current status and recent advances, Agro-Food-Industry Hi-Tech, Mar./Apr. 1994, p. 17-27.

Davis R.H. and de Serres, Genetic and Microbiological Research Techniques for *Neurospora crassa*, Methods Enzymology, 1971, vol. 17A, p. 79-143.

EC 1.1.3.10 (downloaded—Jul. 12, 2010).
EC 1.1.3.4 (downloaded—Jul. 12, 2010).
EC 1.1.3.5 (downloaded—Nov. 16, 2009).
EC 2.4.1.19 (Downloaded Jul. 12, 2010).
EC 3.1.1.26 (downloaded—Dec. 18, 2008).
EC 3.1.1.3 (downloaded—Dec. 18, 2008).
EC 3.1.1.32 (downloaded—May 22, 2008).
EC 3.1.1.4 Phospholipase A2 enzyme Enzyme Entry 1983 (downloaded Apr. 21, 2009).
EC 3.2.1.3 (downloaded Jul. 12, 2010).
EC 3.2.1.32 (Downloaded Jul. 12, 2010).
EC 3.2.1.60 (downloaded Apr. 28, 2009).

Eliasson A-C. and Larssen K., "Cereals in Breadmaking: a molecular colloidal approach," Marcel Dekker Inc, 1993, ISBN0824788168, p. 31-45.

Garzillo et al, "Production, Purification, and Characterization of Glucose Oxidase from Penicillium Variable P16," Biotechnol. Appl. Biochem., 1995, vol. 22, p. 169-178.

Hammond E.G. et al., "Soybean Oil" in Bailey's Industrial Oil and Fat Products, Sixth edition, John Wiley, 2005, vol. 3, chapter 13, p. 577-653. ISBN 978047138401.

Hinchcliffe E., Kenny E., "Yeast as a vehicle for the expression of heterologous genes", Yeasts, 1993, vol. 5, Anthony H. Rose and J. Stuart Harrison, eds. 2nd edition, Academic Press Ltd.

Hinnen A. et al., Transformation of yeast, Proceedings of the National Academy of Sciences of the USA, 1978, vol. 75, p. 1929.

Hollenberg C.P. et al., Production of recombinant proteins by methylotrophic yeasts, Current Opinion in Biotechnology Oct, vol. 8, No. 5, p. 554-560 (1997).

Horwell DC, "The 'peptoid' approach to the design of non-peptide, small molecular agonists and antogonists of neuropeptides", Trends Biotechnol., 1995, vol. 13, No. 4, p. 132-134.

Hossen, Monjur, "Enzyme catalyzed synthesis of structured phospholipids with conjugated linoleic acid and plant sterols, " A Dissertation by MD Monjur Hossen, May 2005, p. 1-152.

Hui, Bailey's Industrial Oil and Fat Products, 5th edition vol. 2, Edible Oil and Fat Products: Oils and Oilseeds, Wiley Interscience 11995, ISBN 0471594261 p. 513-516.

International Dairy Federation Bulletin Document 116, 1979, p. 5, "Definition of recombined milk".

Ito H. et al., "Transformation of Intact Yeast Cells Treated with Alkali Cations," J. Bacteriology, 1983, vol. 153, p. 163-168.

Jost R., Milk and Dairy Products, 2007, Wiley-VCH, pp. 1-62.

Kimmel, A. et al. "Preparation of cDNA and the Generation of cDNA Libraries: Overview," Methods in Enzymology, 1987, vol. 152, p. 307-316.

LaVallie T.M., 2-Methoxyestradiol Inhibits Proliferation and Induces Apoptosis Independently of Estrogen Receptors α and β, Current Opinion in Biotechnology, 1995, vol. 6, No. 5, p. 501-6.

Leon et al., "A new approach to study starchy changes occurring the double-baking process and during bread storage," Z. Lebensn. Unters Forsch A, 1997, vol. 204 p. 316-320.

McIntyre et al., "Distribution of Glycerophospholipid-Cholesterol Acyltransferase in Selected Bacterial Species," Journal of Bacteriology, Jul. 1979, vol. 139, No. p. 132-136.

Kane, "Effects of rare codon clusters on high-level expression of heterolgous proteins in *E.coli*" Current Opinion Biotechnology, 1995, vol. 6, p. 494-500.

Oil Mill Gazetteer, "Enzymatic Degumming Improves Oil Refining in China," Jul. 2005 vol. 111, p. 2-4.

Poldermans B and Schoppink P, "Controlling the baking process and product quality with enzymes", Cereal Foods World, Mar. 1999, 44 (3), p. 132-135.

Potrykus I., Gene Transfer to Plants: assessment of published approaches and results, Annu. Rev. Plant Physiol. Plant Mol. Biol., 1991, vol. 42, p. 205-225.

Seffernick et al, "Melamine Deaminase and Atrazine Chlorohydrolase: 98 Percent Identical but Functionally Different", Journal of Bacteriology, Apr. 2001, vol. 183, No. 8, p. 2405-2410.

Seino et al, "Enzymatic Synthesis of Carbohydrate Esters of Fatty Acid (10 Esterification of Sucrose, Glucose, Fructose and Sorbitol", J. Am. Oil Chem. Soc., Nov. 1984, vol. 61, No. 11, p. 1761-1765.

Simon RJ et al.,"Peptoids: a modular approach to drug discovery", Proc. Natl. Acad. Sci. USA, 1992, vol. 89, No. 20, p. 9367-9371.

Stryer, "Conformation and Dynamics," Biochemistry, 2nd Edition, 1981, WH Freeman & Co., San Francisco, p. 16.

Szuhaj B.F., "Lecithins" in Bailey's Industrial Oil and Fat Products, Sixth edition, John Wiley, 2005, vol. 2, chapter 13, p. 361-456. ISBN 978047138401.

Tanji M.et al., "Lipase hydrolysis of milk fat and its soft fractions", Research Bulletin of Obihiro University, 2001, vol. 22, No. 2, p. 89-94.

Tilden E.B. and Hudson C.S., Preparation and Properties of the Amylases Produced by Bacillus Macerans and Bacillus Polymyxa, J. Bacteriology, 1942, vol. 43, p. 527-544.

Torres C.F. et al., A two steps enzymatic procedure to obtain sterol esters, tocopherols and fatty acid ethyl esters from soybean oil deodorizer distillate, Process Biochemistry, 2007, vol. 42, no., 9, p. 1335-1341.

Trueman L.J., "Heterologous Expression in Yeast," Methods Molecular Biology, vol. 49, p. 341-354 (1995).

Turner G. Vectors for generic manipulation, in Martinelli S.D, Kinghorn J.R. (editors), *Aspergillus*: 50 years on. Progress in industrial microbiology, 1994, vol. 29, p. 641-666.

Verenium Corporation leaflet Purifine® Enzyme"Convert Gums to Oils Significantly Increase Oil Yields no increase in Free Fatty Acids", San Diego, Jan. 2008.

Witkowski et al, "Conversion of a B-Ketoacyl Synthase to a Malonyl Decarboxylase by Replacement of the Active-Site Cysteine with Glutamine," Biochemistry, Sep. 7, 1999, vol. 38, No. 36, p. 11643-11650.

Trueman L.J., "Heterologous Expression in Yeast," Methods Molecular Biology, vol. 49, p. 341-354 (1995).

Turner G., Vectors for Generic Manipulation, in Martinelli S.D., Kinghorn J.R. (editors), Aspergillus: 50 years on. Progress in Industrial Microbiology, 1994, vol. 29, p. 641-666.

Notification of Reasons for Refusal: JP Application No. 526105, Feb. 12, 2003 (Translation).

Notification of Reasons for Refusal: JP Application No. 526105, Jun. 4, 2002 (Translation).

Written Argument: JP Application No. 97181706.5, (Dec. 9, 1997) (Translation).

Acker, L. "Die Lipide des Getreides, ihre Zusammense und inre Bedeutung", Getreide Mehl Brot (1974) 28:181-187.

Adamzcak, Marek, et al., "Application of Enzymatic Glycerolysis for Production of Monoglycerides from Waste Fats", Polish Journal of Food and Nutrition Science, Mar. 1994, p. 129-133.

Adhikari, B., et al., "Stickiness in Foods: A Review of Mechanisms and Test Methods", International Journal of Food Properties, vol. 4, No. 1, 2001, 1pg.

Agarwal et al., "Lipase Activity of Some Fungi Isolated from Groundnut", Current Science, Dec. 5, 1984, vol. 53, No. 23, p. 1253.

Aires-Barros M.R. et al., Isolation and purification of lipases, in "Lipases their structure, biochemistry and application", editors Woolley et al., Cambridge University Press, 1994, ISBN 0521445469 NZAS—00354436 p. 242-270.

Aisaka, Kazuo et al., "Production of Lipoprotein Lipase and Lipase by Rhizopus japonicu", Agri. Biol. Chem., vol. 43, No. 10, pp. 2125-2129, 1979.

Akoh, Casimir C., et al., "GDSL family of serine esterases/lipases" Progress in Lipid Research, vol. 43, 2004, pp. 534-552.

Allan Svendsen et al., "Biochemical properties of cloned lipases from the Pseudomonas family", Biochimica et Biophysica Acta, vol. 1259, 1995, pp. 9-17.

Al-Obaidy, K A, "Dough and Gluten Characteristics of Good and Poor Quality Flours: Lipid-Protein Bindings affected by Mixing time, water absorption, chemicals and heat," Dissertation Abstracts International B (1987) vol. 47(9) 3597, order No. DA8624641, pp. 266.

Amano Enzyme Inc., http://www.amano-enzyme.co.jp/english/productuse/oil_fat.html. Date of visit: Jun. 21, 2004; (Copyright 2003) pp. 1-2.

Amano Enzymes "Enzymes for Gastrointestinal Digestion" Oct 1997, pp. 1-2.

Amano Enzymes, Amano Enzyme Europe Ltd, Sep. 1994, pp. 1-4.

Amin, Neelam S., et al., "Direct transformation of site-saturation libraries in Bacillus subtilis", BioTechniques, Dec. 2003, vol. 35 p. 1134-1140.

Andersson, L., et al., "Hydrolysis of galactolipids by human pancreatic lipolytic enzymes and duidenal contents", Journal of Lipid Research, 1995, vol. 36, pp. 1392-1400.

Sander, Andreas, et al., "Herstellung and Anwendungsmoelichkeiten von Eiweiss-Fettsaeurekondensaten/Production and application of acylated proten hydrolysates", Fett/Lipid 99 (1997) Nr. 4, pp. 115-120.

Arbige, Michael A et al, "Novel lipase for cheddar cheese flavor development" Food Technology, vol. 40, 1996, p. 91-98.

Arcos J.A. et al., "Quantative Enzymatic Production of 6.0-Acylglucose Esters", Biotechnology and Bioengineering 1998 vol. 57, No. 5, p. 505-509.

Assignment Document for Enzymatisk detergent additiv, detergent og vaskemetode, executed Aug. 13, 1986, p. 1-3.

Atomi H, et al., "Microbial lipases-from screening to design", In: Barnes PJ, ed. Oils-Fats-Lipids, 21st World Congress Int Soc Fat Res. England: Bridgwater, 1995: pp. 49-50, vol. 1. NZAS-0016055-NZAS-0016056.

Aunstrup, Knud et al., "Production of Microbiol Enzymes", Microbiol Technology, Academic Press, 1979, 2nd edition, vol. 1, chap. 9, p. 281-309.

Ausubel, Frederick M., et al. (editors), "Short Protocols in Molecular Biology- A Compendium of Methods from Current Protocols in Molecular Biology", 1995, John Wiley & Sons, Inc, NZAS-0028441-NZAS-002844.

"Fat Splitting, Esterification, and Interesterification", in Bailey's Industrial Oils and Fat Products, vol. 2, 4th Edition, John Wiley and Sons, New York pp. 97-173, 1982.

Balcao V.M et. al., "Bioreactors with immobilized lipase: State of the art," Enzyme Microb Technhol, May 1, 1996; 18(6):392-416.

Balcao, V. et. al. "Lipase Catalyzed Modification of Milkfat," (1998), Biotechnology Advances, vol. 16, No. 2, pp. 309-341.

Ballance, "Transformation Systems for Filamentous Fungi and an Overview of Fungal Gene Structure", Molecular Industrial Mycology, Systems and Applications for Filamentous Fungi, Leong and Berka (eds.), Marcel Dekker Inc, New York 1991, pp. 1-29.

Barbesgaard, Peder et al, "On the safety of Aspergillus oryzae: a review," Applied Microbiology and Biotechnology (1992) 36: 569-572.

Barnes, P.J., "Lipids in Cereal Technology", Food and Science Technology, Academic Press, 1983, pp. 167-171.

Basrl, M., et al., "Amidination of Lipase with Hyrdophobic Imidoesters", JAOCS, vol. 69, No. 6, Jun. 1992, p. 579-582.

Bateman A et. al., "HMM-based databases in InterPro," Briefings in Bioinformatics vol. 3,No. 3, pp. 236-245 (2002).

Bateman A et al, (2002), "The Pfam Protein Families Database," Nucleic Acids Res. vol. 30, No. 1, p. 276-280.

Bekkers et al, "The use of genetic engineering to obtain efficient production of porcine pancreatic phospholipase A2 by Saccharomyces cerevisiae," (1991) Biochim Biophys Acta vol. 1089 No. 3 , p. 345-51.

Bengtsson Olivecrona Gunilla et al. "Phospholipase activity of milk lipoprotein lipase," Methods in Enzymology, vol. 197, 1991 p. 345-356.

Beucage S.L. et al, (1981), "Deoxynucleoside Phosphoramidites- A New class of Key Intermediates for Deoxypolynucleotide Synthesis," Tetrahedron Letters 22, p. 1859-1869.

Bieleski R.L., Sugar Alcohols, in Loewus F A & Tanner W (eds), Plant Carbohydrates I. Intercellular Carbohydrates Encyclopedia Plant Physiol. N.S., 1982, 13A, chapter 5, p. 158-192, Springer, Berlin.

Biocatalysts, Limited, Product Sheet for Lipomod(TM) 627P-L627P, published Jan. 9, 2002, Pontypridd UK, p. 1.

Jakobsen, Soren, "Biotekkomet falder hardt til jorden", Borsens, p. 6, Aug. 28, 2002. NZAS-0564031.

Bornscheuer U T et al, "Optimizing lipases and related enzymes for efficient application," Trends in Biotechnology, Elsevier Publications, Cambridge GB, vol. 20, No. 10, Oct. 1, 2002, pp. 433-437.

Brady, Leo, et al., "A serine protease triad forms the catalytic centre of a triacylglycerol lipase", Nature, vol. 343, 1990, p. 767-770.

Brockerhoff, Hans, et al., "Lipolytic Enzymes", Academic Press, 1974, 1 page.

Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.

Brzozowski, A.M., et al., "A model for interfacial activation in lipases from the structure of a fungal lipase-inhibitor comples", Nature, vol. 351, 1991, pp. 491-494.

Buckley J. Thomas et al, "Purification and Partial Characterization of a Bacterial Phospholipid: Cholesterol Acyltransferase," Journal of Biological Chemistry, vol. 257, No. 6, pp. 3320-3325, 1982.

Buckley, "Mechanism of action of a bacterial glycerophospholipid cholesterol acyltransferase," Biochemistry 1983, 22, 5490-5493.

Bulkacz J et al, "Phospholipase A activity in supernatants from cultures of Bacteroides melaninogenicus," Biochim Biophys. Acta (1981) vol. 664, pp. 148-155.

Van Den Berg. G, Regulatory status and use of lipase in various countries, Bulletin of the IDF 294/1994—The use of lipases in cheesemaking, pp. 19-20, (1994).

Butcher, Bronwyn G., et al., "The divergent chromosomal ars operon of Acidithiobacillus ferrooxidans is regulated by an atypical ArsR protein," Microbiology, 2002, vol. 148, pp. 3983-3992.
Buxton et al, "Transformation of Aspergillus niger using the argB gene of Aspergillus nidulans," Gene, 1985, 37:207-214.
Cao, Shu-Gui, et al., "Enzymatic Preparation of Monoglycerides via Glycerolysis of Fats and Oils Catalyzed by Lipase from Pseudomonas Species" National Laboratory of Enzyme Engineering. Monoglycerides, Enzyme Engine, Annals New York Academy of Sciences, 1996, vol. 799, issue 1, p. 670-677.
Caruthers MH et al (1980) "New Chemical methods for Synthesizing polynucleotides," Nuc Acids Res Symp Ser 215-223.
Casimir C A et al "GDSL family of serine esterases/lipases," Progress in Lipid Research, 2004, pp. 534-552.
Castello, P., et al., "Technological and Biochemical effects of exogenous lipases in breadmaking", 2nd European Symposium on enzymes in Grain Processing, Dec. 8-10, 1999, Helsinki, p. 193-199. Published by VTT, Espoo, 2000.
Castello, Phillippe, et al., "Effect of exogenous lipase on dough lipids during mixing of wheat flours", Cereal Chemistry, 1998, vol. 75, No. 5, pp. 595-601.
Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.
Cheng Cheng et al., "Transformation of Trichoderma viride using the Neurospora crassa pyr4 gene and its use in the expression of a Taka-amylase A gene from Aspergillus oryzae", Curr. Genet., 18: 453-456, 1990.
Christensen et al, "A new and simple method to immobilise lipases by means of granulation", 1998 Nachwachsende Rohstoff 10, 98-105.
Christie, William et al., "New Procedures for Rapid Screening of Leaf Lipid Components from Arabidopsis", Phytochemical Analysis, vol. 9, pp. 53-57, 1998.
Christophersen, Claus, et al., "Enzymatic Characterisation of Novamyl a Thermostable α-Amylase", Starch/Sturke, vol. 50, 1998, p. 39-45.
Cloning of rad51 and rad52 homologues from Aspergillus oryzae and the effect of their overexpression on homologous recombination, Novozymes internal document Feb. 9, 2001.
Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.
Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.
Conference May 6-8, 1999 in Santorini, Greece—Lipases & Lipids Structure, Function and Biotechnological Applications—Slides presented by Charlotte Poulsen.
Cordle et al, "The hydrophobic surface of colipase influences lipase activity at an oil-water interface", Journal of Lipid Research, vol. 39 (1998), 1759-1767.
Coteron, A., et al., "Reactions of Olive Oil and Glycerol over Immobilized Lipases", JAOCS, vol. 75, No. 5, 1998, p. 657-660.
Council Directive of Dec. 21, 1988 (89/107/EEC).
Council Regulation (EC) No. 2991/94 May 21, 1994 Official Journal of the European Communities, Sep. 12 1994, No. L316/2-7.
Courtin, Christophe M., et al., "Recent Advances in Enzymes in Grain Processing", Laboratory of Food Chemistry, Leuven, Belgium, 2003, ISBN 90-9016671-8.
Creveld, Lucia D, et al., "Identification of Functional and Unfolding Motions of Cutinase as Obtained from Molecular Dynamics Computer Simulations", Proteins: Structure, Function, and Genetics, 33:253-264, 1998.
Cui et al., "Purification and characterization of an intracellular carboxylesterase from Arthrobacter viscosus NRRL B-1973", Enzyme and Microbial Technology, vol. 24, pp. 200-208, 1999.
Daboussi et al, "Heterologous expression of the Aspergillus nidulans regulatory gene nirA in Fusarium oxysporum," (1991) Gene vol. 109, No. 1, p. 155-60.

Daboussi et al., "Transformation of seven species of filamentous fungi using the nitrate reductase gene of Aspergillus nidulans", Curr. Genet., 15:453-456, 1989.
Daftary R.D. et al., Functional Bread-making Properties of Wheat Flour Lipids, Functional Bread-Making Properties of Lipids chapter 2, in Food Technology, Mar. 1968m vol. 22, No. 327, p. 79-82, NZAS—0487568.
Danisco, Hexose oxidase—nyt enzym med mange mulingheder (advert) Mar. 15, 1999.
Accession No., P10480 "Glycerophosphopholipid-cholesterol acyltransferase" created Jul. 1, 1989, available at www.ncbi.nlm.nih.gov/entrez.
Declaration by Clive Graham Phipps Walter (Dec C) Jul. 4, 2003.
Declaration by Dr Jorn Borch Soe (Dec F) Dec. 2, 2003.
Declaration by Dr Mark Turner (Dec G) Feb. 4, 2005, pp. 1-6.
Declaration by Henrik Pedersen (Dec A) Jul. 7, 2003, pp. 1-3.
Declaration by Henrik Pedersen, Masoud Rajabi Zargahi and Clive Graham Phipps Walter (Dec 2) Feb. 7, 2005, pp. 1-26, D46.
Declaration by Janne Brunstedt (Dec D) Jul. 4, 2003.
Declaration by Kazuko Kato, Henrik Pedersen, Masoud Rajabi Zaghari, Clive Phipps Walter, and Janne Brunstedt (Dec I) Feb. 7, 2005.
Declaration by Kim Borch Oct. 17, 2005.
Declaration by Luise Erlandsen Oct. 21, 2005.
Declaration by Masoud Rajabi Zargahi (Dec B) Jul. 7, 2003.
Declaration by Masoud Rajabi Zargahi (Dec E) Jul. 15, 2003.
Declaration by Tina Spendler Oct. 14, 2005.
Dinkci. N, Mucor miehei den elde edilen lipaz, Ege Univeraitesi Ziraat Fakultesi Dergisi Cilt, 37, Saiy 2-3, 2000, 141-148.
Direct, "The Road to Success: New Stabilizers Rouses Big Interest," A Newsletter from Danisco Ingredients, Sep. 1996, p. 1-4.
Directive 2000/36/EC. Http://europa.eu.int/scadplus/leg/en/lvb/121122b.htm. Dato: Jun. 16, 2004.
Drost-Lustenberger, C and Spendler T Lipopan F BG—Application and Mechanism of a new lipase for baking, Novozymes. Spanish version of EP869167, Novozymes, Oct. 7, 1998.
Drost-Lustenberger, C. et al., Novozymes, "Lipopan F BG- application and mechanism of a new lipase for bread baking" Cereal Food (2003), Novozymes internal draft.
Drost-Lustenberger, Cornelia, et al., "Lipopan F BG-unlocking the natural strengthening potential in dough", Cereal Food, 2004. Novozymes internal draft, p. 1-6.
Dugi KA et al, "Human hepatic and lipoprotein lipase: the loop covering the catalytic site mediates lipase substrate specificity", Journal of Biological Chemistry (1995), vol. 270, pp. 25, 396-pp. 25, 401.
Lorber B & Giegé R, Preparation and handling of biological macromolecules, in Dugruix (Ed), Crystallization of Nucleic Acids and Proteins A Practical Approach, 1992, Oxford University of Press, ISBN 0199632456.
Dutilh & Groger, "Improvement of Product Attributes of Mayonnaise by Enzymic Hydrolysis of Egg Yolk with Phospholipase A2", 1981 J. Sci. Food Agric. 32, 451-458.
Efthymiou CC et al., "Development of domestic feta cheese", Journal of Dairy Science 1964, vol. 47, No. 6, p. 593-598.
Nagodawithana, T. "Enzymes in food processing" (3rd Ed.), Academic press 1993, p. 205-219.
European Parliament and Council Directive No. 95/2/EC of Feb. 20, 1995 on food additives other than colours and sweeteners. OJ No. L61 Mar. 18, 1995 p. 1-53.
European Parliament and Council Directive no. 98/72/Ec of Oct. 15, 1998 amending Directive 95/2/EC on food additives other than colours and sweeteners. OJ No. L295 Nov. 4, 1998 p. 18-30.
Ferrer et al, 2000, "Purification and properties of a lipase from Penicillium chrysogenum isolated from industrial wastes," J. Chem. Technol. Biotechnol. 75, 569-576.
Finizym Technical Information, Novo Enzymes, 1981.
Vafiades D, "Embracing Enzymes", Food R&D, Dairy Fields ingredient technology section, Mar. 1996 p. 39-44.
Forman, Todd, "Enzymes Used in Bread Baking: An Application Update", Technical Bulletin, vol. XXVI, Issue 10, Oct. 2004.
Frenken N. et al (1992) "cloning of the Pseudomonas glumae Lipase Gene and Determination of the Active Site Residues," Appl. Envir. Microbiol. 58 3787-3791.

Freshzyme™, Novozymes Product Sheet Baking/2000-11814, NZAS—0265916. Mar. 12, 2001, p. 1-3.

Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.

Frost & Sullivan leaflet for report #7954-88 U.S. Market for Enzymes for Food Applications, May 2001, NZAS—0413133.

Fugman, Douglas A et al "Lipoprotein Lipase and phospholipase A2-Catalyzed hydrolysis of phospholipid vesicles with an encapsulated fluorescent dye," Biochemica et Biophysica acia 795 (1984) 191-195.

Galliard T and Dennis S (1974) Phospholipase, Galactolipase, and Acyl Transferase Activities of a Lipolytic Enzyme from Potatoe, Phytochemistry vol. 13, pp. 1731-1735.

Gemel J et al., "Comparison of galactoplipase activity and free fatty acid levels in chloroplasts of chill-sensitve and chill-resistant plants", European Journal of Biochemistry, vol. 166, 1987, Published by Springer International on behalf of the Federation of European Biochemical Societies, p. 229-233.

Godfrey, Tony, et al., "Industrial Enzymology Second Edition", Macmillan Press, 1996, ISBN 0333594649, Chapter 2.17, Olive and other Edible Oils, p. 299-300.

Goodey et al, "Expression and secretion of foreign polypeptides in Yeast," Yeast Biotechnology, Berry et al (eds.), Allen and Unwin, London 1987, pp. 401-429.

Graille J, "Possible applications of acyltransferases in Oleotechnology," Lipid Technology, vol. 5, No. 1, 1993, pp. 11-16.

GRAS Notification dated Apr. 11, 2001 by Novozymes for LecitaseR and LipopanTM F. Gregg L. et al., A lipases preparation produced by Aspergillus oryzae expressing the gene encoding a lipases from Fusarium oxyporum. Novo Nordisk A/S product Sheet for Lecitase Novo, Oct. 2000.

Greenough et al (1996) "Safety evaluation of a lipase expressed in Aspergillus oryzae," Food Chem Toxicology 34:161-166 and PubMed abstract in respect thereof.

Greenough R J et al, "Safety Evaluation of a Lipase Expressed in Aspergillus oryzae," Food and Chemical Toxicology, vol. 34(2), 1996, pp. 161-166.

Haas and Berka, 1991, "cloning, expression and characterization of a cDNA encoding a lipase from Phizopus delemar," Gene, 109:107-113.

Marion D et al., "Lipids, Lipid-protein interactions and the quality of baked cereal products", chapter 6 in Hamer, Rob J., et al., "Interaction: The Keys to Cereal Quality", American Association of Cereal Chemists, S Paul, Minnesota, 1998, ISBN 0913250996, p. 131-167.

Hanlin, Richard T., "Illustrated Genera of Ascomycetes"; The American Phytopathological Society, 1992, St Paul, Minnesota, p. 48, 49, 234, 235, 244, 245.

Hansen, Chr., Danisco and Novozymes, Apr. 3, 2002, Food Ingredients day, R&D—the main ingredients for growth.

Hara, et al.; "Comparative Study of Comercially Available Lipases in Hydrolysis Reaction of Phosphatidylcholine"; JAOCS (1997); vol. 74; No. 9, pp. 1129-1132.

Hawker, Kim L., et al., "Heterologous expression and regulation of the Neurospora crassa nit-4 pathway- specific regulartory gene for nitrate assimilation in Aspergillus nidulans", Gene., vol. 100, pp. 237-240, 1991.

Hedin, Eva M.K., et al., "Selective reduction and chemical modification of oxidized lipase cysteine mutants".

Hilton S et al, "Purification and spectral study of a microbial fatty acyltransferase:activation by limited proteolysis," Biochemistry vol. 29, No. 38, 1990, pp. 9072-9078.

Hilton S, Buckley JT, "Studies on the reaction mechanism of a microbial lipase/acyltransferase using chemical modification and site-directed mutagenesis," J Biol Chem. Jan. 15, 1991; 266(2): 997-1000.

Hirayama O et al, "Purification and properties of a lipid acylhydrolase from potato tubers," Biochim Biophys Acta. 1975, vol. 384(1), p. 127-37.

Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.

Horn T et al, Synthesis of oligonucleotides on cellulose. Part II: design and synthetic strategy to the synthesis of 22 oligodeoxynucleotides coding for Gastric Inhibitory Polypeptide (GIP), Nuc Acids Res Symp Ser No. 7, pp. 225-232 (1980).

Hossen, Monjur and Hernandez, Ernesto, "Phospolipase D-Catalyzed Synthesis of Novel Phospholipid-Phytosterol Conjugates", Lipids, vol. 39, Aug. 2004, pp. 777-782.

Hou, Ching T, "pH dependence and thermostability of lipases from cultures from the ARS Culture Collection", Journal of Industrial Microbiology, vol. 13, No. 4, 1994, pp. 242-248.

Humum et al., "Enzyme Catalysed Synthesis in Ambient Temperature Ionic Liquids", Biocatalysis and Biotransformation, 2001, vol. 19, pp. 331-338, NZAS-0215170.

Ikeda H et al, "Complete genome sequence and comparative analysis of the industrial microorganism *Streptomyces avermitilis*", Nature Biotech, vol. 21, pp. 526-531, May 2003.

Godfrey, Tony, et al., editors, Industrial enzymology (2nd Ed.), The Macmillan press, pp. 299-300, (1996).

Ishihara et al., "Studies on Lipase from *Mucor javanicus* I. Purification and Properties", Biochimica et Biophysica Acta vol. 388, pp. 413-422, (1975).

Isobe and Nokihara, "Primary structure determination of mono- and diacylglycerol lipase from *Penicillium camembertti*", Febs. Lett., Federation of European Biochemical Societies, vol. 320, No. 2, pp. 101-106, (1993).

Isobe K et al, "A new enzymatic method for glycoaldehyde production from ethylene glycol", Journal of Molecular Catalysis B: Enzymatic 1 (1995), pp. 37-43.

Iwai and Tsujisaka, "Fungal lipase", (in Lipases, Borgström and Brockman (eds.), Elsevier, Amsterdam, 1984, pp. 443-468.

Iwai, Mieko, et al., "Hydrolytic and Esterifying Actions of Crystalline Lipase of Aspergillus Niger", J. Gen. Appl. Microbiol., 1964, vol. 10, No. 1, p. 13-21.

Izco et al., "Capillary electrophoresis: Evaluation of the effect of added enzymes on casein proteolysis during the ripening of a ewe's-milk cheese", Adv Food Sci, vol. 21, No. 3/4, pp. 110-116, (1999).

Jeng-yen Lin, Matthew, "Wheat Polar Lipids—A Theseis Submitted to the Graduate Faculty of the North Dakota State University of Agriculture and Applied Science", May 1972, pp. 34-45.

Jensen B et al "Effect and Activity of Lipases in Dough and Bread" (translation), 48th Conference on Baking technology and 3rd Conference on Cake & Pastry Technology, Nov. 4-6, 1997, pp. 67-76.

Jensen, B., et al., "Effekt and Wirksamkeit von Lipasen in Teig and Brot" 48th Conference on Baking technology and 3rd Conference on Cake & Pastry Technology, Nov. 4-6, 1997, pp. 67-76.

Owens JJ, "Lecithinase Positive Bacteria in Milk", Process Biochemistry, Jan. 1978, vol. 13, pp. 13-14, 30.

Joerger et al., "Alteration of Chain Length Selectivity of a Rhizopus delemar Lipase through Site-Directed Mutagenesis", Lipids, vol. 29, No. 6, 1994, pp. 377-384.

Jong et al.; "American Type Culture Collection Catalogue of Filamentous FUNGI"; Eighteenth edition (1991) p. 80.

List of Cultures, Fungi and Yeasts, 32 edition, Institute of the Royal Netherlands Academy of Arts and Sciences, p. 38. (1990).

JCM Catalogue of Strains, Fifth Edition, "Filamentous Fungi & Yeasts", p. 246, (1992).

List of Cultures, 1992 Microorganisms Ninth Edition, Institute for Fermentation, Osaka, Japan, p. 325, (1992).

Joshi, et al.; "Specificity of Fungal Lipase in Hydrolytic Cleavage of Oil"; Acta Microbiologica Hungarica (1987); vol. 34(2); pp. 111-114.

Joshi, Sunita, et al., "Specificity of Lipase isolated from Fusarium oxysporum", Department of Chemistry, Indian Institute of Technology, vol. 25, No. 1 & 2, pp. 76-78, (Jan.-Jun. 1985).

Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.

Kaniuga Z, "Galactolipase and chilling sensitivity of plants", Acta Biochim Pol. (1997), vol. 44(1), pp. 21-35.

Kapur J & Sood ML, J. "Effect of pH and Temperature on Lipase and Phospholipase of Adult *Haemonchus contortus* (Nematoda: Trichostrongylidae)" J. Parasit., 1986, vol. 72, No. 2, pp. 346-347.

Kasai, Naoya, et al., "Optically Active Chlorohydrins as Chiral C3 and C4 Building Units: Microbial Resolution and Synthetic Applications", Chirality, vol. 10, pp. 682-692, (1998).

Kawamura, F., et al., "Construction of a *Bacillus subtilis* Double Mutant Deficient in Extracellular Alkaline and Neutral Proteases", J. of Bacteriology, vol. 160, No. 1, Oct 1984, pp. 442-444.

Keum J S et al., "Effect of Commercial Protease and Lipase on the Ripening of Cheddar Cheese", Korean J Dairy Sci 15 (2): pp. 103-117, (1993).

Kindstedt et al., Rapid Quantative test for free oil (Oiling off) in melted Mozzarella cheese, J. Dairy Sci., 1990, vol. 73, p. 867-873.

King et al, "The production of proteins and peptides from *Saccharomyces cervisiae*", Molecular and Cell Biology of Yeasts, Walton and Yarronton (eds.), Blackie, Glasgow, 1989, pp. 107-133.

Kocak et al., Effect of lipase enzyme (palatase A 750 L) on the ripening of tulum cheese, Tr. J. of Agriculture and Forestry, 1995, vol. 19, p. 171-177.

Kocak et al., Effect of added fungal lipase on the ripening of Kasar cheese, Milchwissenschaft 51(1), 1996, p. 13-17.

Kochubei et al., Role of lipids in the organization of the closest surroundings of the reaction centers, Molekulyarnaya Biologiya vol. 12, No. 1, pp. 47-54, Jan.-Feb. 1978.

Kochubei S M et al, "Nature of Longwave Fluorescence of Particles Enriched with Photosytem I", Biophysics (1981), vol. 26(2), pp. 299-304.

Kochubei S M et al, "Differences in the Structure of Long Wave Fluorescence Molecular Aggregates in Photosytems I and II" Institute of Plant Physiology, Academy of Sciences of the Ukranian SSR, Kiev, (Translated from Molekulyarnaya Biologiya vol. 9, No. 2, pp. 190-193, Mar.-Apr. 1975) pp. 150-153, (1975).

Kochubei SM et al, "Role of Lipids in the Organization of the Closest Surroundings of the Reaction Centers of Photosytem 1", Institute of Plant Physiology, Academy of Sciences of the Ukranian SSR, Kiev, (Translated from Molekulyarnaya Biologiya vol. 12, No. 1, pp. 47-54, Jan.-Feb. 1978) pp. 32-37, (1978).

Kolkovski et al., "The Effect of Dietary Enzymes with Age on Protein and Lipid Assimilation and Deposition in *Sparus aurata* Larvae", in Fish Nutrition in Practice, Biarritz (France), Jun. 24-27, 1991, Ed. INRA Paris, 1993, les Colloques, No. 61, p. 569-578.

Kristensen A.C.J., "Preparation of margarine and spreads by enzyme-generated emulsifiers", Master thesis, The Royal Veterinary and Agricultural University, Frederiksberg, Copenhagen, (Jan. 2004) pp. 1-154.

Krog, Niels J., "Dynamic and Unique Monoglycerides", Cereal Foods World, The American Association of Cereal Chemists, Jan. 1979, vol. 24, No. 1, p. 10.

Kuipers, Oscar P., et al., "Enhanced Activity and Altered Specificity of Phospholipase A2 by Deletion of a Surface Loop", Science, vol. 244, 1989, p. 82-85 NZAS-0668767.

Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from Torulaspora delbrueckii", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Kweon et al., "Phospholipid Hydolysate and Antistaling Amylase Effects on Retrogradation of Starch in Bread", Journal of Food Science, vol. 59, No. 5, pp. 1072-1076, 1994.

Larchenkova LP et al. Effect of starter and souring temperature on reproduction of *E coli* and lactobacili in milk, International Dairy Congress XXI, Moscow, Jul. 12-16, 1982, Brief Communications, p. 539.

Larsen N G et al, "The Effect of Ball-milling on Phospholipid Extractability and the Breadmaking Quality of Flour", Journal of Cereal Science (1990), vol. 12(2), p. 155-164.

Lecointe et al., "Ester Synthesis in Aqueous Media in the Presence of Various Lipases" Biotechnology Letters, vol. 18, No. 8 (August) pp. 869-874, (1996).

Lee, Kyung S., et al., the *Saccharomyces cerevisiae* PLB1 Gene Encodes a Protein Required for Lysophospholipase and Phospholipase B Activity, The Journal of Biological Chemistry, vol. 269, No. 31, Issue of August 5, pp. 19725-19730, (1994).

Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.

Lih-ling Wang et al, "Inhibition of Listeria monocytogenes by monoacylglycerols synthesized from coconut oil and milkfat by lipase-catalyzed glycerolysis." Journal of Agricultural Food Chemistry (1993), vol. 41, No. 8, pp. 1000-1005.

Lin S et al, "Purification and characterization of a glycerol oxidase from *Penicillium* sp. TS-622" Enzyme and Microbial Technology 18 (1996), pp. 383-387.

"Lipase A Amano" Technical Bulletin No Lez-1 (Product Specification from Armano Pharmaceutical Co Ltd Nagoya Japan), Dec. 16, 1985, pp. 1-6.

Lipase A "Amano" 6 Assay Note from Armano Pharmaceutical Co Ltd Nagoya Japan, Aug. 27, 1985, p. 1.

Lipase A "Amano" 6 product sheet, Amano Enzyme Inc, Apr. 1, 1999, pp. 1-2.

Lipase SP677 as a Baking Enzyme, from Novo Nordisk, Denmark, Mar. 17, 1994, pp. 1-5.

Lipomod L338P Data Sheet, Biocatalysts Limited, Aug. 15, 2003, pp. 1-2.

Lipopan F: Keep the quality—cut your costs 2000 Novozymes A/S. www.enzymes.novo.dk/cgl-bin/bvisapi.dll/biotimes/one_article. jsp?id=16947&lang=en&t=b1, pp. 1-2. (2000).

Lustenberger, Cornelia et al., Abstract of "Application of lipase in Asian Noodles and Non-durum Pasta" AACC 2000 Annual Meeting, Nov. 5-9, 2000, pp. 1-2, available at http://aaccnet.org/meetings/2000/Abstracts/a00ma031.htm.

Luzi, Paola et al,, "Structure and organization of the human galactocerebrosidase (GALC) gene",Genomics (1995), vol. 26, No. 2, p. 407-409.

Madsen J.S. & Qvist K.B., "Hydrolysis of milk protein by *Bacillus licheniformis* protease specific for acidic amino acid residues" Journal of Food Science, vol. 62, pp. 579-582, (1997).

Marion D et al., "Lipids, Lipid-protein Interactions and the Quality of Baked Cereal Products" from Interactions the Keys to Cereal Quality, Chapter 6, Editors Hamer & Hoseney, American Association of Cereal Chemists, Inc., St. Paul, Minnesota, pp. 131-167, (1998). ISBN 0 913250-99-6.

Marion D et al., Wheat Lipids and Lipid-binding proteins: structure and function, in "Wheat Structure Biochemistry & Functionality", editor Schofield JP, 2000, Royal Society of Chemistry Special publication 212 pp. 245-260 ISBN 085404777-8 (It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physico-chemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of Humicola lanuginosa lipase", Protein Engineering, vol. 9, No. 6, 1996, pp. 519-524.

Martinez, Diego, et al., "Genome sequence of the lignocellulose degrading fungus Phanerochaete chrysosporium strain RP78", Nature Biotechnology, Nature Publishing Group, pp. 1-6, published online on May 2, 2004.

Mason, "Use of Lipolytic Enzyme From *aeromonas* in Detergents", Research Disclosure, Kenneth Mason Publications, Westbourne GB No. 390, Oct. 1996, pp. 661-662.

Matos, A.R., et al., "A patatin-like protein with galactolipase activity is induced by drought stress in Vigna unguiculata leaves", Biochemical Society Transactions, Lipid Catabolism: Lipid Degradation, vol. 28, part 6, p. 779-781, Jun. 30, 2000.

Matos, AR et al, "A novel patatin-like gene stimulated by drought stress encodes a galactolipid acyl hydrolase", FEBS Letters, 491, pp. 188-192, (First published online Feb. 9, 2001).

Matsuda H et al, "Purification and properties of a lipolytic acyl-hydrolase from potato leaves", Biochimica et Biophysica Acta, vol. 573(1), p. 155-165, (1979).

Matthes et al, "Simultaneous rapid chemical synthesis of over one hundred oligonucleotides on a microscale" The EMBO Journal, vol. 3, No. 4, pp. 801-805, (1984).

Reetz M.T., Max-Planck-Institut fur Kohlenforschung et al., "Controlling the enantioselectivity of enzymes by directed evolution: Practical and theoretical ramifications", PNAS, Apr. 20, 2004, vol. 101, No. 16, pp. 5716-5722. NZAS-0441867.

McCoy M G et al, "Characterization of the lipolytic activity of endothelial lipase", Journal of Lipid Research (2002), vol. 43, pp. 921-929.

McNeill G.P. & Berger R.G., Enzymatic glycerolysis of palm oil fractions and palm oil based model mixture: Relationship between fatty acid composition and monoglyceride yield, in Food Biotechnology 7: pp. 75-87, (1993).

McNeill, Gerald P., et al., "Further Improvements in the Yield of Monoglycerides During Enzymatic Glycerolysis of Fats and Oils", JAOCS, Jan. 1991, vol. 68, No. 1, pp. 6-10. NZAS-0213370.

McNeill, Gerald P., et al., "Solid Phase Enzymatic Glycerolysis of Beef Tallow Resulting in a High Yield of Monoglyceride", JAOCS, vol. 67, No. 11, pp. 779-783, (Nov. 1990).

Memo: From Charlotte Johanson, "Short introduction/ status on Ferulic Acid Esterases and Acetyl Xylan Esterases", Protein Biochemistry, pp. 1-2, Jan. 9, 2004.

Meyer, V., et al., "Transcriptional regulation of the Antifungal Protein in Aspergillus giganteus", Mol Genet Genomics, 2002, vol. 266, pp. 747-757.

Meyers, Robert A., "Molecular Biology and Biotechnology—A Comprehensive Desk Reference" VCH Publishers, pp. 731-737, (1995). ISBN1560815698, NZAS-13 015769.

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from Phanerochaete chrysosporium and Bjerkandera sp. BOS55", Enzyme and Microbial Technology, vol. 32, pp. 769-775 (2003).

Miller, Byron S., et al., "A Comparison of Cereal, Fungal, and Bacterial Alpha-Amylases as Supplements for Breadmaking", Food Technology, pp. 38-42, (Jan. 1953). NZAS 0225991.

Mine Y, "Application of the enzymatic methods to the determination of contaminated yolk in egg white", Food Research International, vol. 29, No. 1, pp. 81-84, (1996).

Ministerio da Ciencia e Tecnologia, Diario Oficial da Uniao, No. 134, p. 6, Jul. 15, 2003. ISSN 1677-7042, NZNA-0046369.

Molecular Biological Methods for Bacillus—Chapter 3 Plasmids (Ed. C.R. Harwood and S.M. Cutting) John Wiley and Sons Ltd, Chichester, UK, p. 75-174, 1990.

Mølgaard, Anne, et al., "Rhamnogalacturonan acetylesterase elucidates the structure and function of a new family of hydrolases", Structure, vol. 9, No. 4, pp. 373-383, 2000. NZNA-0056695.

Umanskii M.S. et al., Effect on quality of Kostroma cheese of bacterial cultures selected on phospholipase activity, Molochnaya Promyshlennost 1980 No. 11 21-25, 47—abstract from Food Sci & Tech Abs.

Monick John A., Alcohols, Their Chemistry, Properties and Manufacture, Reinhold Book Cooperation, pp. 3, 6, 14, 47, 48, (1968).

"Mono- and Diglycerides of Edible Fatty Acids", in Monographs for Emulsifiers for Foods, 2nd Edition, The European Food Emulsifier Manufacturers' Association (EFEMA), pp. 47-51, Nov. 1985.

Moore, Charles M., et al., "Metal ion homeostasis in *Bacillus subtilis*", Current Opinion in Microbiology, vol. 8, pp. 188-195, 2005.

Morinaga et al., "Improvement of Oligonucleotide-Directed Site-Specific Mutagenesis Using Double-Stranded Plasmid DNA", Biotechnology 2, pp. 636-639, (1984).

Murakami, Mototake, et al., "Transesterification of Oil by Fatty Acid-Modified Lipase", Technical Research Institute, JAOCS, Jun. 1993, vol. 70, No. 6, p. 571-574 NZAS-0457255.

Murakami, Nobutoshi, et al., "Enzymatic Transformation of Glyceroglycolipids into sn-1 and sn-2 Lysoglyceroglycolipids by use of Rhizopus arrhizus Lipase", Tetrahedron, vol. 50, No. 7, pp. 1993-2002, (1994).

Mustranta, Annikka, et al., "Comparison of Lipases and Phosphlipases in the Hydrolysis of Phospholipids", Process Biochemistry, vol. 30, No. 5, pp. 393-401, 1995.

General Conditions of the company limited by shares N.V. Nederlandsch Octrooibureau, Terms and Conditions, Jan. 2004. NZAS-0012567.

Nagano, et al.; "Cloning and Nucleotide Sequence of cDNA Encoding a Lipase from *Fusarium keteroporum*"; J. Biochem (1994); vol. 116; pp. 535-540.

Nagao T. et al, "C-Terminal Peptide of Fusarium heterosporum Lipase is Necessary for its Increasing Thermostability", J. Biochem., vol. 124, 1124-1129, 1998.

Nagao, T., et al, "Amino Acid Residues Contributing to Stabilization of *Fusarium heterosporum* Lipase", J. of Bioscience and Bioengineering, vol. 89, No. 5, pp. 446-450, 2000.

Nagao, T., et al, "Review: Increase in stability of *Fusarium heterosporum* lipase", J. of Molecular Catalysis B: Enzymatic 17 (2002) pp. 125-132.

Nagao, T., et al, "Use of Thermostable *Fusarium heterosporum* Lipase for Production of Structured Lipid Containing Oleic and Palmitic Acids in Organic Solvent-Free System", JAOCS vol. 78, No. 2, pp. 167-172, (2001).

Nagao, Toshihiro et al., "Cloning and Nucleotide Sequence of CDNA Encoding a Lipase from Fusarium heterosporum", J. Biochem., vol. 116, pp. 535-540, 1994.

Nagao, Toshihiro et al., "Expression of Lipase cDNA from Fusarium heterosporum by Saccharomyces cereviisiae: High-Level Production and Purification", Journal of Fermentation and Bioengineering, 1996, vol. 81, No. 6, pp. 488-492.

Godtfredsen S E, "Lipases", in "Enzymes in food processing" (3rd Ed.), Nagodawithana T and Red G (editors), Academic Press, New York, 1993, ISBN 0125136307, chapter 8, p. 205-219 NZAS-0665885.

Néron, et al., "Effects of lipase and the phosphlipase on the lipids hydrolysis during mixing in correlation with the oxygen consumption by wheat flour dough during kneading", poster 125 Ko at AACC/Tia, San Diego, Calfornia, Sep. 20-22, 2004, available at http://www.cnam.fr/biochimie.

Nielsen et al., "Lipases A and B from the yeast Candida antarctica", in "Biotechnological Applications of Cold-Adapted Organisms" Margesin R & Shimmer F (editors), Springer, 1999, ISBN 3540649727 p. 49-61 NZAS-0214451.

Nierle W et al, Fette Seifen Anstrichmittel (1981), vol. 83(10), p. 391-395.

Nierle, W., et al., "Versuche zur Verlangerung der Haltbarkeit von Dartoffelprodukten", Chem. Mikrobiol. Technol. Lebensm., 1975, vol. 3, pp. 172-175.

Novozymes Memo—Test of lipases for EP1193314B1, Jul. 6, 2005, p. 1-5.

Novozymes Report 2002 Annual Report, "Successfor new baking enzyme," p. 1-2.

Novozymes journal BioTimes, "Biowhitening—a new concept for steamed bread", Jan. 2005 http://vvvvw.biotimes.com/en/Articles/2005/March/Pages/Biowhitening-anewconceptforsteamedbread.aspx, p. 1-2.

Novozymes, "Breakthrough: Less Fattening Fried Food" *BioTimes*, Jun. 2001, No. 2, p. 1-12.

Novozymes, "Enzymes for dough strengthening", 2001, p. 16-21.

Novozymes, "Lipopan F BG- application and mechanism of a new lipase for bread baking" (Draft) *Cereal Food* (2003) (Author: Drost-Lustenberger, C. et al.), p. 1-29.

Novozymes, Drost-Lustenberger, C., "Lipopan F BG: Application and Mechanism of a new Lipase for baking.", *Cereal Foods*, p. 1-9.

Novozymes article, "Mechanism studies of the new lipase,"Cereal Foods, No. 14, p. 1-9.

Novozymes, "Product Sheet for Lipopan F BG", *Cereal Food*, (2001), p. 1-3.

Novozymes, "Product Sheet for Lipopan FS BG", *Cereal Food* (2002), p. 1-3.

Novozymes, "Product Sheet for Lipopan S BG", *Cereal Food* (2002), p. 1-3.
Novozymes, "Product Sheet for Noopazyme", Cereal Food (2002) p. 1-3.
Novozymes, "Product Sheet for Novozym 27016," Baking (2000), p. 1-6.
Novozymes, "Product Sheet for Novozym 27019," Baking (2000), p. 1-6.
Novozymes, "Product Sheet for Novozym 27080," Cereal Food (2003), p. 1-3.
Novozymes, "Product Sheet: Enzyme Business, Noopazyme" p. 1-2.
Novozymes, "Product Sheet: Enzyme Business, Novozym 27019" p. 1-2.
Novozymes, "Product Sheet: Enzyme Business, Novozym 677 BG," p. 1-2.
Novozymes, "Revolutionizing baking", *BioTimes* (Dec. 2002) pp. 6-7.
Novozymes, "Strong sales for lipase that makes dough stronger" *BioTimes*, Dec. 2003, p. 1-2.
Novozymes, "The perfect roll every time for steers", *BioTimes*, Sep. 2003, p. 1-2.
Novozymes, "The value of innovation", *BioTimes*, Mar. 2004, p. 8-9.
Novozymes, "The vital role of technical service in baking", *BioTimes*, Jun. 2004, p. 8-9.
Nylander et al., "Interaction between lipids and lipases A collection of papers presented at the European Meeting on lipid and lipase interaction at Lund University" Sep. 2000.
Ognjenovic Radomir et al, Acceleration of ripening of semi-hard cheese by proteolytic and lipolytic enzymes, Proceedings for Natural Sciences, 1996, vol. 91, p. 5-17.
Okiy D.A. (1978) "Interaction of triglycerides and diglycerides of palm oil," in Oleagineux, vol. 33 p. 625-628.
Okiy D.A., Wright, W.B., Berger, K.G. & Morton I.D. (1978), the physical properties of modified palm oil, in Journal of Science of Food and Agriculture 29:1061-1068.
Oluwatosin, Yemisi E., et al., "Phenotype: a Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.
O'Mahony et al. "Hydrolysis of the lipoprotein fractions of milk by Phospholipase C," Journal of Dairy Science, 1972, vol. 55, No. 4, p. 408-412.
Orberg, Marie-Louise, "Self-assembly Structures Formed by Wheat Polar Lipids and their Interaction with Lipases", Master of Scient Thesis, Apr. 2005.
Ostrovskaya L K et al, "Spectral Features of the Action of Galactolipase on Native Forms of Chlorophyll," Dokl Akad Nauk SSSR, (vol. 186(4), p. 961-3) p. 59-61.
O'Sullivan et al, "A Galactolipase activity associated with the thylakoids of Wheat Leaves (Triticum aestivum L.)," J Plant Physiol, vol. 313, (1987) p. 393-404.
Outtrup, Günther H., et al., "Properties and Application of a Thermostable Maltogenic Amylase Produced by a Strain of Bacillus Modified by Recombinant-DNA Techniques", Starch/Starke, vol. 36, No. 12, pp. 405-411.
Peelman F, et al, "A proposed architecture for lecithin cholesterol acyl transferase (LCAT): Identification of catalytic triad and molecular modeling," Protein Science Mar. 1998; 7(3): 587-99.
Penninga et al, "Site-directed mutations in Tyrosine 195 of Cyclodextrin Glycosyltransferase from Bacillus circulans Strain 251 affect qctivity and product Specificity," Biochemistry (1995), 3368-3376.
Persson, Mattias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the Humicola lanuginosa Lipase", Biochemistry, 1998, vol. 37, pp. 12375-12383.

Peters, G.H., et al.; "Dynamics of Rhizomucor miehei lipase in a lipid or aqueous environment: Functional role of glycines"; Draft for Biophys. J, Nov. 1996, vol. 71, No. 5, p. 2245-2255 NZAS-0031441.
Peters, G.H., et al.; "Essential motions in lipases and their relationship to the biological function", Proceedings of the German Conference on Bioinformatics, GCB '96, Leipzig, Germany, Sep. 30-Oct. 2, 1996, poster, p. 280-282 NZAS-0031438.
Harborne J.B. et al. (editors), *Phytochemical Dictionary: A Handbook of Bioactive Compounds from Plants*, Taylor & Francis, 1993, ISBN 978050667363 Chapter 4, "*Sugar Alcohols and Cyclitols*", p. 20-23.
Picon et al., "Release of Encapsulated Proeinase from Dehydration-Rehydration Liposomes by a Co-encapsulated Phospholipase," Biotechnology Letters, Oct. 1995, vol. 17, No. 10, pp. 1051-1056.
Plijter J and JHGM Mutsaers, "The surface rheological properties of dough and the influence of lipase on it, Gist-brocades," Bakery Ingredients Division, Oct. 1994.
Plou et al, "Enzymatic acylation of di- and trisaccharides with fatty acids: choosing approiate enzyme, support and solvent," J. Biotechnology 92 (2002) 55-66.
Ponte J G, "Note on the Separation and Baking properties of Polar and Nonpolar Wheat Flour Lipids," Cereal Chemistry (1969), vol. 46(3), p. 325-29.
Poulsen, C.H., et al., "Effect and Functionality of Lipases in Dough and Bread", in Angelino SAGF, Hamer RJ, van Hartingsveldt W, Heidekamp F, van der Lugt JP (editors), First European Symposium on Enzymes and Grain Processing, Zeist, The Netherlands, TNO Nutrition and Food Research Institute, ISBN 90-75202-04-0, p. 204-214. Proceedings of ESEGP-1, Noordwijkerhout, The Netherlands, Dec. 2-4, 1996. NZAS-0158559.
Poulsen, Charlotte, et al. "Purification and Characterization of a Hexose Oxidase with Excellent Strenghening Effects in Bread" Cereal Chem. (1998) vol. 75(1); pp. 51-57.
Product Sheet B1324a-GB—"Lecitase$^R$ Novo", Novo Nordisk, Oct. 2000, pp. 1-4.
Punt, P. et. al., "Transformation of Filamentous Fungi Based on Hygromycin B and Phleomycin Resistance Markers," Meth. Enzym., 1992, 216:447-457.
Pyler, E.J., "Baking Science and Technology," Third Edition vol. 1, 1988, p. 1-602.
Pyler, E.J., "Baking Science and Technology," Third Edition, vol. II, 1988, p. 1-784.
Queener et al. (1994), "Improved Expression of a Hybrid: Streptomyces clavuligerus cefE Gene in Penicillium chrysogenum," Ann N Y Acad Sci. 721, p. 178-193.
Rambosek, J., "Recombinant DNA in Filamentous Fungi: Progress and Prospects," CRC Crit. Rev. Biotechnol., 1987, vol. 6, No. 4, p. 357-393.
Reetz M.T et. al., "Overexpression, immobilization and biotechnological application of Pseudomonas lipases," Chem Phys Lipids. Jun. 1998; 93(1-2): 3-14.
Reetz Manfred T, "Lipases as practical biocatalysts," Current Opinion in Chemical Biology, Apr. 2002, vol. 6, No. 2, pp. 145-150.
Reiser J et al.(1990). "Transfer and Expression of Heterologous Genes in Yeasts other than Saccharomyces cerevisiae," Adv Biochem Eng Biotechnol. 43, p. 75-102.
Richardson & Hyslop, "Enzymes", pp. 371-476 in "Food Chemistry Second Edition, Revised and Expanded", 1985, second edition, Owen R. Fennema (ed), Marcel Dekker, Inc, New York and Basel.
Richardson, Toby H., et al., "A Novel, High Performance Enzyme for Starch Liquefaction", The Journal of Biological Chemistry, vol. 277, No. 29, Issue of July 19, pp. 25501-26507, 2002.
Roberts et al. (1992) . "Heterologous gene expression in Aspergillus niger: a glucoamylase-porcine pancreatic prophospholipase A2 fusion protein is secreted and processed to yield mature enzyme," Gene 122(1), 155-161.
Roberts, et al.; "Extracellular Lipase Production by Fungi from Sunflower Seed"; Mycologia(1987); vol. 79(2); pp. 265-273.
Roberts, Ian N., et al., Heterologous gene expression in Aspergillus niger: a glucoamylase-porcine pancreatic prophospholipase A2 fusion protein is secreted and processed to yield mature enzyme.

Robertson et al, "Influence of Active Site and Tyrosine Modification on the Secretion and Activity of the Aeromonas hydrophila Lipase/Acyltransferase," Journal of Biological Chemistry, 1994, vol. 259, No. 3, p. 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via Rhizopus arrhizus Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is a Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in Vigna unguiculata leaves and influence of drought stress", Physiologia Plantarum, vol. 104, pp. 577-586, 1998.
Sahsah, Y., et al., "Purification and characterization of a soluble lipolytic acylhydrolase from Cowpea (vigna unguiculata L.) leaves", Biochimica et Biophysica Acta, vol. 1215, pp. 66-73, 1994.
Saiki R.K. et al, "Primer-Directed Enzymatic Amplification of DNA with a Thermostable DNA Polymerase," Science (1988) 239, pp. 487-491.
Saito, Kunihiko, et al., "Phospholipase B from Penicillium notatum", Methods in Enzymology, 1991, vol. 197, p. 446-456 NZAS-0418833.
Sambrook, J., et al. "Molecular Cloning: a Laboratory Manual, Second Edition", Plasmid Vectors, 1989, p. 1-462.
Shillcock, Julian C., et al., "Tension-induced fusion of bilayer membranes and vesicles", Advance Online Publication Feb. 13, 2005, Nat. Mater., 2005, vol. 4, No. 3, p. 225-228 NZAS-0231181.
Shimada et al, "Enzymatic Purification of Polyunsaturated Fatty Acids," J. of Bioscience and Bioengineering vol. 91, No. 6, 529-538 (2001).
Shimada et al, "Purification and Characterization of a Novel Solvent-Tolerant Lipase from Fusarium heterosporum," J. of Fermentation and Bioengineering vol. 75, No. 5, 349-352 (1993).
Shimada et al, "Enrichment of Polyunsaturated Fatty Acids with Geotrichum candidum Lipase," JAOCS vol. 71, No. 9, (Sep. 1994), p. 951-954.
Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969, p. 93-103.
Si, Joan Qi, "Enzymes, Baking, Bread-Making", Encyclopedia of Bioprocess Technology, Wiley, 1999, ISBN 0471138223 NZAS-0255053, p. 1-18.
Si, Joan Qi, "Synergistic Effect of Enzymes for Breadbaking", Novo Nordisk publication A-06513b, p. 1-18, based on presentation No. 300 at AACC Annual Meeting 1996, Baltimore. Also Encyclopedia of Bioprocess Technology, Wiley, 1999, ISBN 0471138223.
Si, Joan Qi, et al. "Enzymes for bread, noodles and non-durum pasta", Cereal Food 2002 p. 1:3-3:4. Also in Enzymes in Food Technology, RJ Whitehurst & BA Law, Enzymes in Food Technology, Sheffield Academic Press, ISBN 1-84127-223-X, p. 19-54.
Si, Joan Qi, et al., "Novamyl—A true Anti-Staling Enzyme", Cereal Food, Oct. 2001, p. 1-20.
Si, Joan Qi, et al., "Synergistic Effect of Enzymes for Breadbaking", Cereal Food, Oct. 2001, p. 1:21, based on presentation No. 300 at AACC Annual Meeting 1996, Baltimore. Also Encyclopedia of Bioprocess Technology, Wiley, 1999, ISBN 0471138223.
Si, Joan Qi; "New Enzymes for the Baking Industry"; Food Tech Europe (1996) pp. 60-64.
Sias B et al, "Human Pancreatic Lipase-Related Protein 2 Is a Galactolipase," Biochemistry, (2004), vol. 43(31), p. 10138-48.

Siew W.L. et. al. (1999) "Influence of diglycerides on crystalisation of palm oil," in Journal of Science of Food and Agriculture 79:722-726.
Siew W.L. & Ng W.L. (2000) Differential scanning thermograms of palm oil triglycerides in the presence of diglycerides, in Journal of Oil Palm Research 12:107.
Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.
Slotboom et al, "Hydrolysis of Phosphoglycerides by Purified Lipase Preparation," Chem. Phys. Lipids vol. 4 (1970) 15-29.
Smith, George P.; "The Progeny of sexual PCR"; Nature; Vol. 370; No. 18; Aug. 4, 1994 pg. 324-325.
Smith, Timothy L., et al., "The promoter of the glucoamylase-encoding gene of Aspergillus niger functions in Ustilago maydis", Gene. 88, 259-262, 1990.
Soe, J.B., "Analyses of Monoglycerides and Other Emulsifiers by Gaschromatography", Fette, Seifen, Anstrichmittel, 1983, 85 Jahrgang, nr. 2, p72-76NZNA-0005896.
Sorensen, H.R., et al., "Effects of added enzymes on the physicochemical characteristics on fresh durum-pasta", Internal # A-6780.
Sosland, Josh, "Alive and kicking", Milling & Baking News, Feb. 24, 2004. http://www.bakingbusiness.com/co_articles.asp?ArticleID=70026 downloaded Sep. 16, 2004 p. 1-13.
Soumanou, Mohamed M., et al., "Two-Step Enzymatic Reaction for the Synthesis of Pure Structured Triacylglycerides", JAOCS, vol. 75, No. 6, 1998.
Spradling J.E., "Tailoring Enzyme Systems for Food Processing, in Biocatalysis in Agricultural Biotechnology", ACS Symposium Series 389, ed. Whitaker, John R. et al., 1989, ISBN 0 -8412-1571-5 p. 24-43 NZAS-0213683.
Sreekrishna K et al (1988) "High level expression of heterologous proteins in methylotrophic yeast Pichia pastoris," J Basic Microbiol. 28(4), 265-78.
Stadler et al., "Understanding Lipase Action and Selectivity", CCACAA, vol. 68, No. 3, pp. 649-674, 1995.
Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.
Sudbery et al (1988) Biochem Soc Trans. 16(6), 1081-3.
Sugatani, Junko, et al., "Studies of a Phospholipase B from Penicillium Notatum Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Sugiyama et al., "Molecular cloning of a second phospholipase B gene, caPLB2 from Candida albicans", Medical Mycology, vol. 37, 1999.
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the Pseudomonas family", Biochimica et Biophysica Acta, vol. 1259, 1995, pp. 9-17.
Sweigard, James A., et al., "Cloning and analysis of CUT1, a cutinase gene from Magnaporthe grisea", Mol. Gen. Genet., 232:174-182, 1992.
Swinkels et al (1993) Antonie van Leeuwenhoek 64, 187-201.
Talker-Huiber, Cynthia Z., et al., "Esterase EstE from Xanthomonas vesicatoria (Xv_EstE) is an outer membrane protein capable of hydrolyzing long-chain polar esters", Appl. Microbiol Biotechnol, 61:479-487, 2003.
Terasaki, Masaru, et al., "Glycerolipid Acyl Hydrolase Activity in the Brown Alga Cladosiphon okamuranus Tokida", Biosci. Biotechnol. Biochem., vol. 67, No. 9, pp. 1986-1989, 2003.
The New Enzyme Operatives, Ingredient Technology, 50, Aug. 1997.
Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et al 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.

van Nieuqenhuyzen W., "Lecithins Open Doors to baked goods", International Food Ingredients, 1998, No. 2, p. 32-36.

Vaysse et al J. Of Biotechnology 53 (1997) 41-46.

Vujaklija, Dušica, et al., "A novel streptomycete lipase: cloning, sequencing and high-level expression of the Streptomyces rimosus GDS (L)-lipase gene", Arch. Microbiol, vol. 178, pp. 124-130, 2002.

Williams K.R. et al., "Protein Analysis by Integrated Sample Preparation, Chemistry, and Mass Spectrometry", in Molecular Biology and Biotechnology—A Comprehensive Desk Reference, VCH, 1995, ISBN 1-56081-569-8 edited by Meyers R.A., p. 731-737.

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

Helmerich G. et al., Strukur-Wirkungsbeziehehungen von Phospholipiden in Backwaren, Wirkung von Phospholipiden, Getreide Mehl and Brot, 2003, vol. 57, No. 5, p. 270-273 NZAS-0301096.

Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.

Witt, Wolfgang et al., "Secretion of Phospholipase B From Saccharomyces Cerevisiae", Biochimica et Biophysica Acta, vol. 795, 1984, pp. 117-124.

Kelley R.L. and Reddy C.A., Glucose Oxidase of Phanerochaete chrysosporium, in "Biomass, Part B, Lignin, Pectin, and Chitin", Wood et al., Eds., Methods in Enzymology (1988) vol. 161, Academic Press, San Diego, p. 307-316.

WPI Acc No. 93-298906(38) and JP05211852 Preparation of low fat content cream-by adding lipase to mixture of fat and water, Nisshin Oil and Fat Corp. Aug. 24, 1993.

Xu, Jun, et al., "Intron requirement for AFP gene expression in Trichoderma viride", Microbiology, 2003, vol. 149, pp. 3093-3097.

Yamaguchi et al, 1991, Gene 103:61-67.

Yamane et al., "High-Yield Diacylglycerol Formation by Solid-Phase Enzymatic Glycerolysis of Hydrogenated Beef Tallow", JAOCS, vol. 71, No. 3, Mar. 1994.

Yamano Y et al., Surface activity of lysophosphatidyl choline from soybean, 4th World Surfactants Congress, 1996, p. 24-34.

Yamauchi, Asao et al., "Evolvability of random polypetides through functional selection within a small library", Protein Engineering, vol. 15, No. 7, pp. 619-626, 2002.

U.S. Appl. No. 60/083,277, filed Apr. 28, 1998, Spender, T. et. al.

AOCS Official Method Ca 20-99: "Analysis of Phosphorus in oil by inductively Coupled Plasma Optical Emission Spectroscopy", Sampling and Analysis of Commercial Fats and Oils, obtained from The British Library, pp. 1-3, 2001.

Becker T. "Separation and Purification Processes for Recovery of Industrial Enzymes" in R.K. Singh, S.S.H. Rizvi (eds): Bioseparation processes in Foods, Marcel Dekker, New York, pp. 427-445. 1995.

Daftary, R. D. et. al "Functional Bread-Making Properties of Wheat Flour Lipids", Food Technology, vol. 22, p. 327 -330. (1968).

Eliasson A-C. and Larssen K., "Chapter 2: Physiochemical Behavior of the Components of Wheat Flour", *Cereal in Breadmaking: a molecular colloidal approach*, Marcel Dekker Inc, 1993, ISBN0824788168, p. 31-45.

Lo Y-C et al. Crystal structure of *Escherichia coli* Thioesterase I/ProteaseI/Lysophospholipase L1: Consensus sequence blocks constitute the catalytic center of SGNH-hydrolases through a conserved hydrogen bond network. Journal of Molecular Biology, London, GB, vol. 330, No. 3, 539-551. (2003).

Nierle, Von W. et al. "Weizenlipide: Funktion and Einflub bei der Verarbeitung des Mehles" with English abstract "Wheat lipids: Function and Effect in Flour Processing", vol. 83, No. 10, p. 391-395, 1981.

Novozymes brochure "Enzymes at work" 2004, p. 1-60.

Pariza, Michael, et al., "Evaluating the safety of Microbiol Enzyme Preparations Used in Food Processing: Update for a New Century", Regulatory Toxicology and Pharmacology, vol. 33, pp. 173-186, 2001.

PreSens Manual HydroPlate® HP96U and HydroPlate® HP96C, pp. 1-15, Aug. 17, 2004.

Schofield, J. David, "Wheat Structure, Biochemistry and Functionality", Department of Food Science and Technology, p. 243-260., Apr. 2000.

Shehata, A. "Manufacture of Blue Cheese by Direct Acidification Methods," p. 1-90. University of Wisconsin, Nov. 30, 2005.

Tsuchiya, A. et. al., "Cloning and nucleotide sequence of the mono- and diacylglycerol lipase gene (md1B) of Aspergillus oryzae," FEMS Microbiology Letters 143 p. 63-67, (1996).

Van Den Berg. G, "Regulatory status and use of lipase in various countries" Bullentin of the IDF 294, p. 19-20, 1994.

Whitaker, John R., et al., "Biocatalysis in Agricultural Biotechnology", ACS Symposium Series, American Chemical Society, 1989, p. 25-43.

Woolley et al., "Lipases their structure, biochemistry and application", Published by the Press syndicate of the University of Cambridge, Cambridge University Press. 1994, p. 242-270.

Yount, Nannette Y., et al., "Multidimensional signatures in antimicrobial peptides," Proceedings of the National Academy of Sciences, vol. 101 , No. 19, p. 7363-7368, (2004).

* cited by examiner

Figure 1

SEQ ID No. 1

```
  1 ivafGDSlTd geayygdsdg ggwgagladr Ltallrlrar prgvdvfnrg isGrtsdGrl
 61 ivDalvallF laqslglpnL pPYLsgdflr GANFAsagAt Ilptsgpfli QvqFkdfksq
121 vlelrqalgl lqellrllpv ldakspdlvt imiGtNplit saffgpkste sdrnvsvpef
181 kdnlrqlikr Lrsnngarii vlitlvilnl gplGClPlkl alalassknv dasgclerln
241 eavadfneal relaiskled qlrkdglpdv kgadvpyvDl ysifqdldgi qnpsayvyGP
301 ettkaCCGyG gryNynrvCG naglcnvtak aCnpssylls flfwDgfHps ekGykavAea
361 l
```

Figure 2

SEQ ID No. 2

```
  1 mkkwfvcllg lvaltvqaad srpafsrivm fgdslsdtgk myskmrgylp ssppyyegrf
 61 sngpvwleql tnefpgltia neaeggptav aynkiswnpk yqvinnldye vtqflqkdsf
121 kpddlvilwv gandylaygw nteqdakrvr daisdaanrm vlngakeill fnlpdlgqnp
181 sarsqkvvea ashvsayhnq lllnlarqla ptgmvklfei dkqfaemlrd pqnfglsdqr
241 nacyggsyvw kpfasrsast dsqlsafnpq erlaiagnpl laqavaspma arsastlnce
301 gkmfwdqvhp ttvvhaalse paatfiesqy eflah
```

Figure 3

SEQ ID No. 3

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

Figure 4

SEQ ID No. 4

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

Figure 5

SEQ ID No. 5

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

Figure 6

SEQ ID No. 6

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqgeggda
181 wqqlltdglh fsgkgykifh dellkvietf ypqyhpknmq yklkdwrdvl ddgsnims
```

Figure 7

```
Alignment of pfam00657.6 consensus sequence with P10480
            *->ivafGDSlTdg...............eayygdsdgggwgagladrL
               iv+fGDSl+d+++  ++  ++  +++++++  +++s+g  w +l + +
    P10480  28  IVMFGDSLSDTgkmyskmrgylpssppYYEGRFSNGPVWLEQLTNEP  74 tall..rlrarprgvdvfnrgisGrtsdGrlivDalvallFlaqslglpn
                 + l   + +++++++++ +n+   +
    P10480  75  PGLTiaNEAEGGPTAVAYNKISWNPK----------------------- 100

LpPYLsgdflrGANPAsagAtIlptsgpfliQvqFkdfksqvlelrqalg
                                                              ++  ++
    P10480 101  ----------------------------------------------YQVIRN 106 llqellrllpvldakspdlvtimiGtNDlitsaffgpkstesdrnvsvpe
                l++e+ ++l +++ k+ dlv++++G+ND+       ++ ++ ++++++
    P10480 107  LDYEVTQFLQKDSFKPDDLVILWVGANDY--------LAYGWNTEQDAKR 148 fkdnlrqlikrLrsnngariivlitlvilnlgplGClPlklalalasskn
                ++d ++++++r+  nga+        +++nl+ 1G+ P+
    P10480 149  VRDAISDAANRMV-LNGAK-----EILLFNLPDLGQNPS----------- 181 vdasgclerlneavadfnealrelaiskledqlrkdglpdvkgadvpyvD
                ++++ +e +. ++a++n++l +la    +ql+++g++++++++d ++++
    P10480 182  ARSQKVVEAASHVSAYHNQLLLNLA-----RQLAPTGMVKLPEIDKQPAE 226 lysifqdldgiqnpsayv.y....GFe.ttkaCCGyGgr.yNyn.rv.CG
                +  +q+++ + +'+a+++++  +++ +++a+++++++ +N+++r+ ++
    P10480 227  MLRDPQNFGLSDQRNACYgGsyvwKPFaSRSASTDSQLSaFNPQeRLaIA 276 nag.l.c.nvtakaC.npssyll.sflfwDgfHpsekGykavAeal<-*
                +++ 1 + ++++a++ +s+ ++++++fwD++Hp+   ++a+  e
    P10480 277  GNPlLaQaVASPMAArSASTLNCeGKMFWDQVHPTTVVHAALSEPA   322

Alignment of pfam00657.6 consensus sequence with AAG09804
            *->ivafGDSlTdg...............eayygdsdgggwgagladrL
               iv+fGDSl+d+++  ++  ++  +++++++  +++s+g  w ++l + +
  AAG09804  28  IVMFGDSLSDTgkmyskmrgylpssppYYEGRFSNGPVWLEQLTKQF  74 tallrlrarprgvdvfnrgisGrtsdGrlivDalvallFlaqslglpnLp
                        +g+++ n + +G+t
  AAG09804  75  ----------PGLTIANEAEGGAT------------------------- 88

PYLsgdflrGANPAsagAtIlptsgpfliQvqFkdfksqvlelrqa....
                                                  ++++ + ++++ +
  AAG09804  89  ----------------------------------AVAYNKISWNpkyq 102

..lgllqellrllpvldakspdlvtimiGtNDlitsaffgpkstesdrnv
                  ++l++e+ ++l +++ k+ dlv++++G+ND+        ++ ++ ++
  AAG09804 103  vyNNLDYEVTQFLQKDSFKPDDLVILWVGANDY--------LAYGWNTEQ 144 svpefkdnlrqlikrLrsnngariivlitlvilnlgplGClPlklalala
                ++++++d ++++++r+  nga+        +++nl+ 1G+ P+
  AAG09804 145  DAKRVRDAISDAANRMV-LNGAK-----QILLFNLPDLGQNPS------- 181 ssknvdasgclerlneavadfnealrelaiskledqlrkdglpdvkgadv
                     ++++ +e +. ++a++n++l +la    +ql+++g++++++++d
  AAG09804 182  ----ARSQKVVEAVSHVSAYHNKLLLNLA-----RQLAPTGMVKLPEIDK 222 pyvDlysifqdldgiqnpsayv.y....GFe.ttkaCCGyGgr.yNyn.r
                +++++ +q+++ + ++ +++++  +++ t++ +++ +++ + +++r
  AAG09804 223  QFAEMLRDPQNFGLSDVENPCYdGgyvwKPFaTRSVSTDRQLSaFSPQeR 272 v.CGnag.l.c.nvtakaC.npssyll.sflfwDgfHpsekGykavAeal
                + +++++ 1 + ++++a++ +s ++++++fwD++Hp+   ++a+ e+
  AAG09804 273  LaIAGNPlLaQaVASPMARrSASPLNCeGKMFWDQVHPTTVVHAALSERA 322
                                                           <-*
```

Figure 7A

```
Alignment of pfam00657.6 consensus sequence with P10480
              *->ivafGDSlTdg...............eayygdsdgggwgagladrL
                 iv+fGDSl+d+++  ++ ++  +++++++ +++s+g  w ++l + +
    P10480    28   IVMFGDSLSDTgkmyskmrgylpssppYYEGRFSNGPVWLEQLTNEF  74 tall..rlrarprgvdvfnrgisGrtsdGrlivDalvallFlaqslglpn
                 + l    + ++++++++ +n+  +
    P10480    75   PGLTiaNEAEGGPTAVAYNKISWNPK--------------------- 100

LpPYLsgdflrGANFAsagAtIlptsgpfliQvqFkdfksqvlelrqalg
                                                              ++  ++
    P10480   101   -----------------------------------------YQVINN 106 llqellrllpvldakspdlvtimiGtNDlitsaffgpkstesdrnvsvpe
                 l++e+  ++l +++  k+  dlv+++G+ND+        ++ ++ ++++++
    P10480   107   LDYEVTQFLQKDSPKPDDLVILWVGANDY--------LAYGWNTEQDAKR 148 fkdnlrqlikrLrsnngariivlitlvilnlgplGClPlklalalasskn
                 ++d ++++++r+   nga+       ++++nl+ 1G+ P+
    P10480   149   VRDAISDAANRMV-LNGAK-----EILLFNLPDLGQNPS---------- 181 vdasgclerlneavadfnealrelaiskledqlrkdglpdvkgadvpyvD
                 ++++ +e +  ++a++n++l +la      +ql+++g++++++++d ++++
    P10480   182   ARSQKVVEAASHVSAYHNQLLLNLA-----RQLAPTGMVKLFEIDKQFAE 226 lysifqdldgiqnpsayv.y....GFe.ttkaCCGyGgr.yNyn.rv.CG
                 +  +q+++ + + +a+++++    +++ +++a+++++++ +N+++r+ ++
    P10480   227   MLRDPQNFGLSDQRNACYgGsyvwKPFaSRSASTDSQLSaFNPQeRLaIA 276 nag.l.c.nvtakaC.npssyll.sflfwDgfHpsekGykavAeal<-*
                 +++ l +  ++++a++ +s+ ++++++fwD++Hp+   ++a+ e
    P10480   277   GNPlLaQaVASPMAArSASTLNCeGKMFWDQVHPTTVVHAALSEPA     322

Alignment of pfam00657.6 consensus sequence with AAG09804
              *->ivafGDSlTdg...............eayygdsdgggwgagladrL
                 ·iv+fGDSl+d+++  ++ ++  +++++++ +++s+g  w ++l + +
   AAG09804    28   IVMFGDSLSDTgkmyskmrgylpssppYYEGRFSNGPVWLEQLTKQF   74 tallrlrarprgvdvfnrgisGrtsdGrlivDalvallFlaqslglpnLp
                                              +g+++ n + +G+t
   AAG09804    75   ----------PGLTIANEAEGGAT------------------------- 88

PYLsgdflrGANFAsagAtIlptsgpfliQvqFkdfksqvlelrqa....
                                                      ++++ + ++++ +
   AAG09804    89   ---------------------------------AVAYNKISWNpkyq 102

..lgllqellrllpvldakspdlvtimiGtNDlitsaffgpkstesdrnv
                 ++l++e+  ++l +++  k+  dlv+++G+ND+        ++ ++ ++
   AAG09804   103   vyNNLDYEVTQFLQKDSPKPDDLVILWVGANDY--------LAYGWNTEQ 144 svpefkdnlrqlikrLrsnngariivlitlvilnlgplGClPlklalala
                 ++++++d ++++++r+   nga+       ++++nl+ 1G+ P+
   AAG09804   145   DAKRVRDAISDAANRMV-LNGAK-----QILLFNLPDLGQNPS------- 181 ssknvdasgclerlneavadfnealrelaiskledqlrkdglpdvkgadv
                 ++++ +e +  ++a++n++l +la      +ql+++g+++++++d
   AAG09804   182   ----ARSQKVVEAVSHVSAYHNKLLLNLA-----RQLAPTGMVKLFEIDK 222 pyvDlysifqdldgiqnpsayv.y....GFe.ttkaCCGyGgr.yNyn.r
                 +++++  +q+++ +  ++ +++++    +++ t+++ +++ +++ +++r
   AAG09804   223   QFAEMLRDPQNFGLSDVENPCYdGgyvwKPFaTRSVSTDRQLSaFSPQeR 272 v.CGnag.l.c.nvtakaC.npssyll.sflfwDgfHpsekGykavAeal
                 + +++++ l +  ++++a++ +s ++++++fwD++Hp+   ++a+ e+
   AAG09804   273   LaIAGNPlLaQaVASPMARrSASPLNCeGKMFWDQVHPTTVVHAALSERA 322
                 <-*
```

Figure 7B

```
     AAG09804        -   -

Alignment of pfam00657.6 consensus sequence with NP_631558
                *->ivafGDSlTdgeayygdsdgggwgagladrLtallrlrarprgvdvf
                   +va+GDS ++g         +g  +  +++L      + + + ++  +
     NP_631558   42     YVALGDSYSAG---------SGVLPVDPANL----LCLRSTANYPHV 75 nrgisGrtsdGrlivD.a.l.vallPlaqslglpnLpPYLsgdflrGANF
                   +  ++G++         D  +  + +
     NP_631558   76   IADTTGAR-----LTDvTcGaAQ--------------------------- 93

AsagAtIlptsgpfliQvqFkdfksqvlelrqalgllqellrllpvldak
                                         +++       ++  +  ++  +++
     NP_631558   94   ---------------------------TADFTRAQYPGVAPQLDALGT 114 spdlvtimiGtNDl................itsaffgpkstesdrnvsvp
                   + dlvt+ iG+ND ++  +  +  ++ +     ++  + +k     ++ + +++
     NP_631558   115  GTDLVTLTIGGNDNstfinaitacgtagvlSGGKGSPCKDRHGTSFDDEI 164 efkdn..lrqlikrLrs.nngariivlitlvilnlg...........plG
                   e  +++ l++++  +r+++ +ar+ +l  ++i+++   +++   + +     G
     NP_631558   165  EANTYpaLKEALLGVRArAPHARVAALGYPWITPATadpscflklplAAG 214

ClPlklalalassknvdasgclerlneavadfnealrelaiskledqlrk
                   P+                 l+ ++a   n  a+r  ·a
     NP_631558   215  DVPY------------------LRAIQAHLNDAVRRAA---------- 234 dglpdvkgadvpyvDlysifqdldgiqnpsayvyGFettkaCCGyGgryN
                   ++ +  +yvD+ ++
     NP_631558   235  ------EETGATYVDFSGVSDG--------------------------- 250 ynrvCGnaglcnvtakaC.npssyll.sflfwDgf...HpsekGykavAs
                                ++aC+ p +++ +   lf + + +  Hp++ G  +++Ae
     NP_631558   251  --------------HDACeAPGTRWIePLLFGHSLvpvHPNALGERRMAE 286 al<-*
                   +
     NP_631558   287  HT  288

Alignment of pfam00657.6 consensus sequence with CAC42140
                *->ivafGDSlTdgeayygdsdgggwgagladrLtallrlrarprgvdvf
                   +va+GDS ++g         +g  +  +++L      + + + ++  +
     CAC42140    42     YVALGDSYSAG---------SGVLPVDPANL----LCLRSTANYPHV 75 nrgisGrtsdGrlivD.a.l.vallPlaqslglpnLpPYLsgdflrGANF
                   +  ++G++         D  +  + +
     CAC42140    76   IADTTGAR-----LTDvTcGaAQ--------------------------- 93

AsagAtIlptsgpfliQvqFkdfksqvlelrqalgllqellrllpvldak
                                         +++       ++  +  ++  +++
     CAC42140    94   ---------------------------TADFTRAQYPGVAPQLDALGT 114 spdlvtimiGtNDl................itsaffgpkstesdrnvsvp
                   + dlvt+ iG+ND ++  +  +  ++ +     ++  + +k     ++ + +++
     CAC42140    115  GTDLVTLTIGGNDNstfinaitacgtagvlSGGKGSPCKDRHGTSFDDEI 164 efkdn..lrqlikrLrs.nngariivlitlvilnlg...........plG
                   e  +++ l++++  +r+++ +ar+ +l  ++i+++   +++   + +     G
     CAC42140    165  EANTYpaLKEALLGVRArAPHARVAALGYPWITPATadpscflklplAAG 214

ClPlklalalassknvdasgclerlneavadfnealrelaiskledqlrk
                   P+                 l+ ++a   n  a+r   a
     CAC42140    215  DVPY------------------LRAIQAHLNDAVRRAA---------- 234 dglpdvkgadvpyvDlysifqdldgiqnpsayvyGFettkaCCGyGgryN
                   ++ +  +yvD+ ++
     CAC42140    235  ------EETGATYVDFSGVSDG--------------------------- 250 ynrvCGnaglcnvtakaC.npssyll.sflfwDgf...HpsekGykavAs
                                ++aC+ p +++ +   lf + + +  Hp++ G  +++Ae
     CAC42140    251  --------------HDACeAPGTRWIePLLFGHSLvpvHPNALGERRMAE 286
```

Figure 7C

```
                   al<-*
                    +
    CAC42140    287 HT    288

Alignment of pfam00657.6 consensus sequence with P41734
                *->ivafGDSlTdg....eayygdsdgggwgagladrLtallrlrarprg
                   ++fGDS+T+   +++ + +   d+   ga+l + +        +r+
    P41734      6  FLLPGDSITEFafntRPIEDGKDQYALGAALVNEY---------TRK  43 vdvfnrgisGrtsdGrlivDalvallPlaqslglpnLpPYLsgdflrGAN
                   +d+  rg++G+t
    P41734      44 MDILQRGFKGYT-----------------------------------   55

FAsagAtIlptsgpfliQvqFkdfksqvlelrqalgllqeilrllpvlda
                                                  +r+al++l+e+l+     +
    P41734      56 ----------------------------SRWALKILPEILKH-----E  70 kspdlvtimiGtNDlitsaffgpkstesdrnvsvpefkdnlrqlikrLrs
                   +  +  ti++G+ND+         ++ +++ v++pef+dn+rq++++++s
    P41734      71 SNIVMATIPLGANDA---------CSAGPQSVPLPEFIDNIRQMVSLMKS  111 nngariivlitlvilnlgplGClPlklalalassknvdasgclerlneav
                   ++++ii++++lv   ++             ++ k ++ +  + r+ne +
    P41734      112 YHIRPIIIGPGLVDREKW-------------EKEKSEEIALGYFRTNENF  148 sdfnealrelaiskledqlrkdglpdvkgadvpyvDlysifqdldgiqnp
                   a +   al +la                  ++ +vp+v l+++fq+ +g++++
    P41734      149 AIYSDALAKLA---------------NEEKVPFVALNKAPQQEGGDAWQ  182 sayvyGFettkaCCGyGgryNynrvCGnaglcnvtakaCnpssyllsflf
                   +                                                l+
    P41734      183 Q------------------------------------------LL  185 wDgfHpsekGykavAeal<-*
                   Dg+H+s kGyk+++++l
    P41734      186 TDGLHFSGKGYKIFHDEL    203
```

Figure 8

```
A.sal   1   MKKWFVCLLGLIALTVQAADTRPAPSRIVMFGDSLSDTGKMYSKMRGYLPSSPPYYEGRP  60
            +                +
A.hyd   1   MKKWFVCLLGLVALTVQAADSRPAFSRIVMFGDSLSDTGKMYSKMRGYLPSSPPYYEGRP  60

A. sal  61  SNGPVWLEQLTKQPPGLTIANEABGGATAVAYNKISWNPKYQVINNLDYEVTQFLQKDSP 120
                        ++               +
A. hyd  61  SNGPVWLEQLTNFPPGLTIANEAEGGPTAVAYNKISWNPKYQVINNLDYEVTQFLQKDSP 120

A.. sal 121 KPDDLVILWVGANDYLAYGWNTEQDAKRVRDAISDAANRMVLNGAKQILLFNLPDLGQNP 180
                                                              +
A. hyd  121 KPDDLVILWVGANDYLAYGWNTEQDAKRVRDAISDAANRMVLNGAKEILLFNLPDLGQNP 180

A. sal  181 SARSQKVVEAVSHVSAYHNKLLLNLARQLAPTGMVKLFEIDKQFAEMLRDPQNPGLSDVE 240
                      +             +                                         ++
A.hyd   181 SARSQKVVEAASHVSAYHNQLLLNLARQLAPTGMVKLFEIDKQFAEMLRDPQNPGLSDQR 240

A.. sal 241 NPCYDGGYVWKPFATRSVSTDRQLSAFSPQERLAIAGNPLLAQAVASPMARRSASPLNCE 300
               + ++ +       + +  +        +                          +    +
A. hyd  241 NACYGGSYVWKPFASRSASTDSQLSAFNPQERLAIAGNPLLAQAVASPMAARSASTLNCE 300

A. sal  301 GKMFWDQVHPTTVVHAALSERAATFIETQYEFLAH 335
                         +           +
A. hyd  301 GKMFWDQVHPTTVVHAALSEPAATFIESQYEFLAH 335
```

Figure 9

```
  1  ATGAAAAAAT GGTTTGTGTG TTTATTGGGA TTGGTCGCGC TGACAGTTCA GGCAGCCGAC
 61  AGCCGTCCCG CCTTCTCCCG GATCGTGATG TTTGGCGACA GCCTCTCCGA TACCGGCAAG
121  ATGTACAGCA AGATGCGCGG TTACCTCCCC TCCAGCCCCC CCTACTATGA GGGCCGCTTC
181  TCCAACGGGC CCGTCTGGCT GGAGCAGCTG ACCAACGAGT TCCCGGGCCT GACCATAGCC
241  AACGAGGCGG AAGGCGGACC GACCGCCGTG GCTTACAACA AGATCTCCTG GAATCCCAAG
301  TATCAGGTCA TCAACAACCT GGACTACGAG GTCACCCAGT TCCTGCAAAA AGACAGCTTC
361  AAGCCGGACG ATCTGGTGAT CCTCTGGGTC GGCGCCAACG ACTATCTGGC CTATGGCTGG
421  AACACAGAGC AGGATGCCAA GCGGGTGCGC GACGCCATCA GCGATGCGGC CAACCGCATG
481  GTGCTGAACG GCGCCAAGGA GATACTGCTG TTCAACCTGC CGGATCTGGG CCAGAACCCC
541  TCGGCCCGCA GCCAGAAGGT GGTCGAGGCG GCCAGCCATG TCTCCGCCTA CCACAACCAG
601  CTGCTGCTGA ACCTGGCACG CCAGCTGGCT CCCACCGGCA TGGTGAAGCT GTTCGAGATC
661  GACAAGCAGT TTGCCGAGAT GCTGCGTGAT CCGCAGAACT TCGGCCTGAG CGACCAGAGG
721  AACGCCTGCT ACGGTGGCAG CTATGTATGG AAGCCGTTTG CCTCCCGCAG CGCCAGCACC
781  GACAGCCAGC TCTCCGCCTT CAACCCGCAG GAGCGCCTCG CCATCGCCGG CAACCCGCTG
841  CTGGCCCAGG CCGTCGCCAG CCCCATGGCT GCCCGCAGCG CCAGCACCCT CAACTGTGAG
901  GGCAAGATGT TCTGGGATCA GGTCCACCCC ACCACTGTCG TGCACGCCGC CCTGAGCGAG
961  CCCGCCGCCA CCTTCATCGA GAGCCAGTAC GAGTTCCTCG CCCAC
```

Figure 10

```
  1 ATGAAAAAAT GGTTTGTTTG TTTATTGGGG TTGATCGCGC TGACAGTTCA GGCAGCCGAC
 61 ACTCGCCCCG CCTTCTCCCG GATCGTGATG TTCGGCGACA GCCTCTCCGA TACCGGCAAA
121 ATGTACAGCA AGATGCGCGG TTACCTCCCC TCCAGCCCGC CCTACTATGA GGGCCGTTTC
181 TCCAACGGAC CCGTCTGGCT GGAGCAGCTG ACCAAGCAGT TCCCGGGTCT GACCATCGCC
241 AACGAAGCGG AAGGCGGTGC CACTGCCGTG GCTTACAACA AGATCTCCTG GAATCCCAAG
301 TATCAGGTCT ACAACAACCT GGACTACGAG GTCACCCAGT TCTTGCAGAA AGACAGCTTC
361 AAGCCGGACG ATCTGGTGAT CCTCTGGGTC GGTGCCAATG ACTATCTGGC ATATGGCTGG
421 AATACGGAGC AGGATGCCAA GCGAGTTCGC GATGCCATCA GCGATGCGGC CAACCGCATG
481 GTACTGAACG GTGCCAAGCA GATACTGCTG TTCAACCTGC CGGATCTGGG CCAGAACCCG
541 TCAGCCCGCA GTCAGAAGGT GGTCGAGGCG GTCAGCCATG TCTCCGCCTA TCACAACAAG
601 CTGCTGCTGA ACCTGGCACG CCAGCTGGCC CCCACCGGCA TGGTAAAGCT GTTCGAGATC
661 GACAAGCAAT TTGCCGAGAT GCTGCGTGAT CCGCAGAACT TCGGCCTGAG CGACGTCGAG
721 AACCCCTGCT ACGACGGCGG CTATGTGTGG AAGCCGTTTG CCACCGGCAG CGTCAGCACC
781 GACCGCCAGC TCTCCGCCTT CAGTCCGCAG GAACGCCTCG CCATCGCCGG CAACCCGCTG
841 CTGGCACAGG CCGTTGCCAG TCCTATGGCC CGCCGCAGCG CCAGCCCCCT CAACTGTGAG
901 GGCAAGATGT TCTGGGATCA GGTACACCCG ACCACTGTCG TGCACGCAGC CCTGAGCGAG
961 CGCGCCGCCA CCTTCATCGA GACCCAGTAC GAGTTCCTCG CCCACGGATG A
```

Figure 11

```
  1 ATGCCGAAGC CTGCCCTTCG CCGTGTCATG ACCGCGACAG TCGCCGCCGT CGGCACGCTC
 61 GCCCTCGGCC TCACCGACGC CACCGCCCAC GCCGCGCCCG CCCAGGCCAC TCCGACCCTG
121 GACTACGTCG CCCTCGGCGA CAGCTACAGC GCCGGCTCCG GCGTCCTGCC CGTCGACCCC
181 GCCAACCTGC TCTGTCTGCG CTCGACGGCC AACTACCCCC ACGTCATCGC GGACACGACG
241 GGCGCCCGCG TCACGGACGT CACCTGCGGC GCCGCGCAGA CCGCCGACTT CACGCGGGCC
301 CAGTACCCGG GCGTCGCACC CCAGTTGGAC GCGCTCGGCA CCGGCACGGA CCTGGTCACG
361 CTCACCATCG GCGGCAACGA CAACAGCACC TTCATCAACG CCATCACGGC CTGCGGCACG
421 GCGGGTGTCC TCAGCGGCGG CAAGGGCAGC CCCTGCAAGG ACAGGCACGG CACCTCCTTC
481 GACGACGAGA TCGAGGCCAA CACGTACCCC GCGCTCAAGG AGGCGCTGCT CGGCGTCCGC
541 GCCAGGGCTC CCCACGCCAG GGTGGCGGCT CTCGGCTACC CGTGGATCAC CCCGGCCACC
601 GCCGACCCGT CCTGCTTCCT GAAGCTCCCC CTCGCCGCCG GTGACGTGCC CTACCTGCGG
661 GCCATCCAGG CACACCTCAA CGACGCGGTC CGGCGGGCCG CCGAGGAGAC CGGAGCCACC
721 TACGTGGACT TCTCCGGGGT GTCCGACGGC CACGACGCCT GCGAGGCCCC CGGCACCCGC
781 TGGATCGAAC CGCTGCTCTT CGGGCACAGC CTCGTTCCCG TCCACCCCAA CGCCCTGGGC
841 GAGCGGCGCA TGGCCGAGCA CACGATGGAC GTCCTCGGCC TGGACTGA
```

Figure 12

```
  1  TCAGTCCAGG CCGAGGACGT CCATCGTGTG CTCGGCCATG CGCCGCTCGC CCAGGGCGTT
 61  GGGGTGGACG GGAACGAGGC TGTGCCCGAA GAGCAGCGGT TCGATCCAGC GGGTGCCGGG
121  GGCCTCGCAG GCGTCGTGGC CGTCGGACAC CCCGGAGAAG TCCACGTAGG TGGCTCCGGT
181  CTCCTCGGCG GCCCGCCGGA CCGCGTCGTT GAGGTGTGCC TGGATGGCCC GCAGGTAGGG
241  CACGTCACCG GCGGCGAGGG GGAGCTTCAG GAAGCAGGAC GGGTCGGCGG TGGCCGGGGT
301  GATCCACGGG TAGCCGAGAG CCGCCACCCT GGCGTGGGGA GCCCTGGCGC GGACGCCGAG
361  CAGCGCCTCC TTGAGCGCGG GGTACGTGTT GGCCTCGATC TCGTCGTCGA AGGAGGTGCC
421  GTGCCTGTCC TTGCAGGGGC TGCCCTTGCC GCCGCTGAGG ACACCCGCCG TGCCGCAGGC
481  CGTGATGGCG TTGATGAAGG TGCTGTTGTC GTTGCCGCCG ATGGTGAGCG TGACCAGGTC
541  CGTGCCGGTG CCGAGCGCGT CCAACTGGGG TGCGACGCCC GGGTACTGGG CCCGCGTGAA
601  GTCGGCGGTC TGCGCGGCGC CGCAGGTGAC GTCCGTGAGG CGGGCGCCCG TCGTGTCCGC
661  GATGACGTGG GGGTAGTTGG CCGTCGAGCG CAGACAGAGC AGGTTGGCGG GGTCGACGGG
721  CAGGACGCCG GAGCCGGCGC TGTAGCTGTC GCCGAGGGCG ACGTAGTCCA GGGTCGGAGT
781  GGCCTGGGCG GGCGCGGCGT GGGCGGTGGC GTCGGTGAGG CCGAGGGCGA GCGTGCCGAC
841  GGCGGCGACT GTCGCGGTCA TGACACGGCG AAGGGCAGGC TTCGGCAT
```

Figure 13

```
  1 ATGGATTACG AGAAGTTTCT GTTATTTGGG GATTCCATTA CTGAATTTGC TTTTAATACT
 61 AGGCCCATTG AAGATGGCAA AGATCAGTAT GCTCTTGGAG CCGCATTAGT CAACGAATAT
121 ACGAGAAAAA TGGATATTCT TCAAAGAGGG TTCAAAGGGT ACACTTCTAG ATGGGCGTTG
181 AAAATACTTC CTGAGATTTT AAAGCATGAA TCCAATATTG TCATGGCCAC AATATTTTG
241 GGTGCCAACG ATGCATGCTC AGCAGGTCCC CAAAGTGTCC CCCTCCCCGA ATTTATCGAT
301 AATATTCGTC AAATGGTATC TTTGATGAAG TCTTACCATA TCCGTCCTAT TATAATAGGA
361 CCGGGCTAG TAGATAGAGA GAAGTGGGAA AAAGAAAAAT CTGAAGAAAT AGCTCTCGGA
421 TACTTCCGTA CCAACGAGAA CTTTGCCATT TATTCCGATG CCTTAGCAAA ACTAGCCAAT
481 GAGGAAAAAG TTCCCTTCGT GGCTTTGAAT AAGGCGTTTC AACAGGAAGG TGGTGATGCT
541 TGGCAACAAC TGCTAACAGA TGGACTGCAC TTTTCCGGAA AAGGGTACAA AATTTTTCAT
601 GACGAATTAT TGAAGGTCAT TGAGACATTC TACCCCAAT ATCATCCCAA AAACATGCAG
661 TACAAACTGA AAGATTGGAG AGATGTGCTA GATGATGGAT CTAACATAAT GTCTTGA
```

Figure 14

(SEQ ID No. 12)

```
          10         20         30         40         50         60
          |          |          |          |          |          |
    MNLRQWMGAA TAALALGLAA CGGGGTDQSG NPNVAKVQRM VVPGDSLSDI GTYTPVAQAV 70         80         90        100        110        120
          |          |          |          |          |          |
    GGGKFTTNPG PIWAETVAAQ LGVTLTPAVM GYATSVQNCP KAGCFDYAQG GSRVTDPNGI 130        140        150        160        170        180
          |          |          |          |          |          |
    GHNGGAGALT YPVQQQLANF YAASNNTFNG NNDVVFVLAG SNDIFFWTTA AATSGSGVTP 190        200        210        220        230        240
          |          |          |          |          |          |
    AIATAQVQQA ATDLVGYVKD MIAKGATQVY VFNLPDSSLT PDGVASGTTG QALLHALVGT 250        260        270        280        290        300
          |          |          |          |          |          |
    FNTTLQSGLA GTSARIIDFN AQLTAAIQNG ASFGFANTSA RACDATKINA LVPSAGGSSL 310        320        330        340
          |          |          |          |
    FCSANTLVAS GADQSYLFAD GVHPTTAGHR LIASNVLARL LADNVAH
```

Figure 15

(SEQ ID No. 13)

| | | | | | |
|---|---|---|---|---|---|
| atgaacctgc | gtcaatggat | gggcgccgcc | acggctgccc | ttgccttggg | cttggccgcg | 60
| tgcggggcg | gtgggaccga | ccagagcggc | aatcccaatg | tcgccaaggt | gcagcgcatg | 120
| gtggtgttcg | gcgacagcct | gagcgatatc | ggcacctaca | ccccgtcgc | gcaggcggtg | 180
| ggcggcggca | agttcaccac | caacccgggc | ccgatctggg | ccgagaccgt | ggccgcgcaa | 240
| ctgggcgtga | cgctcacgcc | ggcggtgatg | ggctacgcca | cctccgtgca | gaattgcccc | 300
| aaggccggct | gcttcgacta | tgcgcaggc | ggctcgcgcg | tgaccgatcc | gaacggcatc | 360
| ggccacaacg | gcggcgcggg | ggcgctgacc | tacccggttc | agcagcagct | cgccaacttc | 420
| tacgcggcca | gcaacaacac | attcaacggc | aataacgatg | tcgtcttcgt | gctggccggc | 480
| agcaacgaca | ttttcttctg | gaccactgcg | gcggccacca | gcggctccgg | cgtgacgccc | 540
| gccattgcca | cggcccaggt | gcagcaggcc | gcgacggacc | tggtcggcta | tgtcaaggac | 600
| atgatcgcca | agggtgcgac | gcaggtctac | gtgttcaacc | tgcccgacag | cagcctgacg | 660
| ccggacggcg | tggcaagcgg | cacgaccggc | caggcgctgc | tgcacgcgct | ggtgggcacg | 720
| ttcaacacga | cgctgcaaag | cgggctggcc | ggcacctcgg | cgcgcatcat | cgacttcaac | 780
| gcacaactga | ccgcggcgat | ccagaatggc | gcctcgttcg | gcttcgccaa | caccagcgcc | 840
| cgggcctgcg | acgccaccaa | gatcaatgcc | ctggtgccga | gcgccggcgg | cagctcgctg | 900
| ttctgctcgg | ccaacacgct | ggtggcttcc | ggtgcggacc | agagctacct | gttcgccgac | 960
| ggcgtgcacc | cgaccacggc | cggccatcgc | ctgatcgcca | gcaacgtgct | ggcgcgcctg | 1020
| ctggcggata | acgtcgcgca | ctga | | | | 1044

Figure 16 (SEQ ID No. 20)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

Figure 17 (SEQ ID No. 21)

```
  1 gtgatcgggt cgtacgtggc ggtgggggac agcttcaccg agggcgtcgg cgaccccggc
 61 cccgacgggg cgttcgtcgg ctggccgac cggctcgccg tactgctcgc ggaccggcgc
121 cccgagggcg acttcacgta cacgaacctc gccgtgcgcg gcaggctcct cgaccagatc
181 gtggcggaac aggtcccgcg ggtcgtcgga ctcgcgccg acctcgtctc gttcgcggcg
241 ggcggcaacg acatcatccg gccggcacc gatcccgacg aggtcgccga gcggttcgag
301 ctggcggtgg ccgcgctgac cgccgcggcc ggaaccgtcc tggtgaccac cgggttcgac
361 accgggggg tgccgtcct caagcacctg cgcggcaaga tcgccacgta caacgggcac
421 gtccgcgcca tcgccgaccg ctacggctgc ccggtgctcg acctgtggtc gctgcggagc
481 gtccaggacc gcagggcgtg ggacgccgac cggctgcacc tgtcgccgga ggggcacacc
541 cgggtggcgc tgcgcgggg gcaggccctg ggcctgcgcg tcccggccga ccctgaccag
601 ccctggccgc cctgccgcc gcgcggcacg ctcgacgtcc ggcgcgacga cgtgcactgg
661 gcgcgcagt acctggtgcc gtggatcggg cgccggctgc ggggcgagtc gtcgggcgac
721 cacgtgacgg ccaaggggac gctgtcgccg gacgccatca agacgcggat cgccgcggtg
781 gcctga
```

Figure 18
(SEQ ID No. 22)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltgaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

Figure 19 (SEQ ID No. 23)

```
  1 atgcagacga accccgcgta caccagtctc gtcgccgtcg gcgactcctt caccgagggc
 61 atgtcggacc tgctgcccga cggctcctac cgtggctggg ccgacctcct cgccacccgg
121 atggcggccc gctccccgg cttccggtac gccaacctgg cggtgcgcgg gaagctgatc
181 ggacagatcg tcgacgagca ggtggacgtg gccgccgcca tgggagccga cgtgatcacg
241 ctggtcggcg ggctcaacga cacgctgcgg cccaagtgcg acatggcccg ggtgcgggac
301 ctgctgaccc aggccgtgga acggctcgcc ccgcactgcg agcagctggt gctgatgcgc
361 agtcccggtc gccagggtcc ggtgctggag cgcttccggc cccgcatgga ggccctgttc
421 gccgtgatcg acgacctggc cgggcggcac ggcgccgtgg tcgtcgacct gtacggggcc
481 cagtcgctgg ccgaccctcg gatgtgggac gtggaccggc tgcacctgac cgccgagggc
541 caccgccggg tcgcggaggc ggtgtggcag tcgctccggc acgagcccga ggacccccgag
601 tggcacgcgc cgatcccggc gacgccgccg ccggggtggg tgacgcgcag gaccgcggac
661 gtccggttcg cccggcagca cctgctgccc tggataggcc gcaggctgac cgggcgctcg
721 tccggggacg gcctgccggc caagcgcccg gacctgctgc cctacgagga ccccgcacgg
781 tga
```

Figure 20 (SEQ ID No. 24)

```
  1 mtrgrdggag apptkhrall aaivtlivai saaiyagasa ddgsrdhalq aggrlprgda
 61 apastgavvg awatapaaae pgtettglag ravrnvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsgler fqrdvlertn vkavvvvlgv ndvlnspela drdailtglr tlvdraharg
361 lrvvgatitp fggyggytes retmrqevne eiragrvfdt vvdfdkalrd pydprrmrsd
421 ydsgdhlhpg dkgyarmgav idlaalkgaa pvka
```

Figure 21 (SEQ ID No. 25)

```
   1 atgacccggg gtcgtgacgg gggtgcgggg gcgccccca ccaagcaccg tgccctgctc
  61 gcggcgatcg tcacectgat agtggcgatc tccgcggcca tatacgccgg agcgtccgcg
 121 gacgacggca gcagggacca cgcgctgcag gccggaggcc gtctcccacg aggagacgcc
 181 gcccccgcgt ccaccggtgc ctgggtgggc gcctgggcca cccgcaccggc cgcggccgag
 241 ccgggcaccg agacgaccgg cctggcgggc cgctccgtgc gcaacgtcgt gcacacctcg
 301 gtcggcggca ccggcgcgcg gatcaccctc tcgaacctgt acgggcagtc gccgctgacc
 361 gtcacacacg cctcgatcgc cctggccgcc gggcccgaca ccgccgccgc gatcgccgac
 421 accatgcgcc ggctcacctt cggcggcagc gcccgggtga tcatcccggc gggcggccag
 481 gtgatgagcg acaccgcccg cctcgccatc ccctacgggg cgaacgtcct ggtcaccacg
 541 tactccccca tcccgtccgg gccggtgacc taccatccgc aggcccggca gaccagctac
 601 ctggccgacg gcgaccgcac ggcggacgtc accgccgtcg cgtacaccac ccccacgccc
 661 tactgcgcgct acctgaccgc cctcgacgtg ctgagccacg aggccgacgg cacggtcgtg
 721 gcgttcggcg actccatcac cgacggcgcc cgctcgcaga gcgacgccaa ccaccgctgg
 781 accgacgtcc tgccgcacg cctgcacgag gcggcgggcg acggccggga cacgcccgc
 841 tacagcgtcg tcaacgaggg catcagcggc aaccgctcc tgaccagcag gccgggcgg
 901 ccggccgaca cccgagcgg actgagccgg ttccagcggg acgtgctgga acgcaccaac
 961 gtcaaggccg tcgtcgtcgt cctcggcgtc aacgacgtcc tgaacagccc ggaactcgcc
1021 gaccgcgacg ccatcctgac cggcctgcgc accctcgtcg accgggcgca cgcccgggga
1081 ctgcgggtcg tcggcgccac gatcacgccg ttcggcgggct acggcggcta caccgaggcc
1141 cgcgagacga tgcggcagga ggtcaacgag gagatccgct ccggccgggt cttcgacacg
1201 gtcgtcgact tcgacaaggc cctgcgcgac ccgtacgacc cgcgccggat cgctccgac
1261 tacgacagcg gcgaccacct gcacccccggc gacaagggggt acgcgcgcat gggcgcggtc
1321 atcgacctgg ccgcgctgaa gggcgcggcg ccggtcaagg cgtag
```

Figure 22 (SEQ ID No. 26)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdicvimvga ndvthrmpat rsvrhlssav rrlrtagaev
181 vvgtcpdlgt iervrqplrw larrasrqla aaqtigaveq ggrtvslgdl lgpefaqmpr
241 elfgpdnyhp saegyataam avlpsvcaal glwpadeehp dalrregflp varaaaeaas
301 eagtevaaam ptgprgpwal lkrrrrrrvs eaepsspsgv
```

Figure 23 (SEQ ID No. 27)

```
   1 atgacgagca tgtcgagggc gagggtggcg cggcggatcg cggccggcgc ggcgtacggc
  61 ggcggcggca tcggcctggc gggagcggcg gcggtcggtc tggtggtggc cgaggtgcag
 121 ctggccagac gcagggtggg ggtgggcacg ccgaccnggg tgccgaacgc gcagggactg
 181 tacggcggca ccctgcccac ggccgcgac ccgccgctgc ggctgatgat gctgggcgac
 241 tccacggccg ccgggcaggg cgtgcaccgg gccgggcaga cgccgggcgc gctgctggcg
 301 tccgggctcg cggcggtggc ggagcggccg gtgcggctgg ggtcggtcgc ccagccgggg
 361 gcgtgctcgg acgacctgga ccggcaggtg gcgctggtgc tgccgagcc ggaccgggtg
 421 cccgacatct gcgtgatcat ggtcggcgcc aacgacgtca cccaccggat gccggcgacc
 481 cgctcggtgc ggcacctgtc ctcggcggta cggcggctgc gcacggccgg tgcggaggtg
 541 gtggtcggca cctgtccgga cctgggcacg atcgagcggg tgcggcagcc gctgcgctgg
 601 ctggcccggc gggcctcacg gcagctcgcg gcggcacaga ccatcggcgc cgtcgagcag
 661 ggcgggcgca cggtgtcgct gggcgacctg ctgggtccgg agttcgcgca aacccgcgg
 721 gagctcttcg gccccgacaa ctaccacccc tccgccgagg ggtacgccac ggccgcgatg
 781 gcggtactgc cctcggtgtg cgccgcgctc ggcctgtggc cggccgacga ggagcacccg
 841 gacgcgctgc gccgcgaggg cttcctgccg gtggcgcgcg cggcggcgga ggcggcgtcc
 901 gaggcgggta cggaggtcgc cgccgccatg cctacggggc ctcggggggcc ctgggcgctg
 961 ctgaagcgcc ggagacggcg tcgggtgtcg gaggcggaac cgtccagccc gtccggcgtt
1021 tga
```

Figure 24 (SEQ ID No. 28)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswnya
121 vtgarmadlt aqvtraagre pelvavmaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

Figure 25 (SEQ ID No. 29)

```
  1 atgggtcgag ggacggacca gcggacgcgg tacggccgtc gccgggcgcg tgtcgcgctc
 61 gccgccctga ccgccgccgt cctgggcgtg ggcgtggcgg gctgcgactc cgtgggcggc
121 gactcacccg ctccttccgg cagcccgtcg aagcggacga ggacggcgcc cgcctgggac
181 accagccgg cgtccgtcgc cgccgtgggc gactccatca cgcgcggctt cgacgcctgt
241 gcggtgctgt cggactgccc ggaggtgtcg tgggcgaccg gcagcagcgc gaaggtcgac
301 tcgctggccg tacggctgct ggggaaggcg gacgcggccg agcacagctg gaactacgcg
361 gtcaccgggg cccggatggc ggacctgacc gctcaggtga cgcgggcggc gcagcgcgag
421 ccggagctgg tggcggtgat ggccggggcg aacgacgcgt gccggtccac gacctcggcg
481 atgacgccgg tggcggactt ccgggcgcag ttcgaggagg cgatggccac cctgcgcaag
541 aagctcccca aggcgcaggt gtacgtgtcg agcatcccgg acctcaagcg gctctggtcc
601 cagggccgca ccaaccgct gggcaagcag gtgtggaagc tggcctgtg cccgtcgatg
661 ctgggcgacg cggactccct ggactcggcg gcgaccctgc ggcgcaacac ggtgcgcgac
721 cgggtggcgg actacaacga ggtgctgcgg gaggtctgcg cgaaggaccg gcggtgccgc
781 agcgacgacg gcgcggtgca cgagttccgg ttcggcacgg accagttgag ccactgggac
841 tggttccacc cgagtgtgga cggccaggcc cggctggcgg agatcgccta ccgcgcggtc
901 accgcgaaga atccctga
```

Figure 26 (SEQ ID No. 30)

```
  1 mrlsrraata sallltpala lfgasaavsa priqatdyva lgasyssgvg agsydsssgs
 61 ckrstksypa lwaashtgtr fnftacsgar tgdvlakqlt pvnsgtdlvs itiggndsgf
121 adtmttcnlq gesaclaria karayiqqtl paqldqvyda idsrapaaqv vvlgyprfyk
181 lggscavgls eksraainaa addinavtak rsadhgfafg dvnttfaghe lcsgapwlhs
241 vtlpvensyh ptangqskgy lpvlnsat
```

Figure 27 (SEQ ID No. 31)

```
   1 ttcatcacaa cgatgtcaca acaccggcca tccgggtcat ccctgatcgt gggaatgggt
  61 gacaagcctt cccgtgacga aagggtcctg ctacatcaga aatgacagaa atcctgctca
 121 gggaggttcc atgagactgt cccgacgcgc ggccacggcg tccgcgctcc tcctcacccc
 181 ggcgctcgcg ctcttcggcg cgagcgccgc cgtgtccgcg ccgcgaatcc aggccaccga
 241 ctacgtggcc ctcggcgact cctactcctc gggggtcggc gcgggcagct acgacagcag
 301 cagtggctcc tgtaagcgca gcaccaagtc ctaccggcc ctgtgggccg cctcgcacac
 361 cggtacgcgg ttcaacttca ccgcctgttc gggcgcccgc acaggagacg tgctggccaa
 421 gcagctgacc ccggtcaact ccggcaccga cctggtcagc attaccatcg gcggcaacga
 481 cgcgggcttc gccgacacca tgaccacctg caacctccag ggcgagagcg cgtgcctggc
 541 gcggatcgcc aaggcgcgcg cctacatcca gcagacgctg cccgcccagc tggaccaggt
 601 ctacgacgcc atcgacagcc gggcccccgc agcccaggtc gtcgtcctgg gctaccgcg
 661 cttctacaag ctgggcggca gctgcgccgt cggtctctcg gagaagtccc gcgcggccat
 721 caacgccgcc gccgacgaca tcaacgccgt caccgccaag cgcgccgccg accacggctt
 781 cgccttcggg gacgtcaaca cgaccttcgc cgggcacgag ctgtgctccg gcgcccctg
 841 gctgcacagc gtcacccttc ccgtggagaa ctcctaccac cccacggcca acggacagtc
 901 caagggctac ctgccgtc tgaactccgc cacctgatct cgcggctact ccgcccctga
 961 cgaagtcccg ccccgggcg gggcttcgcc gtaggtgcgc gtaccgccgt cgcccgtcgc
1021 gccggtggcc ccgccgtacg tgccgccgcc cccggacgcg gtcggttc
```

Figure 28 (SEQ ID No. 32)

```
  1  MKKWFVCLLG LVALTVQAAD SRPAPSRIVM FGDSLSDTGK MYSKMRGYLP
 51  SSPPYYEGRF SNGPVWLEQL TKQPPGLTIA NEAEGGATAV AYNKISWNPK
101  YQVINNLDYE VTQFLQKDSP KPDDLVILWV GANDYLAYGW NTEQDAKRVR
151  DAISDAANRM VLNGAKQILL PNLPDLGQNP SARSQKVVEA VSHVSAYHNQ
201  LLLNLARQLA PTGMVKLFEI DKQPAEMLRD PQNFGLSDVE NPCYDGGYVW
251  KPPATRSVST DRQLSAFSPQ ERLAIAGNPL LAQAVASPMA RRSASPLNCE
301  GKMFWDQVEP TTVVHAALSE RAATFIANQY EFLAH*
```

Figure 29 (SEQ ID No. 33)

```
   1 ATGAAAAAAT GGTTTGTGTG TTTATTGGGA TTGGTCGCGC TGACAGTTCA
     TACTTTTTTA CCAAACACAC AAATAACCCT AACCAGCGCG ACTGTCAAGT

51 GGCAGCCGAC AGTCGCCCCG CCTTTTCCCG GATCGTGATG TTCGGCGACA
     CCGTCGGCTG TCAGCGGGGC GGAAAAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAACAGT TCCCGGGTCT GACCATCGCC AACGAAGCGG
     CCTCGTCGAC TGGTTTGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC CTATGGCTGG AACACGGAGC AGGATGCCAA GCGGGTTCGC
     TGATAGACCG GATACCGACC TTGTGCCTCG TCCTACGGTT CGCCCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCTCGCA
     CTATGACGAC AAGTTGGACG GCCTAGACCC GGTCTTGGGC AGTCGAGCGT

551 GTCAGAAGGT GGTCGAGGCG GTCAGCCATG TCTCCGCCTA TCACAACCAG
     CAGTCTTCCA CCAGCTCCGC CAGTCGGTAC AGAGGCGGAT AGTGTTGGTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGC GAACCAGTAC GAGTTCCTCG
     GGACTCGCTC GCGCGGCGGT GGAAGTAGCG CTTGGTCATG CTCAAGGAGC

1001 CCCAC TGA
     GGGTG ACT
```

Figure 30 (SEQ ID No. 34)

```
  1  MKKWFVCLLG LIALTVQAAD TRPAFSRIVM FGDSLSDTGK MYSKMRGYLP
 51  SSPPYYEGRF SNGPVWLEQL TKQFPGLTIA NEAEGGATAV AYNKISWNPK
101  YQVINNLDYE VTQFLQKDSF KPDDLVILWV GANDYLAYGW NTEQDAKRVR
151  DAISDAANRM VLNGAKQILL PNLPDLGQNP SARSQKVVEA VSHVSAYHNK
201  LLLNLARQLA PTGMVKLFEI DKQPAEMLRD PQNFGLSDVE NPCYDGGYVW
251  KPFATRSVST DRQLSAFSPQ ERLAIAGNPL LAQAVASPMA RRSASPLNCE
301  GKMFWDQVHP TTVVHAALSE RAATPIETQY EFLAHG*
```

Figure 31 (SEQ ID No. 35)

```
   1  ATGAAAAAAT GGTTTGTTTG TTTATTGGGG TTGATCGCGC TGACAGTTCA
      TACTTTTTTA CCAAACAAAC AAATAACCCC AACTAGCGCG ACTGTCAAGT

51  GGCAGCCGAC ACTCGCCCCG CCTTCTCCCG GATCGTGATG TTCGGCGACA
      CCGTCGGCTG TGAGCGGGGC GGAAGAGGGC CTAGCACTAC AAGCCGCTGT

101  GCCTCTCCGA TACCGGCAAA ATGTACAGCA AGATGCGCGG TTACCTCCCC
      CGGAGAGGCT ATGGCCGTTT TACATGTCGT TCTACGCGCC AATGGAGGGG

151  TCCAGCCCGC CCTACTATGA GGGCCGTTTC TCCAACGGAC CCGTCTGGCT
      AGGTCGGGCG GATGATACT CCCGGCAAAG AGGTTGCCTG GGCAGACCGA

201  GGAGCAGCTG ACCAAGCAGT TCCCGGGTCT GACCATCGCC AACGAAGCGG
      CCTCGTCGAC TGGTTCGTCA AGGGCCCAGA CTGGTAGCGG TTGCTTCGCC

251  AAGGCGGTGC CACTGCCGTG GCTTACAACA AGATCTCCTG GAATCCCAAG
      TTCCGCCACG GTGACGGCAC CGAATGTTGT TCTAGAGGAC CTTAGGGTTC

301  TATCAGGTCA TCAACAACCT GGACTACGAG GTCACCCAGT TCTTGCAGAA
      ATAGTCCAGT AGTTGTTGGA CCTGATGCTC CAGTGGGTCA AGAACGTCTT

351  AGACAGCTTC AAGCCGGACG ATCTGGTGAT CCTCTGGGTC GGTGCCAATG
      TCTGTCGAAG TTCGGCCTGC TAGACCACTA GGAGACCCAG CCACGGTTAC

401  ACTATCTGGC ATATGGCTGG AATACGGAGC AGGATGCCAA GCGAGTTCGC
      TGATAGACCG TATACCGACC TTATGCCTCG TCCTACGGTT CGCTCAAGCG

451  GATGCCATCA GCGATGCGGC CAACCGCATG GTACTGAACG GTGCCAAGCA
      CTACGGTAGT CGCTACGCCG GTTGGCGTAC CATGACTTGC CACGGTTCGT

501  GATACTGCTG TTCAACCTGC CGGATCTGGG CCAGAACCCG TCAGCCCGCA
      CTATGACGAC AAGTTGGACG CCCTAGACCC GGTCTTGGGC AGTCGGGCGT

551  GTCAGAAGGT GGTCGAGGCG GTCAGCCATG TCTCCGCCTA TCACAACAAG
      CAGTCTTCCA CCAGCTCCGC CAGTCGGTAC AGAGGCGGAT AGTGTTGTTC

601  CTGCTGCTGA ACCTGGCACG CCAGCTGGCC CCCACCGGCA TGGTAAAGCT
      GACGACGACT TGGACCGTGC GGTCGACCGG GGGTGGCCGT ACCATTTCGA

651  GTTCGAGATC GACAAGCAAT TTGCCGAGAT GCTGCGTGAT CCGCAGAACT
      CAAGCTCTAG CTGTTCGTTA AACGGCTCTA CGACGCACTA GGCGTCTTGA

701  TCGGCCTGAG CGACGTCGAG AACCCCTGCT ACGACGGCGG CTATGTGTGG
      AGCCGGACTC GCTGCAGCTC TTGGGACGA TGCTGCCGCC GATACACACC

751  AAGCCGTTTG CCACCCGCAG CGTCAGCACC GACCGCCAGC TCTCCGCCTT
      TTCGGCAAAC GGTGGGCGTC GCAGTCGTGG CTGGCGGTCG AGAGGCGGAA

801  CAGTCCGCAG GAACGCCTCG CCATCGCCGG CAACCCGCTG CTGGCACAGG
      GTCAGGCGTC CTTGCGGAGC GGTAGCGGCC GTTGGCGAC GACCGTGTCC

851  CCGTTGCCAG TCCTATGGCC CGCCGCAGCG CCAGCCCCCT CAACTGTGAG
      GGCAACGGTC AGGATACCGG GCGGCGTCGC GGTCGGGGA GTTGACACTC

901  GGCAAGATGT TCTGGGATCA GGTACACCCG ACCACTGTCG TGCACGCAGC
      CCGTTCTACA AGACCCTAGT CCATGTGGGC TGGTGACAGC ACGTGCGTCG

951  CCTGAGCGAG CGCGCCGCCA CCTTCATCGA GACCCAGTAC GAGTTCCTCG
      GGACTCGCTC GCGCGGCGGT GGAAGTAGCT CTGGGTCATG CTCAAGGAGC

1001  CCCACGGATG A
      GGGTGCCTAC T
```

Figure 32

```
            1         10        20        30        40        50
            |---------+---------+---------+---------+---------|
     satA   ADTRPAFSRIVMFGDSLSDTGKMYSKMRGYLPSSPPYYEGRFSN--G
     R.sol  QSGNPNVAKVQRMVVFGDSLSDIGT-------YTPVAQAVGGGKFTTNPG
  Consensus ...adnraafqRiVmFGDSLSDiGk.......YlPsaqaygeGrFsn..G 51        60        70        80        90       100
            |---------+---------+---------+---------+---------|
     satA   PVHLEQLTKQFPGLTIANEAEGGATAVAYNKISHNPKYQVINNLDYEVTQ
     R.sol  PIHAETVAAQL-GVTLTPAVMGYATSVQNCPKAGCFDYAQGGSRVTDPNG
  Consensus P!HaEqlaaQl.GlTianaaeGgATaVannkiagnfdYaqgnnrdt#pnq 101       110       120       130       140       150
            |---------+---------+---------+---------+---------|
     satA   FLQKDSFKPDDLVILHVGANDYLAYG--HNTEQDAKRVRDAISDAANRMV
     R.sol  IGHNGGAGALTYPVQQQLAHFYAASNNTFNGHNDVVFVLAGSNDIFFHTT
  Consensus igqndgagaddlp!qqqgAHdYaAsn..fNg##DakrVraainDaanrmt 151       160       170       180       190       200
            |---------+---------+---------+---------+---------|
     satA   LNGAKQILLFNLPDLGQNPSARSQKVVEAVSHVSAYHNKL-LLNLARQLA
     R.sol  AAATSGSGVTPAIATAQVQQAATDLVGYVKDHIAKGATQVYVFNLPDSSL
  Consensus aaaakqiglfnaialaQnqqAas#lVgeakdh!aaganql.llHLarqla 201       210       220       230       240       250
            |---------+---------+---------+---------+---------|
     satA   PTGMVKLFEIDKQFAEMLRDPQNFGLSDVENPCYDGGYVHKPFATRSVST
     R.sol  TPDGVASGTTGQALLHALVGTFNTTLQSGLAGTSARIIDFNAQLTAAIQN
  Consensus ppdgValgeidqalaeaLrdpqNfgLqdgeagcsargidfnaqaTaa!qn 251       260       270       280       290       300
            |---------+---------+---------+---------+---------|
     satA   DRQLSAFSPQERLAIAG--NPLLAQAVASPM---ARRSASPLNCEGKHFW
     R.sol  GASFGFANTSARACDATKINALVPSAGGSSLFCSANTLVASGADQSYLFA
  Consensus daqlgaanpqaRaadAg..NaLlaqAgaSp$...Arrlaapgad#gk$Fa 301       310       320       330
            |---------+---------+---------|
     satA   DQVHPTTVVHAALSERAATFIETQYEFLAH
     R.sol  DGVHPTTAGHRLIASNVLARLLA--DNVAH
  Consensus DqVHPTTagHaaiaeraaariea..#nlAH
```

Figure 33A

```
Pfam          *->ivafGDSltdggg...............ayygdsdgggwgagladrltsla..rlrargrgvdv
Sriml     38   YVALGDSYSSGVG..............agSYDSSSGSCKRSTKSYPALWAAS..------HTGTRF  81
Scoe1      5   YVAVGDSPTEG--..............--VGDPGPDGAFVGWADRLAVLL..ADRRPEGDFTY  47
Scoe2     10   LVAVGDSPTEG--..............--MSDLLPDGSYRGWADLLATRM..---AARSPGFRY  50
Scoe3    239   VVAFGDSITDG--..............ARSQSDANHRWTDVLAARLHEAA..GDGRDTPRYSV  283
Scoe4     75   LMMLGDSTAAG--..............------QGVHRAGQTPGALLASG..LAAVAERPVRL  113
Scoe5     66   VAAVGDSITRGFD..............acAVLSDCPEVSWATGSSAKVDSLAvrLLGKADAAEHS  116
Ahyd1     28   IVMFGDSLSDTGKmyskmrgylpsappyYEGRFSNGPVWLEQLTNEFPGLTiaNEAEGGPTAVA  91
Asal1     28   IVMFGDSLSDTGKmyskmrgylpsappyYEGRFSNGPVWLEQLTKQF----..------PGLTI  79
Ahyd2     40   IVMFGDSLSDTGKmyskmrgylpsappyYEGRFSNGPVWLEQLTKQFPGLTiaNEAEGGATAVA  103

Pfam          fnrgisGrtsdGrlvvDarlvatllFlaqflGlnlpPYLsgdflrGANFAsagAtIlgtslipflni
Sriml     82   NPTACSGAR-----------------------------------------------------  90
Scoe1     48   TNLAVRGRL-----------------------------------------------------  56
Scoe2     51   ANLAVRGKL-----------------------------------------------------  59
Scoe3    284   VNEGISGNR-----------------------------------------------------  292
Scoe4    114   GSVAQPGAC-----------------------------------------------------  122
Scoe5    117   WNYAVTGAR-----------------------------------------------------  125
Ahyd1     92   YNKISWNPK-----------------------------------------------------  100
Asal1     80   ANEAEGGAT-----------------------------------------------------  88
Ahyd2    104   YNKISWNPK-----------------------------------------------------  112

Pfam          QvqFkdfkskvlelrqa......lgllqellrlvpvldakspdlvtimiGtNDl...itvakfgpks
Sriml     91   -----------------.......---TGDVLAKQLTPVNSGTDLVSITIGGNDAgfaDTMTTCNLQG  131
Scoe1     57   -----------------.......---LDQIVAEQVPRVVGLAPDLVSFAAGGNDI...------I----  86
Scoe2     60   -----------------.......---IGQIVDEQVDVAAAMGADVITLVGGLNDT..---------  88
Scoe3    293   -------LLTSRPGRPA......DNPSGLSRFQRDVLERTNVKAVVVVLGVNDV...----------  333
Scoe4    123   -----------------.......SDDLDRQVALVLAEPDRVPDICVIMVGANDV..----------  153
Scoe5    126   -----------------.......---MADLTAQVTRAAQREPELVAVMAGANDA...--------CR  155
Ahyd1    101   -------------YQVI......NNLDYEVTQFLQKDSFKPDDLVILWVGANDY...--------LA  137
Asal1     89   -------AVAYNKISWNpkygvyNNLDYEVTQFLQKDSFKPDDLVILWVGANDY...--------LA  137
Ahyd2    113   -------------YQVI......NNLDYEVTQFLQKDSFKPDDLVILWVGANDY...--------LA  149

Pfam          .......tksdrnvsvpefrdnlrklikrLrsangariiilitlvllnlpl..........plGCl
Sriml    132   esaclarIAKARAYIQQTLPAQLDQVYDAIDSRAPAA-----QVVVLGYP-...........-----  176
Scoe1     87   ........---RPGTDPDEVAERFELAVAALT-AAAGTVLVTTGPDTRGVP-..........-----  125
Scoe2     89   ........---------LRPKCDMARVRDLLTQAVERLAPHCEQLVLMRSP-...........-----  122
Scoe3    334   ........LNSPELADRDAILTGLRTLVDRAHARGLRVVGATITPFGGYGG-..........-----  376
Scoe4    154   ........---THRMPATRSVRHLSSAVRRLR-TAGAEVVVGTCPDLGTIE-...........-----  192
Scoe5    156   ........STTSAMTPVADFRAQFEEAMATLR-KKLPKAQVYVSSIPDLKRLwsqgrtnplgkQVWKL  214
Ahyd1    138   ........YGWNTEQDAKRVRDAISDAANRMV-LNGAK-----EILLFNLP-...........-----  174
Asal1    138   ........YGWNTEQDAKRVRDAISDAANRMV-LNGAK-----QILLFNLP-...........-----  174
Ahyd2    150   ........YGWNTEQDAKRVRDAISDAANRMV-LNGAK-----QILLFNLP-...........-----  186

Pfam          pq.klalalassknvdatgclerlneavadynealrelaei.ek.l.q.aqlrkdglpdlkeanvpy
Sriml    177   --.RFYKLGGSCAVGLSEKSRAAINAAADDINAVTAKRA--.--.-.-.-----------ADHGFAP  219
Scoe1    126   --.----------------VLKHLRGKIATYNGHVRAIA--.--.-.-.-----------DRYGCPV  152
Scoe2    123   --.----------GRQGPVLERFRPRMEALPAVIDDLA--.--.-.-.-----------GRHGAVV  154
Scoe3    377   --.YTEARETMRQEVNEEIRSGRVFDTVVDFDKALRDPY--.--.-.-.------------------  412
Scoe4    193   --.--------------------RVRQPLRWLaRRaSrQlAAAQTIGAVEQGGRTVSL  227
Scoe5    215   GLcPSMLGDADSLDSAATLRRNTVRDRVADYNEVLREVC--.--.-.AkDRRCRSDDGAVHEFRFGT  273
Ahyd1    175   --.-----DLGQNPSARSQKVVEAASHVSAYHNQLLLNLA--.--.-.-.RQLAPTGMVKLFEIDKQF  224
Asal1    175   --.-----DLGQNPSARSQKVVEAVSHVSAYHNKLLLNLA--.--.-.-.RQLAPTGMVKLFEIDKQF  224
Ahyd2    187   --.-----DLGQNPSARSQKVVEAVSHVSAYHNQLLLNLA--.--.-.-.RQLAPTGMVKLFEIDKQF  236

Pfam          VDlysifqdldgiqnpsayv.y....GPeet.kaCCGyGgr.yNyn.rv.CGnag.l.ck.vtakaC
Sriml    220   GDVNT-----------------.-...-----.----------.-TFAgHElCSGAPwL.HS.VT----  242
Scoe1    153   LDLWSLRSVQDRRA------.-...-.-----.----------.-----.--.------  166
Scoe2    155   VDLYGAQSLADPRM------.-...-.-----.----------.-----.--.------  168
Scoe3    413   ----------------------.-...-.-----.-----;----.----.--.------  413
Scoe4    228   GDLLGPEFAQNPREL------.-...-.-----.----------.-----.--.------  242
```

Figure 33B

```
Scoe5  274 DQL------------------------------------------------- 276
Ahyd1  225 AEMLRDPQNFGLSDQRNACYgGsyvwKPFASrSASTDSQLSaFNPQeRLaIAGNPlLaQAvASPMAA 291
Asal1  225 AEMLRDPQNFGLSDVENPCYdGgyvwKPFATrSVSTDRQLSaFSPQeRLaIAGNPlLaQAvASPMAR 291
Ahyd2  237 AEMLRDPQNFGLSDVENPCYdGgyvwKPFATrSVSTDRQLSaFSPQeRLaIAGNPlLaQAvASPMAR 303

▼
Pfam       .dassyll.atlfwDgf.HpsekGykavAeal<-*
Sriml  243 --------.--LPVENSyHPTANGQSKGYLPV    263
Scoe1  167 --------.--WDADRL.HLSPEGHTRVALRA    186
Scoe2  169 --------.--WDVDRL.HLTAEGHRRVAEAV    188
Scoe3  413 .-DPRRMRsDYDSGDHL.HPGDKGYARMGAVI    441
Scoe4  243 --------.--FGPDNY.HPSAEGYATAAMAV    262
Scoe5  277 --------.--SHWDWF.HPSVDGQARLAEIA    296
Ahyd1  292 rSASTLNCeGKMFWDQV.HPTTVVHAALSEPA    322
Asal1  292 rSASPLNCeGKMFWDQV.HPTTVVHAALSERA    322
Ahyd2  304 rSASPLNCeGKMFWDQV.HPTTVVHAALSERA    334
```

Figure 34

```
Pfam         *->ivafGDSltdggg..............ayygdsdgggwgagladrltsla..rlrargrgvdv
Sriml     38 YVALGDSYSSGVG.............agSYDSSSGSCKRSTKSYPALWAAS..-----HTGTRP  81
Scoe1      5 YVAVGDSFTEG--...........--VGDPGPDGAPVGWADRLAVLL..ADRRPBGDPTY      47
Scoe2     10 LVAVGDSFTEG--.............--MSDLLPDGSYRGWADLLATRM..--AARSPGFRY   50
Ahyd1     28 IVMFGDSLSDTGKmyskmrgylpssppyYEGRFSNGPVWLEQLTNEFPGLTiaNEAEGGPTAVA  91
Asal1     28 IVMFGDSLSDTGKmyskmrgylpssppyYEGRFSNGPVWLEQLTKQF----.------PGLTI   79
Ahyd2     40 IVMFGDSLSDTGKmyskmrgylpssppyYEGRFSNGPVWLEQLTKQFPGLTiaNEAEGGATAVA 103

Pfam         fnrgisGrtsdGrlvvDarlvatllPlsqflGlnlpPYLsgdflrGANPAsagAtIlgtslipflni
Sriml     82 NPTACSGAR---------------------------------------------------  90
Scoe1     48 TNLAVRGRL---------------------------------------------------  56
Scoe2     51 ANLAVRGKL---------------------------------------------------  59
Ahyd1     92 YNKISWNPK--------------------------------------------------- 100
Asal1     80 ANEAEGGAT---------------------------------------------------  88
Ahyd2    104 YNKISWNPK--------------------------------------------------- 112

Pfam         QvqFkdfkskvlelrqa......lgllqellrlvpvldakspdlvtimiGtNDl...itvakfgpks
Sriml     91 -------------------TGDVLAKQLTPVNSGTDLVSITIGGNDAgfaDTMTTCNLQG 131
Scoe1     57 -----------------.....--LDQIVAEQVPRVVGLAPDLVSPAAGGNDI...------I----  86
Scoe2     60 -----------------.....--IGQIVDEQVDVAAAMGADVITLVGGLNDT...----------  88
Ahyd1    101 -------------YQVI......NNLDYEVTQFLQKDSFKPDDLVILWVGANDY...--------LA 137
Asal1     89 -------AVAYNKISWNpkyqvyNNLDYEVTQFLQKDSFKPDDLVILWVGANDY...--------LA 137
Ahyd2    113 -------------YQVI......NNLDYEVTQFLQKDSFKPDDLVILWVGANDY...--------LA 149

Pfam         .......tksdrnvsvpefrdnlrklikrLrsangariiiiltlvllnlplplGCl
Sriml    132 esaclarIAKARAYIQQTLPAQLDQVYDAIDSRAPAA-----QVVVLGYP------ 176
Scoe1     87 .......---RPGTDPDEVAERFELAVAALT-AAAGTVLVTTGPDTRGVP------ 125
Scoe2     89 .......----LRPKCDMARVRDLLTQAVERLAPHCEQLVLMRSP------      122
Ahyd1    138 .......YGWNTEQDAKRVRDAISDAANRMV-LNGAK-----EILLFNLP------ 174
Asal1    138 .......YGWNTEQDAKRVRDAISDAANRMV-LNGAK-----QILLFNLP------ 174
Ahyd2    150 .......YGWNTEQDAKRVRDAISDAANRMV-LNGAK-----QILLFNLP------ 186

Pfam         pqklalalassknvdatgclerlneavadynealrelaeiekIqaqlrkdglpdlkeanvpy
Sriml    177 --RFYKLGGSCAVGLSEKSRAAINAAADDINAVTAKRA--------------ADHGPAP 219
Scoe1    126 ----------------VLKHLRGKIATYNGHVRAIA----------------DRYGCPV 152
Scoe2    123 -------------GRQGPVLERFRPRMEALFAVIDDLA---------------GRHGAVV 154
Ahyd1    175 ------DLGQNPSARSQKVVEAASHVSAYHNQLLLNLA------RQLAPTGMVKLFEIDKQP 224
Asal1    175 ------DLGQNPSARSQKVVEAVSHVSAYHNKLLLNLA------RQLAPTGMVKLFEIDKQP 224
Ahyd2    187 ------DLGQNPSARSQKVVEAVSHVSAYHNQLLLNLA------RQLAPTGMVKLFEIDKQP 236

Pfam         VDlysifqdldgiqnpsayv.y....GPeet.kaCCGyGgr.yNyn.rv.CGnag.l.ck.vtakaC
Sriml    220 GDVNT----------.....-....------.--------.-----.--.------.-------.-- 242
Scoe1    153 LDLWSLRSVQDRRA------.-....------.---------.----.--.------.--.------ 166
Scoe2    155 VDLYGAQSLADPRM------.-....------.---------.----.--.------.--.------ 168
Ahyd1    225 AEMLRDPQNFGLSDQRNACYgGsyvwKPFASrSASTDSQLSaFNPQeRLaIAGNPlLaQAvASPMAA 291
Asal1    225 AEMLRDPQNFGLSDVENPCYdGgyvwKPFATrSVSTDRQLSaFSPQeRLaIAGNPlLaQAvASPMAR 291
Ahyd2    237 AEMLRDPQNFGLSDVENPCYdGgyvwKPFATrSVSTDRQLSaFSPQeRLdIAGNPlLaQAvASPMAR 303

Pfam         .dassyll.atlfwDgf.HpsekGykavAeal<-*
Sriml    243 .-------.--LPVENSyHPTANGQSKGYLPV     263
Scoe1    167 .-------.--WDADRL.HLSPEGHTRVALRA     186
Scoe2    169 .-------.--WDVDRL.HLTAEGHRRVAEAV     188
Ahyd1    292 rSASTLNCeGKMFWDQV.HPTTVVHAALSEPA     322
Asal1    292 rSASPLNCeGKMFWDQV.HPTTVVHAALSERA     322
Ahyd2    304 rSASPLNCeGKMFWDQV.HPTTVVHAALSERA     334
```

A. hydrophila enzyme      A. salmonicida enzyme 2254-82-5. TLC of egg yolk lipid treated with transferase #135

Transferase activity for #178 as a function of % water in the assay.

Figure 71

(SEQ ID No. 36)

```
  1 MPKFKKNFLV GLSAALMSIS LPSATASAAS ADSRPAPSRI VMPGDSLSDT
 51 GKMYSKMRGY LPSSPPYYEG RFSNGPVWLE QLTKQPPGLT IANEAEGGAT
101 AVAYNKISWN PKYQVINNLD YEVTQFLQKD SFKPDDLVIL WVGANDYLAY
151 GWNTEQDAKR VRDAISDAAN RMVLNGAKQI LLFNLPDLGQ NPSARSQKVV
201 EAVSHVSAYH NQLLLNLARQ LAPTGMVKLP EIDKQPAEML RDPQNFGLSD
251 VENPCYDGGY VWKPPATRSV STDRQLSAPS PQERLAIAGN PLLAQAVASP
301 MARRSASPLN CEGKMFWDQV HPTTVVHAAL SERAATPIAN QYEFLAH**
```

Figure 72 (SEQ ID No. 54)

```
   1 ATGTTTAAGT TTAAAAAGAA TTTCTTAGTT GGATTATCGG CAGCTTTAAT
     TACAAATTCA AATTTTTCTT AAAGAATCAA CCTAATAGCC GTCAAATTA

51 GAGTATTAGC TTGTTTTCGG CAACCGCCTC TGCAGCTAGC GCCGA    C
     CTCATAATCG AACAAAAGCC GTTGGCGGAG ACGTCGATCG CGGCTGTCGG

101 GTCCCGCCTT TTCCCGGATC GTGATGTTCG GCGACAGCCT CTCCGATACC
     CAGGGCGGAA AAGGGCCTAG CACTACAAGC CGCTGTCGGA GAGGCTATGG

151 GGCAAAATGT ACAGCAAGAT GCGCGGTTAC CTCCCCTCCA GCCCGCCCTA
     CCGTTTTACA TGTCGTTCTA CGCGCCAATG GAGGGGAGGT CGGGCGGGAT

201 CTATGAGGGC CGTTTCTCCA ACGGACCCGT CTGGCTGGAG CAGCTGACCA
     GATACTCCCG GCAAAGAGGT TGCCTGGGCA GACCGACCTC GTCGACTGGT

251 AACAGTTCCC GGGTCTGACC ATCGCCAACG AAGCGGAAGG CGGTGCCACT
     TTGTCAAGGG CCCAGACTGG TAGCGGTTGC TTCGCCTTCC GCCACGGTGA

301 GCCGTGGCTT ACAACAAGAT CTCCTGGAAT CCCAAGTATC AGGTCATCAA
     CGGCACCGAA TGTTGTTCTA GAGGACCTTA GGGTTCATAG TCCAGTAGTT

351 CAACCTGGAC TACGAGGTCA CCCAGTTCTT GCAGAAAGAC AGCTTCAAGC
     GTTGGACCTG ATGCTCCAGT GGGTCAAGAA CGTCTTTCTG TCGAAGTTCG

401 CGGACGATCT GGTGATCCTC TGGGTCGGTG CCAATGACTA TCTGGCCTAT
     GCCTGCTAGA CCACTAGGAG ACCCAGCCAC GGTTACTGAT AGACCGGATA

451 GGCTGGAACA CGGAGCAGGA TGCCAAGCGG GTTCGCGATG CCATCAGCGA
     CCGACCTTGT GCCTCGTCCT ACGGTTCGCC AAGCGCTAC GGTAGTCGCT

501 TGCGGCCAAC CGCATGGTAC TGAACGGTGC CAAGCAGATA CTGCTGTTCA
     ACGCCGGTTG GCGTACCATG ACTTGCCACG GTTCGTCTAT GACGACAAGT

551 ACCTGCCGGA TCTGGGCCAG AACCCGTCAG CTCGCAGTCA GAAGGTGGTC
     TGGACGGCCT AGACCCGGTC TTGGGCAGTC GAGCGTCAGT CTTCCACCAG

601 GAGGCGGTCA GCCATGTCTC CGCCTATCAC AACCAGCTGC TGCTGAACCT
     CTCCGCCAGT CGGTACAGAG GCGGATAGTG TTGGTCGACG ACGACTTGGA

651 GGCACGCCAG CTGGCCCCCA CCGGCATGGT AAAGCTGTTC GAGATCGACA
     CCGTGCGGTC GACCGGGGGT GGCCGTACCA TTTCGACAAG CTCTAGCTGT

701 AGCAATTTGC CGAGATGCTG CGTGATCCGC AGAACTTCGG CCTGAGCGAC
     TCGTTAAACG GCTCTACGAC GCACTAGGCG TCTTGAAGCC GGACTCGCTG

751 GTCGAGAACC CCTGCTACGA CGGCGGCTAT GTGTGGAAGC CGTTTGCCAC
     CAGCTCTTGG GGACGATGCT GCCGCCGATA CACACCTTCG GCAAACGGTG

801 CCGCAGCGTC AGCACCGACC GCCAGCTCTC CGCCTTCAGT CCGCAGGAAC
     GGCGTCGCAG TCGTGGCTGG CGGTCGAGAG GCGGAAGTCA GGCGTCCTTG

851 GCCTCGCCAT CGCCGGCAAC CCGCTGCTGG CACAGGCCGT TGCCAGTCCT
     CGGAGCGGTA GCGGCCGTTG GCGACGACC GTGTCCGGCA ACGGTCAGGA

901 ATGGCCCGCC GCAGCGCCAG CCCCCTCAAC TGTGAGGGCA AGATGTTCTG
     TACCGGGCGG CGTCGCGGTC GGGGGAGTTG ACACTCCCGT TCTACAAGAC

951 GGATCAGGTA CACCCGACCA CTGTCGTGCA CGCAGCCCTG AGCGAGCGCG
     CCTAGTCCAT GTGGGCTGGT GACAGCACGT GCGTCGGGAC TCGCTCGCGC

1001 CCGCCACCTT CATCGCGAAC CAGTACGAGT TCCTCGCCCA CTGATGA
     GGCGGTGGAA GTAGCGCTTG GTCATGCTCA AGGAGCGGGT GACTACT
```

METHOD OF USING LIPID ACYLTRANSFERASE

REFERENCE TO RELATED APPLICATIONS

This application is a continuation of U.S. patent application Ser. No. 11/182,408 filed Jul. 15, 2005, now U.S. Pat. No. 7,807,398 which is a continuation-in-part of International Patent Application PCT/IB2004/000655 filed Jan. 15, 2004 and published as WO 2004/064537 on Aug. 5, 2004 which claims priority to Great Britain Application Numbers 0301117.8, 0301118.6, 0301119.4, 0301120.2, 0301121.0, 0301122.8, all of which were filed Jan. 17, 2003, U.S. Patent Application No. 60/489,441 filed Jul. 23, 2003, and Great Britain Application Number 0330016.7 filed Dec. 24, 2003. Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

Reference is made to the following related applications: U.S. application Ser. No. 09/750,990 filed on 20 Jul. 1999 and U.S. application Ser. No. 10/409,391. Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("herein cited documents"). Each of the herein cited documents, and each document cited or referenced in the herein cited documents, is hereby incorporated herein by reference.

FIELD OF INVENTION

Sequence Listing

The instant application contains a Sequence Listing which has been submitted via EFS-Web and is hereby incorporated by reference in its entirety. Said ASCII copy, created on Mar. 5, 2010, is named 67451020.txt, and is 111,002 bytes in size.

The present invention relates to a method for the in situ production of an emulsifier within a foodstuff by use of a lipid acyltransferase.

The present invention further relates to a method for the in situ production of an emulsifier within a foodstuff by use of a lipid acyltransferase, wherein the method is such that the emulsifier is produced without increasing or without substantially increasing the free fatty acids in the foodstuff.

The present invention yet further relates to a method for the in situ production of at least two emulsifiers within a foodstuff by use of a lipid acyltransferase.

The present invention also relates to a method for the in situ production of a carbohydrate ester and/or a sterol ester and/or a stanol ester and/or a protein ester and/or glycerol ester and/or a hydroxy acid ester within a foodstuff by use of a lipid acyltransferase.

The present invention relates to a food enzyme composition and/or a feed enzyme composition, which contains a lipid acyltransferase, and the use of such a composition in the methods of the present invention.

The present invention further relates to a method of identifying suitable lipid acyltransferases in accordance with the present invention and to lipid acyltransferases so identified.

The present invention yet further relates to an immobilised lipid acyltransferase.

TECHNICAL BACKGROUND

The beneficial use of phospholipases and lipases (referred to as lipolytic enzymes, (EC. 3.1.1.x) used in food and/or feed industrial applications has been known for many years.

For instance, in EP 0 585 988 it is claimed that lipase addition to dough resulted in an improvement in the anti-stalling effect. It is suggested that a lipase obtained from *Rhizopus arrhizus* when added to dough can improve the quality of the resultant bread when used in combination with shortening/fat. WO94/04035 teaches that an improved softness can be obtained by adding a lipase to dough without the addition of any additional fat/oil to the dough. Castello, P. ESEGP 89-10 December 1999 Helsinki, shows that exogenous lipases can modify bread volume.

Lipolytic enzymes hydrolyse one or more of the fatty acids from lipids present in the food which can result in the formation of powerful emulsifier molecules within the foodstuff which provide commercially valuable functionality. The molecules which contribute the most significant emulsifier characteristics are the partial hydrolysis products, such as lyso-phospholipids, lyso-glycolipids, and mono-glyceride molecules. The polar lipid hydrolysis products, such as lyso-phospholipids and lyso-glycolipids are particularly advantageous. In bread making, such in situ derived emulsifiers can give equivalent functionality as emulsifiers, such as DATEM.

However, the activity of lipolytic enzymes also results in accumulation of free fatty acids, which can lead to detrimental functionality in the foodstuff. This inherent activity of lipolytic enzymes limits their functionality.

Numerous solutions to this problem have been attempted in the art. However, these result in a significant increase in free fatty acids in the foodstuff, particularly food stuffs with high water content, including, but not limited to bread doughs and egg yolk.

Phospholipases, particularly phospholipase A2 (E.C. 3.1.1.4), have been used for many years for the treatment of egg or egg-based products (see U.S. Pat. No. 4,034,124 and Dutihl & Groger 1981 J. Sci. Food Agric. 32, 451-458 for example). The phospholipase activity during the treatment of egg or egg-based products results in the accumulation of polar lysolecithin, which can act as an emulsifier. Phospholipase treatment of egg or egg-based products can improve the stability, thermal stability under heat treatment such as pasteurisation and result in substantial thickening. Egg-based products may include, but are not limited to cake, mayonnaise, salad dressings, sauces, ice creams and the like. Use of phospholipases results in the accumulation of free fatty acids. The accumulation of free fatty acids can result in significant off-flavour. In addition, the accumulation of free fatty acids can result in enhanced susceptibility to oxidation, and hence result in poor shelf-life, product discoloration and alteration of other critical food characteristics such as flavour and texture. Recently, lipolytic enzymes with broader substrate specificity have been marketed for treatment of egg yolk and related food products. These have the advantage that, unlike most of the phospholipase A2s, they do not originate from a mammalian source. However, they result in significant accumulation of free fatty acids, not only due to the hydrolysis of phospholipids, but also triglycerides.

As mentioned above, another area where lipases have been extensively used is in the bakery industry. The use of phospholipases in baking dates bake to the early 1980s.

The substrate for lipases in wheat flour is 1.5-3% endogenous wheat lipids, which are a complex mixture of polar and non-polar lipids. The polar lipids can be divided into glycolipids and phospholipids. These lipids are built up of glycerol esterified with two fatty acids and a polar group. The polar group contributes to surface activity of these lipids. Enzymatic cleavage of one of the fatty acids in these lipids leads to lipids with a much higher surface activity. It is well known that emulsifiers, such as DATEM, with high surface activity are very functional when added to dough.

However, the use of lipases (E.C. 3.1.1.X) in dough products may have a detrimental impact on yeast activity, and/or a negative effect on bread volume. The negative effect on bread volume is often explained by overdosing. Overdosing can lead to a decrease in gluten elasticity which results in a dough which is too stiff and thus results in reduced bread volumes. In addition, or alternatively, such lipases can degrade shortening, oil or milk fat added to the dough, resulting in off-flavour in the dough and baked product. Overdosing and off flavour have been attributed to the accumulation of free fatty acids in the dough.

In EP 1 193 314, EP 0 977 869 and also in WO 01/39602, the use of lipolytic enzymes active on glycolipids was reported to be particularly beneficial in application in bread making as the partial hydrolysis products the lyso-glycolipids were found to have very high emulsifier functionality, apparently resulting in a higher proportion of positive emulsifier functionality compared to the detrimental accumulation of free fatty acids. However, the enzymes were also found to have significant non selective activity on triglyceride which resulted in unnecessarily high free fatty acid.

The same finding was reported in WO 00/32758, which disclosed lipolytic enzyme variants with enhanced activity on phospholipids and/or glycolipids, in addition to variants which had a preference for long rather than short chain fatty acids. This latter feature, also disclosed in WO 01/39602, was deemed of particular importance to prevent the off-flavours associated with the accumulation of free short chain fatty acids. However, significant free fatty acids are produced.

The problem of high triglyceride activity was addressed in WO02/094123, where the use of lipolytic enzymes active on the polar lipids (i.e. glycolipids and phospholipids) in a dough, but substantially not active on triglycerides or 1-mono-glycerides is taught. However, significant free fatty acids are produced.

Some lipolytic enzymes have low or no activity on the lyso form of polar lipids (e.g. glycolipids/phospholipids). The use of such enzymes has been deemed preferable as they ensure the accumulation of the highly polar lyso-lipids, resulting in optimal functionality. Free fatty acids do however accumulate. This selective functionality is characteristic of phospholipase A2 enzymes, and the glycolipases disclosed in EP 0 977 869, EP 1 193 314, and WO01/39602. Variant enzymes of less selective lipolytic enzymes have been produced which have a lower activity on the lyso-polar lipids when compared to the parent enzyme (WO03/060112). However, significant free fatty acids are produced.

WO00/05396 teaches a process for preparing a foodstuff comprising an emulsifier, wherein food material is contacted with an enzyme such that an emulsifier is generated by the enzyme from a fatty acid ester and a second functional ingredient is generated from a second constituent. WO0/05396 teaches the use of in particular a lipase or esterase enzyme. Nowhere in WO00/05396 is the specific use of a lipid acyltransferase taught. In addition, in foodstuffs with high water content, the use of the esterases and lipases as taught in WO00/05396 would result in significant accumulation of free fatty acids.

A disadvantage associated with the use of lipases, including phospholipases and glycolipases, may be caused by the build-up of free fatty acids released from the lipids. Over the past couple of decades the use of lipolytic enzymes in foodstuffs has been limited due to the balance between the detrimental accumulation of free fatty acids and the production of the lyso-lipids which provide positive functionality. Although numerous strategies in the art have been attempted, some of which provided significant improvements in functionality, none have completely addressed and solved the fundamental problem in the art, i.e. the significant accumulation of free fatty acids in foodstuffs prepared using lipolytic enzymes in situ.

The presence of high levels of free fatty acids (FFA) in raw materials or food products is generally recognised as a quality defect and food processors and customers will usually include a maximum FFA level in the food specifications. The resulting effects of excess FFA levels can be in organoleptic and/or functional defects.

A result of lipolysis is hydrolytic rancidity, with the formation of characteristic "soapy" flavour. This "soapy" taste is especially acute with fatty acids of intermediate chain length (C8-C12) which, although not present in high concentrations, may be important constituents of, for example, dairy products or vegetable oils. A more common organoleptic defect is due to the combined effects of lipolytic enzymes and oxidation processes. Unsaturated fatty acids are more susceptible to enzymatic oxidation when unesterified than when esterified in acyl lipids.

Functional defects in food due to high FFA levels are recognised, but less readily explained. Without wishing to be bound by theory, the hydrolysis of unchanged lipids to carboxylic acids will increase [H+] and produce carbonyl groups that can combine with other compounds or metal ions. Free fatty acids also combine proteins by hydrophobic interactions and can complex with starch during cooking. FFA may also interfere with the action of surface-active agents, such as polar lipids and emulsifiers. (Lipid in Cereal Technology, P. J. Barnes, Academic Press 1983.)

WO03/100044 discloses a class of acyl transferases known as PDATs (or ATWAX). These enzymes use a monoglyceride or a diglyceride as the acceptor molecule, and phosphatidylcholine (PC) as the donor molecule to produce the following products: lyso phosphatidylcholine and triacylglycerol and/or diacylglycerol.

In one embodiment, the present invention relates to improvements in the incorporation of whey proteins into food products, providing for improved yields without impairing the qualities—such as the texture—of the food compositions and products.

Cheese compositions are typically prepared from dairy liquids by processes that include treating the liquid with a coagulating or clotting agent. The coagulating agent may be a curding enzyme, an acid or a suitable bacterial culture, or it may include such a culture. The curd that results generally incorporates transformed casein, fats including natural butter fat, and flavourings that arise especially when a bacterial culture is used. The curd may be separated from the liquid whey, which contains soluble proteins not affected by the coagulation and that therefore are not incorporated into the curd.

Whey is thus a by-product of manufacturing in commercial processes that produce food products—such as cheeses. Traditionally, whey is disposed of as unused waste or used as fertiliser or animal feed or processed into a food ingredient.

The inability of whey proteins to be substantially retained in the curd is an important factor contributing to a lack of efficiency in the conventional production of dairy products—such as cheese curds—and to a reduction in overall yield relating to the incorporation of all the protein solids that are present in the starting dairy liquids into resulting cheese curds.

There have been numerous attempts to include whey proteins in cheese e.g. by heat treatment of the milk, heat treatment of whey, or by filtration—such as ultrafiltration.

There are also several descriptions of the use of specific proteases to induce aggregation of whey proteins. A serine protease derived from *Bacillus licheniformis* has been shown to have the ability to induce aggregation of whey proteins (U.S. Pat. No. 5,523,237).

However, there remains many difficulties associated with adding whey proteins in processes such as the manufacture of cheeses. For example, incorporation of whey protein into cheeses is associated with a deterioration in the taste and mouth-feel of the product, and furthermore tends to interfere with curding and subsequent processing of the product. Proteases that have been previously reported that can be added to cheese milk for hydrolysis of whey proteins result in significant hydrolysis of the caseins as described by Madsen, J. S. & Qvist, K. B. (1997) Hydrolysis of milk protein by a *Bacillus licheniformis* protease specific for acidic amino acid residues. *J. Food Sci.* 62, 579-582.

Thus, there is a need in the art for methods and compositions that provide for the improved incorporation of whey protein into food products while maintaining organoleptic and other desirable properties. Such optimisation would result in increased efficiency, higher yields of food products, and reduced overall material costs.

Lipase:cholesterol acyltransferases have been known for some time (see for example Buckley—Biochemistry 1983, 22, 5490-5493). In particular, glycerophospholipid:cholesterol acyl transferases (GCATs) have been found, which like the plant and/or mammalian lecithin:cholesterol acyltransferases (LCATs), will catalyse fatty acid transfer between phosphatidylcholine and cholesterol.

Upton and Buckley (TIBS 20, May 1995 p 178-179) and Brumlik and Buckley (J. of Bacteriology April 1996 p 2060-2064) teach a lipase/acyltransferase from *Aeromonas hydrophila* which has the ability to carry out acyl transfer to alcohol acceptors in aqueous media.

SUMMARY ASPECTS OF THE PRESENT INVENTION

According to a first aspect of the present invention there is provided a method of in situ production of an emulsifier in a foodstuff, wherein the method comprises the step of adding to the foodstuff a lipid acyltransferase as defined herein.

In a further aspect, the present invention provides a method of in situ production of an emulsifier in a foodstuff, wherein the method is such that the emulsifier is produced without increasing or without substantially increasing the free fatty acids in the foodstuff, and wherein the method comprises the step of adding a lipid acyltransferase to the foodstuff.

In another aspect, the present invention provides a method of in situ production of an emulsifier and either a sterol ester and/or a stanol ester in a foodstuff, wherein the method is such that the emulsifier is produced without increasing or without substantially increasing the free fatty acids in the foodstuff, and wherein the method comprises the step of adding a lipid acyltransferase to the foodstuff.

In another aspect, the present invention provides a method of in situ production of an emulsifier and either a sterol ester and/or a stanol ester in a foodstuff, wherein the method comprises the step of adding a lipid acyltransferase to the foodstuff.

According to another aspect of the present invention there is provided a method for the in situ production of at least two emulsifiers in a foodstuff, wherein the method comprises the step of adding to the foodstuff a lipid acyltransferase.

According to a further aspect of the present invention there is provided a method of in situ production of at least two emulsifiers and either a sterol ester and/or a stanol ester in a foodstuff, wherein the method is such that the emulsifiers are produced without increasing or without substantially increasing the free fatty acids in the foodstuff, and wherein the method comprises the step of adding a lipid acyltransferase to the foodstuff.

According to a further aspect of the present invention there is provided a method of in situ production of at least two emulsifiers and either a sterol ester and/or a stanol ester in a foodstuff, wherein the method comprises the step of adding a lipid acyltransferase to the foodstuff.

In a further aspect, the present invention provides a method for the in situ production of a carbohydrate ester in a foodstuff, wherein the method comprises the step of adding a lipid acyltransferase to the foodstuff.

In another aspect, the present invention provides a method for the in situ production of a carbohydrate ester together with an emulsifier in a foodstuff, wherein the method comprises the step of adding a lipid acyltransferase to the foodstuff.

In another aspect, the present invention provides a method of in situ production of an emulsifier, and one or more of a carbohydrate ester; a sterol ester; a stanol ester; a protein ester; a monoglyceride or a diglyceride in a foodstuff, and wherein the method comprises the step of adding a lipid acyltransferase to the foodstuff.

According to a further aspect of the present invention there is provided a method of production of a foodstuff comprising an emulsifier, wherein the method comprises the step of adding to the foodstuff a lipid acyltransferase as defined herein.

In a further aspect, the present invention provides a method of production of a foodstuff comprising an emulsifier, wherein the method is such that the emulsifier is produced without increasing or without substantially increasing the free fatty acids in the foodstuff, and wherein the method comprises the step of adding a lipid acyltransferase to the foodstuff.

In another aspect, the present invention provides a method of the production of a foodstuff comprising an emulsifier and either a sterol ester and/or a stanol ester, wherein the method is such that the emulsifier is produced without increasing or without substantially increasing the free fatty acids in the foodstuff, and wherein the method comprises the step of adding a lipid acyltransferase to the foodstuff.

In another aspect, the present invention provides a method of the production of a foodstuff comprising an emulsifier and either a sterol ester and/or a stanol ester, wherein the method comprises the step of adding a lipid acyltransferase to the foodstuff.

According to a further aspect of the present invention there is provided a method for the production of a foodstuff comprising at least two emulsifiers, wherein the method comprises the step of adding to the foodstuff a lipid acyltransferase.

According to a further aspect of the present invention there is provided a method of the production of a foodstuff comprising at least two emulsifiers and either a sterol ester and/or a stanol ester, wherein the method is such that the emulsifiers are produced without increasing or without substantially increasing the free fatty acids in the foodstuff, and wherein the method comprises the step of adding a lipid acyltransferase to the foodstuff.

According to a further aspect of the present invention there is provided a method of the production of a foodstuff comprising at least two emulsifiers and either a sterol ester and/or a stanol ester, wherein the method comprises the step of adding a lipid acyltransferase to the foodstuff.

In a further aspect, the present invention provides a method for the production of a foodstuff comprising a carbohydrate ester, wherein the method comprises the step of adding a lipid acyltransferase to the foodstuff.

In another aspect, the present invention provides a method for the production of a foodstuff comprising a carbohydrate ester and an emulsifier, wherein the method comprises the step of adding a lipid acyltransferase to the foodstuff.

In another aspect, the present invention provides a method of the production of a foodstuff comprising an emulsifier and one or more of a carbohydrate ester; a sterol ester; a stanol ester; a protein ester; a monoglyceride or a diglyceride, and wherein the method comprises the step of adding a lipid acyltransferase to the foodstuff.

In another aspect, the present invention provides use of a lipid acyltransferase to prepare from a food material a foodstuff comprising an emulsifier, wherein the emulsifier is generated from constituents of the food material by the lipid acyltransferase.

In a further aspect, the present invention provides use of a lipid acyltransferase to prepare from a food material a foodstuff comprising an emulsifier, wherein the emulsifier is produced without increasing or without substantially increasing the free fatty acids in the foodstuff, and wherein the emulsifier is generated from constituents of the food material by the lipid acyltransferase.

In another aspect, the present invention provides use of a lipid acyltransferase to prepare from a food material a foodstuff comprising an emulsifier and either a sterol ester and/or a stanol ester, wherein the emulsifier is produced without increasing or without substantially increasing the free fatty acids in the foodstuff, and wherein the emulsifier and/or sterol ester and/or stanol ester is/are generated from constituents of the food material by the lipid acyltransferase.

In another aspect, the present invention provides use of a lipid acyltransferase to prepare from a food material a foodstuff comprising an emulsifier and either a sterol ester and/or a stanol ester, wherein the emulsifier and/or sterol ester and/or stanol ester is/are generated from constituents of the food material by the lipid acyltransferase.

In another aspect, the present invention provides use of a lipid acyltransferase to prepare from a food material a foodstuff comprising at least two emulsifiers, wherein the two emulsifiers are generated from constituents of the food material by the lipid acyltransferase.

According to a further aspect of the present invention there is provided use of a lipid acyltransferase to prepare from a food material a foodstuff comprising at least two emulsifiers and either a sterol ester and/or a stanol ester, wherein the emulsifiers are produced without increasing or without substantially increasing the free fatty acids in the foodstuff, and wherein one or both of the emulsifiers and/or the sterol ester and/or the stanol ester is/are generated from constituents of the food material by the lipid acyltransferase.

According to a further aspect of the present invention there is provided use of a lipid acyltransferase to prepare from a food material a foodstuff comprising at least two emulsifiers and either a sterol ester and/or a stanol ester, wherein one or both of the emulsifiers and/or the sterol ester and/or the stanol ester is/are generated from constituents of the food material by the lipid acyltransferase.

In a further aspect, the present invention provides use of a lipid acyltransferase to prepare from a food material a foodstuff comprising a carbohydrate ester, wherein the carbohydrate ester is generated from constituents of the food material by the lipid acyltransferase.

In another aspect, the present invention provides use of a lipid acyltransferase to prepare from a food material a foodstuff comprising at least a carbohydrate ester and a further emulsifier, wherein the carbohydrate ester and the emulsifier are generated from constituents of the food material by the lipid acyltransferase.

In another aspect, the present invention provides use of a lipid acyltransferase to prepare from a food material a foodstuff comprising an emulsifier and one or more of a carbohydrate ester; a sterol ester; a stanol ester; a protein ester; a monoglyceride or a diglyceride, and wherein the emulsifier and/or the carbohydrate ester and/or the sterol ester and/or the stanol ester and/or the protein ester and/or the monoglyceride and/or the diglyceride is/are generated from constituents of the food material by the lipid acyltransferase.

In accordance with a further aspect of the present invention there is provided a method of the in situ production of an emulsifier, preferably a lysolecithin and a sterol ester in a egg based foodstuff, wherein the method is such that the emulsifier is produced without increasing or without substantially increasing the free fatty acids in the foodstuff, and wherein the method comprises the step of adding a lipid acyltransferase to the foodstuff.

In accordance with a further aspect of the present invention there is provided a method of the in situ production of an emulsifier, preferably a lysolecithin, and a sterol ester in an egg based foodstuff, wherein the method comprises the step of adding a lipid acyltransferase to the foodstuff.

In another aspect, the present invention provides a method of production of a egg based foodstuff comprising an emulsifier, preferably a lysolecithin, and a sterol ester in an egg based foodstuff, wherein the emulsifier is produced without increasing or without substantially increasing the free fatty acids in the foodstuff, and wherein the method comprises the step of adding a lipid acyltransferase to the foodstuff.

In another aspect, the present invention provides a method of production of an egg based foodstuff comprising an emulsifier, preferably a lysolecithin, and a sterol ester in an egg based foodstuff, wherein the method comprises the step of adding a lipid acyltransferase to the foodstuff.

In a further aspect, the present invention further provides a foodstuff obtainable by, preferably obtained by, a method according to the present invention.

In another aspect the present invention further relates to a food enzyme composition and/or a feed enzyme composition, which contains a lipid acyltransferase, and the use of such a composition in the methods of the present invention.

In accordance with a further aspect of the present invention there is provided a method of identifying a suitable lipid acyltransferase for use in accordance with the present invention, comprising the steps of testing an enzyme of interest using one or more of the "Transferase Assay in a Low Water environment", the "Transferase Assay in High Water Egg Yolk" or the "Transferase Assay in Buffered Substrate", and selecting a lipid acyltransferase if it is one which has one or more of the following characteristics: (a) when tested using the "Transferase Assay in a Low Water Environment", measured after a time period selected from 30, 20 or 120 minutes, has a relative transferase activity of at least 1%; (b) when tested using the "Transferase Assay in High Water Egg Yolk" in an egg yolk with 54% water, has up to 100% relative transferase activity; or (c) when tested using the "Transferase Assay in Buffered Substrate" has at least 2% acyltransferase activity.

The present invention yet further provides a lipid acyltransferase identified using a method according to the present invention.

In accordance with a further aspect, the present invention provides an immobilised lipid acyltransferase enzyme as defined herein.

DETAILED ASPECTS OF THE PRESENT INVENTION

The term "lipid acyltransferase" as used herein means an enzyme which as well as having lipase activity (generally classified as E.C. 3.1.1.x in accordance with the Enzyme Nomenclature Recommendations (1992) of the Nomenclature Committee of the International Union of Biochemistry and Molecular Biology) also has acyltransferase activity (generally classified as E.C. 2.3.1.x), whereby the enzyme is capable of transferring an acyl group from a lipid to one or more acceptor substrates, such as one or more of the following: a sterol; a stanol; a carbohydrate; a protein; a protein subunit; glycerol.

Preferably, the lipid acyltransferase for use in the methods and/or uses of the present invention is capable of transferring an acyl group from a lipid (as defined herein) to one or more of the following acyl acceptor substrates: a sterol, a stanol, a carbohydrate, a protein or subunits thereof, or a glycerol.

For some aspects the "acyl acceptor" according to the present invention may be any compound comprising a hydroxy group (—OH), such as for example, polyvalent alcohols, including glycerol; sterol; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof. Preferably, the "acyl acceptor" according to the present invention is not water.

In one embodiment, the acyl acceptor is preferably not a monoglyceride and/or a diglyceride.

In one aspect, preferably the enzyme is capable of transferring an acyl group from a lipid to a sterol and/or a stanol.

In one aspect, preferably the enzyme is capable of transferring an acyl group from a lipid to a carbohydrate.

In one aspect, preferably the enzyme is capable of transferring an acyl group from a lipid to a protein or a subunit thereof. Suitably the protein subunit may be one or more of the following: an amino acid, a protein hydrolysate, a peptide, a dipeptide, an oligopeptide, a polypeptide.

Suitably in the protein or protein subunit the acyl acceptor may be one or more of the following constituents of the protein or protein subunit: a serine, a threonine, a tyrosine, or a cysteine.

When the protein subunit is an amino acid, suitably the amino acid may be any suitable amino acid. Suitably the amino acid may be one or more of a serine, a threonine, a tyrosine, or a cysteine for example.

In one aspect, preferably the enzyme is capable of transferring an acyl group from a lipid to glycerol.

In one aspect, preferably the enzyme is capable of transferring an acyl group from a lipid to a hydroxy acid.

In one aspect, preferably the enzyme is capable of transferring an acyl group from a lipid to a polyvalent alcohol.

In one aspect, the lipid acyltransferase may, as well as being able to transfer an acyl group from a lipid to a sterol and/or a stanol, additionally be able to transfer the acyl group from a lipid to one or more of the following: a carbohydrate, a protein, a protein subunit, glycerol.

Preferably, the lipid substrate upon which the lipid acyltransferase according to the present invention acts is one or more of the following lipids: a phospholipid, such as a lecithin, e.g. phosphatidylcholine, a triacylglyceride, a cardiolipin, a diglyceride, or a glycolipid, such as digalactosyldiglyceride (DGDG) for example. This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

For some aspects, preferably the lipid substrate upon which the lipid acyltransferase acts is a phospholipid, such as lecithin, for example phosphatidylcholine.

For some aspects, preferably the lipid substrate is a glycolipid, such as DGDG for example.

Preferably the lipid substrate is a food lipid, that is to say a lipid component of a foodstuff.

For some aspects, preferably the lipid acyltransferase according to the present invention is incapable, or substantially incapable, of acting on a triglyceride and/or a 1-monoglyceride and/or 2-monoglyceride.

Suitably, the lipid substrate or lipid acyl donor may be one or more lipids present in one or more of the following substrates: fats, including lard, tallow and butter fat; oils including oils extracted from or derived from palm oil, sunflower oil, soya bean oil, safflower oil, cotton seed oil, ground nut oil, corn oil, olive oil, peanut oil, coconut oil, and rape seed oil. Lecithin from soya, rape seed or egg yolk is also a suitable lipid substrate. The lipid substrate may be an oat lipid or other plant based material containing galactolipids.

In one aspect the lipid acyl donor is preferably lecithin (such as phosphatidylcholine) in egg yolk.

For some aspects of the present invention, the lipid may be selected from lipids having a fatty acid chain length of from 8 to 22 carbons.

For some aspects of the present invention, the lipid may be selected from lipids having a fatty acid chain length of from 16 to 22 carbons, more preferably of from 16 to 20 carbons.

For some aspects of the present invention, the lipid may be selected from lipids having a fatty acid chain length of no greater than 14 carbons, suitably from lipids having a fatty acid chain length of from 4 to 14 carbons, suitably 4 to 10 carbons, suitably 4 to 8 carbons.

Suitably, the lipid acyltransferase according to the present invention may exhibit one or more of the following lipase activities: glycolipase activity (E.C. 3.1.1.26), triacylglycerol lipase activity (E.C. 3.1.1.3), phospholipase A2 activity (E.C. 3.1.1.4) or phospholipase A1 activity (E.C. 3.1.1.32). The term "glycolipase activity" as used herein encompasses "galactolipase activity".

Suitably, the lipid acyltransferase according to the present invention may have at least one or more of the following activities: glycolipase activity (E.C. 3.1.1.26) and/or phospholipase A1 activity (E.C. 3.1.1.32) and/or phospholipase A2 activity (E.C. 3.1.1.4).

For some aspects, the lipid acyltransferase according to the present invention may have at least glycolipase activity (E.C. 3.1.1.26).

Suitably, for some aspects the lipid acyltransferase according to the present invention may be capable of transferring an acyl group from a glycolipid and/or a phospholipid to one or more of the following acceptor substrates: a sterol, a stanol, a carbohydrate, a protein, glycerol.

For some aspects, preferably the lipid acyltransferase according to the present invention is capable of transferring an acyl group from a glycolipid and/or a phospholipid to a sterol and/or a stanol to form at least a sterol ester and/or a stanol ester.

For some aspects, preferably the lipid acyltransferase according to the present invention is capable of transferring an acyl group from a glycolipid and/or a phospholipid to a carbohydrate to form at least a carbohydrate ester.

For some aspects, preferably the lipid acyltransferase according to the present invention is capable of transferring an acyl group from a glycolipid and/or a phospholipid to a protein to form at least protein ester (or a protein fatty acid condensate).

For some aspects, preferably the lipid acyltransferase according to the present invention is capable of transferring an acyl group from a glycolipid and/or a phospholipid to glycerol to form at least a diglyceride and/or a monoglyceride.

For some aspects, preferably the lipid acyltransferase according to the present invention does not exhibit triacylglycerol lipase activity (E.C. 3.1.1.3).

In some aspects, the lipid acyltransferase may be capable of transferring an acyl group from a lipid to a sterol and/or a stanol. Thus, in one embodiment the "acyl acceptor" according to the present invention may be either a sterol or a stanol or a combination of both a sterol and a stanol.

In one embodiment suitably the sterol and/or stanol may comprise one or more of the following structural features:
i) a 3-beta hydroxy group or a 3-alpha hydroxy group; and/or
ii) A:B rings in the cis position or A:B rings in the trans position or $C_5$-$C_6$ is unsaturated.

Suitable sterol acyl acceptors include cholesterol and phytosterols, for example alpha-sitosterol, beta-sitosterol, stigmasterol, ergosterol, campesterol, 5,6-dihydrosterol, brassicasterol, alpha-spinasterol, beta-spinasterol, gamma-spinasterol, deltaspinasterol, fucosterol, dimosterol, ascosterol, serebisterol, episterol, anasterol, hyposterol, chondrillasterol, desmosterol, chalinosterol, poriferasterol, clionasterol, sterol glycosides, and other natural or synthetic isomeric forms and derivatives.

In one aspect of the present invention suitably more than one sterol and/or stanol may act as the acyl acceptor, suitably more than two sterols and/or stanols may act as the acyl acceptor. In other words, in one aspect of the present invention, suitably more than one sterol ester and/or stanol ester may be produced. Suitably, when cholesterol is the acyl acceptor one or more further sterols or one or more stanols may also act as the acyl acceptor. Thus, in one aspect, the present invention provides a method for the in situ production of both a cholesterol ester and at least one sterol or stanol ester in combination. In other words, the lipid acyltransferase for some aspects of the present invention may transfer an acyl group from a lipid to both cholesterol and at least one further sterol and/or at least one stanol.

In one aspect, preferably the sterol acyl acceptor is one or more of the following: alpha-sitosterol, beta-sitosterol, stigmasterol, ergosterol and campesterol.

In one aspect, preferably the sterol acyl acceptor is cholesterol. When it is the case that cholesterol is the acyl acceptor for the lipid acyltransferase, the amount of free cholesterol in the foodstuff is reduced as compared with the foodstuff prior to exposure to the lipid acyltransferase and/or as compared with an equivalent foodstuff which has not been treated with the lipid acyltransferase.

Suitable stanol acyl acceptors include phytostanols, for example beta-sitostanol or ss-sitostanol.

In one aspect, preferably the sterol and/or stanol acyl acceptor is a sterol and/or a stanol other than cholesterol.

In some aspects, the foodstuff prepared in accordance with the present invention may be used to reduce blood serum cholesterol and/or to reduce low density lipoprotein. Blood serum cholesterol and low density lipoproteins have both been associated with certain diseases in humans, such as atherosclerosis and/or heart disease for example. Thus, it is envisaged that the foodstuffs prepared in accordance with the present invention may be used to reduce the risk of such diseases.

Thus, in one aspect the present invention provides the use of a foodstuff according to the present invention for use in the treatment and/or prevention of atherosclerosis and/or heart disease.

In a further aspect, the present invention provides a medicament comprising a foodstuff according to the present invention.

In a further aspect, the present invention provides a method of treating and/or preventing a disease in a human or animal patient which method comprising administering to the patient an effective amount of a foodstuff according to the present invention.

Suitably, the sterol and/or the stanol "acyl acceptor" may be found naturally within the foodstuff. Alternatively, the sterol and/or the stanol may be added to the foodstuff. When it is the case that a sterol and/or a stanol is added to the foodstuff, the sterol and/or stanol may be added before, simultaneously with, and/or after the addition of the lipid acyltransferase according to the present invention. Suitably, the present invention may encompass the addition of exogenous sterols/stanols, particularly phytosterols/phytostanols, to the foodstuff prior to or simultaneously with the addition of the enzyme according to the present invention.

For some aspects, one or more sterols present in the foodstuff may be converted to one or more stanols prior to or at the same time as the lipid acyltransferase is added according to the present invention. Any suitable method for converting sterols to stanols may be employed. For example, the conversion may be carried out by chemical hydrogenation for example. The conversion may be conducted prior to the addition of the lipid acyltransferase in accordance with the present invention or simultaneously with the addition of the lipid acyltransferase in accordance with the present invention. Suitably enzymes for the conversion of sterol to stanols are taught in WO00/061771.

Suitably the present invention may be employed to produce phytostanol esters in situ in a foodstuff. Phytostanol esters have increased solubility through lipid membranes, bioavailability and enhanced health benefits (see for example WO92/99640).

In some embodiments of the present invention the stanol ester and/or the sterol ester may be a flavouring and/or a texturiser. In which instances, the present invention encompasses the in situ production of flavourings and/or texturisers.

For some aspects of the present invention, the lipid acyltransferase according to the present invention may utilise a carbohydrate as the acyl acceptor. The carbohydrate acyl acceptor may be one or more of the following: a monosaccharide, a disaccharide, an oligosaccharide or a polysaccharide. Preferably, the carbohydrate is one or more of the following: glucose, fructose, anhydrofructose, maltose, lactose, sucrose, galactose, xylose, xylooligosacharides, arabinose, maltooligosaccharides, tagatose, microthecin, ascopyrone P, ascopyrone T, cortalcerone.

Suitably, the carbohydrate "acyl acceptor" may be found naturally within the foodstuff. Alternatively, the carbohydrate may be added to the foodstuff. When it is the case that the carbohydrate is added to the foodstuff, the carbohydrate may be added before, simultaneously with, and/or after the addition of the lipid acyltransferase according to the present invention.

Carbohydrate esters can function as valuable emulsifiers in foodstuffs. Thus, when it is the case that the enzyme functions to transfer the acyl group to a sugar, the invention encompasses the production of a second in situ emulsifier in the foodstuff.

In some embodiments, the lipid acyltransferase may utilise both a sterol and/or stanol and a carbohydrate as an acyl acceptor.

The utilisation of lipid acyltransferase which can transfer the acyl group to a carbohydrate as well as to a sterol and/or a stanol is particularly advantageous for foodstuffs comprising eggs. In particular, the presence of sugars, in particular glucose, in eggs and egg products is often seen as disadvantageous. Egg yolk may comprise up to 1% glucose. Typically, egg or egg based products may be treated with glucose oxidase to remove some or all of this glucose. However, in accordance with the present invention this unwanted sugar can be readily removed by "esterifying" the sugar to form a sugar ester.

For some aspects of the present invention, the lipid acyltransferase according to the present invention may utilise a protein as the acyl acceptor. Suitably, the protein may be one or more of the proteins found in a food product, for example in a dairy product and/or a meat product. By way of example only, suitable proteins may be those found in curd or whey, such as lactoglobulin. Other suitable proteins include ovalbumin from egg, gliadin, glutenin, puroindoline, lipid transfer proteins from grains, and myosin from meat.

Thus in accordance with the present invention, one or more of the following advantageous properties can be achieved: in situ production of an emulsifier without an increase in free fatty acids; a reduction in the accumulation of free fatty acids in the foodstuff; a reduction in free cholesterol levels in the foodstuff; an increase in sterol esters and/or stanol esters; a reduction in blood serum cholesterol and/or low density lipoproteins; an increase in carbohydrate esters; a reduction in unwanted free carbohydrates.

An advantage of the present invention is that the emulsifier(s) is/are prepared in situ in the foodstuff without an increase, or a substantial, increase, in the free fatty acid content of the foodstuff. The production of free fatty acids can be detrimental to foodstuffs. In particular, free fatty acids have been linked with off-odours and/or off-flavours in foodstuffs, as well other detrimental effects, including a soapy taste in cheese for instance. Preferably, the method according to the present invention results in the in situ preparation of an emulsifier(s) wherein the accumulation of free fatty acids is reduced and/or eliminated. Without wishing to be bound by theory, in accordance with the present invention the fatty acid which is removed from the lipid is transferred by the lipid acyltransferase to an acyl acceptor, for example a sterol and/or a stanol. Thus, the overall level of free fatty acids in the foodstuff does not increase or increases only to an insignificant degree. This is in sharp contradistinction to the situation when lipases (E.C. 3.1.1.x) are used to produce emulsifiers in situ. In particular, the use of lipases can result in an increased amount of free fatty acid in the foodstuff, which can be detrimental. In accordance with the present invention, the accumulation of free fatty acids is reduced and/or eliminated when compared with the amount of free fatty acids which would have been accumulated had a lipase enzyme, in particular a phospholipase A enzyme, been used in place of the lipid acyltransferase in accordance with the present invention.

The utilisation of a lipid acyltransferase which can transfer the acyl group to a sterol and/or stanol may be particularly advantageous for foodstuffs comprising eggs. In particular, it has been found that an egg-based product with significantly better properties can be obtained following treatment with a lipid acyltransferase as defined herein compared with egg-based products treated with conventional phospholipases, such as LipopanF® (Novozymes A/S, Denmark)), Lecitase Ultra® (Novozymes A/S, Denmark) or Lipomod 22 L from Biocatalysts, for instance.

Preferably, the lipid acyltransferase enzyme according to the present invention may be characterised using the following criteria:

(i) the enzyme possesses acyl transferase activity which may be defined as ester transfer activity whereby the acyl part of an original ester bond of a lipid acyl donor is transferred to an acyl acceptor to form a new ester; and (ii) the enzyme comprises the amino acid sequence motif GDSX (SEQ ID NO: 71), wherein X is one or more of the following amino acid residues L, A, V, I, F, Y, H, Q, T, N, M or S.

Preferably, X of the GDSX (SEQ ID NO: 71) motif is L. Thus, preferably the enzyme according to the present invention comprises the amino acid sequence motif GDSL (SEQ ID NO: 16).

The GDSX (SEQ ID NO: 71) motif is comprised of four conserved amino acids. Preferably, the serine within the motif is a catalytic serine of the lipid acyltransferase enzyme. Suitably, the serine of the GDSX (SEQ ID NO: 71) motif may be in a position corresponding to Ser-16 in *Aeromonas hydrophila* lipolytic enzyme taught in Brumlik & Buckley (Journal of Bacteriology April 1996, Vol. 178, No. 7, p 2060-2064).

To determine if a protein has the GDSX (SEQ ID NO: 71) motif according to the present invention, the sequence is preferably compared with the hidden markov model profiles (HMM profiles) of the pfam database.

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft D H (2002) Brief Bioinform 3; 236-245.

For a detailed explanation of hidden Markov models and how they are applied in the Pfam database see Durbin R, Eddy S, and Krogh A (1998) Biological sequence analysis; probabilistic models of proteins and nucleic acids. Cambridge University Press, ISBN 0-521-62041-4. The Hammer software package can be obtained from Washington University, St Louis, USA.

Alternatively, the GDSX (SEQ ID NO: 71) motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

The PFAM database can be accessed, for example, through several servers which are currently located at the following websites:
Wellcome Trust Sanger Institute
Washington University St. Louis
Institut National de la Recherche Agronomique The database offers a search facility where one can enter a protein sequence. Using the default parameters of the database the protein sequence will then be analysed for the presence of Pfam domains. The GDSX (SEQ ID NO: 71) domain is an established domain in the database and as such its presence in any query sequence will be recognised. The database will return the alignment of the Pfam00657 consensus sequence to the query sequence.

A multiple alignment, including *Aeromonas salmonicida* or *Aeromonas hydrophila* can be obtained by:
a) manual
   obtain an alignment of the protein of interest with the Pfam00657 consensus sequence and obtain an alignment of P10480 with the Pfam00657 consensus sequence following the procedure described above;
or
b) through the database
   After identification of the Pfam00657 consensus sequence the database offers the option to show an alignment of the query sequence to the seed alignment of the Pfam00657 consensus sequence. P10480 is part of this seed alignment and is indicated by GCAT_AERHY. Both the query sequence and P10480 will be displayed in the same window.

The *Aeromonas hydrophila* reference sequence:

The residues of *Aeromonas hydrophila* GDSX (SEQ ID NO: 71) lipase are numbered in the NCBI file P10480, the numbers in this text refer to the numbers given in that file which in the present invention is used to determine specific amino acids residues which, in a preferred embodiment are present in the lipid acyltransferase enzymes of the invention.

The Pfam alignment was performed (FIGS. 33 and 34):

The following conserved residues can be recognised and in a preferable embodiment may be present in the enzymes for use in the compositions and methods of the invention;

```
Block 1 - GDSX (SEQ ID NO: 71) block
hid hid hid hid Gly Asp Ser hid (SEQ ID NO: 72)
 28  29  30  31  32  33  34  35
```

-continued

```
Block 2 - GANDY (SEQ ID NO: 73) block
hid Gly hid Asn Asp hid (SEQ ID NO: 74)
130 131 132 133 134 135
```

Where 'hid' means a hydrophobic residue selected from Met, Ile, Leu, Val, Ala, Gly, Cys, His, Lys, Trp, Tyr, Phe.

Preferably the lipid acyltransferase enzyme for use in the compositions/methods of the invention can be aligned using the Pfam00657 consensus sequence.

Preferably, a positive match with the hidden markov model profile (HMM profile) of the pfam00657 domain family indicates the presence of the GDSL (SEQ ID NO: 16) or GDSX (SEQ ID NO: 71) domain according to the present invention.

Preferably when aligned with the Pfam00657 consensus sequence the lipid acyltransferase for use in the compositions/methods of the invention have at least one, preferably more than one, preferably more than two, of the following, a GDSx (SEQ ID NO: 71) block, a GANDY (SEQ ID NO: 73) block, a HPT block. Suitably, the lipid acyltransferase may have a GDSX (SEQ ID NO: 71) block and a GANDY (SEQ ID NO: 73) block. Alternatively, the enzyme may have a GDSX (SEQ ID NO: 71) block and a HPT block. Preferably the enzyme comprises at least a GDSX (SEQ ID NO: 71) block.

Preferably, when aligned with the Pfam00657 consensus sequence the enzyme for use in the compositions/methods of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophila* polypeptide sequence, namely SEQ ID No. 32: 28hid, 29hid, 30hid, 31hid, 32gly, 33Asp, 34Ser, 35hid, 130hid, 131Gly, 132Hid, 133Asn, 134Asp, 135hid, 309His The pfam00657 GDSX (SEQ ID NO: 71) domain is a unique identifier which distinguishes proteins possessing this domain from other enzymes.

The pfam00657 consensus sequence is presented in FIG. 1 as SEQ ID No. 1. This is derived from the identification of the pfam family 00657, database version 6, which may also be referred to as pfam00657.6 herein.

The consensus sequence may be updated by using further releases of the pfam database.

For example, FIGS. 33 and 34 show the pfam alignment of family 00657, from database version 11, which may also be referred to as pfam00657.11 herein.

The presence of the GDSx (SEQ ID NO: 71), GANDY (SEQ ID NO: 73) and HPT blocks are found in the pfam family 00657 from both releases of the database. Future releases of the pfam database can be used to identify the pfam family 00657.

Preferably, the lipid acyltransferase enzyme according to the present invention may be characterised using the following criteria:
(i) the enzyme possesses acyl transferase activity which may be defined as ester transfer activity whereby the acyl part of an original ester bond of a lipid acyl donor is transferred to acyl acceptor to form a new ester;
(ii) the enzyme comprises the amino acid sequence motif GDSX (SEQ ID NO: 71), wherein X is one or more of the following amino acid residues L, A, V, I, F, Y, H, Q, T, N, M or S.;

(iii) the enzyme comprises His-309 or comprises a histidine residue at a position corresponding to His-309 in the Aeromonas hydrophila lipolytic enzyme shown in FIG. 2 (SEQ ID No. 2 or SEQ ID No. 32).

Preferably, the amino acid residue of the GDSX (SEQ ID NO: 71) motif is L.

In SEQ ID No. 2 or SEQ ID No. 32 the first 18 amino acid residues form a signal sequence. His-309 of the full length sequence, that is the protein including the signal sequence, equates to His-291 of the mature part of the protein, i.e. the sequence without the signal sequence.

Preferably, the lipid acyltransferase enzyme according to the present invention comprises the following catalytic triad: Ser-34, Asp-134 and His-309 or comprises a serine residue, an aspartic acid residue and a histidine residue, respectively, at positions corresponding to Ser-34, Asp-134 and His-309 in the Aeromonas hydrophila lipolytic enzyme shown in FIG. 2 (SEQ ID No. 2) or FIG. 28 (SEQ ID No. 32). As stated above, in the sequence shown in SEQ ID No. 2 or SEQ ID No. 32 the first 18 amino acid residues form a signal sequence. Ser-34, Asp-134 and His-309 of the full length sequence, that is the protein including the signal sequence, equate to Ser-16, Asp-116 and His-291 of the mature part of the protein, i.e. the sequence without the signal sequence. In the pfam00657 consensus sequence, as given in FIG. 1 (SEQ ID No. 1) the active site residues correspond to Ser-7, Asp-157 and His-348.

Preferably, the lipid acyltransferase enzyme according to the present invention may be characterised using the following criteria:

(i) the enzyme possesses acyl transferase activity which may be defined as ester transfer activity whereby the acyl part of an original ester bond of a first lipid acyl donor is transferred to an acyl acceptor to form a new ester; and (ii) the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-134 and His-309, respectively, in the Aeromonas hydrophila lipolytic enzyme shown in FIG. 2 (SEQ ID No. 2) or FIG. 28 (SEQ ID No. 32).

Suitably, the lipid acyltransferase enzyme according to the present invention may be obtainable, preferably obtained, from organisms from one or more of the following genera: Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas and Candida.

Suitably, the lipid acyltransferase enzyme according to the present invention may be obtainable, preferably obtained, from one or more of the following organisms: Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Lactobacillus helveticus, Desulfitobacterium dehalogenans, Bacillus sp, Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis and Candida parapsilosis.

In one aspect, preferably the lipid acyltransferase enzyme according to the present invention is obtainable, preferably obtained, from one or more of Aeromonas hydrophila or Aeromonas salmonicida.

Suitably, the lipid acyltransferase enzyme according to the present invention comprises one or more of the following amino acid sequences:

(i) the amino acid sequence shown as SEQ ID No. 2 (see FIG. 2)
(ii) the amino acid sequence shown as SEQ ID No. 3 (see FIG. 3)
(iii) the amino acid sequence shown as SEQ ID No. 4 (see FIG. 4)
(iv) the amino acid sequence shown as SEQ ID No. 5 (see FIG. 5)
(v) the amino acid sequence shown as SEQ ID No. 6 (see FIG. 6)
(vi) the amino acid sequence shown as SEQ ID No. 12 (see FIG. 14)
(vii) the amino acid sequence shown as SEQ ID No. 20 (FIG. 16)
(viii) the amino acid sequence shown as SEQ ID No. 22 (FIG. 18)
(ix) the amino acid sequence shown as SEQ ID No. 24 (FIG. 20)
(x) the amino acid sequence shown as SEQ ID No. 26 (FIG. 22)
(xi) the amino acid sequence shown as SEQ ID No. 28 (FIG. 24)
(xii) the amino acid sequence shown as SEQ ID No. 30 (FIG. 26)
(xiii) the amino acid sequence shown as SEQ ID No. 32 (FIG. 28)
(xiv) the amino acid sequence shown as SEQ ID No. 34 (FIG. 30) or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, or SEQ ID No. 34.

Suitably, the lipid acyltransferase enzyme according to the present invention comprises either the amino acid sequence shown as SEQ ID No. 2 or as SEQ ID No. 3 or SEQ ID No. 32 or SEQ ID No. 34 or comprises an amino acid sequence which has 75% or more, preferably 80% or more, preferably 85% or more, preferably 90% or more, preferably 95% or more, identity with the amino acid sequence shown as SEQ ID No. 2 or the amino acid sequence shown as SEQ ID No. 3 or the amino acid sequence shown as SEQ ID No. 32 or the amino acid sequence shown as SEQ ID No. 34.

For the purposes of the present invention, the degree of identity is based on the number of sequence elements which are the same. The degree of identity in accordance with the present invention may be suitably determined by means of computer programs known in the art, such as GAP provided in the GCG program package (Program Manual for the Wisconsin Package, Version 8, August 1994, Genetics Computer Group, 575 Science Drive, Madison, Wis., US53711) (Needleman & Wunsch (1970), J. of Molecular Biology 48, 443-45) using the following settings for polypeptide sequence comparison: GAP creation penalty of 3.0 and GAP extension penalty of 0.1.

Suitably the lipid acyltransferase enzyme according to the present invention comprises an amino acid sequence which has 80% or more, preferably 85% or more, more preferably 90% or more and even more preferably 95% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, or SEQ ID No. 34.

Suitably, the lipid acyltransferase enzyme according to the present invention comprises one or more of the following amino acid sequences:
(a) an amino acid sequence shown as amino acid residues 1-100 of SEQ ID No. 2 or SEQ ID No. 32;
(b) an amino acid sequence shown as amino acids residues 101-200 of SEQ ID No. 2 or SEQ ID No. 32;
(c) an amino acid sequence shown as amino acid residues 201-300 of SEQ ID No. 2 or SEQ ID No. 32; or
(d) an amino acid sequence which has 75% or more, preferably 85% or more, more preferably 90% or more, even more preferably 95% or more identity to any one of the amino acid sequences defined in (a)-(c) above.

Suitably, the lipid acyltransferase enzyme according to the present invention comprises one or more of the following amino acid sequences:
(a) an amino acid sequence shown as amino acid residues 28-39 of SEQ ID No. 2 or SEQ ID No. 32;
(b) an amino acid sequence shown as amino acids residues 77-88 of SEQ ID No. 2 or SEQ ID No. 32;
(c) an amino acid sequence shown as amino acid residues 126-136 of SEQ ID No. 2 or SEQ ID No. 32;
(d) an amino acid sequence shown as amino acid residues 163-175 of SEQ ID No. 2 or SEQ ID No. 32;
(e) an amino acid sequence shown as amino acid residues 304-311 of SEQ ID No. 2 or SEQ ID No. 32; or
(f) an amino acid sequence which has 75% or more, preferably 85% or more, more preferably 90% or more, even more preferably 95% or more identity to any one of the amino acid sequences defined in (a)-(e) above.

Suitably, the lipid acyltransferase enzyme according to the present invention may comprise an amino acid sequence produced by the expression or one or more of the following nucleotide sequences:
(a) the nucleotide sequence shown as SEQ ID No. 7 (see FIG. 9);
(b) the nucleotide sequence shown as SEQ ID No. 8 (see FIG. 10);
(c) the nucleotide sequence shown as SEQ ID No. 9 (see FIG. 11);
(d) the nucleotide sequence shown as SEQ ID No. 10 (see FIG. 12);
(e) the nucleotide sequence shown as SEQ ID No. 11 (see FIG. 13);
(f) the nucleotide sequence shown as SEQ ID No. 13 (see FIG. 15);
(g) the nucleotide sequence shown as SEQ ID No. 21 (see FIG. 17);
(h) the nucleotide sequence shown as SEQ ID No. 23 (see FIG. 19);
(i) the nucleotide sequence shown as SEQ ID No. 25 (see FIG. 21);
(j) the nucleotide sequence shown as SEQ ID No. 27 (see FIG. 23);
(k) the nucleotide sequence shown as SEQ ID No. 29 (see FIG. 25);
(l) the nucleotide sequence shown as SEQ ID No. 31 (see FIG. 27);
(m) the nucleotide sequence shown as SEQ ID No. 33 (see FIG. 29);
(n) the nucleotide sequence shown as SEQ ID No. 35 (see FIG. 31);
(o) or
a nucleotide sequence which has 75% or more identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33 or SEQ ID No. 35.

Suitably the nucleotide sequence may have 80% or more, preferably 85% or more, more preferably 90% or more and even more preferably 95% or more identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33 or SEQ ID No. 35.

In one aspect, the lipid acyltransferase according to the present invention may be a lecithin:cholesterol acyltransferases (LCAT) or variant thereof (for example a variant made by molecular evolution)

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the lipid acyltransferase enzyme according to the present invention may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NICMB 41204 and NCIMB 41205, respectively.

Preferably, when carrying out a method according to the present invention the product is produced without increasing or substantially increasing the free fatty acids in the foodstuff.

The term "transferase" as used herein is interchangeable with the term "lipid acyltransferase".

Suitably, the lipid acyltransferase as defined herein catalyses one or more of the following reactions: interesterification, transesterification, alcoholysis, hydrolysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule. Acyl transfer which results from hydrolysis requires the separation of the water molecule.

The term "without increasing or without substantially increasing the free fatty acids" as used herein means that preferably the lipid acyl transferase according to the present invention has 100% transferase activity (i.e. transfers 100% of the acyl groups from an acyl donor onto the acyl acceptor, with no hydrolytic activity); however, the enzyme may transfer less than 100% of the acyl groups present in the lipid acyl donor to the acyl acceptor. In which case, preferably the acyltransferase activity accounts for at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following protocol:

Protocol for the Determination of % acyltransferase Activity:

A foodstuff to which a lipid acyltransferase according to the present invention has been added may be extracted following the enzymatic reaction with $CHCl_3:CH_3OH$ 2:1 and the organic phase containing the lipid material is isolated and analysed by GLC and HPLC according to the procedure detailed hereinbelow. From the GLC and HPLC analyses the amount of free fatty acids and one or more of sterol/stanol esters; carbohydrate esters, protein esters; diglycerides; or monoglycerides are determined. A control foodstuff to which no enzyme according to the present invention has been added, is analysed in the same way.

Calculation:

From the results of the GLC and HPLC analyses the increase in free fatty acids and sterol/stanol esters and/or carbohydrate esters and/or protein esters and/or diglycerides and/or monoglycerides can be calculated:

Δ% fatty acid=% Fatty acid(enzyme)–% fatty acid (control); Mv fatty acid=average molecular weight of the fatty acids;

$A$=Δ% sterol ester/$Mv$ sterol ester (where Δ% sterol ester=% sterol/stanol ester(enzyme)–% sterol/stanol ester(control) and Mv sterol ester=average molecular weight of the sterol/stanol esters)—applicable where the acyl acceptor is a sterol and/or stanol;

$B$=Δ% carbohydrate ester/Mv carbohydrate ester (where Δ% carbohydrate ester=% carbohydrate ester(enzyme)–% carbohydrate ester(control) and Mv carbohydrate ester=average molecular weight of the carbohydrate ester)—applicable where the acyl acceptor is a carbohydrate;

$C$=Δ% protein ester/Mv protein ester (where Δ% protein ester=% protein ester(enzyme)–% protein ester(control) and Mv protein ester=average molecular weight of the protein ester)—applicable where the acyl acceptor is a protein; and $D$=absolute value of diglyceride and/or monoglyceride/$Mv$ di/monoglyceride (where Δ% diglyceride and/or monoglyceride=% diglyceride and/or monoglyceride (enzyme)–% diglyceride and/or monoglyceride (control) and Mv di/monoglyceride=average molecular weight of the diglyceride and/or monoglyceride)—applicable where the acyl acceptor is glycerol.

The transferase activity is calculated as a percentage of the total enzymatic activity:

% transferase activity =
$$\frac{A^* + B^* + C^* + D^* \times 100}{A^* + B^* + C^* + D^* + \Delta \text{ \% fatty acid}/(Mv \text{ fatty acid})}$$

*–delete as appropriate.

If the free fatty acids are increased in the foodstuff they are preferably not increased substantially, i.e. to a significant degree. By this we mean, that the increase in free fatty acid does not adversely affect the quality of the foodstuff.

In some aspects of the present invention, the term "without substantially increasing free fatty acids" as used herein means that the amount of free fatty acid in a foodstuff or composition treated with an lipid acyltransferase according to the present invention is less than the amount of free fatty acid produced in the foodstuff or composition when an enzyme other than a lipid acyltransferase according to the present invention had been used, such as for example as compared with the amount of free fatty acid produced when a conventional phospholipase enzyme, e.g. LipopanF® (Novozymes A/S, Denmark), had been used.

The term "in situ" as used herein means that the emulsifier(s) and/or the sterol/stanol esters and/or the carbohydrate esters and/or the protein esters and/or the mono- or diglycerides are produced within the foodstuff or fraction of the foodstuff. This contrasts the situation where the emulsifier(s) and/or the sterol/stanol esters and/or the carbohydrate esters and/or the protein esters and/or the mono- or diglycerides are produced separately of the foodstuff and are added as formed products to the foodstuff during preparation of the same. In other words, the term "in situ" as used herein means that by the addition of the lipid acyltransferase enzyme according to the present invention to a foodstuff, or to the food ingredients/materials constituting the foodstuff, an emulsifier and/or a sterol ester and/or a stanol ester and/or a carbohydrate ester and/or a protein ester and/or a mono- or diglyceride may be produced from components of the foodstuff. Suitably, the components of the foodstuff may be the substrate(s) for the enzyme. If necessary, the components of the foodstuff may be supplemented by addition of one or more further components which further components may be the same as those present in the foodstuff or may be additional to those components already present in the foodstuff. For the avoidance of doubt, in one embodiment, the method according to the present invention may be a method for the production of an emulsifier and/or a sterol ester and/or a stanol ester and/or a carbohydrate ester and/or a protein ester and/or a mono- or diglyceride in situ in a foodstuff and is not a method for preparing an emulsifier and/or a sterol ester and/or a stanol ester (for example is an isolated and/or purified form) for subsequent addition to a foodstuff.

In another embodiment the lipase acyl-transferase may be used during the food processing, but not remain in the foodstuff. For example, the lipase acyl transferase may be immobilised, allowing it to be reused.

Preferably, the lipid acyltransferase according to the present invention is capable of transferring an acyl group from a lipid to a sterol and/or stanol and/or a carbohydrate and/or a protein and/or glycerol when present in a polar environment, preferably in an aqueous environment, preferably a water containing foodstuff. Suitably, the aqueous environment may be an aqueous buffer or may be the aqueous phase in a foodstuff. The term "aqueous environment" as used herein preferably means an environment which is absent an organic solvent, preferably absent a polar organic solvent, more preferably absent an non-edible organic solvent. In particular, the term "aqueous environment" may refer to an environment to which no exogenous organic solvents, preferably no polar organic solvents, have been added. The term organic solvent as used herein does not encompass food oils, preferably does not encompass food oils that are high in non-polar lipids. In one embodiment the term organic solvent may exclude edible organic solvents, such as ethanol, propylene glycol and/or glycerol. Suitably, the aqueous environment according to the present invention may comprise less than 80% by volume organic solvents, less than 70% by volume organic solvents, less than 50% by volume organic solvents, less than 30% by volume organic solvents, more preferably less than 15% by volume organic solvents, more preferably less than 5%. Suitably the foodstuff may comprise between 1 and 5% organic solvent, for example ethanol. However, when the foodstuff comprises such an organic solvent, preferably it is produced endogenously within the foodstuff. That is to say, when the foodstuff comprises such an organic solvent, preferably the organic solvent is not an exogenous organic solvent.

The term "foodstuff" as used herein means a substance which is suitable for human and/or animal consumption.

Suitably, the term "foodstuff" as used herein may mean a foodstuff in a form which is ready for consumption. Alternatively or in addition, however, the term foodstuff as used herein may mean one or more food materials which are used in the preparation of a foodstuff. By way of example only, the term foodstuff encompasses both baked goods produced from dough as well as the dough used in the preparation of said baked goods.

In a preferred aspect the present invention provides a foodstuff as defined above wherein the foodstuff is selected from one or more of the following: eggs, egg-based products, including but not limited to mayonnaise, salad dressings, sauces, ice creams, egg powder, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

Suitably the foodstuff in accordance with the present invention may be a "fine foods", including cakes, pastry, confectionery, chocolates, fudge and the like.

In one aspect the foodstuff in accordance with the present invention may be a dough product or a baked product, such as a bread, a fried product, a snack, cakes, pies, brownies, cookies, noodles, snack items such as crackers, graham crackers, pretzels, and potato chips, and pasta.

In a further aspect, the foodstuff in accordance with the present invention may be a plant derived food product such as flours, pre-mixes, oils, fats, cocoa butter, coffee whitener, salad dressings, margarine, spreads, peanut butter, shortenings, ice cream, cooking oils.

In another aspect, the foodstuff in accordance with the present invention may be a dairy product, including butter, milk, cream, cheese such as natural, processed, and imitation cheeses in a variety of forms (including shredded, block, slices or grated), cream cheese, ice cream, frozen desserts, yoghurt, yoghurt drinks, butter fat, anhydrous milk fat, other dairy products. The enzyme according to the present invention may improve fat stability in dairy products.

It is particularly advantageous to utilise the present invention in cheese as the production of free fatty acids in cheese is associated with a "soapy" taste. Thus, the use of a lipid acyltransferase in accordance with the present invention advantageously produces cheese without a "soapy" taste.

In another aspect, the foodstuff in accordance with the present invention may be a food product containing animal derived ingredients, such as processed meat products, cooking oils, shortenings.

In a further aspect, the foodstuff in accordance with the present invention may be a beverage, a fruit, mixed fruit, a vegetable or wine. In some cases the beverage may contain up to 20 g/l of added phytosterols.

In another aspect, the foodstuff in accordance with the present invention may be an animal feed. The animal feed may be enriched with phytosterol and/or phytostanols, preferably with beta-sitosterol/stanol. Suitably, the animal feed may be a poultry feed. When the foodstuff is poultry feed, the present invention may be used to lower the cholesterol content of eggs produced by poultry fed on the foodstuff according to the present invention.

In one aspect preferably the foodstuff is selected from one or more of the following: eggs, egg-based products, including mayonnaise, salad dressings, sauces, ice cream, egg powder, modified egg yolk and products made therefrom.

Preferably the foodstuff according to the present invention is a water containing foodstuff. Suitably the foodstuff may be comprised of 10-98% water, suitably 14-98%, suitably of 18-98% water, suitably of 20-98%, suitably of 40-98%, suitably of 50-98%, suitably of 70-98%, suitably of 75-98%.

For some aspects, preferably the foodstuff in accordance with the present invention is not a pure plant derived oil, such as olive oil, sunflower oil, peanut oil, rapeseed oil for instance. For the avoidance of doubt, in some aspects of the present invention the foodstuff according to the present invention may comprise an oil, but preferably the foodstuff is not primarily composed of oil or mixtures of oil. For some aspects, preferably the foodstuff comprises less than 95% lipids, preferably less than 90% lipids, preferably less than 85%, preferably less than 80% lipids. Thus, for some aspects of the present invention oil may be a component of the foodstuff, but preferably the foodstuff is not an oil per se.

The claims of the present invention are to be construed to include each of the foodstuffs listed above.

When it is the case that a carbohydrate ester is produced in accordance with the present invention, the carbohydrate ester is preferably an oligosaccharide ester, a monosaccharide ester or a disaccharide ester.

Suitably, the carbohydrate ester when produced in accordance with the present invention may be one or more of the following: glucose ester, fructose ester, anhydrofructose ester, maltose ester, lactose ester, galactose ester, xylose ester, xylooligosaccharide ester, arabinose ester, maltooligosaccharide ester, tagatose ester, sucrose ester, microthecin ester, ascopyrone P ester, ascopyrone T ester or cortalcerone ester.

Preferably, the carbohydrate ester when produced in accordance with the present invention is one or more of the following: a carbohydrate mono-ester, a sugar mono-ester, an oligosaccharide mono-ester, a trisaccharide mono-ester, a disaccharide mono-ester, a monosaccharide mono-ester, a glucose mono-ester, a fructose mono-ester, anhydrofructose mono-ester, maltose mono-ester, lactose mono-ester, galactose mono-ester, xylose mono-ester, xylooligosacchride mono-ester, arabinose mono-ester, maltooligosacchride mono-ester, tagatose mono-ester, sucrose mono-ester, microthecin ester, ascopyrone P ester, ascopyrone T ester or cortalcerone ester.

In one embodiment, the microthecin ester, ascopyrone P ester, ascopyrone T ester and/or cortalcerone ester may function as an antimicrobial agent. Alternatively or in addition thereto, the microthecin ester, ascopyrone P ester, ascopyrone T ester and/or cortalcerone ester may function as one or both of an antioxidant and/or emulsifier.

Preferably, the formation of the carbohydrate ester (if any) in accordance with the present invention is independent of UDP-glucose.

Preferably, the foodstuff according to the present invention does not comprise UDP-glucose, or only comprises UDP-glucose in insignificant amounts.

Suitably, the emulsifier in accordance with the present invention may be for example one or more of the following: a diglyceride, a monoglyceride, such as 1-monoglyceride or a lysolecithin, such as lysophosphatidylcholine for example, a digalactosyl monoglyceride (DGMG). The emulsifier is preferably produced from the lipid acyl donor following removal of one or more acyl groups from said lipid acyl donor. The term lysolecithin as used herein encompasses lysophosphatidylcholine, lysophosphatidylethanolamine, lysophosphatidylinositol, lysophosphatidylserine and lysophosphatidylglycerol Where one of the emulsifiers is a carbohydrate ester, the second emulsifier may be for example one or more of the following: a diglyceride, a monoglyceride, such as 1-monoglyceride, lysophosphatidylcholine, or digalactosyl monoglyceride (DGMG). The second emulsifier is preferably produced from the lipid acyl donor following removal of one or more acyl groups from said lipid acyl donor. The term lysophosphatidylcholine as used herein is synonymous with the term lysolecithin and these terms may be used herein interchangeably.

Preferably the second emulsifier is DGMG. Suitably, the DGMG is produced in situ by the removal of an acyl group from DGDG with the transfer of the removed acyl group onto a carbohydrate to form a carbohydrate ester.

Where one of the emulsifiers is a protein ester and/or a diglyceride and/or a monoglyceride, the second emulsifier may be for example one or more of the following: a diglyceride, a monoglyceride, such as 1-monoglyceride, lysophosphatidylcholine, or digalactosyl monoglyceride (DGMG). The second emulsifier is preferably produced from the lipid acyl donor following removal of one or more acyl groups from said lipid acyl donor. The term lysophosphatidylcholine as used herein is synonymous with the term lysolecithin and these terms may be used herein interchangeably.

In one embodiment the lipid acyl transferase of the invention can be used in a process for the preparation of a foodstuff such as a cooking oil, margarine or spread, whereby the foodstuff naturally contains, or has been supplemented with, glycerol, at least one phospholipid (for example lecithin) and/or glycolipid (for example digalactosyl-diglyceride), and optionally a phytosterol or phytostanol.

When used as a cooking oil or margarine, the foodstuff may have enhanced anti-plattering properties. In addition or alternatively the foodstuff may have one or more beneficial technical properties, for example improved oxidative stability, improved emulsification properties, or health benefits.

In one embodiment the lipid acyl transferase of the invention can be in the preparation of low fat foodstuffs, such as low fat spreads, low fat salad dressings, low fat mayonnaise, low fat margarines etc. In such low fat food products, the fat content is typically reduced by the addition of emulsifiers and additional water compared to the higher fat equivalent.

The lipid acyl transferases used in the compositions and methods of the invention have been found to have unique properties when compared to lipolytic enzymes in that they have a marked preference for transfer of acyl groups from lipids to acceptors other than water, even in the presence of significant water. In a comparison with prior art enzymes, the lipid acyl transferase used in the invention were found to have a high relative transferase activity in the presence of 6% water, 54% water, 73% water, 89% water and approximately 95%. Lipolytic enzymes tested had virtually no significant relative transferase activity at these water concentrations.

The lipase and acyltransferase activity of an enzyme may be evaluated using the following assays. In this way, a lipid acyltransferase having the enzyme characteristics defined herein may be obtained/identified.

Transferase Assay in Buffered Substrate (see Example 12)

Enzymes which function as lipid acyltransferases for use in the compositions and methods of the invention can be routinely identified using the assay taught herein in Example 12. This assay will be hereinafter referred to as the 'Transferase Assay in Buffered Substrate'. In Example 12 the lipid acyltransferase enzyme from *Aeromonas salmonicida* in accordance with the present invention was analysed and compared with a range of lipolytic enzymes not encompassed by the present invention. As can be seen, of the lipolytic enzymes only LIPOPAN® F (Novozymes, Denmark) was found to have any transferase activity and then only a very low level (1.3%).

Enzymes suitable for use in the compositions and methods of the invention can be routinely identified using the Transferase Assay in Buffered Substrate. Using this assay, in which there is a very high water content—approximately 95%, lipid acyltransferases in accordance with the present invention are those which have at least 2% acyltransferase activity (relative transferase activity), preferably at least 5% relative transferase activity, preferably at least 10% relative transferase activity, preferably at least 15%, 20%, 25% 26%, 28%, 30%, 40% 50%, 60% or 75% relative transferase activity. Suitably, the lipid acyltransferase in accordance with the present invention may have less than 28%, less than 30%, preferably less than 40%, 50%, 60%, 70%, 80%, 90% or 100% acyltransferase activity.

Transferase Assay in High Water Egg Yolk (see Example 11)

As an alternative to (or in addition to) using the "Transferase Assay in Buffered Substrate" (see above), a lipid acyltransferase for use in accordance with the present invention may be identified using the "Transferase Assay in High Water Egg Yolk" taught in Example 11.

In one embodiment, the lipid acyltransferase suitable for use in the methods and/or compositions according to the present invention is one which when tested using the Transferase Assay in High Water Egg Yolk in an egg yolk with 54% water, has up to 100% relative transferase activity. Indeed, experiments in high water egg yolk have shown that at the start of the experiment the initial transferase rate was calculated to be 100% transferase activity, i.e. no hydrolytic activity was observed. In contrast, the lipolytic enzymes used as control, i.e. LIPOPAN® F and phospholipase A2, showed no detectable transferase activity in egg yolk with 54% water, or egg yolk with enriched water content (namely egg yolk with 73% water or 89% water). Preferably the increase in water content does not significantly decrease the percentage acyl transferase activity of a lipid acyltransferase for use in the methods or compositions according to the present invention.

In a preferable embodiment, with reference to the Transferase Assay in High Water Egg Yolk, with a water content of 54%, a lipid acyltransferase for use in the present invention will have an initial percentage acyltransferase activity (initial relative transferase activity) measured after 10% consumption of the donor molecule (i.e. phospholipid) of at least 0.1% relative transferase activity, preferably at least 1% relative transferase activity, preferably at least 5% relative transferase activity, preferable at least 10% relative transferase activity, preferably at least 20% relative transferase activity, preferably at least 30% relative transferase activity, preferably at least 40% relative transferase activity, preferably at least 50% relative transferase activity, preferably at least 60%, preferably at least 70%, preferably at least 80%, preferably at least 90%, preferably at least 95%, preferably at least 99%, preferably about 100% acyl transferase activity.

In a preferable embodiment, with reference to the Transferase Assay in High Water Egg Yolk, with a water content of 54%, and measured after 10% consumption of the donor molecule (i.e. phospholipid), the lipid acyltransferase for use in the compositions and methods of the invention has detectable transferase activity, i.e. relative transferase activity of between 0.1 and 100%, preferably at least 1% relative transferase activity, preferably at least 5% relative transferase activity, preferable at least 10% relative transferase activity, preferably at least 20% relative transferase activity, preferably at least 30% relative transferase activity, preferably at least 40% relative transferase activity, preferably at least 45%, 50%, 60%, 70%, 80%, or 90% relative transferase activity. Suitably, the lipid acyl transferase in accordance with the present invention may have, when using the Transferase Assay in High Water Egg Yolk with 54% water content and measured after 10% consumption of the donor molecule (i.e. phospholipid), a percentage acyl transferase activity (relative transferase activity) of less than 45%, 47%, 50%, 60%, 70%, 80%, 90% or 100%.

In a preferable embodiment, with reference to the Transferase Assay in High Water Egg Yolk, with a water content of 73%, measured after 10% consumption of the donor molecule (i.e. phospholipid), the lipid acyltransferase for use in the compositions and methods of the invention has detectable transferase activity, i.e. relative transferase activity of between 0.1 and 100%, preferably at least 1% relative transferase activity, preferably at least 5% relative transferase activity, preferable at least 10% relative transferase activity, preferably at least 20% relative transferase activity, preferably at least 30% relative transferase activity, preferably at least 40% relative transferase activity, preferably at least 45%, 50%, 58%, 60%, 70%, 80%, or 90% relative transferase activity. Suitably, the lipid acyl transferase in accordance with the present invention may have, when using the Transferase Assay in High Water Egg Yolk with 73% water content and measured after 10% consumption of the donor molecule (i.e. phospholipid), a percentage acyl transferase activity (relative transferase activity) of less than 45%, 47%, 50%, 58%, 60%, 70%, 80%, 90% or 100%.

In a preferable embodiment, with reference to the Transferase Assay in High Water Egg Yolk, with a water content of 89%, and measured after 10% consumption of the donor molecule (i.e. phospholipid), the lipid acyltransferase for use in the compositions and methods of the invention has detectable transferase activity, i.e. relative transferase activity of between 0.1 and 100%, preferably at least 1% relative transferase activity, preferably at least 5% relative transferase activity, preferable at least 10% relative transferase activity, preferably at least 20% relative transferase activity, preferably at least 30% relative transferase activity, preferably at least 40% relative transferase activity, preferably at least 45%, 50%, 60%, 70%, 80%, or 90% relative transferase activity. Suitably, the lipid acyl transferase in accordance with the present invention may have, when using the Transferase Assay in High Water Egg Yolk with 89% water content and measured after 10% consumption of the donor molecule (i.e. phospholipid), a percentage acyl transferase activity (relative transferase activity) of less than 45%, 47%, 50%, 60%, 70%, 80%, 90% or 100%.

In a preferable embodiment, with reference to the Transferase Assay in High Water Egg Yolk, a lipid acyltransferase for use in the compositions and methods of the invention has significant relative transferase activity (i.e. at least 0.1% at both water contents), and has an equivalent relative transferase activity in egg yolk with a water content of 54% as in an egg yolk with a water content of 73%, when measured after 10% consumption of the donor molecule (i.e. phospholipid).

In a preferable embodiment, with reference to the Transferase Assay in High Water Egg Yolk, a lipid acyltransferase for use in the compositions and methods of the invention has significant relative transferase activity (i.e. at least 0.1% at both water contents), and has an equivalent relative transferase activity in egg yolk with a water content of 54% as in an egg yolk with a water content of 89%, when measured after 10% consumption of the donor molecule (i.e. phospholipid).

In a preferable embodiment, with reference to the Transferase Assay in High Water Egg Yolk, a lipid acyltransferase for use in the compositions and methods of the invention has significant relative transferase activity (i.e. at least 0.1% at both water contents), and has an equivalent relative transferase activity in egg yolk with a water content of 73% as in an egg yolk with a water content of 89%, when measured after 10% consumption of the donor molecule (i.e. phospholipid).

The term "equivalent relative transferase activity" as referred to herein means that the enzyme has a relative transferase activity (% acyltransferase activity) which is at least 2% lower, preferably at least 5%, 10%, 20%, 30%, 40%, 50%, 60%, 70%, 80% or 90% lower, in the egg yolk with the higher water content compared with that in the egg yolk with the lower water content.

Transferase Assay in a Low Water Environment

As an alternative to (or in addition to) using the "Transferase Assay in High Water Egg Yolk" and/or the "Transferase Assay in Buffered Substrate", lipid acyltransferases for use in accordance with the present invention may be identified using the "Transferase Assay in a Low Water Environment".

In order to determine if an enzyme is a lipid acyltransferase according to the present invention, one may carry out a "Transferase Assay in a Low Water Environment", namely in an oily environment with 6% water as taught in Example 22. This example illustrates that in an oily environment with 6% water content the lipid acyltransferase of the invention has a high relative transferase activity, where the prior art lipolytic enzymes have hydrolytic activity.

In one embodiment, the lipid acyltransferase suitable for use in the methods and/or compositions according to the present invention is one which when tested using the "Transferase Assay in a Low Water Environment", measured after a time period selected from 30, 20 or 120 minutes, has a relative transferase activity of at least 1%, preferably at least 2%, preferably at least 5%, preferably at least 10%, preferably at least 20%, preferably at least 30%, preferably at least 40%, preferably at least 50%, preferably at least 60%, preferably at least 70%, preferably at least 75%. Suitably, the lipid acyl transferase in accordance with the present invention may have less than 30%, 40%, 50%, 60%, 70%, or 80% activity when measured after a time period of 10, 20, 30 or 120 minutes using the "Transferase Assay in a Low Water Environment".

As described above, the lipase acyltransferase of the invention can be identified using either the "Transferase Assay in Buffered Substrate" or in the "Transferase Assay in Low Water Environment" using cholesterol as the acyl acceptor. Of course, the skilled person would be readily aware that, with obvious amendments to the analytical methods the 'Transferase Assay in Buffered Substrate' or the "Transferase Assay in Low Water Environment" may be used to determine the lipid acyltransferase activity for any lipid acyl donor or any acyl acceptor combination. The skilled person would, if necessary, simply replace the acyl donor substrate (e.g. phospholipid) with an alternative acyl donor substrate (e.g. glycolipid, triacylglyceride) and/or replace the acyl acceptor (e.g. cholesterol) with an alternative acyl acceptor substrate (e.g. a carbohydrate, a protein, another sterol, a stanol or glycerol).

The term "high water" as used herein means any substrate or foodstuff with more than 2% water content, preferably more than 3%, 4%, 5%, 6%, 7%, 8%, 9%, 10%, 20%, 30%, 40%, 50%, 60%, 70%, 80% or 90%.

The term "low water" as used herein means any substrate or foodstuff with less than 6% water content, preferably less than 5%, 4%, 3%, 2%, 1% or 0.5%.

Preferably the method and/or use according to the present invention may be carried out, for example, in foodstuff at a temperature of 15-60° C., preferably at a temperature of 20-60° C., preferably 20-50° C., preferably 20-45° C., preferably 20-40° C. For some aspects, for example in dough, preferably the temperature of the food during which the acyltransferase reaction takes place is between 20 and 40° C. For other aspects, for example with regard to dairy products, such as cheese, the temperature of the food may suitably be between 30° C. and 60° C. In yet other aspects, for example with regard to mayonnaise, the temperature of the food may suitably be between 20 and 40° C., more preferably between 25 and 30° C.

Preferably, the emulsifier produced according to the present invention comprises less than 5 wt % of the foodstuff.

Preferably, the emulsifier produced according to the present invention comprises from 0.01 to 4 wt % of the foodstuff.

Preferably, the emulsifier produced according to the present invention comprises from 0.01 to 2 wt % of the foodstuff.

Preferably, the emulsifier produced according to the present invention comprises from 0.01 to 1 wt % of the foodstuff.

Preferably, the emulsifier produced according to the present invention comprises from 0.01 to 0.5 wt % of the foodstuff.

Preferably, the emulsifier produced according to the present invention comprises from 0.01 to 0.3 wt % of the foodstuff.

Suitably, the method according to the present invention includes inactivating or denaturing the enzyme to provide a foodstuff comprising the enzyme in an inactive or denatured form. Suitably the enzyme may be denatured by either baking or by pasteurisation.

The present invention may further encompass the use of a lipid acyltransferase as defined herein in food and/or feed enzyme compositions, and may encompass food and/or feed enzyme compositions comprising a lipid acyltransferase as defined herein. Such compositions may contain one or more further enzymes, such as those listed herein. Alternatively, the enzyme composition of the invention may be used in combination with other food ingredients/additives, such as those listed herein, including other enzyme compositions. By formulation of the lipid acyl transferase of the invention within a food and/or feed composition, the enzyme can be stabilised to allow for prolonged storage (under suitable conditions) prior to use in food and/or feed production. In addition the enzyme composition of the present invention provides the enzyme in a suitable form for safe use for the 'in situ' application in the preparation of foodstuffs and/or feedstuffs, or ingredients for use in food and/or feed preparation. Such compositions may be in either liquid, semi-liquid or solid/granular form.

In one embodiment the food enzyme composition may suitable be a dough improving composition. The dough improving composition may comprise other beneficial components such as an emulsifier and/or other enzymes as listed herein.

Food enzymes are sold as stabilised liquid concentrates or as particulate solids. Formulation into food enzyme composition minimises losses in enzymatic activity during transport, storage, and use. Enzymes are often exposed to humid, hot, or oxidative environments in food and beverage processing. Formulations enhance stability by counteracting the primary forces of deactivation: denaturation, catalytic-site deactivation, and proteololysis. Denaturation occurs by physical unfolding of an enzyme's tertiary protein structure under thermal or chemical stress. Once an enzyme begins to unfold it becomes dramatically more vulnerable to deactivation and proteolysis. To minimise unfolding, the formulator can alter the protein's environment so as to induce a compact protein structure; this is done most effectively by "preferential exclusion" of water from the protein surface by adding water-associating compounds such as sugars, polyhydric alcohols, and lyotropic salts. The best ways to combat active site inactivation are to ensure sufficient levels of any required cofactors, to add reversible inhibitors, and to exclude oxidising or reactive species from the formulation.

Besides enzymatic stability, a formulation should meet several key secondary requirements, including preservation against microbial contamination, avoidance of physical precipitation or haze formation, minimising the formation of sensitising dusts or aerosols, and the optimisation of aesthetic criteria such as colour and odour. Many of these problems are best addressed by focusing as far "upstream" as possible, including the choice of raw materials in the fermentation or enzyme recovery process. Downstream operations such as diafiltration, adsorption, chromatography, crystallization, and extraction can be used to remove impurities responsible for colour, odour, and precipitation. The risk of physical precipitation is minimised by formulating near the isoelectric point of the enzyme with hydrophilic solvents such as glycerol or propylene glycol. One can effectively also add moderate levels of solvating salts to avoid either salting-out or "reverse salting-in". To prevent microbial contamination, one can use a combination of filtration, acidification, and the minimisation of free water; biocides can be effective, but the range of acceptable chemicals for controlling or killing microbes is increasingly circumscribed by health and safety regulations.

Two processes producing the most attrition-resistant granules to date are high-shear granulation and fluidised-bed spray coating, see for example T. Becker: "Separation and Purification Processes for Recovery of Industrial Enzymes" in R. K. Singh, S. S. H. Rizvi (eds.): *Bioseparation Processes in Foods*, Marcel Dekker, New York, pp. 427-445. These processes use various binders, coatings, and particle morphologies to produce nonfriable particles which still protect enzymes during storage but allow for their ready release in solution during use.

Food enzyme compositions containing the lipid acyl transferase of the invention may be made using standard formulation techniques, such as spray drying or liquid formulation.

The lipid acyl-transferase of the invention can be expressed in any suitable expression host. For example the lipid acyltransferase of the invention may be expressed in *Bacillus subtilis* and may be purified by ultrafiltration and/or by precipitation in ethanol and/or centrifugation, and may be subsequently spray dried using starch (maltodextrin) as carrier for the enzyme. The spray dried enzyme may be standardised to specified PLU activity by adding further carrier in powder form. The techniques involved are well established and routine in the art.

Alternatively, lipid acyltransferase for use in accordance with the present invention, for example the heterologously produced lipid acyl-transferase of the invention, once purified, may be stabilised in a suitable liquid formulation, such as those based on glycerol. Other methods of making stabilised enzyme formulations are described in EP0770037 and EP0702 712.

The acyl transferase in powder form can also be used in combination with other enzymes as listed herein, for the production of enzyme compositions with defined activity according to the product specification.

Typically the dosage of the food enzyme formulation is between 10 g and 1000 g per 1000 kg of foodstuff, preferably 50-200 g per 1000 kg of foodstuff, preferably, 75-125 gm per 1000 kg of foodstuff.

Preferably the enzyme according to the present invention is present in an inactive form or in a denatured form in the foodstuff.

In one embodiment, the enzyme according to the present invention is preferably not immobilised, in particular is not immobilised on a solid support.

In an alternative embodiment, the enzyme may be immobilised.

Immobilised lipid acyl transferase can be prepared using immobilisation techniques known in the art. There are numerous methods of preparing immobilised enzymes, which will be apparent to a person skilled in the art (for example the techniques referred to in EP 0 746 608; or Balcao V M, Paiva A L, Malcata F X., Enzyme Microb Technol. 1996 May 1; 18(6):392-416; or Reetz M T, Jaeger K E. Chem Phys Lipids. 1998 June; 93(1-2):3-14; or Bomscheuer U T, Bessler C, Srinivas R, Krishna S H. Trends Biotechnol. 2002 October; 20(10):433-7 (each of which is incorporated herein by reference).

In one embodiment, the foodstuff of the invention may contain food ingredients, which have been prepared using immobilised lipid acyltransferase, but do not contain the lipid acyltransferase in the food ingredient or foodstuff. For example the foodstuff may contain one or more of the following: an emulsifier, more than one emulsifier, one or more flavouring agents, one or more textural enhancers and/or one or more sterol esters, such as phytosterol esters or phytostanol esters.

The enzyme according to the present invention may be used with one or more conventional emulsifiers, including for example monoglycerides, diacetyl tartaric acid esters of mono- and diglycerides of fatty acids, and lecithins e.g. obtained from soya.

The enzyme according to the present invention may be used with one or more other suitable food grade enzymes. Thus, it is within the scope of the present invention that, in addition to the enzyme of the invention, at least one further enzyme is added to the foodstuff. Such further enzymes include starch degrading enzymes such as endo- or exoamylases, pullulanases, debranching enzymes, hemicellulases including xylanases, cellulases, lipases, phospholipases, and proteases.

The enzyme according to the present invention may be used with one or more other suitable food grade enzymes.

Thus, it is within the scope of the present invention that, in addition to the enzyme of the invention, at least one further enzyme is added to the foodstuff. Such further enzymes include starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases and hexose oxidase, and proteases.

In one preferred embodiment the lipid acyltransferase is used in combination with a lipase having one or more of the following lipase activities: glycolipase activity (E.C. 3.1.1.26, triacylglycerol lipase activity (E.C. 3.1.1.3), phospholipase A2 activity (E.C. 3.1.1.4) or phospholipase A1 activity (E.C. 3.1.1.32). Suitably, lipase enzymes are well know within the art and include by way of example the following lipases: LIPOPAN®° F. and/or LECITASE® ULTRA (Novozymes A/S, Denmark), phospholipase A2 (e.g. phospholipase A2 from LIPOMOD™ 22L from Biocatalysts, LIPOMAX™ from Genecor), LIPOLASE® (Novozymes A/S, Denmark), the lipases taught in WO03/97835, EP 0 977 869 or EP 1 193 314. This combination of a lipid acyl transferase as defined herein and a lipase may be particularly preferred in dough or baked products or in fine food products such as cakes and confectionary.

The use of lipases in combination with the enzyme of the invention may be particularly advantageous in instances where some accumulation of free fatty acids maybe desirable, for example in cheese where the free fatty acids can impart a desirable flavour, or in the preparation of fine foods. The person skilled in the art will be able to combine proportions of lipolytic enzymes, for example LIPOPAN® F. and/or LECITASE® ULTRA (Novozymes A/S, Denmark), phospholipase A2 (e.g. phospholipase A2 from LIPOMOD™ 22L from Biocatalysts, LIPOMAX™ from Genecor), LIPOLASE® (Novozymes A/S, Denmark), the lipases taught in WO03/97835, EP 0 977 869 or EP 1 193, 314 and the lipid acyltransferase of the present invention to provide the desired ratio of hydrolytic to transferase activity which results in a preferred technical effect or combination of technical effects in the foodstuff (such as those listed herein under 'Technical Effects').

Traditionally the cake industry uses cake improvers for the production of cakes and to secure high quality cakes in terms of taste, structure, eating quality and appearance. These cake improvers are normally based on emulsifiers spray dried on a carrier like starch and malto dextrin. Some cake improvers are also in a gel form based on emulsifiers, sugars and water. These cake improvers are very important for the cake industry in order to produce cake of high quality. Cake improvers however contain emulsifiers and other "non-natural" ingredients with an E-number. Because of demand for the consumers to reduce the numbers of E-numbers, the cake industry has asked for alternative ways to produce cakes of high quality without using emulsifiers.

An alternative way to produce cake is to use an enzyme, i.e. the lipid acyltransferase defined herein or an enzyme composition according to the present invention.

The lipid acyltransferase as defined herein and/or the food enzyme composition of the present invention may be used in the preparations of a fine food, such as a cake. In such instances, the following constituents may be formed in the fine food:

i) sugar esters and lysolecithin (from the carbohydrate in the cake recipe and the lecithin in egg which also form part of the cake recipe); and/or ii) acylated peptides and lysolecithin (by transferring a fatty acid from lecithin to a protein or peptide during formation of protein-fatty acid condensates, which are known to be highly efficient emulsifiers (Herstellung und Anvendungmöglichkeiten von Eiweiss-Fettsäurekondensaten. Andreas Sander, Eberhard Eilers, Andrea Heilemann, Edith von Kreis.Fett/lipid 99 (1997) Nr. 4, 115-120).

It is considered that in the production of some fine foods, particularly high fat fine foods, such as cakes, it may be desirable to have some accumulation of fatty acids. Therefore the combination of the use of lipolytic enzymes and the lipid acyl transferase as defined herein may be particularly beneficial for production of high fat fine foods. Alternatively, additional free fatty acids or fatty acid soap (E470a) may be selected and used in combination with the lipid acyl transferase.

The foodstuff according to the present invention may suitably comprise one or more of the following additives:
soy protein material; carotenoids, flavenoids, antioxidant and phytochemical (especially anthocyanonide, carotenoid, bioflavinoid, glutathione, catechin, isoflavone, lycopene, ginsenoside, pycnogenol, alkaloid, pygeum phytosterol, sulphoraphane, resveretol, grape seed extract or food containing stanol esters), vitamin (especially vitamin C, vitamin A, vitamin B3, vitamin D, vitamin E, thiamine, riboflavin, niacin, pyridoxine, cyanocobalamin, folic acid, biotin, pantothenic acid or vitamin K), minerals (especially calcium, iodine, magnesium, zinc, iron, selenium, manganese, chromium, copper, cobalt, molybdenum or phosphorus), fatty acid (especially gamma-linoleic acid, ucospentaenoic acid or decosahexaenoic acid), oil (especially borage oil, high carotenoid canola oil or flax seed oil), amino acid (especially tryptophan, lysine, methionine, phenylalanine, threonine, valine, leucine, isoleucine, alanine, arginine, aspartic acid, cystine, cysteine, glutamic acid, glutamine, glycine, histidine, proline, hydroxyproline, serine, taurine or tyrosine), enzyme (especially bromelain, papain, amylase, cellulase or coenzyme Q), lignin, stanol ester or friendly bacteria (especially *Lactobacillus acidophilus, Lactobacillus bulgaricus, Lactobacillus bifidus, Lactobacillus plantarum* or *Streptococcus faecium*), folic acid, and soluble fibre.

TECHNICAL EFFECT

Surprisingly lipid acyltransferases have significant acyltransferase activity in foodstuffs. This activity has surprising beneficial applications in methods of preparing foodstuffs.

The present invention is predicated upon the surprising finding that the lipid acyltransferases according to the present invention can perform carbohydrate-esterification via alcoholosis, i.e. acyl transfer from a lipid, in a foodstuff with a significant water content. Prior art suggests that such enzymes if they would function at all in this manner would only function in a solvent environment (i.e. in environments with low or no water content).

The present invention may provide one or more of the following unexpected technical effects in egg products, particularly mayonnaise: an improved heat stability during pasteurisation; improved organoleptic properties, an improved consistency.

The present invention may provide one or more of the following unexpected technical effects in dough and/or baked products: an improved specific volume of either the dough or the baked products (for example of bread and/or of cake); an improved dough stability; an improved crust score (for example a thinner and/or crispier bread crust), an improved crumb score (for example a more homogenous crumb distribution and/or a finer crumb structure and/or a softer crumb); an improved appearance (for example a smooth surface without blisters or holes or substantially without blisters or holes); a reduced staling; an enhanced softness; an improved odour; an improved taste.

The present invention may provide a beneficial effect from formation of highly surface-active materials in a foodstuff without formation of substantial amount of free fatty acids, which reduce the ability of the foodstuff to oxidize upon storage, because free fatty acids are more prone to oxidation than the corresponding fatty acid esters.

Suitably, the present invention may provide one or more of the following unexpected technical effects in a foodstuff: an improved appearance, an improved mouthfeel, an improved stability, in particular an improved thermal stability, an improved taste, an improved softness, an improved resilience, an improved emulsification.

Suitably, the present invention may provide one or more of the following unexpected technical effects in dairy products, such as ice cream for example: an improved mouthfeel (preferably a more creamy mouthfeel); an improved taste; an improved meltdown.

Suitably, the present invention may provide one or more of the following unexpected technical effects in egg or in egg products: improved stability of emulsion; thermal stability of emulsion; improved flavour; reduced mal-odour; improved thickening properties, improved consistency.

Specific technical effects associated with the use of a lipid acyltransferase as defined herein in the preparation of a foodstuff are listed in the table below:

| | Foodstuff | Effect |
|---|---|---|
| 1 | Bread, Muffins and Doughnuts | Strengthens dough and increases mechanical resistance and increases water absorption capacity. Increases volume of bakery products and maintains softness of crumb |
| 2 | Frozen dough | Prevents spoiling during refrigeration |
| 3 | Sponge cake | Makes good cake volume and a uniform soft texture |
| 4 | Biscuit, cracker and cookie | Makes stable emulsions of fat and prevents stickiness to the machine. Prevents blooming of high fat products |
| 5 | Batter and breading | Improves texture of fried products. |
| 6 | Noodles | Prevents dough from sticking to the machine. Increases water content, and decreases cooking loss |
| 7 | Instant noodles | Prevent noodles form adhering to each other |
| 8 | Pasta | Dough conditioner prevents adhesion on cooking. |
| 9 | Custard cream | Makes starch paste with a smooth and creamy texture, and prevents dehydration. |
| 10 | Coffee whitener | Prevent oil and water separation |
| 11 | Whipping cream | Provides stable emulsion |
| 12 | Chocolate | Prevents or reduced blooming |
| 13 | Caramel, candy and nougat | Improves emulsification of molten sugar and oil. Prevents separation of oil. |
| 14 | Processed meat, sausages | Improves water holding capacity of sausages and pressed ham, and prevents separation of oil phase of pastes and pâté. |

Suitably, the present invention may provide one or more of the following unexpected technical effects in cheese: a decrease in the oiling-off effect in cheese; an increase in cheese yield; an improvement in flavour; a reduced mal-odour; a reduced "soapy" taste.

In food production, in particular cheese production, the use of the lipid acyltransferase in accordance with the present invention provides a significant advantage in the ability to recover soluble proteins from dairy products. For example, in cheese production nearly 20% of all milk protein is removed in the whey (i.e. the watery part of the milk that remains after the formation of curds). The whey comprises the soluble milk proteins, whereas the hydrophobic proteins are maintained in the curd. By use of the lipid acyltransferase in accordance with the present invention it is possible to transfer an acyl group from a lipid (preferably from a glycolipid or a phospholipid), to a protein (in particular to a whey protein such as lactoglobulin) to from a protein fatty acid condensate. Thus, producing a product which is more hydrophobic and which will stay in the curd rather than being eluted in the whey. In this way, more of the milk protein can be maintained in the final foodstuff, i.e. the final dairy product such as the cheese.

In one aspect, the present invention is based in part on the realisation that yields of foods—such as cheese—may be improved by the use of a lipid acyl transferase. In addition or alternatively, the flavour, texture, oxidative stability and/or shelf life of the food may be improved. In addition or alternatively, the food may have a reduced cholesterol level or enhanced content of phytosterol/stanol esters.

Without wishing to be bound to a particular theory it is considered that the increase in yield may be the result of the transesterification of whey proteins and peptides, resulting in significant increase in the hydrophobicity of the whey proteins and precipitation of the acylated whey proteins in the cheese curd.

In biological systems, for example, the deposition of membrane bound proteins and enzymes are achieved by two different mechanisms. The membrane bound proteins either possess a number of membrane-spanning or hydrophobic domains, or they have alternatively a fatty acid linked to the polypeptide chain. The fatty acids have normally a chain length of 14 or 16 carbon atoms. The fatty acids are covalently linked to the polypeptide chain at 3 different position, the N-terminal amino acid as an amide-bond, a cysteine residue as a thioester linkage, or a serine or threonine amino acid as an ester linkage. Only one fatty acid per polypeptide molecule is necessary to incorporate the protein into the cell membrane.

When a fatty acid is covalently linked to a non-membrane protein, the physical and functional properties will change drastically. WO97/14713 describes the transformed soy and gluten proteins into acyl derivatives by treatment with a lipase from *Mucor miehei* (Lipozyme™, Novozymes), and a fatty acid in organic solvent. The lipid acyl transferase according to the present invention may be used in the production of acylated proteins is a low or high water environment.

We note that acylated proteins form amphiphilic complexes that can be used for a number of cosmetic products. The acylated protein can form gels, bind water by retaining moisture, have emulsifying properties and is very active in the interphase between water and lipid.

Thus, the present invention may in one aspect provide a cosmetic composition comprising a lipid acyl transferase as defined herein.

In addition, the present invention may provide the use of an acyltransferase as defined herein to produce a cosmetic composition.

In a further aspect, the present invention provides a method of in situ production of a protein ester in a cosmetic composition, wherein the method comprises the step of adding to the cosmetic composition (or components thereof) a lipid acyltransferase as defined herein.

Many food proteins are soluble in aqueous solutions and are therefore suitable for in situ modification by the lipase acyl transferase. In the cheese production, β-lactoglobulin is lost to the whey fraction. After acylation with a lipase acyl transferase, or a lipase acyl transferase variant, initial results indicate that b-lactoglobulin may however, be deposited in the casein micelle surface during rennet coagulation. β-lactoglobulin has three potential acylation sites (serine residues) on three surface loops. Milk contains sufficient amounts of lecithin, a suitable substrate for a lipid acyl transferase enzyme to acylate the β-lactoglobulin. The lysolecithin formed may have an additional emulsifying effect.

The improvements observed with lipid acyltransferase according to the present invention are in comparison to when lipolytic enzymes without acyltransferase activity, such as triacylglycerol lipases and phospholipases, are used.

ADVANTAGES

The generation of an emulsifier and a sterol/stanol ester in situ from at least one constituent of the food material, means that the food material will contain at least one less additive material. This is advantageous because of the improvement in the ease of production. For example, no further processing or addition of ingredients or addition of emulsifiers may be required. Moreover, the foodstuff may contain less "additives". The reduction or elimination of "additives" is desirable to consumers and inclusion of additives often must be declared to the consumer in the ingredients listing on the foodstuff. Thus, the present invention is further advantageous.

An advantage of the present invention may be the production in situ of an emulsifier in a foodstuff without a detrimental increase in the free fatty acid content of the foodstuff.

The generation of two emulsifiers and/or a carbohydrate ester in situ from at least one constituent of the food material, means that the food material will contain at least one less additive material.

In addition, when the lipid acyltransferase acts on a glycolipid it is possible to advantageously produce the emulsifier DGMG in situ without a detrimental increase in the free fatty acid content of the foodstuff. Thus, reducing detrimental effects attributed to an increase in free fatty acids, including but not limited to a reduction in "soapy" taste in cheese, prevention of overdosing in dough and dough baked properties.

For some aspects, an advantage of the present invention is the reduction in free cholesterol levels in the foodstuff.

For other aspect, an advantage of the present invention is the increase in stanol and/or sterol esters in the foodstuff. Some sterol/stanol esters may be effective flavourants and/or texturisers. Thus, the present invention may not only results in the in situ production of an emulsifier in a foodstuff, but also the in situ production of a flavourant and/or a texturiser. Some sterol/stanol esters are known to reduce blood serum cholesterol and/or low density lipoproteins when consumed in a foodstuff. Thus, the present invention may be used to prepare a foodstuff with increased levels of sterol esters and/or stanol esters.

For some aspects, particularly when the enzyme according to the present invention is used in egg based products, an advantage is the removal of unwanted free carbohydrates.

Also advantageously the emulsification properties of the foodstuff are enhanced, leading to improved appearance and/or handling properties and/or structure and/or consistency and/or heat stability without a negative impact on taste.

In addition, for some embodiments advantageously the effect of "overdosing" observed when using lipases per se, is effectively overcome by the addition of an enzyme in accordance with the present invention. This is due at least in part to the fact that free fatty acids are not produced or only produced to an insignificant degree when using the enzyme according to the present invention.

Isolated

In one aspect, preferably the polypeptide or protein for use in the present invention is in an isolated form. The term "isolated" means that the sequence is at least substantially free from at least one other component with which the sequence is naturally associated in nature and as found in nature.

Purified

In one aspect, preferably the polypeptide or protein for use in the present invention is in a purified form. The term "purified" means that the sequence is in a relatively pure state— e.g. at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labelled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characterisitics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate.

As will be apparent to a person skilled in the art, using molecular evolution tools an enzyme may be altered to improve the functionality of the enzyme.

Suitably, the lipid acyltransferase used in the invention may be a variant, i.e. may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx (SEQ ID NO: 71), GANDY (SEQ ID NO: 73) and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the lipid acyltransferase for use in the invention may be a variant with enhanced enzyme activity on polar lipids, preferably phospholipids and/or glycolipids when compared to the parent enzyme. Preferably, such variants also have low or no activity on lyso polar lipids. The enhanced activity on polar lipids, phospholipids and/or glycolipids may be the result of hydrolysis and/or transferase activity or a combination of both.

Variant lipid acyltransferases for use in the invention may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme for use in the invention may have increased activity on triglycerides, and/or may also have increased activity on one or more of the following, polar lipids, phospholipids, lecithin, phosphatidylcholine, glycolipids, digalactosyl monoglyceride, monogalactosyl monoglyceride.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J. Biol. Chem. 1991 January 15: 266 (2): 997-1000; Robertson et al J. Biol. Chem. 1994 Jan. 21; 269(3):2146-50; Brumlik et al J. Bacteriol 1996 April; 178 (7): 2060-4; Peelman et al Protein Sci. 1998 March; 7(3):587-99.

Amino Acid Sequences

The present invention also encompasses amino acid sequences of polypeptides having the specific properties as defined herein.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software that can perform sequence comparisons include, but are not limited to, the BLAST package (see Ausubel et al 1999 Short Protocols in Molecular Biology, 4$^{th}$ Ed—Chapter 18), FASTA (Altschul et al 1990 J. Mol. Biol. 403-410) and the GENEWORKS suite of comparison tools. Both BLAST and FASTA are available for offline and online searching (see Ausubel et al 1999, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

The nucleotide sequence of the present invention or coding for a polypeptide having the specific properties as defined herein may be present in a vector, in which the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide having the specific properties as defined herein.

The choice of vector, e.g. plasmid, cosmid, virus or phage vector, will often depend on the host cell into which it is to be introduced.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, a nucleotide sequence for use in the present invention or a nucleotide sequence encoding a polypeptide having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions.

Preferably, the nucleotide sequence of the present invention may be operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Host Cells

The term "host cell"—in relation to the present invention includes any cell that comprises either a nucleotide sequence encoding a polypeptide having the specific properties as defined herein or an expression vector as described above and which is used in the recombinant production of a polypeptide having the specific properties as defined herein.

Thus, a further embodiment of the present invention provides host cells transformed or transfected with a nucleotide sequence of the present invention or a nucleotide sequence that expresses a polypeptide having the specific properties as defined herein. The cells will be chosen to be compatible with the said vector and may for example be prokaryotic (for example bacterial), fungal, yeast or plant cells. Preferably, the host cells are not human cells.

Examples of suitable bacterial host organisms are gram negative bacterium or gram positive bacteria.

Depending on the nature of the nucleotide sequence encoding a polypeptide having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

Organism

The term "organism" in relation to the present invention includes any organism that could comprise a nucleotide sequence according to the present invention or a nucleotide sequence encoding for a polypeptide having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus: 50 years on. Progress in industrial microbiology vol 29*. Elsevier Amsterdam 1994. pp. 641-666).

Gene expression in filamentous fungi has been reviewed in Punt et al. (2002) Trends Biotechnol 2002 May; 20(5):200-6, Archer & Peberdy Crit Rev Biotechnol (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

For the transformation of yeast, several transformation protocols have been developed.

For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp. including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO01/39544).

Transformed Plants/Plant Cells

A host organism suitable for the present invention may be a plant. A review of the general techniques may be found in articles by Potrykus (*Annu Rev Plant Physiol Plant Mol Biol* [1991] 42:205-225) and Christou (Agro-Food-Industry Hi-Tech March/April 1994 17-27), or in WO01/16308. The transgenic plant may produce enhanced levels of phytosterol esters and phytostanol esters, for example.

Therefore the present invention also relates to a method for the production of a transgenic plant with enhanced levels of phytosterol esters and phytostanol esters, comprising the steps of transforming a plant cell with a lipid acyltransferase as defined herein (in particular with an expression vector or construct comprising a lipid acyltransferase as defined herein), and growing a plant from the transformed plant cell.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

A polypeptide having the specific properties as defined herein may be produced as a fusion protein, for example to aid in extraction and purification thereof. Examples of fusion protein partners include glutathione-5-transferase (GST), 6×His (SEQ ID NO: 17), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

In another embodiment of the invention, the amino acid sequence of a polypeptide having the specific properties as defined herein may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The invention will now be described, by way of example only, with reference to the following Figures and Examples.

FIG. 1 shows a pfam00657 consensus sequence from database version 6 (SEQ ID No. 1);

FIG. 2 shows an amino acid sequence (SEQ ID No. 2) obtained from the organism *Aeromonas hydrophila* (P10480; GI:121051);

FIG. 3 shows an amino acid sequence (SEQ ID No. 3) obtained from the organism *Aeromonas salmonicida* (AAG098404; GI:9964017);

FIG. 4 shows an amino acid sequence (SEQ ID No. 4) obtained from the organism *Streptomyces coelicolor* A3(2) (Genbank accession number NP_631558);

FIG. 5 shows an amino acid sequence (SEQ ID No. 5) obtained from the organism *Streptomyces coelicolor* A3(2) (Genbank accession number: CAC42140);

FIG. 6 shows an amino acid sequence (SEQ ID No. 6) obtained from the organism *Saccharomyces cerevisiae* (Genbank accession number P41734);

FIG. 7 shows an alignment of selected sequences (SEQ ID NOS: 55-59 respectively, in order of appearance) to pfam00657 consensus sequence (SEQ ID NO: 1);

Figure 35:
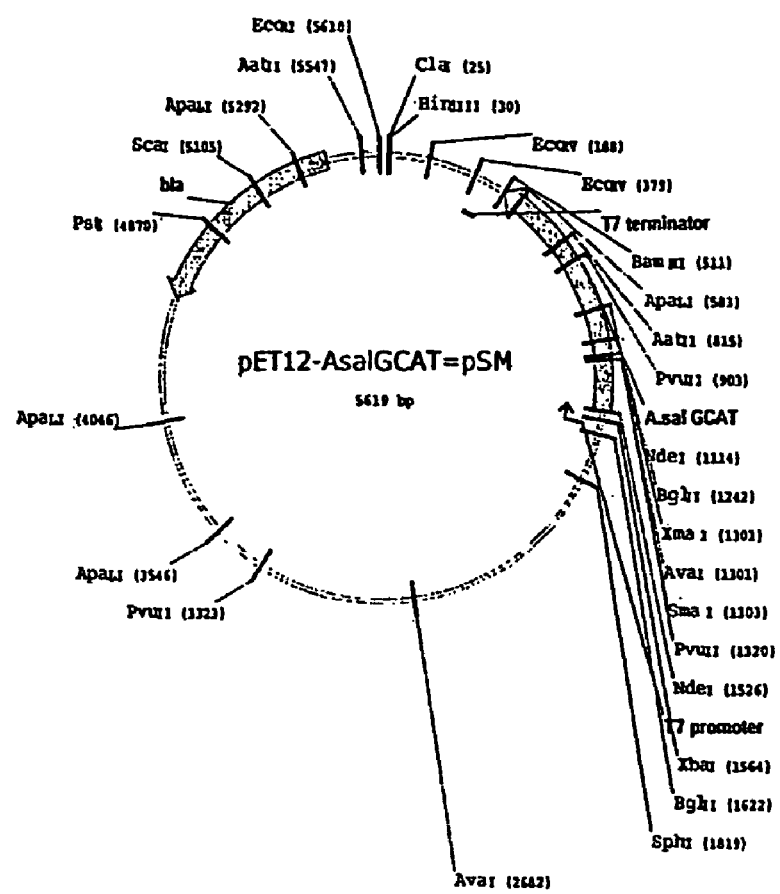

FIG. 8 shows a pairwise alignment of residues 1-335 of SEQ ID No. 3 with SEQ ID No. 2 showing 93% amino acid sequence identity. The signal sequence is underlined. + denotes differences. The GDSX (SEQ ID NO: 71) motif containing the active site serine 16, and the active sites aspartic acid 116 and histidine 291 are highlighted (see shaded regions). Numbers after the amino acid is minus the signal sequence;

FIG. 9 shows a nucleotide sequence (SEQ ID No. 7) encoding a lipid acyl transferase according to the present invention obtained from the organism *Aeromonas hydrophila*;

FIG. 10 shows a nucleotide sequence (SEQ ID No. 8) encoding a lipid acyl transferase according to the present invention obtained from the organism *Aeromonas salmonicida*;

FIG. 11 shows a nucleotide sequence (SEQ ID No. 9) encoding a lipid acyl transferase according to the present invention obtained from the organism *Streptomyces coelicolor* A3(2) (Genbank accession number NC_003888.1: 8327480..8328367);

FIG. 12 shows a nucleotide sequence (SEQ ID No. 10) encoding a lipid acyl transferase according to the present invention obtained from the organism *Streptomyces coelicolor* A3(2) (Genbank accession number AL939131.1: 265480..266367);

FIG. 13 shows a nucleotide sequence (SEQ ID No. 11) encoding a lipid acyl transferase according to the present invention obtained from the organism *Saccharomyces cerevisiae* (Genbank accession number Z75034);

FIG. 14 shows an amino acid sequence (SEQ ID No. 12) obtained from the organism Ralstonia (Genbank accession number: AL646052);

FIG. 15 shows a nucleotide sequence (SEQ ID No. 13) encoding a lipid acyl transferase according to the present invention obtained from the organism Ralstonia;

FIG. 16 shows SEQ ID No. 20. Scoe1 NCBI protein accession code CAB39707.1 GI:4539178 conserved hypothetical protein [*Streptomyces coelicolor* A3(2)];

FIG. 17 shows a nucleotide sequence shown as SEQ ID No. 21 encoding NCBI protein accession code CAB39707.1 GI:4539178 conserved hypothetical protein [*Streptomyces coelicolor* A3(2)];

FIG. 18 shows an amino acid shown as SEQ ID No. 22. Scoe2 NCBI protein accession code CAC01477.1 GI:9716139 conserved hypothetical protein [*Streptomyces coelicolor* A3(2)];

FIG. 19 shows a nucleotide sequence shown as SEQ ID No. 23 encoding Scoe2 NCBI protein accession code CAC01477.1 GI:9716139 conserved hypothetical protein [*Streptomyces coelicolor* A3(2)];

FIG. 20 shows an amino acid sequence (SEQ ID No. 24) Scoe3 NCBI protein accession code CAB88833.1 GI:7635996 putative secreted protein. [*Streptomyces coelicolor* A3(2)];

FIG. 21 shows a nucleotide sequence shown as SEQ ID No. 25 encoding Scoe3 NCBI protein accession code CAB88833.1 GI:7635996 putative secreted protein. [*Streptomyces coelicolor* A3(2)];

FIG. 22 shows an amino acid sequence (SEQ ID No. 26) Scoe4 NCBI protein accession code CAB89450.1 GI:7672261 putative secreted protein. [*Streptomyces coelicolor* A3(2)];

FIG. 23 shows an nucleotide sequence shown as SEQ ID No. 27 encoding Scoe4 NCBI protein accession code CAB89450.1 GI:7672261 putative secreted protein. [*Streptomyces coelicolor* A3(2)];

FIG. 24 shows an amino acid sequence (SEQ ID No. 28) Scoe5 NCBI protein accession code CAB62724.1 GI:6562793 putative lipoprotein [*Streptomyces coelicolor* A3(2)];

FIG. 25 shows a nucleotide sequence shown as SEQ ID No. 29, encoding Scoe5 NCBI protein accession code CAB62724.1 GI:6562793 putative lipoprotein [*Streptomyces coelicolor* A3(2)];

FIG. 26 shows an amino acid sequence (SEQ ID No. 30) Srim1 NCBI protein accession code AAK84028.1 GI: 15082088 GDSL-lipase [*Streptomyces rimosus*];

FIG. 27 shows a nucleotide sequence shown as SEQ ID No. 31 encoding Srim1 NCBI protein accession code AAK84028.1 GI:15082088 GDSL-lipase [*Streptomyces rimosus*];

FIG. 28 shows an amino acid sequence (SEQ ID No. 32) A lipid acyl transferase from *Aeromonas hydrophila* (ATCC #7965);

FIG. 29 shows a nucleotide sequence (SEQ ID No. 33) encoding a lipid acyltransferase from *Aeromonas hydrophila* (ATCC #7965);

FIG. 30 shows an amino acid sequence (SEQ ID No. 34) of a lipid acyltransferase from *Aeromonas salmonicida* subsp. *Salmonicida* (ATCC#14174);

FIG. 31 shows a nucleotide sequence (SEQ ID No 35) encoding a lipid acyltransferase from *Aeromonas salmonicida* subsp. *Salmonicida* (ATCC#14174);

FIG. 32 shows that homologues of the *Aeromonas* genes can be identified using the basic local alignment search tool service at the National Center for Biotechnology Information, NIH, MD, USA and the completed genome databases. The GDSX (SEQ ID NO: 71) motif was used in the database search and a number of sequences/genes potentially encoding enzymes with lipolytic activity were identified. Genes were identified from the genus *Streptomyces*, *Xanthomonas* and *Ralstonia*. As an example below, the *Ralstonia solanacearum* was aligned to the *Aeromonas salmonicida* (satA) gene. Pairwise alignment showed 23% identity. The active site serine is present at the amino terminus and the catalytic residues histidine and aspartic acid can be identified (SEQ ID NOS 60-61);

FIG. 33 shows the Pfam00657.11 [family 00657, database version 11] consensus sequence (SEQ ID NO: 70) (hereafter called Pfam consensus) and the alignment of various sequences (SEQ ID NOS 62-68, and 14-15 respectively, in order of appearance) to the Pfam consensus sequence. The arrows indicate the active site residues, the underlined boxes indicate three of the homology boxes indicated by [Upton C and Buckley J T (1995) Trends Biochem Sci 20; 179-179]. Capital letters in the Pfam consensus indicate conserved residues in many family members. The − symbol indicates a position where the hidden Markov model of the Pfam consensus expected to find a residue but did not, so a gap is inserted. The . symbol indicates a residue without a corresponding residue in the Pfam consensus. The sequences are the amino acid sequences listed in FIGS. 16, 18, 20, 22, 24, 26, 28 and 30.

FIG. 34 shows the Pfam00657.11 [family 00657, database version 11] consensus sequence (SEQ ID NO: 70) (hereafter called Pfam consensus) and the alignment of various sequences (SEQ ID NOS 62-64, 68, and 14-15 respectively, in order of appearance) to the Pfam consensus sequence. The arrows indicate the active site residues, the underlined boxes indicate three of the homology boxes indicated by [Upton C and Buckley J T (1995) Trends Biochem Sci 20; 179-179]. Capital letters in the Pfam consensus indicate conserved residues in many family members. The − symbol indicates a position where the hidden Markov model of the Pfam consensus expected to find a residue but did not, so a gap is inserted. The · symbol indicates a residue without a corresponding residue in the Pfam consensus. The sequences are the amino acid sequences listed in FIGS. 2, 16, 18, 20, 26, 28 and 30. All these proteins were found to be active against lipid substrates.

Figure 36:
Figure 37:
Figure 38:
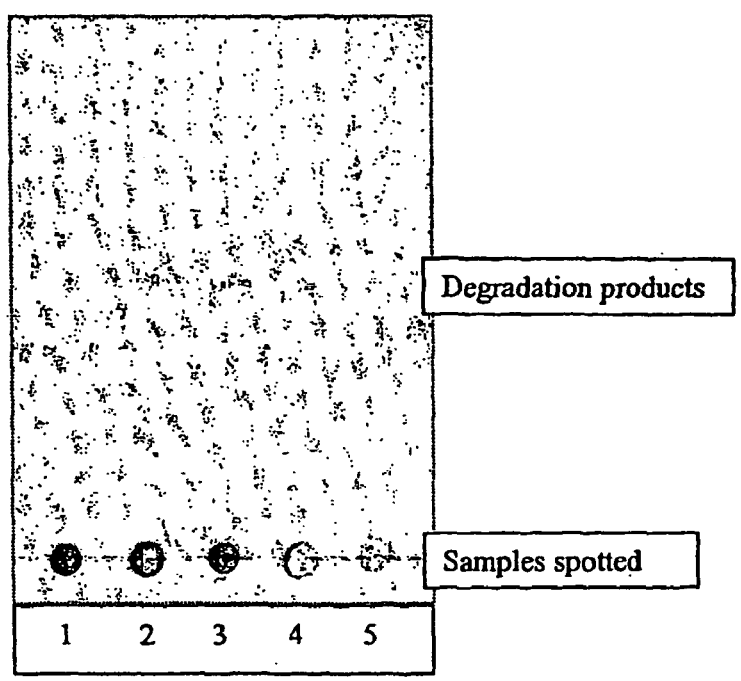
Figure 39:
Figure 40:
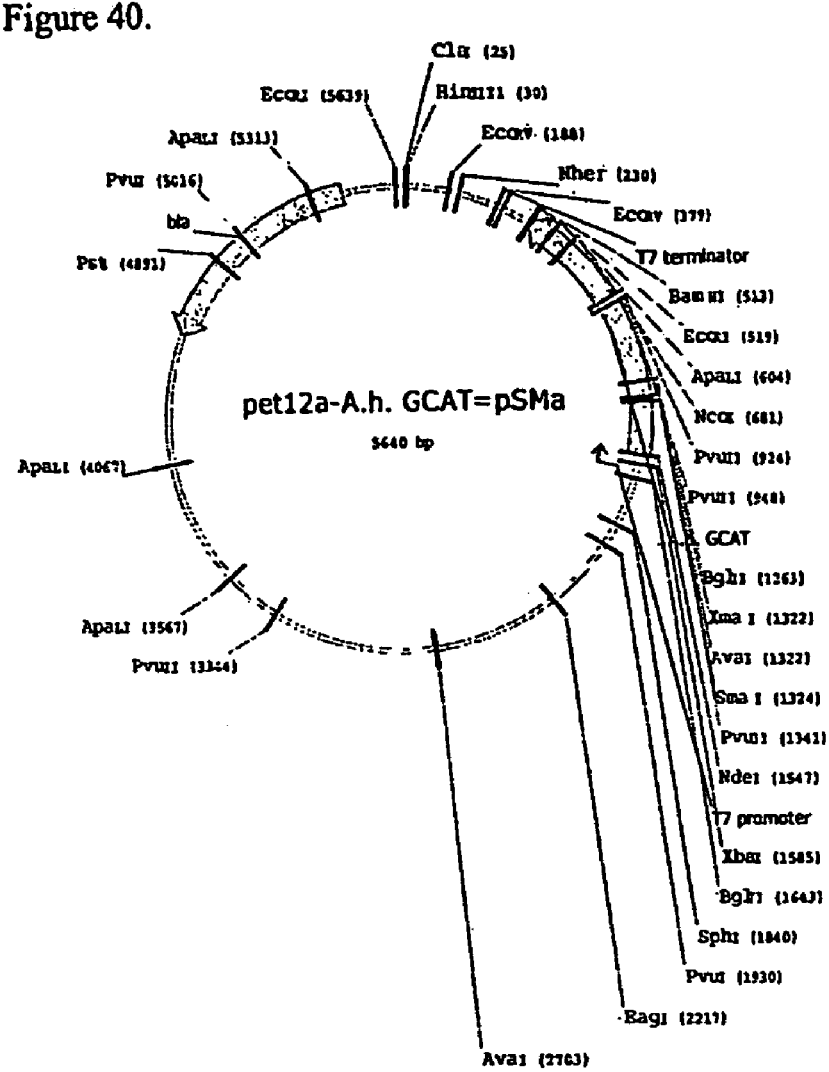
Figure 41:
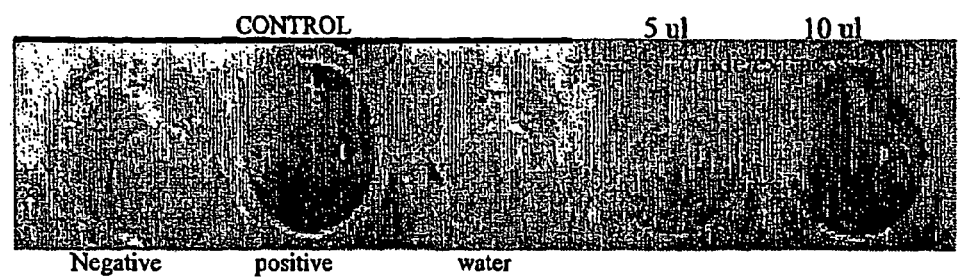
Figure 42:
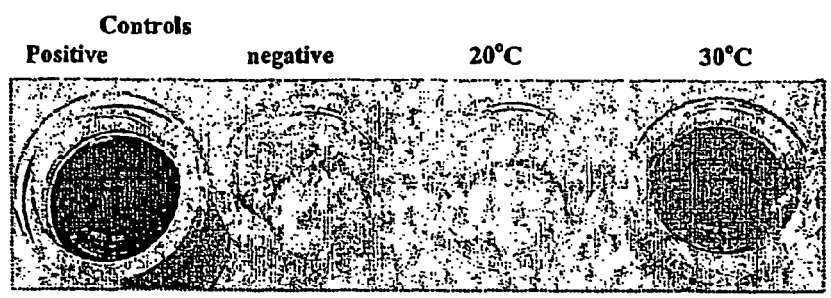
Figure 43:
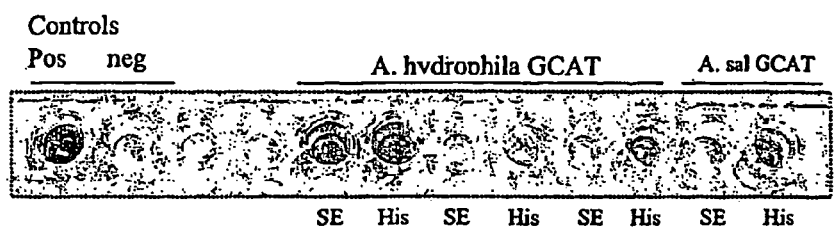
Figure 44:
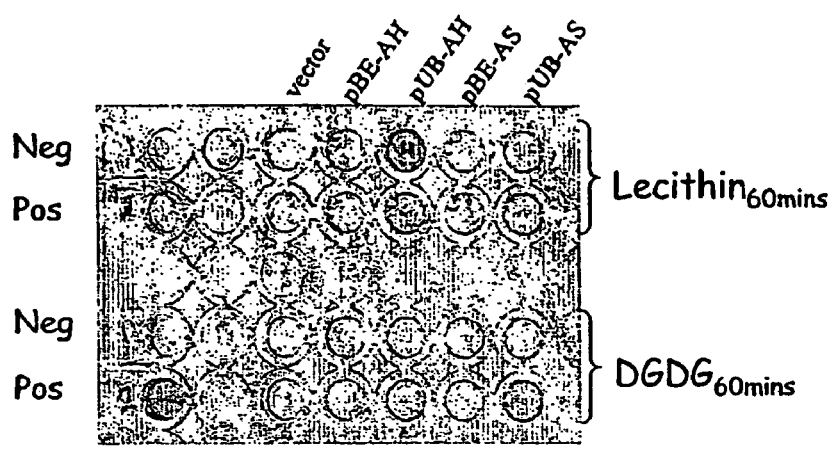

FIG. 35 shows a expression vector pet12-AsalGCAT=pSM containing the C-terminal His-tagged *Aeromonas salmonicida* lipid acyltransferase gene;

FIG. 36 shows the results of testing cell extracts in a NEFA Kit Assay, which depicts the activity of a recombinant, *A. salmonicida* lipid acyltransferase, towards lecithin. The wells from left to right indicate: a positive control, a negative control (i.e. extracts from empty plasmid) and samples collected after 0, 1, 2 and 3 hours cultivation after IPTG induction;

FIG. 37 shows growth optimisation of BL21(DE3)pLysS harboring the expression vector pet12-AsalGCAT=pSM showing cultivation at 30° C. resulted in the production of enzyme with high activity towards lecithin. Cell extracts were tested for phospholipase activity using the NEFA kit assay. Wells from left to right: positive control; negative control; 20° C.; 30° C.;

FIG. 38 shows crude cell extracts from BL21(DE3)pLysS expressing active lipid acyltransferase incubated with the substrate lecithin and reaction mixture was analyzed using thin layer chromatography showing the presence of degradation products. Lanes: 1. No enzyme; 2. +A.sal−10 ul 37° C.; 3. +A. sal−20 ul 37° C.; 4. +A.sal−10 ul 24° C.; 5. +A.sal−20 u 24° C.;

FIG. 39 shows partial purification of the *Aeromonas salmonicida* Acyl Transferase showing the phospholipase activity associated with purified His-tag protein. SE=Sonicated extracts, His=Purified with Ni-NTA spin-kit from Qiagen;

FIG. 40 shows the expression vector pet12-A.h. GCAT=pSMa containing the C-terminal His-tagged *Aeromonas hydrophila* Glycerolipid Acyl Transferase (GCAT) gene was used to transform *E. coli* strain BL21(DE3)pLysS;

FIG. 41 shows the activity of the crude extracts (5 & 10 ul) containing the recombinant *Aeromonas hydrophila* GCAT enzyme was tested towards lecithin using Non-Esterified Fatty Acid (NEFA) kit (Roche, Switzerland), showing the presence of active enzyme towards the phospholipid, lecithin;

FIG. 42 shows growth optimisation of BL21(DE3)pLysS harboring the expression vector pet12-AsalGCAT=pSM showing cultivation at 30° C. resulted in the production of enzyme with high activity towards lecithin. Cell extracts were tested for phospholipase activity using the NEFA kit assay;

FIG. 43 shows the partial purification of the *Aeromonas hydrophila* & *A. salmonicida* Acyl Transferases showing the phospholipase activity associated with purified His-tag protein. SE=Sonicated extracts, His=Purified with Ni-NTA spin-kit from Qiagen);

FIG. 44 shows the expression of the *Aeromonas* genes in *Bacillus subtilis* 163 showing the production of secreted enzyme with activity towards both lecithin and DGDG. pUB-AH=construct containing the *A. hydrophila* gene and pUB-AS, construct with the *A. salmonicida* gene, Culture filtrate was incubated with the substrates for 60 minutes.

Figure 45:
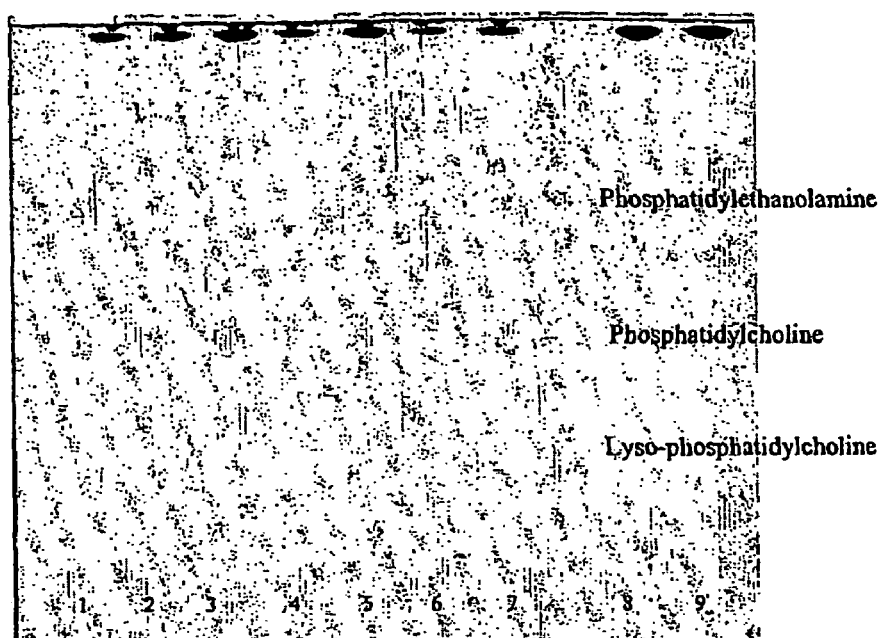
Figure 46:
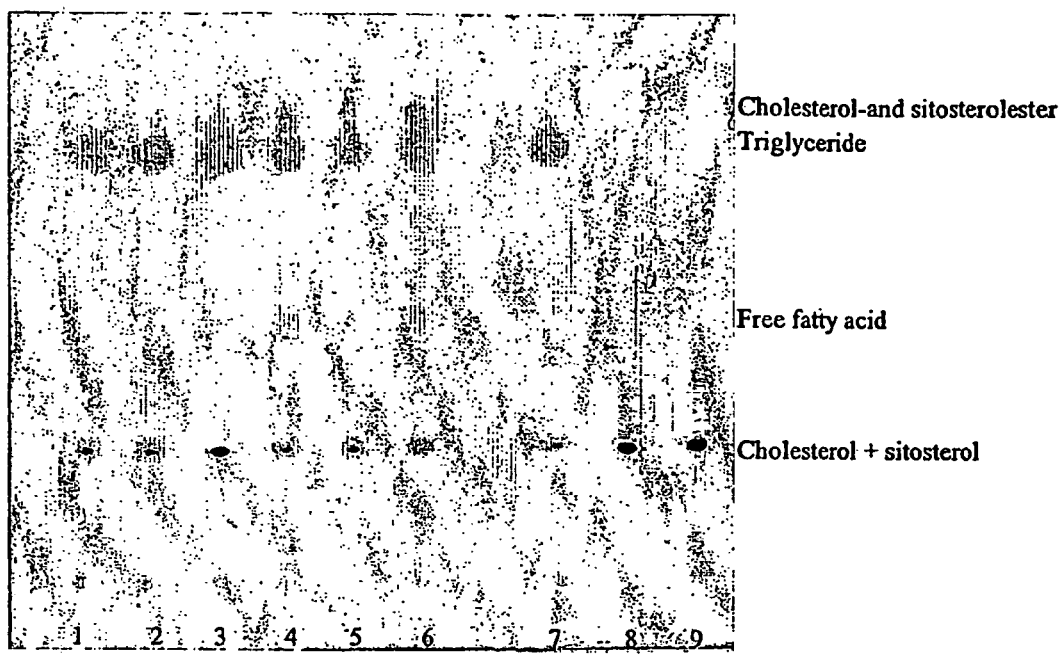
Figure 47:
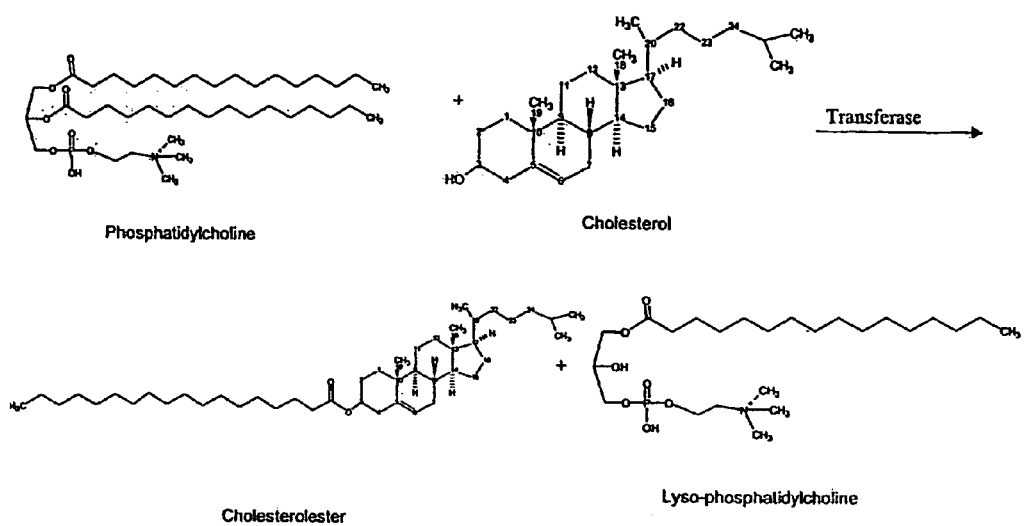
Figure 48:
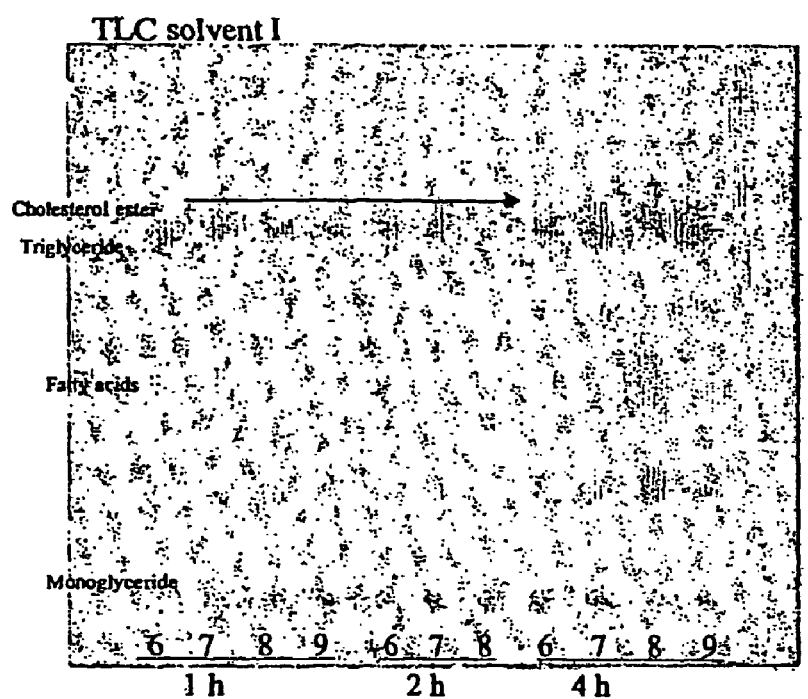

FIG. 45 and FIG. 46 show a TLC plate in developing solvent IV (chloroform:methanol:water (65:25:4)); Lane 1: 40 mg sitosterol 30 min: Lane 2: Transferase+40 mg sitosterol 30 min; Lane 3: Transferase+80 mg sitosterol 30 min; Lane 4: Transferase+40 mg sitosterol 120 min; Lane 5: Transferase+80 mg sitosterol 120 min; Lane 6: Transferase+40 mg sitosterol 300 min; Lane 7: 40 mg sitosterol 300 min; Lane 8: Cholesterol; Lane 9: Sitosterol;

FIG. 47 depicts the reaction between phosphatidylcholine and cholesterol which is catalysed by a lipid acyltransferase;

FIG. 48 shows a TLC analysis of lipids extracted from enzyme treated or untreated egg yolk., 6) 0.31 PLU/g Transferase #179, 7) 1.25 PLU/g Transferase #178-9., 8) 23.25 PLU/g Phospholipase #3108., 9) Control.

Figure 49:
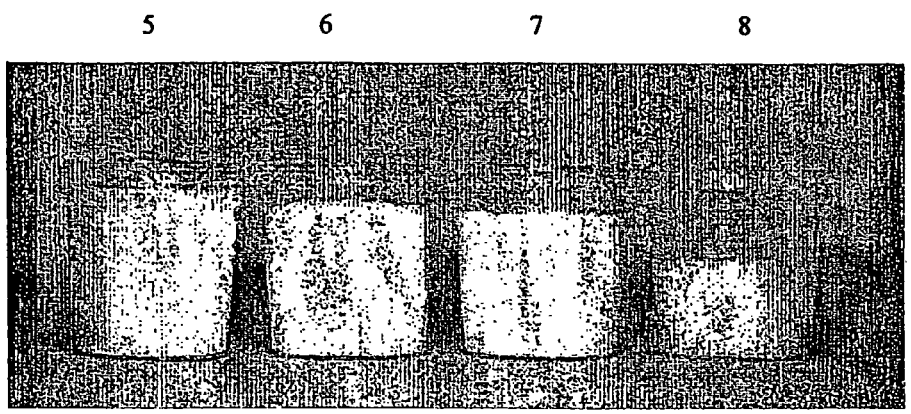
Figure 50:
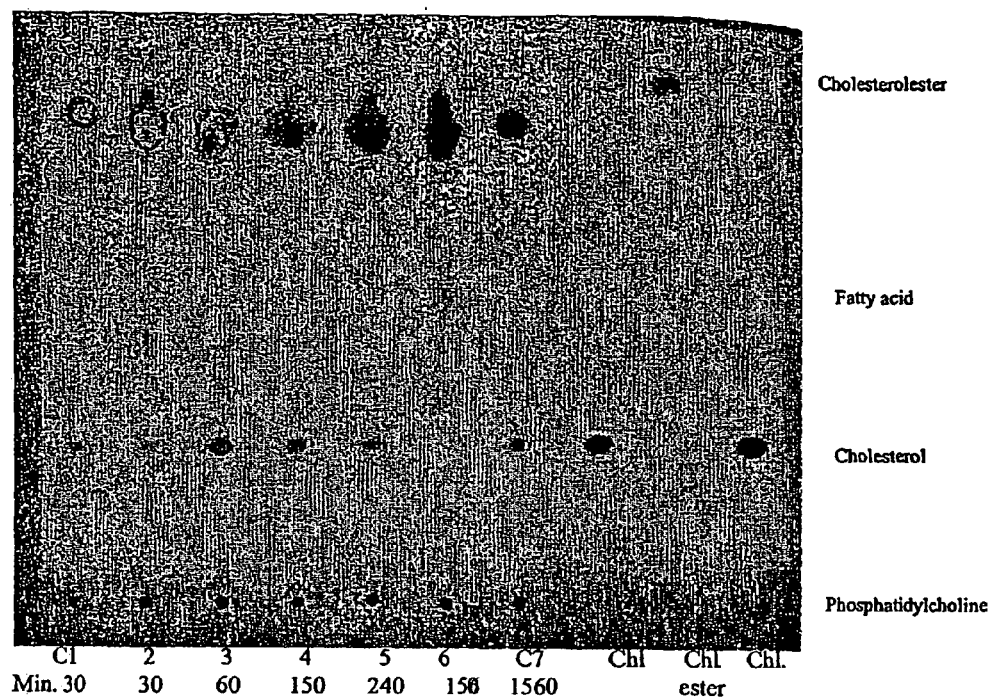
Figure 51:
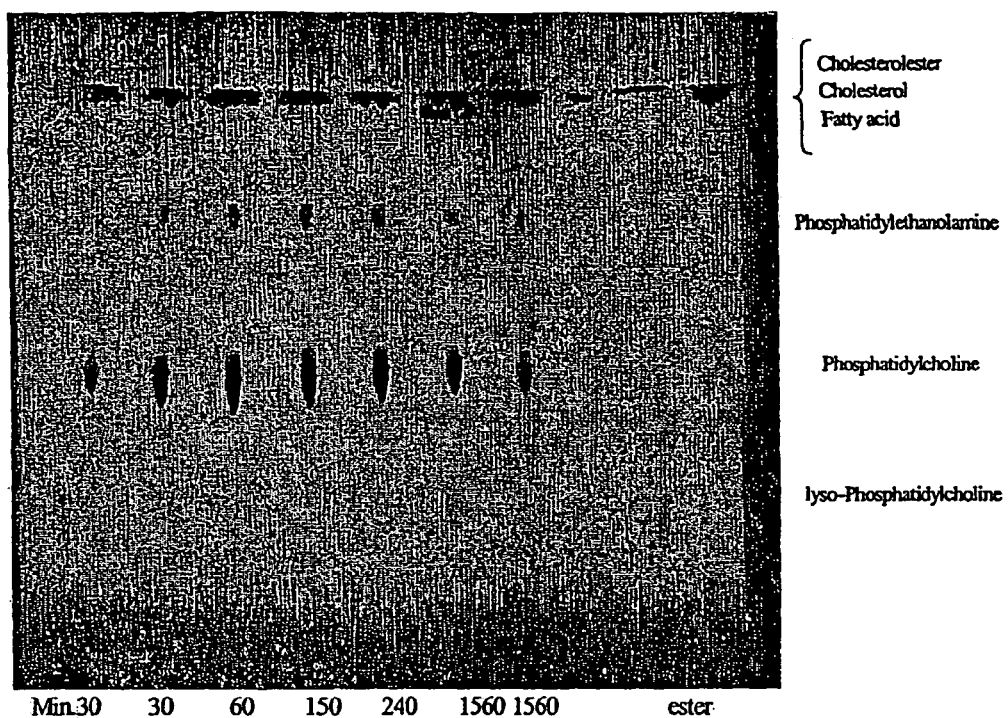
Figure 52:
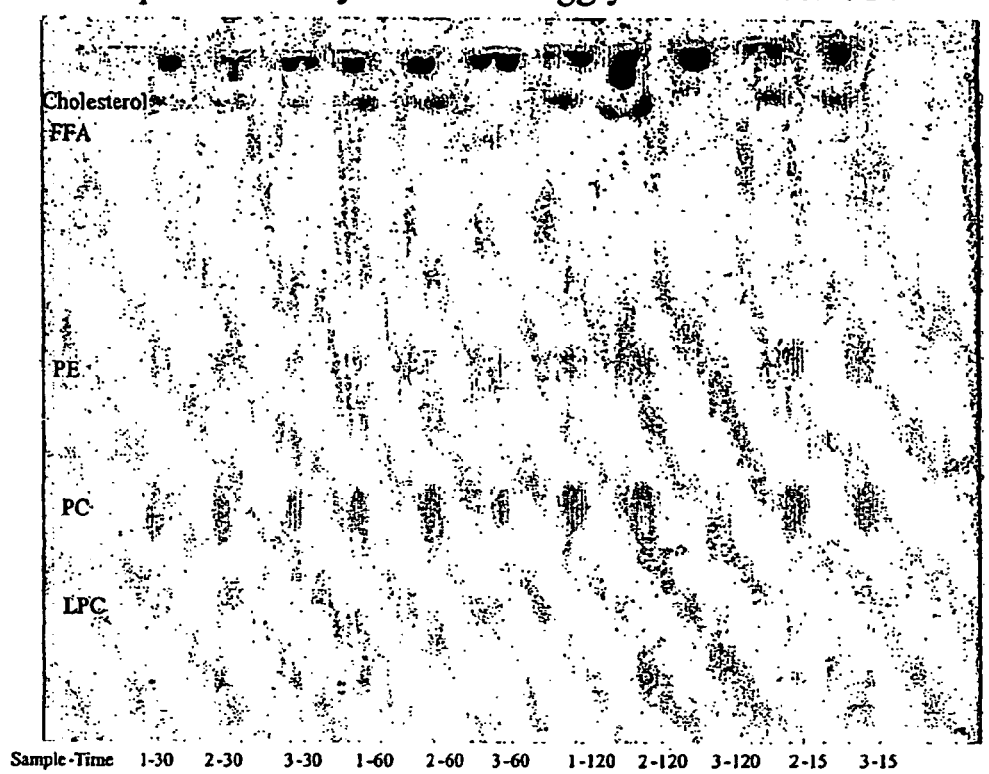
Figure 53:
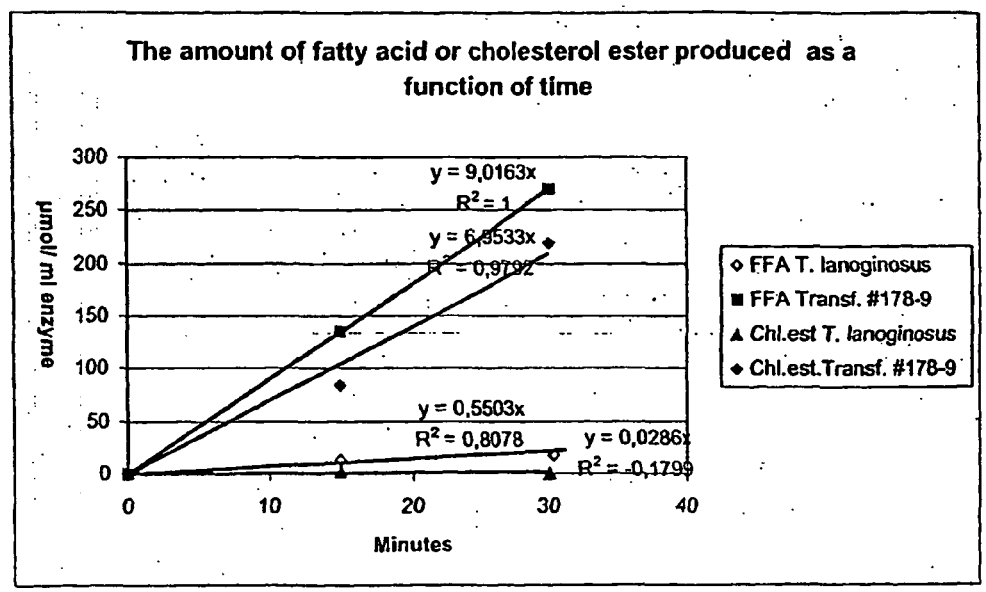
Figure 54:
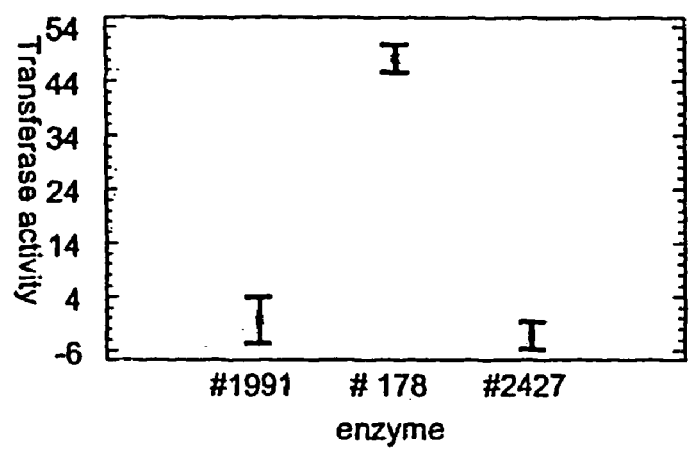
Figure 55:
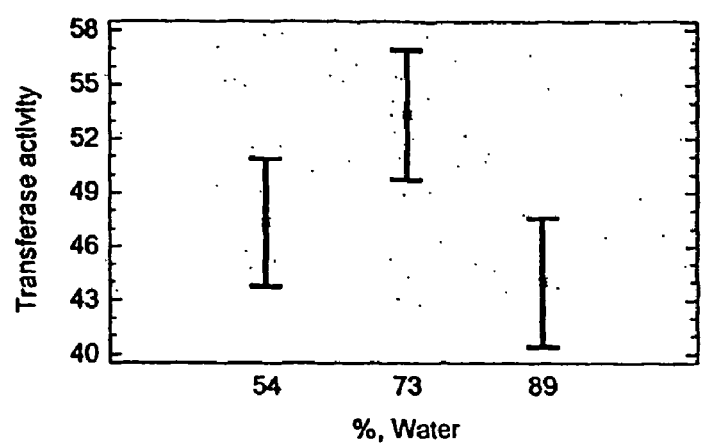
Figure 56:
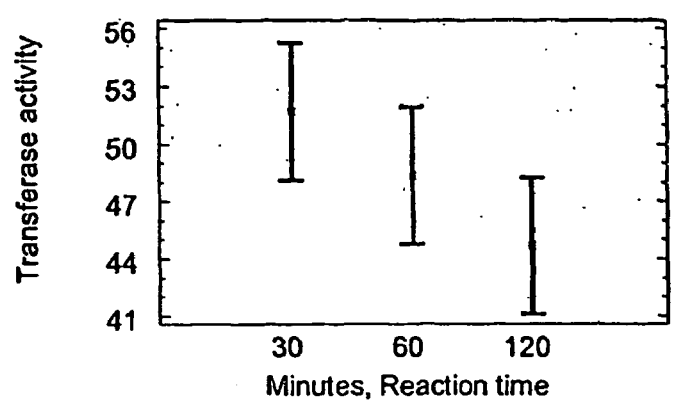
Figure 57:
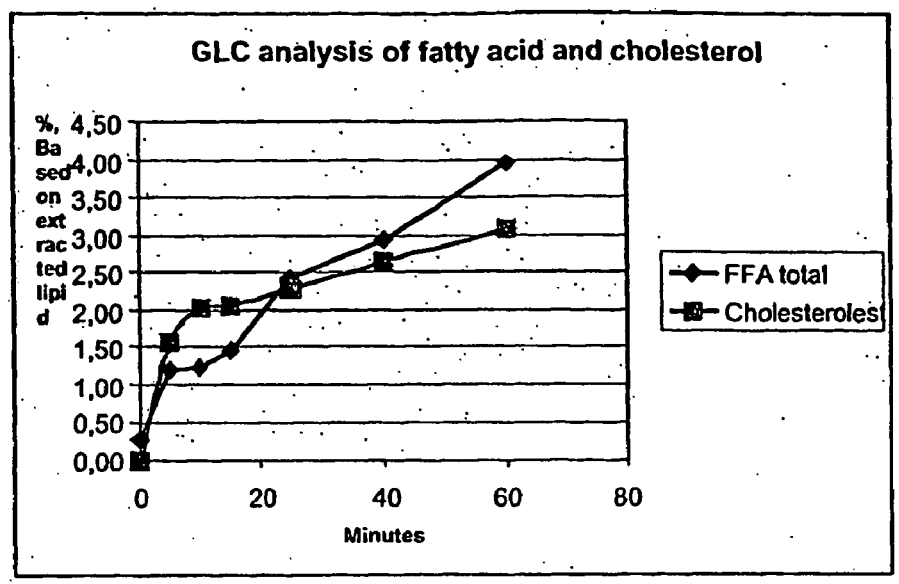
Figure 58:
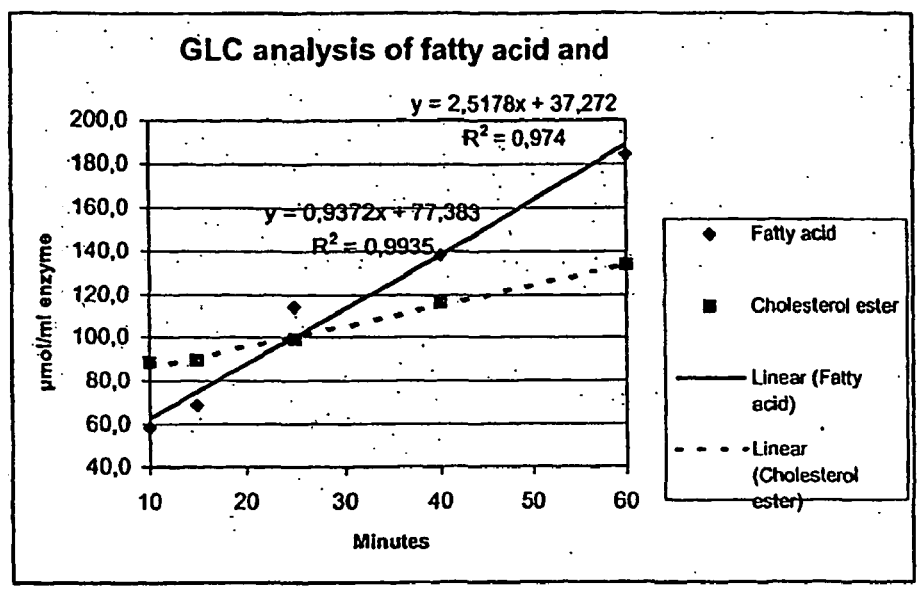
Figure 59:
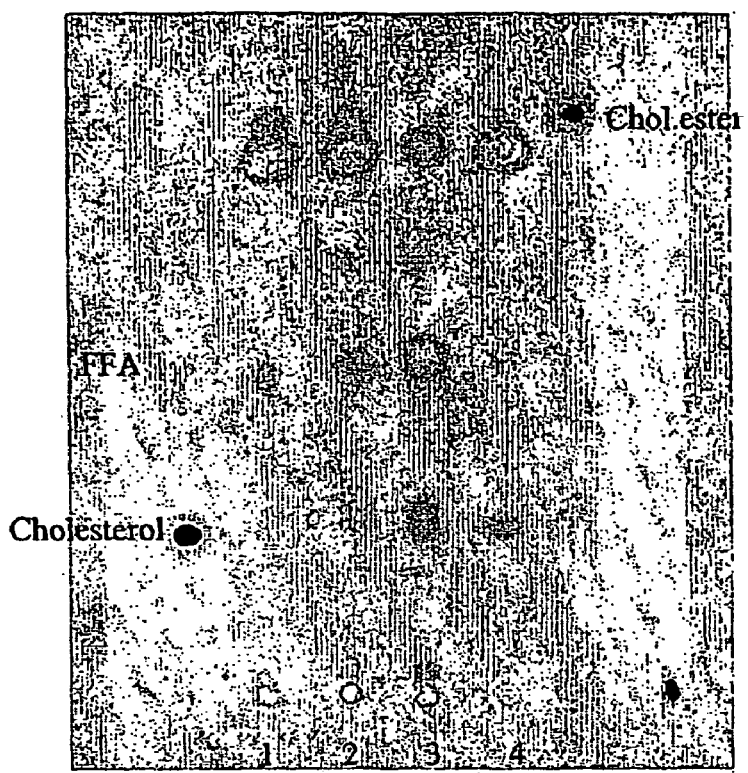
Figure 60:
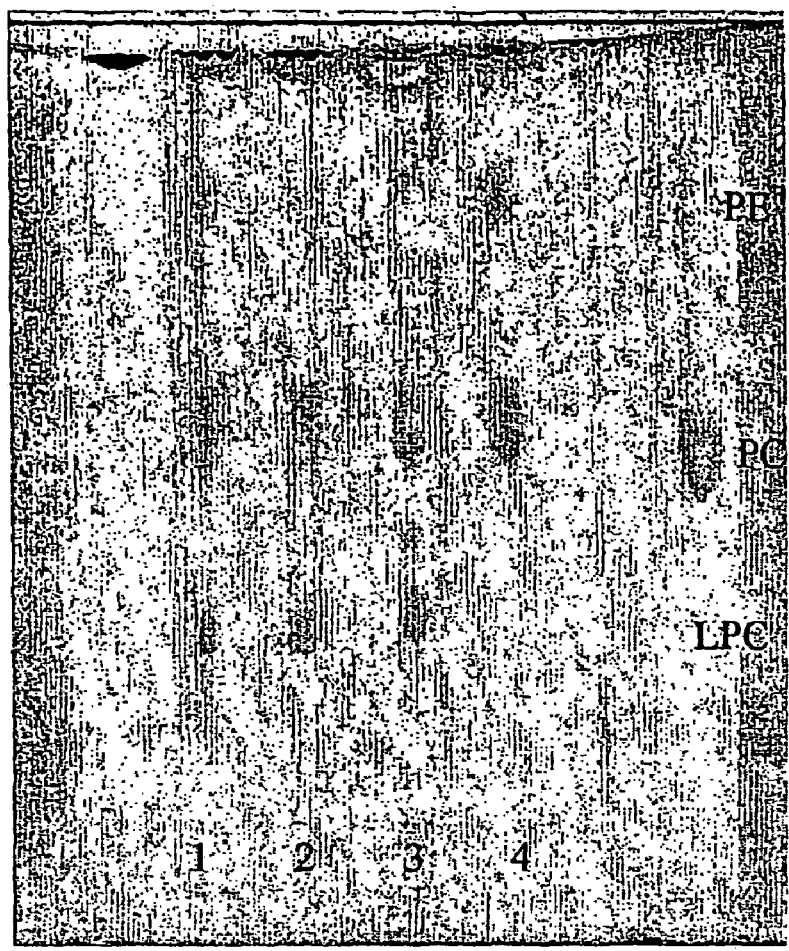
Figure 61:
Figure 62:
Figure 63:
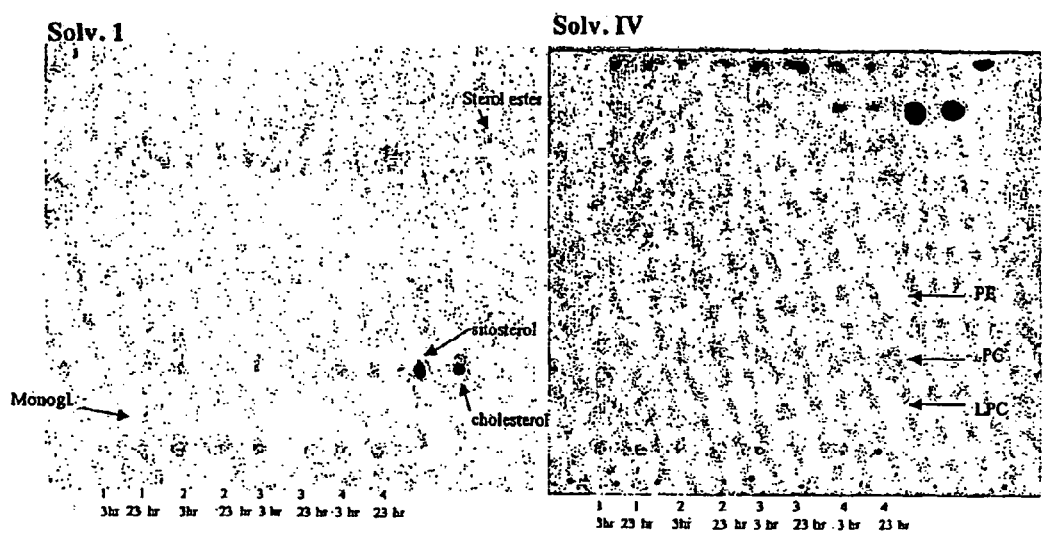
Figure 64:
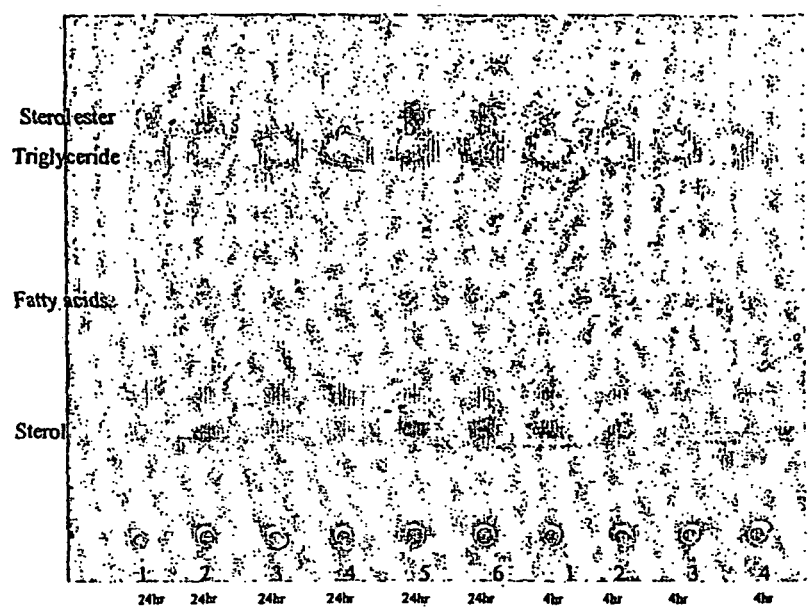
Figure 65:
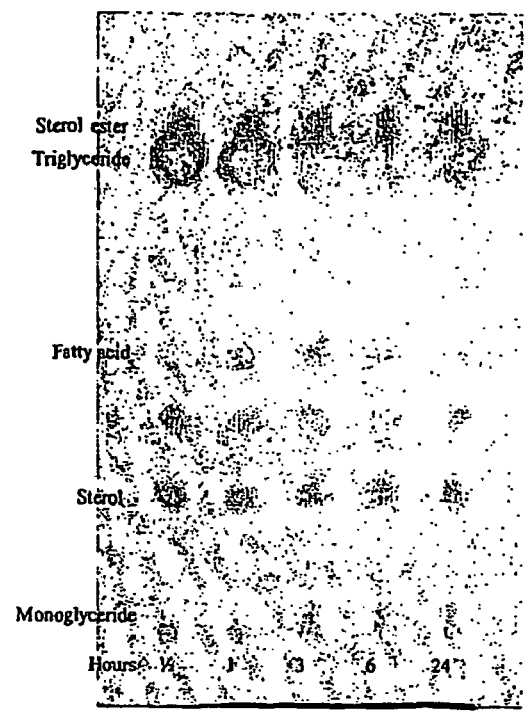
Figure 66:
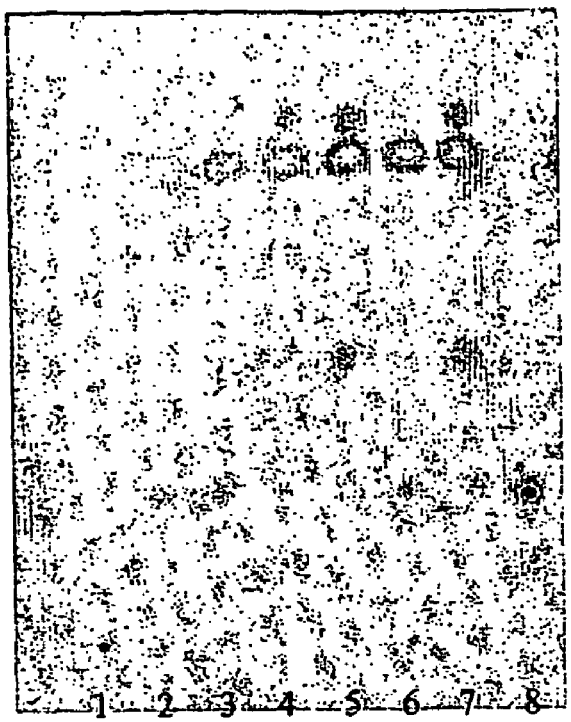
Figure 67:
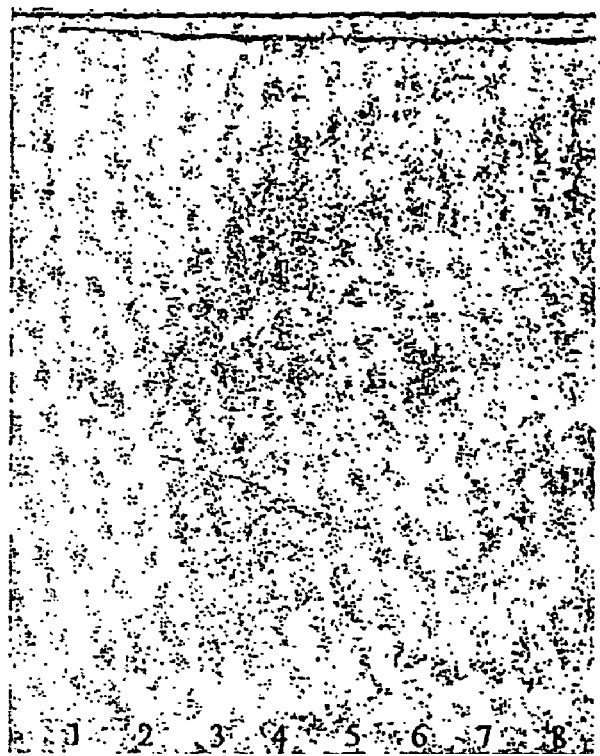
Figure 68:
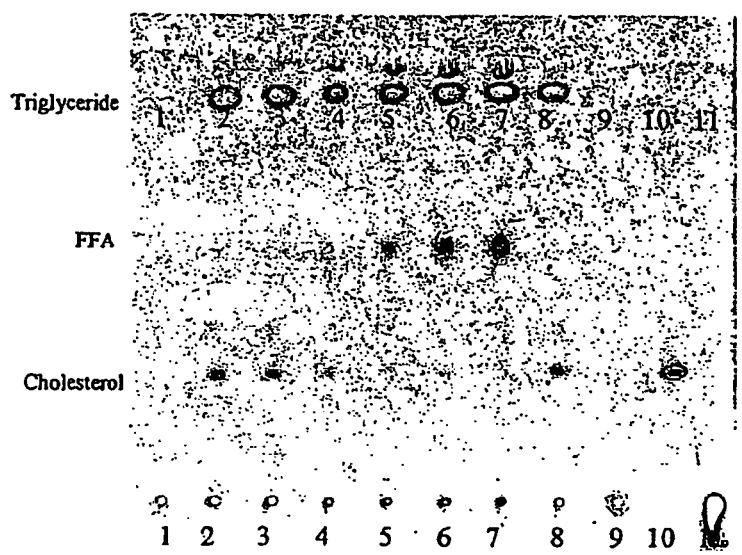
Figure 69:
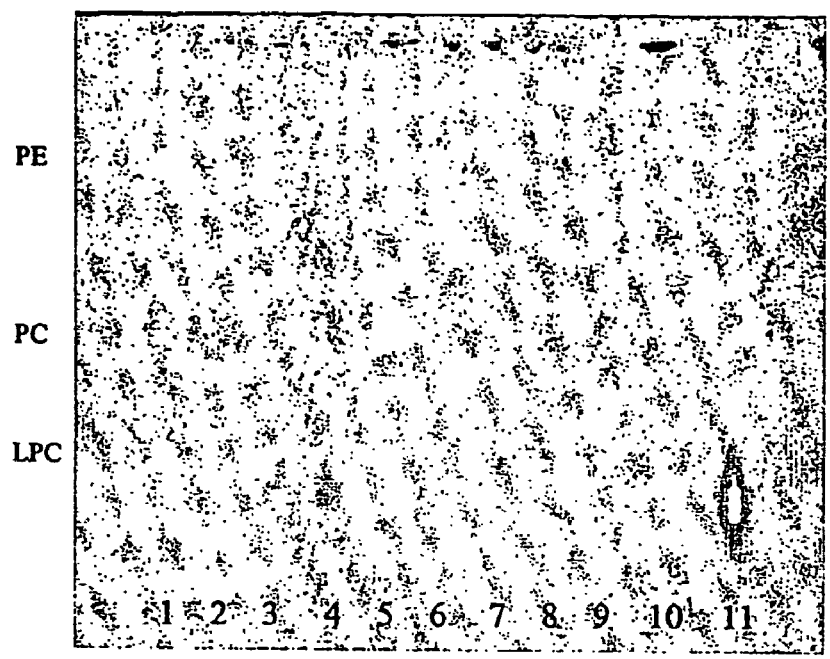
Figure 70:
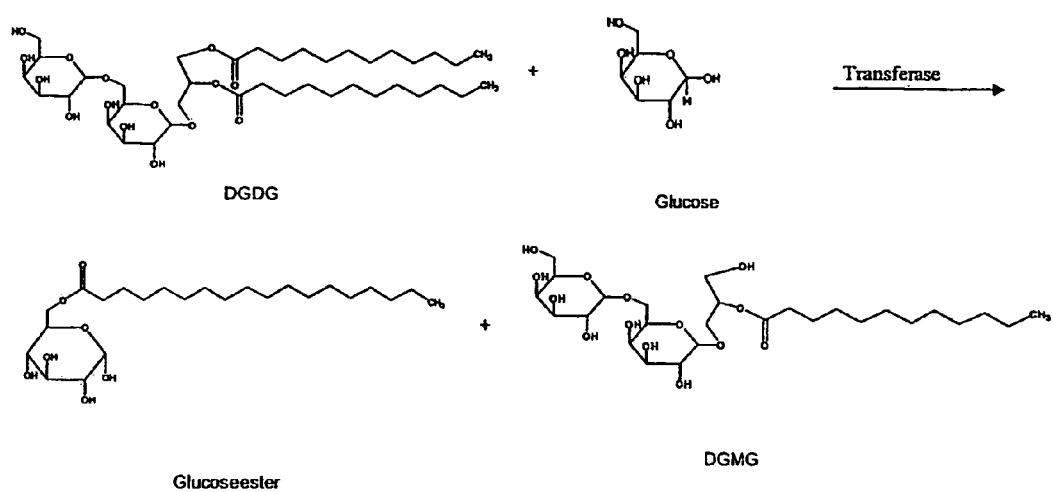
Figure 73:
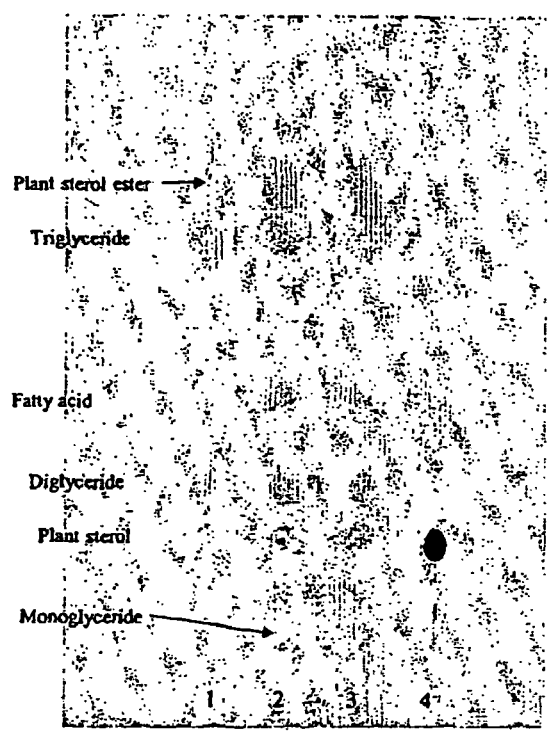

FIG. 49 shows mayonnaise test samples produced by enzyme treated or untreated egg yolk: 5) Transferase #179, 0.31 PLU/g. 6) Transferase #178-9, 1.25 PLU/g, 7) Phospholipase #3108, 23.3 PLU/g 8) Control, water FIG. 50 shows a TLC (in solvent I) of egg yolk lipid treated with a lipid acyl transferase from *A. hydrophila*;

FIG. 51 shows a TLC (in solvent IV) of egg yolk lipid treated with a lipid acyl transferase from *A. hydrophila*;

FIG. 52 shows a TLC analysis of transferase treated lipid from egg yolk over a time course;

FIG. 53 shows the amount of fatty acid and cholesterol ester produced as a function of time when using a lipid acyltransferase (Tranf #178-9) compared with when using a control lipolytic enzyme, *Thermomyces lanuginosus*;

FIG. 54 shows relative transferase activity as % of transferase and hydrolytic activity in enzymatic reactions in egg yolk with high water content, #1991 (phospholipase A2) and #2427 (phospholipase A1) are control phospholipases, #178 is a lipid acyltransferase;

FIG. 55 shows the effect of water content in the assay on the transferase activity of the transferase #178 in transferase reactions in egg yolk with high water content;

FIG. 56 shows the transferase activity for a lipid acyltransferase (#178) as a function of reaction time in transferase reactions in egg yolk with high water;

FIG. 57 and FIG. 58 show graphs depicting fatty acid and cholesterol ester as a function of time. The graphs depict results obtained for GLC analysis in the assay for measurement of acyltransferase activity using lecithin and cholesterol in buffer as substrate;

FIG. 59 shows a TLC in solvent I. Egg yolk treated with lipid acyltransferase #138 from *Aeromonas salmonidica* (lane no. 1 and 2) or with a phospholipase #2938 (LIPO-PAN® F) (lane no. 3) or Untreated egg yolk (lane no. 4);

FIG. 60 shows a TLC in solvent IV. Egg yolk treated with lipid acyltransferase #138 (lane no. 1 and 2) or with Phospholipase #2938 (lane no. 3). Untreated egg yolk (lane no. 4);

FIG. 61 shows egg yolk treated with lipid acyltransferase #138 (sample nos. 1 and 2) and with phospholipase #2938 (sample no. 3). Untreated egg yolk (sample no. 4);

FIG. 62 shows a food emulsion after 2 hours at 100° C., 0) Untreated egg yolk 1) Egg yolk treated with lipid acyl transferase #138 for 210 minutes. 3) Egg yolk treated with the control phospholipase #2938 for 210 minutes;

FIG. 63 shows TLC plates showing the screening of transferase activity on plant sterol and glycerol. PC=phosphatidylcholine, LPC=lysophosphatidylcholine; PE=phosphatidylethanolamine; monogl=monoglyceride;

FIG. 64 shows a TLC plate in solvent I, Samples 1 to 6 after 24 hours and samples 1 to 4 after 4 hours reaction time. The TLC analysis confirms the formation of sterol ester in samples 1, 2, 5 and 6;

FIG. 65 shows a TLC plate in solvent I where the transferase activity of an immobilised acyltransferase from *Aeromonas salmonicida* was tested in an oil mixture—with samples taken at 0.5, 1, 3, 6 and 24 h;

FIGS. 66 and 67 show TLC plates in solvent I and IV. Lane 1=lecithin; Lane 2=control—10 mins; Lane 3=0.75 PLU, 10 mins; Lane 4=0.75 PLU, 60 mins; Lane 5=0.75 PLU, 220 mins; Lane 6=control, 20 h; Lane 7=0.75 PLU, 20 h; and Lane 8=cholesterol ester;

FIGS. 68 and 69 show TLC plates in solvent IV. Lane 1=lecithin; Lane 2=control—10 mins; Lane 3=1 PLU, 10 mins; Lane 4=1 PLU, 60 mins; Lane 5=1 PLU, 180 mins; Lane 6=IPLU, 220 mins; Lane 7=IPLU, 1200 min; Lane 8=control, 1200 min; Lane 9=glucose ester; Lane 10=cholesterol; and Lane 11=glucose;

FIG. 70 shows the reaction between DGDG and glucose when catalysed by a lipid acyltransferase;

FIG. 71 shows an amino acid sequence (SEQ ID No. 36) of the fusion construct used for mutagenesis of the *Aeromonas hydrophila* lipid acyltransferase gene in Example 17. The underlined amino acids is a xylanase signal peptide;

FIG. 72 shows a nucleotide sequence (SEQ ID No. 54) encoding an enzyme from *Aeromonas hydrophile* including a xylanase signal peptide; and FIG. 73 shows a TLC plate clearly showing the formation of plant sterol ester and monoglyceride. Lane 1 is after 1 hour reaction time, Lane 2 is after 4 hours reaction time, Lane 3 is after 24 hours reaction time and Lane 4 is a plant sterol.

EXAMPLES

Except where stated TLC analysis was performed as described in Example 6 and GLC analysis was performed as described in Example 11.

Example 1

The Cloning, Sequencing and Heterologous Expression of a Transferase from *Aeromonas salmonicida* subsp. *Salmonicida*

Strains Used:

*Aeromonas salmonicida* subsp. *Salmonicida* (ATCC 14174) was obtained from ATCC and grown overnight at 30° C. in Luria-Bertani medium (LB). The cells were centrifuged and genomic DNA was isolated using the procedures for genomic DNA isolation from Qiagen Ltd. Genomic DNA buffer set (cat.19060), protease K (cat. 19131) and RNAse A (cat. 19101) were all obtained from Qiagen Ltd. (Boundary court Gatwick Court, West Sussex, RH10 2AX).

Host bacterial strain BL21(DE3)pLysS (Novagen) was used for production of the recombinant *Aeromonas* enzymes. Competent cells of BL21(DE3)pLysS were used as host for transformation with the expression vector pet12-AsalGCAT=pSM. Transformants containing the appropriate plasmid were grown at 37° C. in LB agar medium containing 100-ug ampicillin/ml.

Construction of Expression Vector pet12-Asalgcat-pSM:

For all DNA amplifications of the transferase genes from *Aeromonas*, genomic DNA (0.2-1 ul) was used as template and pfu DNA polymerase (2.5 units) was used with 10 ul of 10× pfu buffer, 1 ul each primer (50 pmol/ul), 200 uMdNTP in a total reaction volume of 100 ul. PCR reactions were performed in a programmable thermal cycler using the following conditions: 95° C. for 30 seconds, 30 cycles of 95° C. for 30 seconds, 60° C. for 1 minute and 68° C. for 2 minutes. An additional extension of 5 minutes at 72° C. was applied.

The PCR amplification of the transferase gene from *A. salmonicida* was carried in 2 separate PCR reactions. PCR reaction 1 was performed using primer pairs, as1USNEW (5'AGCATATGAAAA AATGGTTTGT TTGTTTATTG GGG 3' [SEQ ID No. 69]) and as1s950new (5' GTG ATG GTG GGC GAG GAA CTC GTA CTG3' [SEQ ID No. 37]). A second PCR reaction was performed to incorporate a C-terminal Histidine tag using the PCR product from the first reaction and the primers: as1USNEW(5'AGCATATGAAAA AATGGTTTGT TTGTTTATTG GGG 3' [SEQ ID No. 38]) and AHLS1001 (5'TTGGATCC GAATTCAT CAATG GTG ATG GTG ATG GTG GGC3' [SEQ ID No. 39]). The PCR product from the second reaction was purified and digested with restriction enzymes Nde1 and BamHI. 2 ug of pET 12a vector DNA was also digested with restriction enzymes Nde1 and BamHI and treated with phosphatase. The restriction enzyme-treated pet12a and PCR product from reaction 2 were purified and ligated using the Rapid Ligation Kit (Roche, Switzerland). The ligation mix was used to transform *E. coli* TOP10 cells. Transformants were plated on LB agar medium containing 100 ug/ml ampicillin.

The T7 promoter primer (5'TAATACGACTCACTATAG3' [SEQ ID No. 40]) and the T7 terminator primer (5'CTAGTTATTGCTCAGCGG3' [SEQ ID No. 41]) were used to verify the sequences and the orientation of the cloned transferase genes in pET12a vector. DNA sequencing was performed using ABI Prism® BigDye™ Terminators Cycle sequencing kit with 500 ng plasmid DNA as template and 3.2 pmol T7 promoter and terminator primers.

The construct shown in FIG. 35 was used to transform competent bacterial host strain BL21(DE3)pLysS (Novagen) and ampicillin resistant transformants were picked and used for expression analysis.

Expression of the Recombinant *Aeromonas salmonicida* Lipid Acyltransferase

Quantification of enzyme activity towards lecithin was determined on cell extracts using Non-Esterified Fatty Acid (NEFA) kit (Roche, Switzerland).

In FIG. 36, BL21(DE3)pLysS harboring the expression vector pet12-AsalGCAT=pSM was grown in LB medium+100 ug/ml ampicillin and incubated with shaking at 37° C. until $OD_{600}$=0.6 to 1.0 is reached. The cultures are then induced using IPTG (0.4 mM) and incubation was continued for the next 3 hours. Samples where taken at 0 hour, 1, 2, and 3 hours after IPTG induction. Enzyme Activity was tested using the NEFA kit and lecithin as substrate.

Growth Optimisation for the Production of More Active Enzymes

BL21(DE3)pLysS harboring the expression vector pet12-AsalGCAT=pSM was grown in LB medium+100 ug/ml ampicillin and incubated with shaking at different growth temperatures (37° C., 30° C., & 20° C.). The optimal condition for the production of active lipid acyltransferase enzyme was when cultures are grown at 30° C. as shown in FIG. 37.

Partial Purification of Recombinant *Aeromonas salmonicida* Transferase

Strain BL21(DE3)pLysS harboring the expression vector pet12-AsalGCAT=pSM was grown at 37° C. & crude cell extracts were prepared by sonication. The recombinant enzyme was further purified from the sonicated crude cell extracts using the Ni-NTA spin kit from Qiagen. Phospholipase activity using the NEFA kit & Lecithin as substrate. Crude cell extracts from BL21(DE3)pLysS expressing active transferase incubated with the substrate lecithin and reaction mixture was analysed using thin layer chromatography showing the presence of degradation products (see FIG. 38).

Partial Purification of recombinant *Aeromonas salmonicidae* transferase. Strain BL21(DE3)pLysS harbouring the expression vector pet12-AsalGCAT=pSM was grown at 37° C. and crude cell extracts were prepared by sonication. The recombinant enzyme ware further purified from the sonicated crude cell extract using the Ni-NTA spin kit from Qiagen. Phospholipase activity using the NEFA kit and lecithin as substrate was tested (see FIG. 39).

Example 2

Cloning and Expression of *Aeromonas hydrophila* Transferase in *E. coli*

*Aeromonas hydrophila* (ATCC #7965) was obtained from ATCC and grown overnight at 30° C. in Luria-Bertani medium (LB). The cells were centrifuged and genomic DNA was isolated using the procedures for genomic DNA isolation from Qiagen Ltd. Genomic DNA buffer set (cat. 19060), protease K (cat. 19131) and RNAse A (cat. 19101) were all obtained from Qiagen Ltd. (Boundary court Gatwick Court, West Sussex, RH10 2AX).

Host bacterial strain BL21(DE3)pLysS (Novagen) was used for production of the recombinant *Aeromonas* enzymes. Competent cells of BL21(DE3)pLysS were used as host for transformation with the expression vector pet12a-A.h.GCAT=pSMa. Transformants containing the appropriate plasmid were grown at 37° C. in LB agar medium containing 100-ug ampicillin/ml.

Construction of Expression Vector pet12a-A.h.GCAT-pSMa:

For all DNA amplifications of the transferase gene from *Aeromonas*, genomic DNA (0.2-1 ul) was used as template and pfu DNA polymerase (2.5 units) was used with 10 ul of 10× pfu buffer, 1 ul each primer (50 pmol/ul), 200 uMdNTP in a total reaction volume of 100 ul. PCR reactions were performed in a programmable thermal cycler using the following conditions: 95° C. for 30 seconds, 30 cycles of 95° C. for 30 seconds, 60° C. for 1 minute and 68° C. for 2 minutes. An additional extension of 5 minutes at 72° C. was applied.

The PCR amplification of the transferase gene from *A. hydrophila* (ATCC #7965) was carried out in 2 separate PCR reactions.

PCR reaction 1 was performed using primer pairs, AHUS1 (5'GTCATATGAAAAAATGGTTTGTGTGTT-TATTGGGATTGGTC3', SEQ ID No. 42) and ah1s950 (5'ATGGTGATGGTGGGCGAGGAACTCGTACTG3', SEQ ID No. 43).

A second PCR reaction was performed to incorporate a C-terminal Histidine tag using the PCR product from the first reaction and the primer pairs:

```
AHUS1
(5'GTCATATGAAAAAATGGTTTGTGTGTT-         SEQ ID No. 44)
TATTGGGATTGGTC3',
and AHLS1001
(5'TTGGATCCGAATTCATCAATGGTGATGGTGATGGTGGGC3'.SEQ ID No. 45)
```

The PCR product from the second reaction was purified and digested with restriction enzymes Nde1 and Bam-HI. 2 ug of pET 12a vector DNA was also digested with restriction enzymes Nde1 and BamHI and treated with phosphatase. The restriction enzyme-treated pet12a and PCR product from reaction 2 were purified and ligated using the Rapid Ligation Kit (Roche, Switzerland). The ligation mix was used to transform *E. Coli* TOP10 cells. Transformants were plated on LB agar medium containing 100 ug/ml ampicillin.

The T7 promoter primer (5'TAATACGACTCAC-TATAG3') (SEQ ID NO: 18) and the T7 terminator primer (5'CTAGTTATTGCTCAGCGG3') (SEQ ID NO: 19) were used to verify the sequences and the orientation of the cloned GCAT genes in pET12a vector. DNA sequencing was performed using ABI Prism® BigDye™ Terminators Cycle sequencing kit with 500 ng plasmid DNA as template and 3.2 pmol T7 promoter and terminator primers.

The construct shown in FIG. 40 was used to transform competent bacterial host strain BL21 (DE3)pLysS (Novagen) and ampicillin resistant transformants were picked and used for expression analysis.

Expression of the *Aeromonas hydrophila* Transferase in BL21(DE3)pLysS

The *E. coli* strain BL21(DE3)pLysS harboring the expression vector pet12a-A.h.GCAT=pSMa was grown in LB medium+10 ug/ml ampicillin and incubated with shaking at 37° C. until $OD_{600}$=0.6 to 1.0 is reached. The cultures are then induced using IPTG (0.4 mM) and incubation was continued for the next 3 hours. Samples where taken at 0 hour, 1, 2, and 3 hours after IPTG induction. Enzyme Activity was tested using the NEFA kit and lecithin as substrate (FIG. 41).

Growth Optimisation for the Production of More Active Enzymes

BL21(DE3)pLysS harboring the expression vector pet12a-A.h.GCAT=pSMa was grown in LB medium+100 ug/ml ampicillin and incubated with shaking at different growth temperatures (37° C., 30° C., & 20° C.). The optimal condition for the production of active GCAT enzyme was when cultures are grown at 30° C. as shown in FIG. 42.

Partial Purification of Recombinant *A. hydrophila* Transferase (GCAT)

Strain BL21(DE3)pLysS harboring the expression vector pet12a-A.h.GCAT=pSMa was grown at 37° C. & crude cell extracts were prepared by sonication. The recombinant enzyme was further purified from the sonicated crude cell extracts using the Ni-NTA spin kit from Qiagen. Phospholipase activity assay using the NEFA kit & Lecithin as substrate. (FIG. 43).

Example 3

Expression of *Aeromonas* Transferases in *Bacillus subtilis* 163

Plasmid Construction

Two different *Bacillus subtilis* expression vectors (pUB 110 & pBE5) were used for the heterologous expression of the *Aeromonas* genes in *Bacillus subtilis*. The pUB110 vector contains the alpha amylase promoter while the pBE vector has the P32 promoter as the regulatory region for the expression of the fused *Aeromonas* genes. In pUB110, the first amino acid of the mature GCAT genes of *Aeromonas* were fused in frame with the last amino acid of the xylanase signal peptide sequence from *Bacillus subtilis* via the restriction site Nhe1, creating an additional 2 amino acids in front of the mature proteins. pBE5 contains the cgtase signal sequence fusion at the Nco1 site for secretion of the recombinant proteins into the culture filtrate.

PCR reactions were carried out to obtain the *Aeromonas* genes fuse in frame to the signal sequences of the pUB 110 and the pBE5 vectors. PCRs were performed using the following primer pairs for *A. hydrophila* gene:

```
PCR reaction 1:
usAHncol
(5'ATGCCATGGCCGACAGCCGTCCCGCC3',    SEQ ID No. 46)
and 1sAH
(5'TTGGATCCGAATTCATCAATGGTGATG3',   SEQ ID No. 47)

PCR reaction 2:
US-AhnheI
(5'TTGCTAGCGCCGACAGCCGTCCCGCC3',    SEQ ID No. 48.)
and 1sAH
(5'TTGGATCCGAATTCATCAATGGTGATG3,    SEQ ID No. 49)
```

PCRs were performed using the following primer pairs for *A. salmonicida* gene:

```
PCR reaction 3:
US-Asncol
(5'TTGCCATGGCCGACACTCGCCCCGCC3',    SEQ ID No. 50)
and 1sAH
(5'TTGGATCCGAATTCATCAATGGTGATG3',   SEQ ID No. 51)

PCR reaction 4:
US-ASnhe1
(5'TTGCTAGCGCCGACACTCGCCCCGCC3',    SEQ ID No. 52)
and 1sAH
(5'TTGGATCCGAATTCATCAATGGTGATG3',   SEQ ID No. 53)
```

All the PCR products were cloned into PCR blunt II (TOPO vector) and sequenced with reverse & forward sequencing primers.

Clones from PCR reactions 1 & 3 were cut with Nco1 & Bam HI and used as inserts for ligation to the pBE5 vector cut with Nco1/BamHI/phosphatase. Clones from PCR reactions 2 & 4 were cut with Nhe1 & Bam HI and used as inserts for ligation to the pUB vector that was cut with Nhe1/BamH1/phosphatase.

Expression of the *Aeromonas* Transferase Genes in *Bacillus subtilis* and Characterization of the Enzyme Activity.

The acyl transferases from the two *Aeromonas* species have been successfully expressed in *E. coli* (results above). The *Bacillus* pUB110 & pBE5 gene fusion constructs were used to transform *Bacillus subtilis* and transformants were selected by plating on kanamycin plates. The kanamycin resistant transformants isolated and grown in 2xYT are capable of heterologous expression of the *Aeromonas* genes in *Bacillus*. The culture filtrates have digalactosyldiacylglycerol (DGDG) galactolipase activity, in addition to having both acyl transferase and phospholipase activities. The activity towards digalactosyldiacylglycerol (DGDG) was measured after 60 minutes of incubation of culture supernatant with the substrate, DGDG from wheat flour (obtainable form Sigma) as well as the activity towards lecithin as shown in FIG. 44. *Bacillus* produced the enzyme after overnight (20-24 hours) to 48 hours of cultivation in the culture medium as a secreted protein. In some instances, the expression of the *Aeromonas* genes has been shown to interfere with cell viability and growth in *Bacillus* & *E. coli*, it is therefore necessary to carefully select expression strains and optimise the growth conditions to ensure expression. For example, several *Bacillus* host strains (B.s 163, DB104 and OS 21) were transformed with the expression vectors for growth comparison. B.s163 is transformable with the 2 *Aeromonas* genes and is capable of expressing active protein. DB104 is transformable with all the constructs but is only able to express *A. salmonicida* transferase.

Example 4

Fermentation and Purification of *Aeromonas* Lipid Acyltransferases Produced in *E. coli*

*E. coli* Fermentations:
Microorganisms

Two strains of *Eschericia coli*, one containing an *Aeromonas hydrophila* (Example 2) lipid acyltransferase and two containing *Aeromonas salmonicida* lipid acyltransferases, (Example 1) were used in this study.

The *E. coli* strain containing the *A. hydrophila* gene was named DIDK0124, and the *E. coli* strain containing the *A. salmonicida* gene was named DIDK0125. The fermentation with DIDK0124 was named HYDRO0303 and the fermentation with DIDK0125 was named SAL0302. The purified protein from HYDRO025 was named REF#138. The purified protein from HYDRO0303 was named REF#135.

Growth Media and Culture Conditions
LB-Agar

The LB agar plates used for maintaining the strains contained: 10 g/L tryptone, 5 g/L yeast extract, 5 g/L NaCl, 15 g/L agar, 100 mg/L ampicillin and 35 mg/L chloramphenicol. The agar plates were incubated at 30° C.

LB Shake Flask

The LB medium (50 mL pr shake flask) used for production of inoculum material for the bioreactor cultivations contained: 10 g/L tryptone, 5 g/L yeast extract, 5 g/L NaCl, 100 mg/L ampicillin and 35 mg/L chloramphenicol. The shake flasks were inoculated from the LB agar plates, and incubated at 30° C. and 200 rpm.

Bioreactor Cultivation

The bioreactor cultivations were carried out in 6 L in-house built bioreactors filled with 4 L medium containing: 10 g/L tryptone, 5 g/L yeast extract, 5 g/L NaCl, 8 g/L $KH_2PO_4$, 0.9 g/L $MgSO_4.7H_2O$, 40 g/L glucose monohydrate, 0.4 mL/ADD APT® Foamstop Sin 260 (ADD APT Chemicals AG, Helmond, The Netherlands), 10 mg/L $(NH_4)_2Fe(SO_4)_2$. $6H_2O$, 0.7 mg/L $CuSO_4.5H_2O$, 3 mg/L $ZnSO_4.7H_2O$, 3 mg/L $MnSO_4.H_2O$, 10 mg/L EDTA, 0.1 mg/L $NiSO_4.6H_2O$, 0.1 mg/L $CoCl_2$, 0.1 mg/L $H_3BO_4$, 0.1 mg/L KI, 0.1 mg/L $Na_2MoO_4.2H_2O$, 1 g/L ampicillin and 35 mg/L chloramphenicol.

The bioreactors were inoculated with an amount of LB culture ensuring end of growth after approximately 20 hours of cultivation (calculated from the maximum specific growth rate of 0.6 $h^{-1}$, the $OD_{600}$ of the LB shake flask and the final $OD_{600}$ in the bioreactor of approximately 20).

SAL0302 was inoculated with 10 mL of LB culture, and HYDRO0303 was inoculated with 4 mL of LB culture.

The bioreactors were operated at the following conditions: temperature 30° C., stirring 800-1000 rpm (depending on experiment), aeration 5 L/min, pH 6.9, pH control 8.75% (w/v) $NH_3$-water and 2 M $H_2SO_4$. Induction was achieved by addition of isopropyl β-D-thiogalactoside to a final concentration of 0.6 mM, when 0.4 moles (HYDRO0303) and 0.7 moles $CO_2$ was produced respectively.

Harvest

The following procedure was used for harvest and homogenisation of the biomass:
1) The fermentation broth from the fermentations was centrifuged at 5000×g and 4° C. for 10 minutes, and the supernatant was discharged. The biomass was stored at −20° C. until use. The biomass was thawed and resuspended in 500 mL of 20 mM $NaH_2PO_4$, pH 7.4, 500 mM NaCl, 10 mM Imidazole and Complete (EDTA-free) protease inhibitor (Roche, Germany).
2) The suspended biomass was homogenized at 2 kbar and 4° C. in a cell disrupter from Constant Systems Ltd (Warwick, UK).
3) The cell debris was removed by centrifugation at 10.000×g and 4° C. for 30 minutes followed by collection of the supernatant.
4) The supernatant was clarified further by centrifugation at 13.700×g and 4° C. for 60 minutes, followed by collection of the supernatant.
5) The supernatant was filtered through 0.2 μm Vacu Cap filters (Pall Life Sciences, UK) and the filtrate was collected for immediate chromatographic purification.

Chromatographic Purification of the Transferases

A column (2.5×10 cm) was packed with 50 ml of Chelating Sepharose ff. gel and charged with Ni-sulphate (according to the method described by manufacturer, Amersham Biosciences). The column was equilibrated with 200 ml of 20 mM $NaH_2PO_4$, pH 7.4, 500 mM NaCl, 10 mM Imidazole. 400 ml of crude was applied to the column at a flow rate of 5 ml/min. The column was then washed with 20 mM $NaH_2PO_4$, pH 7.4, 500 mM NaCl, 10 mM Imidazole until the $UV_{280}$ reached the base line. The GCAT was then eluted with 40 ml of 20 mM $NaH_2PO_4$, pH 7.4, 500 mM NaCl and 500 mM Imidazole.

Example 5

Fermentation and Purification of *Aeromonas* Lipid Acyltransferases Produced in *Bacillus subtilis*

Fermentations
BAC0318-19, BAC0323-24
Microorganism

The microorganisms used in this study originate from transformation of a *Bacillus subtilis* host strain, #163 with a plasmid containing the gene encoding the *Aeromonas salmonicida* transferase inserted in the vector pUB110OIS. The expression of the gene is controlled by an alpha-amylase promoter, and the secretion of the transferase is mediated by the *B. subtilis* xylanase signal sequence (Example 3). The strains were named DIDK0138 (fermentation BAC0318-19) and DIDK0153 (fermentation BAC0323-24).

Growth Media and Culture Conditions
Pre Culture Medium

A shake flask (500 mL total volume, with baffles) was added 100 mL of a medium containing:

| | |
|---|---|
| NaCl | 5 g/L |
| $K_2HPO_4$ | 10 g/L |
| Soy flour | 20 g/L |
| Yeast extract, BioSpringer 106 | 20 g/L |
| Antifoam, SIN260 | 5 mL/L | pH was adjusted to 7.0 before autoclaving
After autoclaving 6 mL 50% (w/w) Nutriose were added pr flask. Kanamycin was added at a concentration of 50 mg/L after autoclaving.

Inoculation

A pre culture shake flask was inoculated with frozen culture directly from a 25% (w/v) glycerol stock. The shake flask was incubated at 33° C. and 175 rpm for approximately 16 hours, whereupon 50 mL was used to inoculate the fermentor.

Fermentations

The fermentations were carried out in 6 L in house built fermentors.

The batch medium (3 L) contained:

| | |
|---|---|
| Corn steep liquor (50% dw) | 40 g/L |
| Yeast extract BioSpringer 153 (50% dw) | 10 g/L |
| NaCl | 5 g/L |
| $CaCl_2, 2H_2O$ | 0.25 g/L |
| $Mn(NO_3)_2, H_2O$ | 0.2 g/L |
| Antifoam SIN260 | 1 mL/L |
| Kanamycin (filter sterilised to the fermentor after autoclaving | 50 mg/L |

The feed contained:

| | |
|---|---|
| Glucose monohydrate | 540 g/kg |
| $MgSO_4, 7H_2O$ | 4.8 g/kg |
| Antofoam SIN260 | 4 mL/kg |
| Yeast extract, BioSpringer 153 (50% dw) (autoclaved separately) | 150 g/kg |

The feed in fermentation BAC0318 and BAC0323 was started based on the accumulated $CO_2$, according to the equations below:

Feed–flow[g/h]=0, $AcCO_2$<0.15

Feed–flow[g/h]=2.85+t·1.54, $AcCO_2$≥0.15 and t<12

Feed–flow[g/h]=21.3, t>12 t: time (hours) from the point when the accumulated $CO_2$ ($AcCO_2$) reached 0.15 moles.

The feed in fermentation BAC0319 and BAC0324 was started based on the accumulated $CO_2$, according to the equations below:

Feed-flow[g/h]=0, AcCO$_2$<0.15

Feed-flow[g/h]=2.0+t·1.08, AcCO$_2$≧0.15 and t<12

Feed-flow[g/h]=15, t>12 t: time (hours) from the point when the accumulated CO$_2$ (AcCO$_2$) reached 0.15 moles.

The pH was controlled at 7.0 by adding 12.5% (w/v) NH$_3$-water or 2M phosphoric acid.

The aeration was 3 L/min corresponding to 1 vvm.

The temperature was 33° C.

The fermentor was equipped with two 8 cm φ Rushton impellers placed with a distance of 10 cm.

Harvest

The biomass was removed by centrifugation at 16,000×g for 10 minutes at room temperature. The supernatant was filter sterilized, and the filtrate was used for purification and application tests.

Example 6

Application Tests in Egg Yolk

In the following experiments the isolated transferase from Aeromonas salmonicida expressed in E-coli was tested in egg yolk alone and in egg yolk where a plant sterol had been added.

Material

Transferase from Aeromonas salmonicida REF#138

Egg yolk: from fresh egg (hens eggs)

Plant sterol: β-sitosterol, Sigma S 5753

TLC plates: Silica plates Merck nr. 1.05715.0001

TLC Analysis.

TLC-plate was activated in a heat cupboard (110° C.) for ½ h.

100 ml developing solvent was poured into a chromatography camber with lid. The walls of the chamber were covered with filter paper (Whatman 2) in order to saturate the chamber with the solvent vapor.

The TLC-plate was placed in a frame and the sample was applied onto the TLC plate 2 cm from the bottom. The TLC plate was then placed in the TLC chamber with the developing solvent. When the developing solvent reached 14 cm from the bottom of the plate. The TLC plate was taken out and dried in fume board, and then placed in the heat cupboard at 110° C. for 10 minutes.

The TLC-plate was then immersed in the developing reagent, and dried in the heat cupboard at 110° C. for 15 minutes Developing Solvent:

Nr. IV: Chloroform:Methanol: H$_2$O (65:25:4)

Nr. I: P-ether: MTBE: Acetic acid (60:40:1)

Developing Buffer (Vanadate-Buffer):

32 g Na$_2$CO$_3$ ad 300 ml H$_2$O (1M)

18.2 g vanadate pentoxide (V$_2$O$_5$) is added and dissolved during gentle heating.

The solution is cooled to ambient.

Carefully 460 ml 2.5 M H$_2$SO$_4$. (460 ml H$_2$O+61 ml H$_2$SO$_4$) is added

Water is added to 1000 ml.

Phospholipase Activity.

Substrate:

0.6% L-α Phosphatidylcholine 95% Plant (Avanti #441601)+0.4% Triton-X 100(Sigma X-100)+5 mM CaCl$_2$ is dissolved in 0.05M HEPES buffer pH 7.

Procedure.

400 µl substrate was added to an 1.5 ml Eppendorf tube and placed in a Eppendorf thermomixer at 30° C. for 5 minutes.

To the time T=0 50 µl enzyme solution was added. Also a blank with water instead of enzyme was analysed.

The sample was mixed at 1000 rpm on Eppendorf Termomixer at 30° C. for 10 minutes. To the time T=10 min. The Eppendorf tube was placed in another termomixer at 99° C. for 10 minutes to stops the reaction.

Free fatty acid in the samples were analyzed by using the NEFA kit from WAKO GmbH.

Enzyme activity PLU-7 pH 7 was calculated as micromole fatty acid produced per minute under assay conditions.

Lipid Extraction.

1 g egg yolk and 7.5 ml Chloroform:Methanol 2:1 was mixed on a Whirley and centrifuged at 750×g for 10 minutes.

3 ml of the chloroform phase was isolated and used for further lipid analysis.

Results:

The transferase (REF#138), from Aeromonas salmonicida expressed in E-coli was analysed for phospholipase activity as described above, and was also tested in egg yolk with and without β-sitosterol. The sample was stirred with a magnetic stirrer during the reaction. The experimental design is shown in Table 1

TABLE 1

| Test Nr | Reaction time at 37° C. Minutes | Egg yolk gram | Sitosterol mg | Transferase #138 Units |
|---|---|---|---|---|
| 1 | 30 | 1 | 40 | |
| 2 | 30 | 1 | 40 | 0.75 PLU |
| 3 | 30 | 1 | 80 | 0.75 PLU |
| 4 | 120 | 1 | 40 | 0.75 PLU |
| 5 | 120 | 1 | 80 | 0.75 PLU |
| 6 | 300 | 1 | 40 | 0.75 PLU |
| 8 | 300 | 1 | 40 | |

The reaction was stopped by adding 7.5 ml Chloroform: Methanol (2:1) and mixed on a Whirley mixer for 30 seconds. The chloroform phase was isolated by centrifugation and 2 µl of the chloroform phase was transferred to a pre-activated silica TLC plate and eluted with developing solvent nr. I, and another TLC-plate in developing solvent IV.

The results from the TLC analysis are shown in FIGS. 45 and 46.

Transferase reaction with a transferase from Aeromonas salmonicida in egg yolk where plant sterol was added has shown that the enzyme transfers fatty acid from lecithin in the egg yolk to the cholesterol during formation of cholesterolester. The TLC chromatogram also indicated that part of the sterol added to egg yolk was transferred to sterol ester.

The amount of sterol ester relative to the amount of cholesterol ester formed during the reaction can be analysed by HPLC or GLC.

It is known that plant sterol esters reduce the absorption of cholesterol in the intestine. It is also indicated in the literature that cholesterolesters are absorbed less than free cholesterol in the intestine. When a transferase and plant sterol is added to egg yolk a product with causes reduced cholesterol absorption is obtained, and at the same time lysolecithin is produced which improves the emulsification properties of the egg yolk. A further advantage of adding transferase and plant sterol to egg yolk is that plant sterol ester is ingested together with the natural available cholesterol, which is expected to have the highest effect on the reduction of cholesterol absorption.

Example 7

Modification of Egg Yolk by Lipid Acyl Transferase from *Aeromonas salmonicida*

In accordance with the present invention it has now been shown that it is possible to produce lysolecithin from egg yolk without substantial free fatty acid formation by use of a transferase.

The lecithin content of egg yolk is an important emulsifier for the production of mayonnaise with the limitation that the mayonnaise is not heat stable. It has therefore been known for several years to use a phospholipase from pancreas to modify lecithin in egg yolk to lysolecithin, which is a more efficient emulsifier. The use of enzyme modified egg yolk in mayonnaise production contributes to better heat stability of the mayonnaise during pasteurisation. A limitation of using pancreas phospholipase in egg yolk is that the amount of free fatty acid also increases, which contributes to reduced oxidative stability because free fatty acids are more prone to oxidation than the corresponding ester. Free fatty acid may also contribute to a soapy off taste.

The transferase from *Aeromonas salmonicida* was successfully expressed in *B. subtilis* and fermented in lab scale as described in Example 5, purified by liquid chromatography and used to modify egg yolk lipids. The enzyme modified egg yolk was used to produce heat stable mayonnaise.

The transferase from *A. salmonicida* can be used to produce lysolecithin and cholesterolester in egg yolk without production of significant amounts of free fatty acids. That is to say without increasing or substantially increasing the free fatty acids in the foodstuff.

The enzyme modified egg yolk produced by transferase showed improved emulsification properties and can be used for heat stable mayonnaise.

This enzyme was highly functional in modification of egg yolk by catalysing the lipid transfer reaction between lecithin and cholesterol FIG. 47.

This study further investigated the use of transferase for modification of egg yolk and the use of modified egg yolk in the production of heat stable mayonnaise.

This example describes the fermentation, isolation, and application of the transferase in egg yolks as well as the application of the enzyme modified egg yolk in mayonnaise. The example is divided into two parts:

A. Application of transferase in egg yolk
B. Testing of enzyme modified egg yolk in mayonnaise

EXPERIMENTAL

A. Application
Enzyme and Substrate
Transferase #178-9 from *A. salmonicida*, purification 2554-100 C73, 15 PLU-7/ml.
Transferase #179 from *A. salmonicida*, 18.5 PLU-7/ml.
Phospholipase A1 LECITASE™ Ultra (Novozymes A/S, Denmark)
Egg yolk: Liquid egg yolk with 8% salt, SANOVA FOODS, DK
TLC analysis was performed as described previously (see above Example 6).
Phospholipase activity: See previous examples.
Lipid Extraction
1 g egg yolk and 7.5 ml Chloroform:Methanol 2:1 was mixed on a Whirley for 30 sec. and centrifuged at 750×g for 10 minutes.
4 ml of the chloroform phase was isolated and used for further lipid analysis.
Oxidation Stability Test
Oxidation stability of mayonnaise was measured in an ML OXIPRESS equipment where the sample is oxidative stressed by means of heat under pressure in an oxygen atmosphere.
After a certain time, called the induction period (IP), the oxidation of the sample causes a certain consumption of oxygen, which is registered as pressure change of a pressure transducer. Higher induction period indicates better oxidation stability.
Procedure.
5-gram mayonnaise is placed in a glass container and the glass container is closed with the pressure transducer. The container is filled with oxygen to 5 bars. The valve is opened to empty the container. This procedure is repeated twice and the sample with 5 bar oxygen atmosphere is placed at 80° C. The oxygen pressure as a function of time is measured and the induction period (IP) calculated in hours.
Results
Purified transferase from *Aeromonas salmonicide* sample no. #179 and #178-9 were used to treat egg yolk as outlined in Table 2. The initial test has shown that GCAT transferase should be added with much lower phospholipase (PLU) activity, than a commercial Phospholipase. This is explained by the fact that GCAT is a transferase and therefore has much lower hydrolytic activity than a normal phospholipase.

TABLE 2

| nr | Sanofo egg yolk 8% salt Egg yolk gram | 2344-44 C89 18.5 PLU-7/ml Transferase #179 gram | Transferase #178-9 18.5 PLU-7/ml gram | #3108, Lecitase Ultra 1500 PLU-7/ml ml | Water gram | PLU-7/ml |
|---|---|---|---|---|---|---|
| 6 | 120 | 2.00 | | | 8.00 | 0.31 |
| 7 | 120 | | 10 | | 0 | 1.25 |
| 8 | 120 | | | 1.86 | 8.14 | 23.25 |
| 9 | 120 | | | | 10 | 0 |

The enzymatic reactions were conducted by scaling the egg yolk and the enzyme in a beaker. The samples were placed in a heating cabinet at 37° C. during slow agitation. After 1, 2 and 4 hours reaction time a sample was taken out for TLC analysis. After 4 hours reaction time the product was stored at 5° C. and used for mayonnaise experiments.

The TLC analyses of lipids extracted from enzyme treated egg yolk is shown in FIG. 48.

The TLC analysis in FIG. 48 shows a clear hydrolytic effect of Phospholipase #3108 on triglyceride during formation of free fatty acids, as well as some mono- and diglyceride. Phospholipase #3108 seem to have no effect on cholesterol. Both transferase samples clearly contribute to the formation of cholesterol ester concomitant with the reduction of the cholesterol content.

D. Enzyme Modified Egg Yolk in Mayonnaise

In order to investigate the effect of the modification of the egg yolk samples mentioned in Table 2, application trials were performed on mayonnaise with a fat content of 50%. A mayonnaise containing untreated egg yolk was also produced.

The aim of the investigation was to determine the impact of enzymatically modified egg yolks' emulsification properties and the impact on heat stability. All mayonnaise samples contained the same oil level and were emulsified with only egg yolk. The mayonnaise samples were all produced using a Koruma mixer (Disho V60/10) and heated during processing to 95° C. for 5 minutes.

Samples of the mayonnaises (FIG. 49) produced by enzyme treated egg yolk were nice and homogenous with no oil separation. The control sample separated in an oil and a water phase.

The particle size of oil droplet in the mayonnaise samples with enzyme treated egg yolk was measured on a Malvern Mastersizer. The sample was mixed with 0.1% SDS in 0.1 M phosphate buffer pH 7 prior to measurement. Reading was mean size of all particles as shown in Table 3.

TABLE 3

| Experiment | Enzyme | Mean particle size, μm |
|---|---|---|
| 6 | Transferase #179, 0.31 PLU-7/g | 12.9 |
| 7 | Transferase #178-9, 1.25 PLU-7/g | 7.2 |
| 8 | #3108, Lecitase Ultra, 23 PLU-7/g | 5.2 |

The results from the particle size measurement clearly show the effect of increased dosage of transferase from *A. salmonicida*. With the high dosage of transferase the particle size is close to the mayonnaise produced by Lecitase Ultra. It should however be kept in mind that Lecitase Ultra produces a lot of fatty acids, which might contribute to a finer particle distribution.

The oil droplet size of the mayonnaise prepared with the enzyme is significantly smaller than the oil droplet size of the mayonnaise prepared without the enzyme (i.e. the control mayonnaise).

Oxidation Stability

The oxidation stability of the mayonnaise samples 7 and 8 were analyzed on a ML OXIPRES with results shown in Table 4.

TABLE 4

| Sample | Induction period 1. determination hours | Induction period 2. determination hours |
|---|---|---|
| 7 | 37.44 | 38.08 |
| 8 | 35.68 | 35.52 |

Measurement of oxidation stability gave a clear significant difference in oxidation stability. The mayonnaise with transferase 179-8 treated egg yolk had a significant better oxidation stability than the mayonnaise with Lecitase Ultra treated egg yolk. This might be explained by the fact that Lecitase Ultra produces more free fatty acids which are more prone to oxidation that the corresponding fatty acid esters.

A sample of the egg yolks used for mayonnaise production were extracted with chloroform, and the lipids from the egg yolk were analysed by GLC with results shown in Table 5.

TABLE 5

| Experiment | Enzyme | Fatty acid | Cholesterol | Cholesterol ester | Triglyceride |
|---|---|---|---|---|---|
| 6 | Transferase #179 | 0.96 | 0.94 | 0.49 | 23.95 |
| 7 | Transferase #178-9 | 1.84 | 0.60 | 1.06 | 24.54 |
| 8 | #3108, Lecitase Ultra | 14.05 | 1.16 | 0.12 | 2.45 |
| 9 | Control | 0.48 | 1.16 | 0.13 | 22.87 |

The GLC results in Table 5 confirm the results form the TLC analysis that Lecitase Ultra produces a very high amount of free fatty acids and a large part of the triglyceride is hydrolysed. On the other hand the transferase produces only modest amount of free fatty acids and no triglycerides are hydrolysed. It is also clearly shown that transferase produce cholesterol ester from cholesterol.

The results indicate that the amount of PC in the "enzyme treated" mayonnaise is reduced as compared with the control mayonnaise, whilst the amount of LPC is increase in the enzyme treated mayonnaise as compared with the control mayonnaise. The increase in the amount of LPC may well explain the improved emulsification properties of the enzyme treated mayonnaise as compared with the control mayonnaise. The HPLC and GLC analyses also indicate a lower level of free cholesterol in the enzyme treated mayonnaise as compared with the control mayonnaise, probably due to the cholesterol being used as an acceptor molecule in the transferase reaction resulting in an increase in the amount of cholesterol esters in the enzyme treated mayonnaise as compared with the control mayonnaise. In addition, the results indicate that the amount of free fatty acids do not increases significantly when egg yolk is treated with the transferase. The results further indicate that the amount of free fatty acids produced in the foodstuff treated with the lipid acyltransferase is significantly lower than in the foodstuff treated with the control phospholipase, this is true even if the amount of lysolecithin formed in the foodstuffs is the same.

Example 8

Effect of *Aeromonas salmonicida* Transferase in Cakes

The effect of GCAT acyl-transferase form *Aeromonas salmonicida* is tested in a cake recipe. The enzyme is tested alone and in combination with other lipolytic enzymes. The enzymes are added to some of the cake ingredients or added together with the other cake ingredients before mixing the cake.

Preliminary results show that acyl-transferase combined with a triglyceride-hydrolysing enzyme improves the cake volume and crumb structure compared with a control.

In the following experiments a transferase from *A. salmonicida* and variants are tested alone and in combination with triglyceride hydrolysing enzymes. These enzymes are active on the lipid components in the egg and the shortening as well as on the carbohydrates, protein, glycerol and cholesterol (in egg), which forms part of the cake recipe.

Materials and Method
Enzyme
179, Acyl-transferase from *Aeromonas salmonicida*
Grindamyl EXEL 16, Lipase from *Thermomyces lanuginisus*
Cake Recipe:

| Ingredients | % | g |
|---|---|---|
| Sugar 35/20 | 20.37 | 204 |
| Cake flour, Albatros | 18.11 | 181 |
| Wheat starch | 5.21 | 52 |
| Baking powder | 0.36 | 4 |
| Pasteurised liquid whole egg | 22.63 | 226 |
| Shortening Vegao (Aarhus United) | 18.11 | 181 |
| Whey powder | 0.68 | 7 |
| Glucose sirup, 75% 42 DE | 4.53 | 45 |
| Glycerol | 1.36 | 14 |
| Salt | 0.32 | 3 |
| Rape seed oil | 6.34 | 63 |
| Potassium sorbate | 0.18 | 1.8 |

Equipment:
Mixer: Hobart N50 with a spatula
Oven: Simon cake oven
Procedure:
All ingredients must be tempered to room temperature.
1. Cream up sugar and shortening for 3 minutes—start at $2^{nd}$ speed and move to $3^{rd}$ speed within 30 sec
2. Add remaining ingredients—start at $1^{st}$ speed and move to $2^{nd}$ speed within 30 sec—mix total 5 min
3. Measure the volume of the batter in 1 dl cup
4. The pound cake tins are sprayed with "Babette" oil spread, and covered with paper
5. Scale 2×350 g into the pound cake tins
6. Spread out the mass evenly with a spatula
7. Before put in the oven—add a string of oil on top of the cake (lengthwise in the middle—to make the cake break in the middle
8. Bake for 50 min. at 180° C.
9. After baking take the tins out of the oven, and "drop" it on the table, before taking the cakes out of the tins
10. Take paper off the cakes and turn the right side up
11. The cakes are cooled on a grating for 60 min. before weighing and measuring of the volume Remarks:
The enzyme(s) used is/are added at the beginning of mixing or is/are added to some of the cake ingredients before added to the other cake ingredients.

The enzymes are only active during the mixing or reaction of cake components, and the enzymes are inactivated during baking of the cake.

Results.
The following experiments are conducted as shown in the following table:

|  |  | 1 | 2 | 3 | 4 |
|---|---|---|---|---|---|
| Whole egg | G | 250 | 250 | 250 | 250 |
| Glucose syrup, 75% DE 42 | G | 10 | 10 | 10 | 10 |
| #179 acyl-transferase, 26 PLU/ml | Ml | 25 |  | 25 |  |
| Grindamyl EXEL 16, | Mg |  | 37.5 | 37.5 |  |
| Water |  |  |  |  | 25 |

Egg, Glucose syrup and enzyme are reacted for 30 minutes at 37° C. and shortly after the eggs are use to produce cake according to the recipe mentioned above.

Preliminary results show that a combination of acyltransferase and a triglyceride hydrolysing lipase from *Thermomyces lanoginosus* improves the cake volume, and also the crumb structure, eating quality and appearance is improved compared with a water control. Preliminary results indicate in cake it may be preferably to use a combination of lipid acyl-transferase and a lipase.

Example 9

The purpose of These Experiments was to Test a Transferase from *A. hydrophila* Expressed in *E. coli*

The transferase reaction of *A. hydrophila* #135 (0.5 NEFA-PLU/ml) was tested in egg yolk. The experimental set-up is shown in Table 6.

TABLE 6

| Nr | Reaction time Minutes | Egg yolk Gram | #135 conc. Units, PLU-NEFA |
|---|---|---|---|
| 1 | 30 | 1 | 0.000 |
| 2 | 30 | 2 | 0.100 |
| 3 | 60 | 2 | 0.100 |
| 4 | 150 | 2 | 0.100 |
| 5 | 240 | 2 | 0.100 |
| 6 | 1560 | 2 | 0.100 |
| 7 | 1560 | 1 | 0.000 |

The egg yolk was heated to 37° C. and the enzyme added. After reaction time 7 ml $CHCl_3$:Methanol 2:1 was added and mixed on a Whirley for 30 sec.

The sample was centrifuged 800×g for 10 minutes and the lower solvent phase isolated. 2 µl of this sample was applied onto a TLC Silica plate and eluted in elution solvent IV. The results from the TLC analysis is shown in FIGS. 50 and 51.

The methods and materials mentioned in this Example are those detailed in Examples above.

Samples from this experiment was also analysed by GLC as TMS derivatives. The results from the GLC analysis are shown in Table 7.

TABLE 7

GLC analysis of lipid from egg yolk

| No. | Reaction time min | Transferase #135 conc. Units/g egg yolk | Free fatty acid % | Cholesterol % | Cholesterolester % |
|---|---|---|---|---|---|
| 7 | control | 0 | 0.25 | 2.88 | 0.34 |
| 3 | 60 | 0.025 | 0.25 | 2.68 | 0.56 |
| 4 | 150 | 0.025 | 0.29 | 1.85 | 1.72 |
| 5 | 240 | 0.025 | 0.53 | 1.42 | 3.54 |
| 6 | 1560 | 0.025 | 0.95 | 0.3 | 4.43 |

From the GLC analysis of free fatty acid, cholesterol and cholesterolester it is possible to calculate the molar concentration of each component and calculate % transferase activity as shown in Table 7.

Calculation of % Transferase Activity

From the results the increase in free fatty acid, sterol esters are calculated $\Delta$% fatty acid=% Fatty acid(enzyme)−% fatty acid (control)

$\Delta$% sterol ester=% sterol/stanol ester(enzyme)−% sterol/stanol ester(control)

The transferase activity is calculated as % of the total enzymatic activity:

$$\% \text{ transferase activity} = \frac{(\Delta \% \text{ sterol ester}/(Mv \text{ sterol ester}) \times 100}{\Delta \% \text{ sterol ester}/(Mv \text{ sterol ester}) + \Delta \% \text{ fatty acid}/(Mv \text{ fatty acid})}.$$

where:
Mv sterol ester=average molecular weight of the sterol esters
Mv fatty acid=average molecular weight of the fatty acids

TABLE 8

Transferase activity in egg yolk of *A. hydrophila* #135

| No. | Reaction Time min | Transferase #135 conc. Units/g egg yolk | Free fatty acid mM | Cholesterol mM | Cholesterol-ester mM | Transferase activity % |
|---|---|---|---|---|---|---|
| 7 | Control | 0 | 8.9 | 74.5 | 5.3 | — |
| 3 | 60 | 0.05 | 8.9 | 69.3 | 8.7 | 100 |
| 4 | 150 | 0.05 | 10.4 | 47.8 | 26.5 | 93 |
| 5 | 240 | 0.05 | 18.9 | 36.7 | 54.6 | 77 |
| 6 | 1560 | 0.05 | 33.9 | 7.8 | 68.4 | 48 |

Both TLC and GLC analysis confirm that initially the transferase reaction of *A. hydrophila* #135 is the dominating reaction. After 150 minutes reaction time some hydrolytic activity occurs. After 1560 minutes the transferase reaction and the hydrolytic reaction has almost reached the same level. The results also indicate that as long as the acceptor molecule cholesterol is available the transferase reaction is the dominating reaction. When the concentration of cholesterol decreases the hydrolytic activity becomes more dominant.

Example 10

Assay for Measurement of Transferase Activity Using Egg Yolk as Substrate—Hereinafter Referred to as the "Egg Yolk Assay"

A lipid acyltransferase was isolated from *Aeromonas salmonicida* and expressed in *Bacillus subtilis*. The purpose of this work is to develop an analytical method, which is able to measure both transferase and hydrolytic activity of enzymes and from these analyses it is possible to define both transferase and hydrolytic activity of enzymes using a substrate which contain lecithin and cholesterol.

In this work egg yolk was used as substrate for the enzyme assay because egg yolk contain both lecithin and cholesterol and it is known that transferases and phospholipases works very well in this substrate.

The drawback by using egg yolk is that this substrate is a complex mixture of water, lipids, and proteins. Lipid components include glycerides, 66.2%; phospholipids, 29.6%; and cholesterol, 4.2%. The phospholipids consist of 73% lecithin, 15% cephalin, and 12% other phospholipids. Of the fatty acids, 33% are saturated and 67% unsaturated, including 42% oleic acid and 7% linoleic acid (ref. Kirk-Othmer Encyclopedia of Chemical Technology, John Wiley & Sons, Inc.)

Some variations in the egg yolk composition might be expected. In the literature (Biochimica et Biophysica Acta, 1124 (1992) 205-222) it is however mentioned that "The mature egg yolk of the domestic hen possesses remarkably constant lipid and lipoprotein composition despite much variation in dietary and environmental conditions", and further it is quoted "As a result the egg yolk continues to provide a food product of nearly constant composition, which serves to maintain its chemical and physical-chemical properties for reliable utilization in the baking, cosmetic and pharmaceutical industries"

This reference indicates that egg yolk composition is very constant and it was therefore decided to use hens egg yolk as substrate for the Egg Yolk Assay.

Quantification of lipid reaction products from enzymatic treatment of egg yolk was made by extraction of lipids from the substrate followed by GLC analysis of the lipid components Procedure
Materials.
Egg yolk: Pasteurised liquid egg yolk from Danæg Products A/S, DK-4000 Roskilde. .

HEPES buffer Sigma cat. no. H 3375
Chloroform, Analytical grade
Enzymes.
Purified lipid acyltransferase from A. salmonicida #178-9
Thermomyces lanuginosus lipase. GRINDAMYL EXEL 16, item nr. 147060 tion because lysolecithin is very polar and therefore could be partly distributed in the water phase.

The lipids isolated by solvent extraction was also analysed by GLC in order to quantify the amount of free fatty acid, cholesterol and cholesterol ester. The GLC results are shown in Table 10.

TABLE 10

GLC analysis of lipid from enzyme treated egg yolk. Results are in % based on lipid content.

|  |  |  | 15 Minutes | 30 Minutes | 60 Minutes | 120 Minutes | 1080 Minutes |
|---|---|---|---|---|---|---|---|
| Free fatty acids | Control | 1 | 0.328 | 0.304 | 0.332 | 0.333 | 0.369 |
|  | T. lanuginosus | 2 | 0.391 | 0.376 | 0.459 | 0.627 | 22.909 |
|  | A. salmonicida #178-9 | 3 | 1.007 | 1.668 | 4.013 | 6.761 | 15.098 |
| Cholesterol | Control | 1 | 3.075 | 2.968 | 3.103 | 3.056 | 3.099 |
|  | T. lanuginosus | 2 | 3.130 | 3.032 | 3.045 | 3.026 | 3.225 |
|  | A. salmonicida #178-9 | 3 | 2.835 | 1.912 | 0.356 | 0.220 | 0.206 |
| Cholesterol ester | Control | 1 | 0.416 | 0.397 | 0.422 | 0.408 | 0.437 |
|  | T. lanuginosus | 2 | 0.436 | 0.400 | 0.425 | 0.419 | 0.416 |
|  | A. salmonicida #178-9 | 3 | 1.414 | 2.988 | 6.107 | 6.694 | 5.760 |
| Triglyceride | Control | 1 | 76.153 | 73.505 | 75.565 | 79.344 | 77.382 |
|  | T. lanuginosus | 2 | 74.099 | 74.413 | 77.079 | 74.284 | 21.781 |
|  | A. salmonicida #178-9 | 3 | 73.781 | 73.342 | 77.857 | 82.040 | 72.117 |

(Control)
Enzyme Assay with Egg Yolk Substrate.
5 gram liquid egg yolk was scaled in a 20 ml Wheaton glass and heated to 35° C.
0.25 ml enzyme solution was added and a stopwatch is started.
At regular intervals 0.5 g samples were transferred to a 10 ml Dram glass.
20 µl 4M HCl was added in order to stop the enzyme reaction and acidify the fatty acid soap.
3 ml Chloroform was added. And the sample was mixed on a Whirley mixer for 30 sec.
The sample was centrifuged at 3000 g for 10 min and 0.8 ml of the chloroform phase was transferred to a tarred Dram glass. Chloroform was evaporated at 60° C. under a steam of nitrogen. The dram glass was scaled again.
The isolated lipids were analysed by GLC and TLC.
TLC analysis—as described herein.
GLC analysis—as described herein.
Results
For the Egg Yolk Assay using egg yolk as substrate the experiment shown in Table 9 was conducted.

TABLE 9

|  |  | 1 | 2 | 3 |
|---|---|---|---|---|
| Egg yolk, liquid. | gram | 5 | 5 | 5 |
| Transferase# 178-9, 32 PLU-7/ml* | ml |  |  | 0.25 |
| T. lanuginosus lipase, 200 LIPU/ml | ml |  | 0.25 |  |
| Water | ml | 0.25 |  |  |

0.5 g samples were taken out after 15, 30, 60 120 and 1080 minutes, and the lipid isolated by solvent extraction. The lipids were analysed by TLC using solvent I and IV respectively. Picture of the TLC plate is shown in FIG. 52.
The TLC analysis clearly indicates the activity of transferase #178-9 from A. salmonicida (sample 3). This can be seen from the decrease in the phospholipids PC and PE. The results also indicate that the amount of lysolecithin LPC is not as high as expected. This might indicate hydrolytic activity on lysolecithin or it might also be caused by insufficient extrac- From the results it was observed that almost all the cholesterol was esterified after 60 minutes in sample 3. It was concluded that for the first 30 minutes there was surplus substrate for the reaction. The results form samples taken out after 15 and 30 minutes were therefore used to calculate the activities of the enzymes.

Based on the information in table 10 and the fact that egg yolk contain 27% lipid the amount of micromole fatty acid and cholesterol ester produced per ml enzyme was calculated with results shown in Table 11

The results in Table 11 were obtained be the following calculations of the results from fatty acids in sample no. 3 (A. salmonicida, 15 min.)

Lipid in 5 g egg yolk=5*0.27=1.35 gram 1.35 gram lipid contain 1.007% fatty acids=1.35*1.007/100=0.01359 gram Average molecular weight of fatty acids is 272

0.01359 gram=0.01359*1000000/272 µmol=49.9798 µmol 0.25 ml enzyme is added

µmol Fatty acid/ml enzyme=49.9798/0.25=199.9

TABLE 11

| Micromole/ml enzyme |  | 0 min | 15 min | 30 min |
|---|---|---|---|---|
| Free fatty acid | Control |  | 65.01 | 60.37 |
|  | T. lanuginosa |  | 77.61 | 74.71 |
|  | Transferase #178-9 |  | 199.86 | 331.06 |
| Cholesterol ester | Control |  | 35.09 | 33.50 |
|  | T. lanuginosa |  | 36.77 | 33.73 |
|  | Transf. #178-9 |  | 119.29 | 252.15 |

From the results in Table 11 it is possible to calculate the change in amount of fatty acid and cholesterol ester caused by the enzyme relative to control as shown in Table 12.

TABLE 12

| Δ Micromole/ml enzyme | | 0 min | 15 min | 30 min |
|---|---|---|---|---|
| Free fatty acid | T. lanuginosus | 0 | 12.593 | 14.340 |
| | Transf. #178-9 | 0 | 134.843 | 270.691 |
| Cholesterol ester | T. lanuginosus | 0 | 1.677 | 0.235 |
| | Transf. #178-9 | 0 | 84.196 | 218.652 |

The amount of fatty acid or cholesterol ester produced as a function of time is shown in FIG. 53.

From the slope of the curve the hydrolytic activity (FFA formation) and the lipid acyltransferase activity (cholesterol ester formation) as a function of time was calculated. The relative transferase activity (% acyltransferase activity) and the relative hydrolytic activity were then calculated as shown in Table 13. The relative transferase activity was determined using the protocol for the determination of % acyltransferase activity as described hereinbefore. For example, calculation of relative activity for #178-9: Total activity is FFA activity+ transferase activity=9,023+7,2884=16,311 μmol/min/ml, Relative transferase activity=7,2884*100/16,311=44,7, Relative hydrolytic activity=9,023*100/16,311=55,3

TABLE 13

| T. lanuginosus | FFA activity | 0.4780 | μmol/min/ml |
|---|---|---|---|
| A. salmonicida #178-9 | FFA activity | 9.0230 | μmol/min/ml |
| T. lanuginosus | Cholesterol ester. Activity | 0.0078 | μmol/min/ml |
| A. salmonicida #178-9 | Cholesterol ester. Activity | 7.2884 | μmol/min/ml |
| T. lanuginosus | Relative transferase activity | 1.6 | |
| A. salmonicida #178-9 | | 44.7 | |
| T. lanuginosus | Relative hydrolytic activity | 98.4 | |
| A. salmonicida #178-9 | | 55.3 | |

The results in Table 13 confirmed that the transferase enzyme from *A. salmonicida* has a significant transferase activity, but the results also confirmed that this enzyme has a significant hydrolytic activity.

The lipase from *T. lanuginosus* mainly has hydrolytic activity, and the relative transferase activity 1.6 was not a proof of any transferase activity but was explained by the uncertainty of the analysis.

Conclusion.

Egg yolk was used as substrate for the measurement of transferase and hydrolase activity of lipid acyltransferase from *Aeromonas salmonicida* and a lipase from *Thermomyces lanuginosus*. Under assay conditions there was initially a linear relation between cholestererol ester and free fatty acid formation and time for the lipid acyltransferase enzyme. Based on this linear relationship it was possible to calculate the hydrolytic activity (FFA formation) and the transferase activity (cholesterol ester formation). The relative hydrolytic and transferase activity was also calculated. The lipid acyltransferase (in this case a GCAT) from *Aeromonas salmonicida* showed almost equal hydrolytic and transferase activity under these assay conditions.

Lipase from *Thermomyces lanuginosus* showed very low hydrolytic activity and the transferase activity was not significant.

Example 11

Transferase Assay in High Water Egg Yolk

Introduction

A lipid acyltransferase in accordance with the present invention was isolated from *Aeromonas salmonicida* and expressed in *Bacillus subtilis*. Initial experiments have shown that this enzyme is very efficient in transferring fatty acid from lecithin to cholesterol using egg yolk as a substrate.

In the following experiments the transferase reaction was studied in further detail using egg yolk as a substrate with special focus on the water concentration in the substrate.

Procedure

Materials.

Egg yolk: Pasteurised liquid egg yolk from Danæg Products A/S, DK-4000 Roskilde.

HEPES buffer Sigma cat. no. H 3375

Chloroform, Analytical grade

Squalane, analytival grade

Enzymes.

178-9 Lipid acyl transferase in accordance with present invention from *A. salmonicida*

2427 Phospholipase A1 from *Fusarium oxysporum*. LIPOPAN® F from Novozymes, DK (comparative lipolytic enzyme)

1991 Phospholipase A2 from Pancreas, LIPOMOD 22L from Biocatalysts, UK (comparative lipolytic enzyme)

Enzyme Assay with Egg Yolk Substrate.

5 gram liquid egg yolk substrate was scaled in a 20 ml Wheaton glass and heated to 35° C.

Water and enzyme solution was added and a stopwatch is started.

At regular intervals 0.5 g samples was transferred to a 10 ml Dram glass.

20 μl 4M HCl was added in order to stop the enzyme reaction and acidify the fatty acid soap.

3 ml Chloroform was added. And the sample was mixed on a Whirley mixer for 30 sec.

The sample was centrifuged at 3000 g for 10 min and 0.8 ml of the chloroform phase was transferred to a tarred Dram glass. Chloroform was evaporated at 60° C. under a steam of nitrogen. The dram glass is scaled again.

The isolated lipids are analysed by GLC

GLC Analysis

Perkin Elmer Autosystem 9000 Capillary Gas Chromatograph equipped with WCOT fused silica column 12.5 m×0.25 mm ID×0.1μ film thickness 5% phenyl-methyl-silicone (CP Sil 8 CB from Chrompack).

Carrier gas: Helium.

Injector. PSSI cold split injection (initial temp 50° C. heated to 385° C.), volume 1.0 μl Detector FID: 395° C.

| Oven program: | 1 | 2 | 3 |
|---|---|---|---|
| Oven temperature, ° C. | 90 | 280 | 350 |
| Isothermal, time, min. | 1 | 0 | 10 |
| Temperature rate, ° C./min. | | 15 | 4 |

Sample preparation: 30 mg of sample was dissolved in 9 ml Heptane:Pyridin, 2:1 containing internal standard heptadecane, 0.5 mg/ml. 300 μl sample solution was transferred to a crimp vial, 300 μl MSTFA (N-Methyl-N-trimethylsilyl-trifluoraceamid) was added and reacted for 20 minutes at 60° C.

Calculation: Response factors for mono-di-triglycerides and free fatty acid were determined from Standard 2 (mono-di-triglyceride), for Cholesterol, Cholesteryl palmitate and Cholesteryl stearate the response factors were determined from pure reference material (weighing for pure material 10 mg).

Results

Egg yolk containing 2% squalane was used as substrate for the reactions. Squalane was added as an internal standard for the GLC analysis, in order to quantify the lipid components in egg yolk.

The experiment was set up as shown in Table 14.

The results in Table 16. were also analysed statistically using a Statgraphic Multifactor ANOVA. The statistical results in FIG. 54 confirm that Phospholipase A1; #2427 and phospholipase A2, #1991 have no transferase activity

TABLE 14

|  |  | 1 | 2 | 3 | 4 | 5 | 6 | 7 | 8 |
|---|---|---|---|---|---|---|---|---|---|
| Substrate, egg yolk with 2% squalane | g | 5 | 5 | 5 | 5 | 5 | 5 | 2.5 | 2.5 |
| Transferase # 178-9, 14 PLU-7/ml | ml |  | 0.25 |  |  | 0.25 |  | 0.13 |  |
| LIPOPAN ® Fsolution, 200 PLU-7/ml | ml |  |  | 0.25 |  |  |  |  | 0.13 |
| #1991 Phospholipase A2, 6300 PLU/ml | ml |  |  |  | 0.25 |  | 0.25 |  |  |
| Water | ml | 0.25 |  |  |  | 3.8 | 3.8 | 8.75 | 8.75 |

Samples were taken out after 30, 60 and 120 minutes and analysed according the method described above (0.5 ml (exp 1-4) 0.86 ml (exp. 5-6) and 2.2 ml (exp. 7-8) samples were taken).

The results from the GLC analysis are shown in Table 15. The GLC results were expressed in percent of the substrate (egg yolk). The table also indicate the reaction time and the total amount of water in the reaction mixture.

whereas the transferase #178-9 showed almost 50% transferase activity under these assay conditions.

The effect of water content in the assay on the transferase activity of the transferase #178 was also analysed statistically as shown in FIG. 55. These results indicate that in the range from 54 to 89% water in the assay there was no strong effect of the water content on the relative transferase activity.

TABLE 15

| Enzyme | Reaction time minutes | Water % in reaction | GLC % Fatty acid | GLC % cholesterol | GLC % cholesterol ester |
|---|---|---|---|---|---|
| Control | 120 | 54 | 0.247 | 0.863 | 0.083 |
| #178 | 30 | 54 | 0.422 | 0.669 | 0.445 |
| #178 | 60 | 54 | 0.515 | 0.549 | 0.672 |
| #178 | 120 | 54 | 0.711 | 0.364 | 1.029 |
| #2427 | 30 | 54 | 2.366 | 0.848 | 0.090 |
| #2427 | 60 | 54 | 3.175 | 0.837 | 0.088 |
| #2427 | 120 | 54 | 3.926 | 0.833 | 0.082 |
| #1991 | 30 | 54 | 1.606 | 0.911 | 0.083 |
| #1991 | 60 | 54 | 1.701 | 0.838 | 0.080 |
| #1991 | 120 | 54 | 1.781 | 0.763 | 0.053 |
| #178 | 30 | 73 | 0.377 | 0.764 | 0.495 |
| #178 | 60 | 73 | 0.488 | 0.665 | 0.719 |
| #178 | 120 | 73 | 0.626 | 0.426 | 0.931 |
| #2427 | 30 | 73 | 2.471 | 0.853 | 0.092 |
| #2427 | 60 | 73 | 3.284 | 0.858 | 0.087 |
| #2427 | 120 | 73 | 4.176 | 0.837 | 0.081 |
| #178 | 30 | 89 | 0.344 | 0.720 | 0.308 |
| #178 | 60 | 89 | 0.443 | 0.725 | 0.446 |
| #178 | 120 | 89 | 0.610 | 0.597 | 0.607 |
| #2427 | 30 | 89 | 0.510 | 0.167 | 0.010 |
| #2427 | 60 | 89 | 0.602 | 0.133 | 0.010 |
| #2427 | 120 | 89 | 0.867 | 0.147 | 0.009 |

Based on the analyses of fatty acid, cholesterol and cholesterol ester it was possible to calculate the amount of free fatty acid, and cholesterol ester produced as a function of reaction time and water content. Based on these results it was then possible to calculate the total enzymatic activity as the sum of the fatty acid formation and the cholesterol ester formation. The relative hydrolytic activity and the relative transferase activity (i.e. % acyltransferase activity) were then calculated with the results shown in Table 16.

The impact of reaction time on transferase activity for transferase #178 was evaluated with results shown in Table 16 and FIG. 56. The results in FIG. 56 indicate that the relative transferase activity decreases as a function of reaction time. This might be explained by the fact that most of the acceptor molecule cholesterol is consumed and therefore the relative hydrolytic activity increases. The negative values for transferase reaction for #2427 only indicate no transferase activity within the variation for the analytical method.

TABLE 16

| Enzyme | Reaction time minutes | Water % in reaction mixture | Fatty acid Produced | Cholesterol Consumed | Cholesterol ester produced | Hydrolytic activity % | Transferase activity % |
|---|---|---|---|---|---|---|---|
| #178 | 30 | 54 | 0.175 | 0.194 | 0.362 | 53 | 47 |
| #178 | 60 | 54 | 0.268 | 0.314 | 0.589 | 52 | 48 |

TABLE 16-continued

| Enzyme | Reaction time minutes | Water % in reaction mixture | Fatty acid Produced | Cholesterol Consumed | Cholesterol ester produced | Hydrolytic activity % | Transferase activity % |
|---|---|---|---|---|---|---|---|
| #178  | 120 | 54 | 0.464 | 0.499  | 0.946  | 53  | 47  |
| #2427 | 30  | 54 | 2.119 | 0.015  | 0.007  | 100 | 0   |
| #2427 | 120 | 54 | 2.928 | 0.026  | 0.005  | 100 | 0   |
| #2427 | 60  | 54 | 3.679 | 0.030  | −0.001 | 100 | 0   |
| #1991 | 30  | 54 | 1.359 | −0.048 | 0.000  | 100 | 0   |
| #1991 | 60  | 54 | 1.454 | 0.025  | −0.003 | 100 | 0   |
| #1991 | 120 | 54 | 1.534 | 0.100  | −0.030 | 101 | −1  |
| #178  | 30  | 73 | 0.130 | 0.099  | 0.412  | 42  | 58  |
| #178  | 60  | 73 | 0.241 | 0.198  | 0.636  | 47  | 53  |
| #178  | 120 | 73 | 0.379 | 0.437  | 0.848  | 51  | 49  |
| #2427 | 30  | 73 | 2.224 | 0.010  | 0.009  | 100 | 0   |
| #2427 | 60  | 73 | 3.037 | 0.005  | 0.004  | 100 | 0   |
| #2427 | 120 | 73 | 3.929 | 0.026  | −0.002 | 100 | 0   |
| #178  | 30  | 89 | 0.097 | 0.143  | 0.225  | 50  | 50  |
| #178  | 60  | 89 | 0.196 | 0.138  | 0.363  | 56  | 44  |
| #178  | 120 | 89 | 0.363 | 0.266  | 0.524  | 62  | 38  |
| #2427 | 30  | 89 | 0.263 | 0.696  | −0.073 | 113 | −13 |
| #2427 | 60  | 89 | 0.355 | 0.730  | −0.073 | 110 | −10 |
| #2427 | 120 | 89 | 0.620 | 0.716  | −0.074 | 105 | −5  |

Conclusion.

The lipid acyltransferase from *Aeromonas salmonicida* was tested in egg yolk as substrate and with different levels of water content. This enzyme was compared with control lipolytic enzymes, namely Phospholipase A1 from *Fusarium oxysporum* and a Phospholipase A2 from pancreas.

The results have proved that only the transferase catalysed the transferase reaction between lecithin and cholesterol during formation of cholesterol ester. The results showed that in the range from 54% to 89% water in the substrate the relative transferase activity was almost the same for transferase from *Aeromonas salmonicida*.

Example 12

The "Transferase Assay in Buffered Substrate" for Measurement of Acyltransferase Activity (e.g. for Use in a Foodstuff Using Lecithin and Cholesterol)

The lipid acyltransferase was isolated from *Aeromonas salmonicida* and expressed in *Bacillus subtilis*. This enzyme is very efficient in transferring fatty acid from lecithin to cholesterol during formation of cholesterol esters. It has also been shown that the enzyme has some hydrolytic activity, which is observed by the formation of free fatty acid. Traditional phospholipases (EC3.1.1.4 and EC3.1.1.32) have the ability to hydrolyse lecithin during formation of free fatty acids and lysolecithin, and no transferase reactions has been reported for these enzymes.

We detail herein an assay that is able to measure both transferase and hydrolytic activity of enzymes and thus to identify lipid acyltransferases in accordance with the present invention, the assay uses a substrate which contains lecithin and cholesterol. In this work a substrate based on phosphatidylcholine and cholesterol dispersed in a buffer was used. Quantification of reaction products was made by extraction of lipids from the substrate followed by GLC analysis of the lipid components.

Procedure
Materials
L-alpha-Phosphatidylcholine 95% (Plant) Avanti no. 441601
Cholesterol: Sigma cat. C 8503
Cholesteryl Palmitate, Sigma C 6072
Cholesteryl Stearate, Sigma C 3549
HEPES buffer Sigma cat. No. H 3375
Chloroform, Analytical Grade.
Enzymes
Purified GCAT from *A. salmonicida* #178-9

TLC analysis was carried out as described in Example 6.

GLC analysis was carried out as described in Example 11.

Results: Transferase assay based on phosphatidylcholine and cholesterol as substrate.

In the following the transferase activity of the transferase was tested in a substrate based on phosphatidylcholine and cholesterol according to the following procedure.

450 mg phosphatidylcholine (>95% PC Avanti item no. 441601) and 50 mg cholesterol was dissolved in chloroform and evaporated to dryness under vacuum. 300 mg cholesterol/phosphatidylcholine mixture was transferred to a Wheaton glass and 15 ml 50 mM HEPES buffer pH 7 was added. The lipid was dispersed in the buffer during agitation.

The substrate was heated to 35° C. during mixing with a magnetic stirrer and 0.25 ml enzyme solution was added. This is a very high water environment of approximately 95% water.

Samples of 2 ml were taken out after 0, 5, 10, 15, 25, 40 and 60 minutes reaction time. Immediately 25 µl 4M HCl was added to acidify the free fatty acid and stop the enzyme reaction. 3.00 ml chloroform was added, and the sample was shaken vigorously on a Whirley for 30 seconds. The sample was centrifuged and 2 ml of the chloroform phase was isolated and filtered through 0.45-µm filters into a 10 ml tared Dram glass. The chloroform was evaporated under a stream of nitrogen at 60° C., and the samples were scaled again. The extracted lipid was analysed by GLC.

The results from the GLC analysis are shown in Table 17. The results are expressed in % calculated on extracted lipid. The amount of fatty acid and cholesterol ester formed as a function of time is illustrated in. FIG. 57 It can be concluded from FIG. 57 that the enzyme reaction is not linear as a function of time, because an initially strong both hydrolytic and transferase activity is observed. After approximately 10 minutes and until approximately 60 minutes the reaction shows an almost linear response of fatty acid and cholesterol ester formation as a function of time. It was therefore decided to look at the enzymatic reaction in this time interval.

TABLE 17

|  | Minutes | | | | | | |
| --- | --- | --- | --- | --- | --- | --- | --- |
|  | 0 | 5 | 10 | 15 | 25 | 40 | 60 |
| Cholesterol, % | 10.064 | 8.943 | 8.577 | 8.656 | 8.102 | 7.856 | 7.809 |
| Cholesterol ester, % | 0.000 | 1.571 | 2.030 | 2.058 | 2.282 | 2.659 | 3.081 |
| FFA total, % | 0.260 | 1.197 | 1.239 | 1.466 | 2.445 | 2.943 | 3.940 |

From the knowledge about the amount of lipid in the reaction mixture and the amount of enzyme added it was possible to calculate the formation of fatty acid and cholesterol ester expressed in μmol/ml enzyme (Table 18 and FIG. 58)

TABLE 18

|  | Minutes | | | | |
| --- | --- | --- | --- | --- | --- |
|  | 10 μmol/ml | 15 μmol/ml | 25 μmol/ml | 40 μmol/ml | 60 μmol/ml |
| FFA total | 58.1 | 68.7 | 114.6 | 138.0 | 184.7 |
| Cholesterol ester | 88.8 | 90.0 | 99.3 | 115.6 | 133.8 |

From the results in Table 18 and the slope of the curves in FIG. 58 it was possible to calculate the amount of fatty acid and cholesterol ester as a function of time expressed in μmol/min per ml enzyme.

The calculation of the hydrolytic activity and the transferase activity is shown in Table 19. The relative transferase activity was determined using the protocol for the determination of % acyltransferase activity as described hereinbefore.

TABLE 19

| Hydrolytic activity (fatty acid) | 2.52 | μmol/min per ml enzyme |
| --- | --- | --- |
| Transferase activity(cholesterol ester) | 0.94 | μmol/min per ml enzyme |
| Total activity | 3.45 | μmol/min per ml enzyme |
| Relative Transferase activity | 27.1 | % |
| Relative hydrolytic activity | 72.9 | % |

Screening of Other Enzymes for Transferase Activity.

The method mentioned above was used to screen different lipolytic enzymes for transferase and hydrolytic activity. The enzymes were tested as shown in Table 20

TABLE 20

|  |  | 1 | 2 | 3 | 4 | 5 |
| --- | --- | --- | --- | --- | --- | --- |
| Substrate | ml | 15 | 15 | 15 | 15 | 15 |
| #178-9Transferase | ml | 0.25 |  |  |  |  |
| *A. salmonicida* 32 PLU-7/ml |  |  |  |  |  |  |
| 5% #3016, LIPOPAN ® F | ml |  | 0.25 |  |  |  |
| (*F. oxysporum*) |  |  |  |  |  |  |
| 5%, *Thermomyces lanuginosus* | ml |  |  | 0.25 |  |  |
| 5% *Candida rugosa* #2983 | ml |  |  |  | 0.25 |  |
| 5% *Candida cylindracea* #3076 | ml |  |  |  |  | 0.25 |

The substrate containing 300 mg phosphatidylcholine/cholesterol dispersed in 50 mM HEPES buffer pH 7.0 was heated to 35° C. with agitation. Enzyme solution was added and the sample was kept at 35° C. with agitation. Samples were taken out with regular interval and extracted with Chloroform. The isolated lipids were analysed by GLC with results shown in Table 21.

TABLE 21

| Sample | | | | | | | | |
| --- | --- | --- | --- | --- | --- | --- | --- | --- |
| 1 | Transferase 178-9 | | | | | | | |
|  | Minutes | 0 | 5 | 10 | 15 | 25 | 40 | 60 |
|  | FFA | 1.216 | 2.516 | 2.983 | 2.62 | 2.894 | 3.448 | 3.911 |
|  | Cholesterol | 7.547 | 6.438 | 6.365 | 6.15 | 6.136 | 5.936 | 5.662 |
|  | Chl. Ester | 0 | 1.835 | 2.177 | 2.44 | 2.58 | 2.851 | 3.331 |
| 2 | *Fusarium oxysporum* (LIPOPAN ® F) | 0 | 5 | 10 | 15 | 25 | 40 | 60 |
|  | FFA | 1.216 | 1.345 | 1.796 | 1.95 | 2.487 | 2.424 | 2.977 |
|  | Cholesterol | 7.547 | 7.309 | 7.366 | 7.33 | 7.429 | 7.341 | 7.326 |
|  | Chl. Ester | 0 | 0.26 | 0.386 | 0.35 | 0.267 | 0.36 | 0.394 |
| 3 | *Thermomyces lanuginosus* | 0 | 5 | 10 | 15 | 25 | 40 | 60 |
|  | FFA | 1.216 | 0.853 | 0.875 | 1 | 0.896 | 1.105 | 1.009 |
|  | Cholesterol | 7.547 | 7.384 | 7.639 | 7.63 | 7.675 | 7.603 | 7.529 |
|  | Chl. Ester | 0 | 0 | 0 | 0 | 0 | 0 | 0 |
| 4 | *Candida rugosa* (#2938) | 0 | 5 | 10 | 15 | 25 | 40 | 60 |
|  | FFA | 1.216 | 0.982 | 0.987 | 1.02 | 1.135 | 1.131 | 1.15 |
|  | Cholesterol | 7.547 | 7.438 | 7.656 | 7.66 | 7.638 | 7.575 | 7.585 |
|  | Chl. Ester | 0 | 0 | 0 | 0 | 0 | 0 | 0 |
| 5 | *Candida cylandracea* (#3076) | 0 | 5 | 10 | 15 | 25 | 40 | 60 |
|  | FFA | 1.216 | 1.032 | 1.097 | 1.07 | 1.203 | 1.131 | 1.43 |
|  | Cholesterol | 7.547 | 7.502 | 7.425 | 7.65 | 7.619 | 7.502 | 7.411 |
|  | Chl. Ester | 0 | 0 | 0 | 0 | 0 | 0 | 0 |

From the GLC analysis it was observed that only the lipid acyltransferase (178-9) produced significant amount of cholesterol ester and fatty acids. Phospholipase from *Fusarium oxysporum* also gave a steady increase in free fatty acid but only an initial small amount formation of cholesterol ester was formed but no increase in cholesterol ester as a function of time was observed.

Based on the knowledge about the amount of lipid substrate and the GLC analyses it was possible to calculate the relative transferase activity and the relative hydrolytic activity based on the results from 10 to 60 minutes reaction time. The results from Transferase 178-9 and *Fusarium oxysporum* lipase are shown in Table 21. The other enzymes tested showed no activity.

TABLE 21

|  | Transferase 178-9 | *Fusarium oxysporum* |
|---|---|---|
| Hydrolytic activity, micromole/min per ml enzyme | 1.03 | 0.96 |
| Transferase activity, micromole/min per ml enzyme | 0.40 | 0.01 |
| Total activity, micromole/min per ml enzyme | 1.43 | 0.98 |
| Relative hydrolytic activity | 71.8 | 98.7 |
| Relative transferase activity | 28.2 | 1.3 |

The result shown in Table 21 confirm a significant transferase activity from the lipid acyltransferase (sample 178-9). It is also observed that the relative transferase activity is in good agreement with the experiment mentioned in Table 19

A very low transferase activity form *Fusarium oxysporum* phospholipase is however observed. This transferase level is so low that it falls within the uncertainty of the analysis. As expected *Fusarium oxysporum* phospholipase has a significant hydrolytic activity.

Conclusion.

Instead of egg yolk (shown in Example 11) an artificial substrate based on purified phosphatidylcholine and cholesterol was used as a substrate to measure the activity of transferase from *Aeromonas salmonicida*. Between 10 minutes and 60 minutes reaction time the assay gave an almost linear formation of free fatty acids and cholesterol ester as a function of time. Based on the activity between 10 and 60 minutes reaction time the hydrolytic activity and the transferase activity was calculated.

The concentration of substrates in this assay was relatively lower than in egg yolk, and the amount of water in the assay was relatively higher.

Based on the results from the assay of the lipid acyltransferase (in this instance a GCAT) from *Aeromonas salmonicida* in a artificial substrate of phosphatidylcholine/cholesterol in buffer it is concluded that this enzyme has very good transferase activity also in a system with a very high water content.

Both assays based on egg yolk (see Example 11) and phosphatidylcholine/cholesterol in buffer (Example 12), can be used to measure the transferase and hydrolytic activity of enzymes. The egg yolk is preferred from the point of view that the hydrolytic and the transferase activity is linear as a function of time, but the phosphatidylcholine/cholesterol in buffer is only linear within a certain time limit.

Example 13

Food Emulsions

The effect of enzyme modified liquid egg yolk was tested in a standard Food emulsion recipe with 60% oil.

Standard methods and materials are as per those detailed in the Examples above.

The egg yolk was treated with a lipid acyl transferase from *Aeromonas salmonicida* (#138) or phospholipase, namely a commercially available enzyme LipopanF® (Novozymes A/S, Denmark) (#2938) as shown in Table 22.

TABLE 22

Enzyme treatment of egg yolk.

|  |  | 1 | 2 | 3 | 4 |
|---|---|---|---|---|---|
| Egg Yolk, Sanofo product no 1123P2 | Gram | 10 | 10 | 10 | 10 |
| #138, 10 PLU/ml | Ml | 1 | 1 |  |  |
| #2938, 200 PLU/ml | Ml |  |  | 1 |  |
| Water | Ml |  |  |  | 1 |
| Reaction time | Minutes | 210 | 360 | 210 | 210 |

TLC analysis of the egg yolk lipids from enzyme treated egg yolk (Table 9) is shown in FIGS. 59 and 60.

In this experiment the dosage of #2938 was increased by a factor of 10 and this gave a very clear activity on egg yolk. The amount of free fatty acid increased significantly and lecithin (PC) was hydrolysed to lysolecithin (LPC). The transferase #138 gave a clear transferase reaction because free cholesterol was converted to cholesterol ester and part of the lecithin was converted to lysolecithin.

Another interesting aspect of the enzyme modification was the consistency of the product. The sample treated with Phospholipase #2938 became very solid, whereas the samples treated with the lipid acyltransferase #138 kept the same liquid consistency as the control sample (see FIG. 61).

These modified egg yolks were tested in a Food Emulsion recipe shown in Table 23.

TABLE 23

Mayonnaise with enzyme modified egg yolk.

|  | 0 % | 1a % | 2a % | 3a % | 4a % |
|---|---|---|---|---|---|
| Rapsolie | 60 | 60 | 60 | 60 | 60 |
| Egg yolk, Sanofo product no. 1123P2 | 2.8 |  |  |  |  |
| Enz. Modified egg yolk no. 1 |  | 2.8 |  |  |  |
| Enz. Modified egg yolk no. 2 |  |  | 2.8 |  |  |
| Enz. Modified egg yolk no. 3 |  |  |  | 2.8 |  |
| Control (untreated) egg yolk no. 4 |  |  |  |  | 2.8 |
| Water | 39 | 36.2 | 36.2 | 36.2 | 36.2 |
| Vinegar, 10% acetic acid | 1 | 1 | 1 | 1 | 1 |

Modified egg yolks 1 and 2 were treated with the lipid acyl transferase; and modified egg yolk 3 was treated with the commercially available phospholipase.

The food emulsion was produced as an oil in water emulsion according to the following procedure: Egg yolk and water was scaled in a beaker. The oil was scaled separately.

A Turrax mixer (20000 rpm) was immersed in the water phase. Oil was pumped to the water phase at a constant speed over 2 minutes. The mixing continued for further 1 minute. The vinegar was then added and mixed for 5 seconds.

The stability of the emulsion was tested in a heating cabinet at 100° C. After 2 hours at 100° C. the emulsion was evaluated (see FIG. 62).

The emulsion stability of untreated egg yolk was quite good in this experiment. Treatment of egg yolk with the lipid acyltransferase #138 however improved the stability because the amount of water separation was reduced. Egg yolk treated with phospholipase #2938 gave a very unstable emulsion with almost complete separation of the oil- and the water phase at 100° C.

It is considered that in some applications the use of the compositions and methods of the invention can provide enhanced thermal stability of emulsions, such as oil in water salad dressings and the like. This is particularly important in food emulsions which are pasturised to ensure long shelf life and/or are heated prior to serving, e.g. in pre-prepared meals for re-heating prior to serving (e.g. microwave meals). Although not wishing to be bound by any particular theory, it is considered that in some applications the accumulation of free fatty acid may be determental to the thermal stability of such emulsions. It should be recognised that the enhanced thermal stability of the food emulsions produced using the methods of the invention, may not be found, or even desirable, in all food applications. It will be apparent to the person skilled in the art in which applications such characteristics are desirable, and the stability of the emulsions can be easily determined using a simple heat tests, equivalent to, for example pasturisation and or microwave reheating. The inventors have discovered that in a preferable embodiment the food emulsions obtained using the enzymes of the invention have enhanced thermal stability.

Example 14

Transferase Reaction in Plant Sterol Enriched Egg Yolk

Transferase form *Aeromonas salmonicida* was able to catalyse to formation of lysolecithin, monoglyceride and plant sterol esters in egg yolk enriched with plant sterol and glycerol. The same enzyme was also tested in a low water system containing palm oil, lecithin, plant sterol and glycerol By TLC and GLC analyses it was shown that monoglyceride, and plant sterol esters were produced under these reaction conditions.

Introduction:

The transferase from *Aeromonas salmonicida* was tested for transferase activity in almost water free system of lecithin, fat, plant sterol and glycerol.

Materials:

Egg yolk: Pasteurised liquid egg yolk from Danæg Products A/S, DK-4000 Roskilde
GCAT transferase purification 178-9, 32 PLU-7/ml(Journal 2254-100)
Soya lecithin. Yolkin from Aarhus United, Denmark.
Palm oil 43, from Aarhus United, Denmark.
L-α Phosphatidylcholine 95% Plant (Avanti #441601)
Sitosterol, Sigma no S5753
Plant Sterol: Generol N122 from Cognis, Germany
Glycerol Item no. 085915

Results

Initial screening of transferase activity on plant sterol and glycerol was conducted in egg yolk as shown in Table 24.

TABLE 24

|  |  | 1 | 2 | 3 | 4 |
|---|---|---|---|---|---|
| Egg yolk | Gram | 1 | 1 | 1 | 1 |
| Glycerol | Gram | 0.1 | 0.1 |  |  |
| Sitosterol:olie 3:7 | Gram |  |  | 0.13 | 0.13 |
| Transferase #178-9 | Units | 1 |  | 1 |  |
| Water |  |  | * |  | * |

* Water corresponding to the amount of water in the enzyme solution = 83 μl

The ingredients were mixed and heated to 37° C. and kept at this temperature during agitation with a magnetic stirrer.

0.1 gram samples were taken out after 3 and 23 hours and analysed by TLC.

The results from the TLC analysis is shown in FIG. 63.

The result in FIG. 63 indicated that both cholesterol and plant sterols were esterified by the transferase reaction, concomitant with the formation of lysolecithin (sample 3 and 4), because almost all free sterol and cholesterol was converted to the corresponding ester in sample 3.

The results also indicated that the sample with only glycerol and egg yolk produced monoglyceride. The amount of monoglyceride needs to be confirmed by GLC analysis. When sterol was added together with glycerol (sample 3) the amount of monoglyceride was very low and not detectable by TLC. This indicated that as long as there were surplus of sterol or cholesterol the transferase reaction using glycerol was modest.

In another experiment the transferase enzyme 178-9 was added to a mixture soybean lecithin, glycerol and plant sterol, in order to study the catalytic activity of the enzyme in this reaction mixture.

The composition of the reaction mixtures in these experiments are shown in Table 25

TABLE 25

|  |  | 1 | 2 | 3 | 4 | 5 | 6 |
|---|---|---|---|---|---|---|---|
| Soya lecithin | gram | 1.875 | 2.25 | 1.875 | 2.5 | 3.5 | 3.5 |
| Plantesterol; Generol N 122 | gram | 0.225 | 0.225 | 0 | 0 | 0.225 | 0.5 |
| Palm oil 43 | gram | 2.675 | 2.25 | 2.8 | 2.125 | 1.062 | 0.831 |
| Glycerol | gram | 0.225 | 0.275 | 0.325 | 0.375 | 0.248 | 0.238 |
| Transferase #178-9, 32 PLU/ml | ml | 0.2 | 0.2 | 0.2 | 0.2 | 0.2 | 0.2 |

The experiment was conducted by mixing the lipid components during agitation at 46° C. The enzyme was added and samples were taken out after 4 and 24 hours.

The samples were analysed by TLC as shown in FIG. 64.

Sample from experiment 2, 4 and 5 after 24 hours reaction time were also analysed by GLC with results shown in Table 26

TABLE 26

|  |  | 2 | 4 | 5 |
|---|---|---|---|---|
| Glycerol | % | 3.16 | 5.71 | 4.17 |
| Fatty acids | % | 4.23 | 5.36 | 6.67 |
| Mono | % | 2.24 | 3.87 | 3.92 |
| Sterol | % | 2.13 |  | 2.62 |
| Sterolester | % | 2.89 |  | 2.14 |

The results confirmed that transferase 178-9 was able to catalyse to formation plant sterol esters and monoglyceride from a reaction mixture containing soybean lecithin, glycerol and plant sterol. Such reaction mixture could be of interest for use in margarine production where monoglyceride is wanted for their emulsification properties and plant sterol esters for their cholesterol lowering effect.

Conclusion

CGAT transferase from *Aeromonas salmonicida* was able to catalyse the formation of plant sterol esters and monoglyceride in egg yolk where plant sterol and glycerol was added. The same enzyme also catalysed the formation of plant sterol esters and monoglyceride in a mixture of palm oil, lecithin, plant sterol and glycerol. This enzyme therefore is of interest for use in margarine and other oil containing food products where monoglyceride and lysolecithin are needed for improved emulsification and the plant sterol ester for their cholesterol lowering effects.

Example 15

Immobilisation of a Lipid Acyltransferase from *Aeromonas salmonicida* and the Use in the Synthesis of Sterol Esters A lipid acyltransferase (in this instance a GCAT) from *A. salmonicida* was immobilised on Celite by acetone precipitation. 10 ml enzyme solution in 20 mM TEA buffer pH 7 was agitated slowly with 0.1 gram Celite 535 535 (from Fluka) for 2 hours at room temperature.

50 ml cool acetone was added during continued agitation. The precipitate was isolated by centrifugation 5000 g for 1 minute.

The precipitate was washed 2 times with 20 ml cold acetone.

The Celite was tried at ambient temperature for about 1 hour

The immobilised transferase was tested in a oil mixture containing 13% Phosphatidylcholin and 7% plant sterol. (Table 27)

TABLE 27

|  | % |
|---|---|
| Avanti lecithin | 12.0 |
| Plant sterol, Generol 122N | 6.6 |
| Palm 43 | 71.4 |
| Glycerol | 5.0 |
| Immobilised Transferase #178, 45 U/g | 2.0 |
| Water | 3.0 |

Lecithin, plant sterol and soybean oil was heated to 46° C. and the plant sterol was dissolved. The immobilised transferase was added.

The transferase reaction continued at 46° C. during gentle agitation with a magnetic stirrer. Samples were taken out for analyses after ½, 1 3 6 and 24 hours and analysed by TLC. The reaction was stopped after 24 hours reaction time and the immobilised enzyme was filtered off.

The samples were analysed by TLC as shown in FIG. 65.

The TLC analysis clearly shows the effect of immobilised transferase from *A. salmonicida* in the transformation of cholesterol into cholesterol ester. It is also observed that small amount of monoglyceride is formed. The enzyme has also been shown to have a high activity in environments with high water content (6-89%) water environments, the use of the transferase, and other transferases for use in the invention can therefore also be used in immobilised enzyme applications with a significant water content. This allows the replacement of the solvents used by the current immobilised lipases in the bioconvertion of lipids using transferases.

Example 16

The *Aeromonas hydrophilia* Transferase can Transfer from a Phospholipid to a Sterol to Form a Sterol Ester, and/or a Sugar Molecule to Form a Sugar Ester A lipid acyltransferase from *Aeromonas hydrophila* expressed in *E. coli* (Hydro 0303 HVP), labelled #139 was purified on a Chelating Sepharose FF, HR 2.5/10 column and analysed for Phospholipase activity. The transferase activity was evaluated in egg yolk for enzyme activity and functionality in egg yolk. The enzyme was also tested in egg yolk containing glucose.

Phospholipase Activity.

Transferase #139 isolated from a Chelating Sepharose FF, HR 2.5/10 column was assayed by NEFA-PLU (pH7) The activity was 1.15 Units NEFA-PLU/ml.

Egg Yolk

In an initial application test transferase #139 was tested in egg yolk according to the following procedure.

1-gram fresh egg yolk was scaled in a 10 ml flask with screw lid. The enzyme preparation was added and mixed on a Vortex mixer. The sample was placed at 37° C. and agitated with a magnetic stirrer.

The reaction was stopped by adding 7.5 ml Chloroform: Methanol (2:1) and mixed on a Whirley mixer for 30 seconds. The chloroform phase was isolated by centrifugation and 2 µl of the chloroform phase was transferred to a pre-activated silica TLC plate and eluted with running buffer nr. I and another TLC-plate in running buffer IV, The experimental setup is shown in table 28

TABLE 28

| Test no. | Reaction time min. | Egg yolk gram | Transferase #139 units |
|---|---|---|---|
| 1 | 10 | 1 |  |
| 2 | 10 | 1 | 0.75 NEFA-PLU |
| 3 | 60 | 1 | 0.75 NEFA-PLU |
| 4 | 300 | 1 | 0.75 NEFA-PLU |
| 5 | 1200 | 1 |  |
| 6 | 1200 | 1 | 0.75 NEFA-PLU |

TLC analysis are shown in FIG. 66 and FIG. 67. The TLC analysis clearly demonstrates the transferase reaction of transferase #139. The cholesterol is converted to cholesterol ester and the amount of lecithin is reduced. The results however also indicate that lysolecithin are only accumulated in very small amount because transferase #139 also is active on lysolecithin. This observation is supported by the formation of free fatty acids(FFA).

Egg Yolk and Glucose

It was earlier shown that a transferase from *Aeromonas salmonicida* (#138) was able to use glucose as acceptor molecule in a transferase reaction. It has also been tested if transferase #139 can use glucose as acceptor molecule. The experimental set up is seen in Table 29.

TABLE 29

| Test no. | Reaction time Minutes | Egg yolk gram | Glucose, 70% mg | Transferase #139 units |
|---|---|---|---|---|
| 1 | 10 | 1 | 500 |  |
| 2 | 10 | 1 | 500 | 1 NEFA-PLU |
| 3 | 60 | 1 | 500 | 1 NEFA-PLU |
| 4 | 180 | 1 | 500 | 1 NEFA-PLU |
| 5 | 300 | 1 | 500 | 1 NEFA-PLU |
| 6 | 1200 | 1 | 500 | 1 NEFA-PLU |
| 7 | 1200 | 1 | 500 |  |

The reaction products were analysed by TLC (FIG. 68 and FIG. 69).

The TLC analysis indicates formation of glucose ester after 220 min. reaction time (FIG. 69 lane 6) but after 1200 min reaction time no glucose ester is seen.

It must therefore be concluded that transferase #139 has both transferase and hydrolytic activity. This is also supported by the fact that the amount of free fatty acids steadily increases as a function of reaction time.

Resume:

Transferase from *Aeromonas hydrophila* was tested in egg yolk. The results confirm that this enzyme catalyses the formation of cholesterol ester concomitant with the formation of lysolecithin. After extended reaction time when most of the cholesterol is consumed free fatty acid are also formed. It can therefore be concluded that the enzyme has primary transferase activity but also hydrolytic activity was observed when only water was available as donor molecule.

In an experiment with egg yolk and glucose it has been observed that transferase from *Aeromonas hydrophila* is able to catalyse the formation of glucose ester in situ in a high water food environment (FIG. 70).

Example 17

Variants of a Lipid Acyltransferase from *Aeromonas hydrophila* (Ahyd2) (SEQ ID No. 36 (see FIG. 71))

Mutations were introduced using the QuikChange® Multi-Site Directed Mutagenesis kit from Stratagene, La Jolla, Calif. 92037, USA following the instructions provided by Stratagene.

Variants at Tyr256 showed an increased activity towards phospholipids.

Variants at Tyr256 and Tyr260 showed an increased activity towards galactolipids.

Variants at Tyr265 show an increased transferase activity with galactolipids as the acyl donor.

The numbers indicate positions on the following sequence: An enzyme from *Aeromonas hydrophila* the amino acid sequence of which is shown as SEQ ID No. 36 in FIG. 71 (the underlined amino acids show a xylanase signal peptide). The nucleotide sequence is as shown as SEQ ID No 54 in FIG. 72.

Example 18

Use of Acyl-Transferase Reaction for the Production of Plant Sterol Ester and Monoglyceride for Margarine Production An acyltransferase from *Aeromonas salmonicida* expressed in *Bacillus subtilis* was tested in a palm oil mixture containing plant lecithin, plant sterol and glycerol. The acyltransferase showed the ability to utilise both plant sterol and glycerol as acceptor molecules during production of plant sterol ester and monoglyceride. The reaction mixture was used to produce table margarine of good quality based on the monoglyceride in the reaction mixture and at the same time the margarine was enriched with plant sterol ester, which has been shown to have a cholesterol lowering effect.

The aim of this work was to study to possibility to produce monoglyceride and plant sterol ester by enzymatic reaction of lecithin, plant sterol and glycerol dissolved in vegetable fat.

Initial experiments has shown that it was possible to use acyl-transferase from *Aeromonas salmonicida* to produce monoglyceride and plant sterol ester from lecithin, glycerol and plant sterol.

In this experiment such reaction mixture was used to produce table margarine.

Materials:
Lipid acyltransferase from *Aeromonas salmonicida*, #196 C101, 18.6 PLU/g (Journal 2254-104)
Palm Oil 43, from Aarhus United, DK
L-α Phosphatidylcholine 95% Plant (Avanti #441601)
Plant Sterol: Generol N122 from Cognis, Germany
Glycerol Item no. 085915
Distilled Monoglyceride, Dimodan HP from Danisco.

Margarine Production.
1. Blend the water phase ingredients. (If required, pasteurise the water phase by heating to approx. 80° C.). Adjust pH 5.5.
2. Melt the fat phase, and temper to approx. 40-45° C.
3. Heat the emulsifier with some of the oil in a ratio of 1 part emulsifier to 5 parts oil to a temperature (75-80°), which is 5-10° C. higher than the melting point of the emulsifier. When this blend is fully melted and well stirred, add it to the remaining heated oil, stirring continuously.
4. Add the flavouring.
5. Add the water phase to the fat phase, stirring continuously.
6. Cool in a tube chiller (normal capacity, normal cooling) to an outlet temperature of 8-10° C.

Results

Acyltransferase from *A. salmonicida* was tested in an palm oil mixture as shown in Table 30. Lecithin, plant sterol, glycerol and palm oil was heated to 60° C. during agitation in order to solubilize plant sterol and lecithin.

TABLE 30

| Substrate: | % |
| --- | --- |
| Avanti lecithin | 12 |
| Plant sterol, Generol 122N | 6.6 |
| Palm oil, melting point 43 | 76.4 |
| Glycerol | 5 |

The substrate was cooled to 48° C. and acyl-transferase #196 was added in the amount shown in Table 31. The reaction mixture was kept at 48° C. for 24 hours during slow agitation.

TABLE 31

|  | gram |
| --- | --- |
| Substrate | 220 |
| Transferase # 196 C101, 18.6 PLU/g | 15 |

Samples from the reaction mixture were taken out after 1, 4 and 24 hours reaction time, and analysed by TLC in solvent I (FIG. 73). The TLC results clearly show the formation of plant sterol ester and monoglyceride. In FIG. 73, the first lane is after 1 hour reaction time, Lane 2 is 4 hours reaction time, Lane 3 is 24 hours reaction time and Lane 4 is a plant sterol.

The reaction was stopped after 24 hours reaction time and residues of undissolved plant sterol was removed, and the clear solution was used to produce margarine.

Margarine.

The reaction mixture containing monoglyceride and plant sterol ester was used to produce table margarine according to the recipe shown in Table 32.

TABLE 32

|  | Jour. No 3734 | |
| --- | --- | --- |
|  | 1 | 2 |
| Water phase | | |
| Water phase | 16 | 16 |
| Salt | 0.5 | 0.5 |
| Skim milk powder | 1 | 1 |
| Potassium sorbate | 0.1 | 0.1 |
| EDTA | 0.015 | 0.015 |
| PH | 5.5 | 5.5 |

TABLE 32-continued

| | Jour. No 3734 | |
|---|---|---|
| | 1 | 2 |
| Water phase total | 16.6 | 16.6 |
| Fat phase | | |
| Palm 43 | 25 | 25 |
| Rapeseed Oil | 75 | 75 |
| Fat phase total | 83.2 | 78.4 |
| Dimodan HP | 0.2 | |
| Reaction mixture | | 5 |

The margarine produced from the reaction mixture was evaluated of good quality with good spreadability, and good mouth feel and without any off flavour. The margarine was compared to be on quality level with the reference margarine produced by using distilled monoglyceride Dimodan HP.

The only difference observed was that the margarine jour. 3734 no 2 with the reaction mixture was slightly more firm, which was explained by the fact that this recipe contained more Palm 43 than the reference margarine.

Example 19

Use of a Lipid Acyltransferase During Bread Production

One of the limitations of using lipases in bread making is that free fatty acid is formed during the lipase reaction. It is well known that formation of too much free fatty acid will have a negative impact on the baking performance of flour, because the gluten gets too stiff and a bucky (i.e. less elastic) dough is formed which can not expand during fermentation and baking.

Formation of free fatty acid should also be avoided from the point of oxidative stability, because free fatty acids are more prone to lipid oxidation than the corresponding triglyceride.

In the present invention the problems with free fatty acid formation when adding a lipolytic enzyme to a dough has been overcome by using a lipid acyltransferase which, instead of producing free fatty acids, transfers one or more fatty acids from the lipid acyl donor to a non water acceptor molecule present in the dough, such as a carbohydrate, a protein or peptide, or if used in bread with milk fat, a sterol, alternatively or in combination other acceptors listed above mat be added to a dough, for example phytosterols or phytostanols. Preferably, the acceptor molecule in a dough may be one or more of glucose, sucrose or maltose and/or other carbohydrates normally available in a dough.

In the following experiments acyl transferase is tested in mini scale baking experiments. The formation of reaction products, and the lipid components in fully proved dough is extracted by water saturated butanol and analysed by HPLC and GLC analysis.

Materials and Methods
Enzymes:
Acyl Transferase, 550 PLU-7/ml
Lipopan™ F BG, a commercial lipase from Novozymes. 12000 LIPU/g or Grindamyl
Exel 16. 12000 LIPU/g
Lecithin powder, 95% phospholipid (available from Danisco A/S Denmark)
Digalactosyldiglyceride from whole wheat flour (from Sigma D4651)
Flour: Sølvmel nr. 2001084 (Danish wheat flour, obtained from Havnemøllerne, Odense, Denmark)
Mini Baking Test.

Flour, 50 gram, Dry yeast 10 gram, glucose 0.8 gram, salt 0.8 gram, 70 ppm ascorbic acid and, water 400 Brabender units was kneaded in a 50 g Brabender mixing bowl for 5 min at 30° C.

Resting time was 10 min. at 34° C. The dough was scaled 15 gram per dough. Then moulded on a special device where the dough is rolled between a wooden plate and a plexiglas frame. The doughs were proofed in tins for 45 min. at 34° C., and baked in a Voss household oven 8 min. 225° C.

After baking the breads are cooled to ambient temperature and after 20 min. the breads are scaled and the volume is determined by rape seed displacement method. The breads are also cut and crumb and crust evaluated.
Results and Conclusion:

Preliminary results indicate that the lipid acyltransferase clearly demonstrates a positive effect on both bread volume and bread appearance. In particular, preliminary results indicate that the use of the lipid acyltransferase results in increased specific bread volume as compared with that obtained with the control (no enzyme) and that obtained with the use of a commercially available lipolytic enzyme, namely Grindamyl Exel 16 or LipopanF™.

Example 20

Standard Ice Cream with Dairy Fat

The function of emulsifiers used in ice cream is to bring about controlled fat crystallisation and mild destabilization due to protein desorbtion during ageing of the ice cream. This change improves the ice cream quality. Mono-diglycerides are normally used for the production of ice cream, but is also known to use polar emulsifiers like polysorbate and sugar esters in ice cream production in combination with mono-diglyceride to facilitate controlled fat destabilization and produce ice cream with very good creamy and smooth eating texture.

Emulsifiers used for ice cream are normally added the ice cream mix as a powder. Recently it has however been shown that mono-diglyceride can bee produced by enzymatic reaction of the fat in the ice cream recipe using lipases. The problem by using lipases is however that lipases also catalyse the formation of free fatty acids, when water is available in the reaction mixture.

It has however surprisingly been shown that lipid acyltransferase overcomes the limitation by lipase because acyltransferase is able to transfer fatty acid from lecithin and other lipids to acceptor molecules like sterol, cholesterol, glucose, glycerol and proteins/peptides without formation of significant amount of free fatty acids.

One of the main ingredients in ice cream is dairy cream containing 38% milk fat. Dairy cream also contains smaller amount of lecithin, which is a donor molecule for acyl-transferase. ("Complex milk lipids account for about 1% of the total milk fat and are mainly composed of phospholipids". Ref. Ullmann's Encyclopedia of Industrial ChemistryCopyright© 2003 by Wiley-VCH Verlag GmbH & Co. KGaA.). Dairy cream also contains small amount of cholesterol, which is an acceptor molecule for acyl-transferase.

From the constituents of ice cream it is thus possible to produce both monoglyceride and polar emulsifiers like lysolecithin and sugar ester, which are known for the beneficial effects in ice cream production.

A further beneficial effect form the reaction of acyl-transferase in dairy cream is the formation of cholesterol ester, which might slow down the absorption of cholesterol in the intestine.

| Ice cream Recipe | With emulsifier | With enzyme |
|---|---|---|
| Dairy cream, 38% | 23.65 | 23.65 |
| Skimmed milk | 53.30 | 53.30 |
| Skimmed milk powder | 4.90 | 11.30 |
| Sugar | 12.00 | 12.00 |
| Glucose sirup, DE 42, 75% TS | 4.25 | 4.25 |
| Glycerol | 1.0 | 1.0 |
| Stabilizer blend | 0.2 | 0.2 |
| Cremodan SE 30 | 0.6 | |
| Lipid acyl transferase, 500 PLU/g | | 0.1 |
| Grindsted Flavouring 2976 | 0.1 | 0.1 |
| Colour | + | + |

Ice Cream Production Process.
1. Heat dairy cream, glucose syrup and glycerol to approx. 40° C. Add the lipid acyl transferase and let the mixture react for 30 minutes. A sample is taken out for analysis
2. Heat all the other liquid ingredients to approx. 40°
3. Add the other dry ingredients. (stabiliser blend is mixed with sugar before addition)
4. When the dry ingredients are dissolved add the dairy cream-glucose mixture.
5. Pasteurise at 80-85° C./20-40 seconds
6. Homogenise at 80° C. (190 bar for recipe 1 and 175 bar for recipe 2)
7. Cool to ageing temperature, 4° C.
8. Freeze in continuous freezer to desired overrun (100% recommended)
9. Harden in tunnel at −40° C.
10. Store below −25° C.

Results:
Uses of Acyl-transferase in the production of ice cream contribute to the production of ice cream with very good taste and excellent creamy mouth feel comparable the ice cream produced by using a commercial emulsifier Cremodan SE 30. The melt down of the ice cream produced by the lipid acyl transferase is also improved.

Example 21

Acyl transferase in Cheese

Cheese is the fresh or matured solid or semisolid product obtained by coagulating milk, skimmed milk, partly skimmed milk, cream, whey cream, or buttermilk, or any combination of these materials, through the action of rennet or other suitable coagulating agents, and partially draining the whey that results from such coagulation.

The cheese yield depends primarily on the fat and protein contents of the milk. The salt (particularly calcium salts) and protein concentrations, as well as the acidity, are very important for coagulation. (ref. *Ullmann's Encyclopedia of Industrial Chemistry* Copyright© 2003 by Wiley-VCH Verlag GmbH & Co).

Such effort has been made in order to optimise and increase the cheese yield by optimisation of the cheese making procedure (U.S. Pat. No. 4,959,229) or by using improved clotting method (U.S. Pat. No. 4,581,240), which increase the amount of whey protein in the curd.

In the present invention the amount of whey protein in the curd is increased by enzymatic modification of the whey protein by treatment of the milk during cheese making with a lipid acyl transferase.

When a fatty acid is covalently linked to a non-membrane protein like β-lactoglobulin, the physical and functional properties will change drastically.

For cheese production of the present invention acyl transferase is added to the milk before or at the same time as rennet is added to the milk.

During casein precipitation acyl transferase is able to use lecithin and other lipids in the milk as donor and peptides or protein as acceptor molecule during formation of acylated protein or acylated peptides.

The change in hydrophobic properties of milk protein contributes to increased protein precipitation in the curd during cheese production.

Since the increase in cheese yield obtained by the present invention originates from increased retention in the cheese coagulum of proteins that are normally lost in the whey, a suitable method, directly related to the mechanism of the invention, is based on determination of the amount of protein that ends up in the whey. Less protein in the whey necessarily means more protein in the curd, and higher cheese yield.

The test for the amount of protein in the whey can be performed in the following way. Skim or whole milk is warmed to a temperature suitable for rennet coagulation, typically 30-35° C. in a 100 ml beaker. Optionally 1% of a bulk lactic acid bacteria starter is added, and standard rennet is added in an amount corresponding to e.g. 0.03-0.05%. When the milk has turned into a coagulum solid enough to allow it to be cut into cubes with a side length of about 0.5 cm, such cutting is performed with a sharp knife. Syneresis is thereby initiated, and after 30 min holding period, that allows the curd to settle, a whey sample is withdrawn, and centrifuged in a laboratory centrifuge for 10 min. This sample is analyzed for protein content, using e.g. the Kjeldahl method. Alternatively, and/or as a supplement, the sample may be analyzed with methods that allow the type and quantity of the individual protein components to be established.

Example 22

"Assay in Low Water Environment"

Transferase reactions of lipolytic enzymes in low water environment.
Procedure
Materials.
Cholesterol Sigma cat. C 8503
L-alpha-Phosphatidylcholine 95% (Plant) Avanti #441601
Soybean oil, Aarhus United, DK.
Chloroform, Analytical grade
Enzymes.
179, GCAT from *A. salmonicida*
2427, Phospholipase A1 from *Fusarium oxysporum*. LIPOPAN® F from Novozymes, Denmark
1991, Phospholipase A2 from Pancreas, LIPOMOD 22L from Biocatalysts, UK
2373, *Candida Antarctica* lipase, Novozyme 525 L from Novozymes Denmark.
Enzyme Assay
13.1% Lecithin and 6.6% cholesterol was dissolved in soybean oil by heating to 60° C. during agitation
The substrate was scaled in a 20 ml Wheaton glass and heated to 46° C.
Water and enzyme solution was added and a stopwatch is started.
At regular intervals 50 mg samples ware transferred to a 10 ml Dram glass and frozen.
The isolated lipids were analysed by GLC GLC Analysis GLC analysis was carried out as described in Example 11

Results

The experiment was set up as shown in Table 33

The substrate based on soybean oil containing 13.1% lecithin and 6.6% cholesterol was heated to 46° C. The enzyme solution was added and a stopwatch started.

After 30, 60 and 120 minutes reaction time samples were taken out for GLC analysis.

TABLE 33

|  |  | 1 | 2 | 3 | 4 | 5 |
|---|---|---|---|---|---|---|
| Substrate | gram | 5 | 5 | 5 | 5 | 5 |
| Transferase #179-C72, 56 PLU-7/ml | ml |  | 0.3 |  |  |  |
| #2427, 200 PLU-7/ml | ml |  |  | 0.3 |  |  |
| Pancreas PLA 2 #1991 6300 PLU/ml | ml |  |  |  | 0.3 |  |
| Novozyme 525 L, #2373, 200 LIPU/ml | ml |  |  |  |  | 0.3 |
| Water | ml | 0.3 |  |  |  |  |
| % water |  |  | 6 | 6 | 6 | 6 |

The results from the GLC analysis is shown in Table 34. The results are expressed in percent based total sample composition. Based on the GLC results it was possible to calculate the amount of fatty acid and cholesterol ester produced by enzymatic reaction relative to the control sample without enzyme added. Under these experimental conditions the total enzymatic activity was estimated as the hydrolytic activity measured as free fatty acid formation and the transferase activity estimated as cholesterol ester formation. From these results and the information about molecular weight of fatty acid and cholesterol ester it was possible to calculate to relative molar hydrolytic activity and the relative molar transferase activity as shown in Table 35.

TABLE 34

| Enzyme | Reaction time minutes | Fatty acid % | cholesterol % | Cholesterol ester % |
|---|---|---|---|---|
| Control | 120 | 0.533 | 7.094 | 0.000 |
| #179 | 30 | 0.770 | 5.761 | 2.229 |
| #179 | 60 | 0.852 | 5.369 | 2.883 |
| #179 | 120 | 0.876 | 4.900 | 3.667 |
| #2427 | 30 | 3.269 | 7.094 | 0.000 |
| #2427 | 60 | 3.420 | 7.094 | 0.000 |
| #2427 | 120 | 3.710 | 7.094 | 0.000 |
| #1991 | 30 | 2.871 | 7.094 | 0.000 |
| #1991 | 60 | 3.578 | 7.094 | 0.000 |
| #1991 | 120 | 3.928 | 7.094 | 0.000 |
| #2373 | 30 | 1.418 | 7.094 | 0.000 |
| #2373 | 60 | 1.421 | 7.094 | 0.000 |
| #2373 | 120 | 1.915 | 7.094 | 0.000 |

TABLE 35

| Enzyme | Reaction time minutes | Fatty acid produced | Cholesterol Used | Cholesterol ester produced | Hydrolytic activity % | Transferase activity % |
|---|---|---|---|---|---|---|
| #179 | 30 | 0.238 | 1.334 | 2.229 | 20 | 80 |
| #179 | 60 | 0.319 | 1.725 | 2.883 | 21 | 79 |
| #179 | 120 | 0.343 | 2.195 | 3.667 | 18 | 82 |
| #2427 | 30 | 2.737 | 0.000 | 0.000 | 100 | 0 |
| #2427 | 60 | 2.887 | 0.000 | 0.000 | 100 | 0 |
| #2427 | 120 | 3.177 | 0.000 | 0.000 | 100 | 0 |
| #1991 | 30 | 2.338 | 0.000 | 0.000 | 100 | 0 |
| #1991 | 60 | 3.046 | 0.000 | 0.000 | 100 | 0 |
| #1991 | 120 | 3.395 | 0.000 | 0.000 | 100 | 0 |
| #2373 | 30 | 0.885 | 0.000 | 0.000 | 100 | 0 |
| #2373 | 60 | 0.888 | 0.000 | 0.000 | 100 | 0 |
| #2373 | 120 | 1.383 | 0.000 | 0.000 | 100 | 0 |

Conclusion

In these experiments it was observed that all the tested enzymes showed hydrolytic activity because the amount of fatty acid increased. However the only enzyme which showed transferase activity was GCAT from *A. salmonicida*. It is therefore concluded that in an oily system with lecithin and cholesterol containing 6% water phospholipase A1 from *Fusarium oxysporum*, phospholipase A2 from pancreas and a lipase from *Candida antarctica* only showed hydrolytic activity.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for producing a dough product or a baked product comprising an emulsifier from a water-containing food material comprising 10-98% water, comprising:
adding a lipid acyltransferase to the food material whereby the emulsifier is generated in situ from the constituents of the food material by the lipid acyltransferase, wherein the lipid acyltransferase is an enzyme
  (i) having acyltransferase activity, and
  (ii) which, when tested using a Transferase Assay in Buffered Substrate has at least 5% acyltransferase activity (relative acyltransferase activity),
    wherein the Transferase Assay in Buffered Substrate comprises:
      (a) heating to 35° C. a substrate solution comprising:
        phosphatidylcholine;
        cholesterol;
        water; and
        HEPES buffer; and
        wherein the substrate solution comprises approximately 95% water and has pH 7.0,
      (b) adding an enzyme to the substrate solution, and
      (c) determining acyltransferase activity of the enzyme based upon cholesterol and fatty acids formed, and
  (iii) which transfers an acyl group from a lipid in the food material to one or more acceptor substrates having a hydroxy group in the food material to form the emulsifier in situ;
    wherein the lipid is a phospholipid, a triacylglyceride, a diglyceride, or a glycolipid, and
    wherein the acyl acceptor is a sterol, a stanol, a carbohydrate, or a protein or subunit thereof.

2. The method according to claim 1 wherein the dough product or the baked product is a bread, a fried product, a snack, cakes, pies, brownies, cookies, noodles, snack items or pasta.

3. The method according to claim 1 wherein the dough product or the baked product is a bread.

4. The method according to claim 1 wherein at least 2 emulsifiers are produced.

5. The method according to claim 4 wherein one or more the emulsifiers is selected from the group consisting of: a sterol ester, a stanol ester, a protein ester, a carbohydrate ester, a diglyceride, and a monoglyceride is produced in situ in the foodstuff.

6. The method according to claim 1 wherein the lipid acyltransferase possesses acyl transferase activity and which comprises the amino acid sequence motif GDSX (SEQ ID NO: 71), wherein X is an amino acid residue selected from the group consisting of: L, A, V, I, F, Y, H, Q, T, N, M and S.

7. The method according to claim 1 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

8. The method according to claim 1 wherein the lipid acyltransferase is from an organism in the genera selected from the group consisting of: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

9. The method according to claim 1 wherein the lipid acyltransferase comprises an amino acid sequence selected from the group consisting of: (i) SEQ ID No. 2; (ii) SEQ ID No. 3; (iii) SEQ ID No. 4; (iv) t SED ID No. 5; (v) SEQ ID No. 6; (vi) SEQ ID No. 12, (vii) SEQ ID No. 20, (viii) SEQ ID No. 22, (ix) s SEQ ID No. 24, (x) SEQ ID No. 26, (xi) SEQ ID No. 28, (xii) SEQ ID No. 30, (xiii) SEQ ID No. 32, (xiv) SEQ ID No. 34, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 and SEQ ID No. 34.

10. The method according to claim 1, wherein the emulsifier is selected from the group consisting of: a monoglyceride, a lysophosphatidylcholine, and DGMG.

11. The method according to claim 1 wherein the lipid acyltransferase, when tested using the Transferase Assay in High Water Egg Yolk in an egg yolk with 54% water, has up to 100% relative transferase activity.

12. The method according to claim 1, wherein the lipid from which the acyl group is transferred is a donor molecule and wherein the lipid acyltransferase has an initial percentage acyltransferase activity measured after 10% consumption of the donor molecules of at least 1% relative transferase activity.

13. The method according to claim 1, wherein the lipid acyltransferase when tested using the Transferase Assay in a Low Water Environment has a relative transferase activity of at least 1%.

14. A method for producing a dough product or a baked product comprising an emulsifier from a water-containing food material comprising 10-98% water, comprising:
  adding a lipid acyltransferase to the food material whereby the emulsifier is generated in situ from the constituents of the food material by the lipid acyltransferase, wherein the lipid acyltransferase is an enzyme
    (i) having acyltransferase activity, and
    (ii) which, when tested using a Transferase Assay in High Water Egg Yolk in an egg yolk with 54% water, has up to 100% relative transferase activity,
    wherein the Transferase Assay in High Water Egg Yolk comprises:
      (a) heating to 35° C. a substrate solution comprising:
        egg yolk;
        water; and
        HEPES buffer; and
      wherein the substrate solution comprises approximately 54% water,
      (b) adding an enzyme to the substrate solution, and
      (c) determining acyltransferase activity of the enzyme based upon cholesterol and fatty acids formed, and
    (iii) which transfers an acyl group from a lipid in the food material to one or more acceptor substrates having a hydroxy group in the food material to form the emulsifier in situ;
    wherein the lipid is a phospholipid, a triacylglyceride, a diglyceride, or a glycolipid,
    wherein the acyl acceptor is a sterol, a stanol, a carbohydrate, or a protein or subunit thereof;
    wherein the lipid from which the acyl group is transferred is a donor molecule; and
    wherein the lipid acyltransferase has an initial percentage acyltransferase activity measured after 10% consumption of the donor molecule of at least 1% relative transferase activity.

15. The method according to claim 14 wherein the dough product or the baked product is a bread, a fried product, a snack, cakes, pies, brownies, cookies, noodles, snack items or pasta.

16. The method according to claim 14 wherein the dough product or the baked product is a bread.

17. The method according to claim 14 wherein at least 2 emulsifiers are produced.

18. The method according to claim 17 wherein one or more the emulsifiers is selected from the group consisting of a sterol ester, a stanol ester, a protein ester, a carbohydrate ester, a diglyceride, and a monoglyceride is produced in situ in the foodstuff.

19. The method according to claim 14 wherein the lipid acyltransferase possesses acyl transferase activity and which comprises the amino acid sequence motif GDSX (SEQ ID NO: 71), wherein X is an amino acid residue selected from the group consisting of: L, A, V, I, F, Y, H, Q, T, N, M and S.

20. The method according to claim 14 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

21. The method according to claim 14 wherein the lipid acyltransferase is from an organism in the genera selected from the group consisting of: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

22. The method according to claim 14 wherein the lipid acyltransferase comprises an amino acid sequence selected from the group consisting of: (i) SEQ ID No. 2; (ii) SEQ ID No. 3; (iii) SEQ ID No. 4; (iv) t SED ID No. 5; (v) SEQ ID No. 6; (vi) SEQ ID No. 12, (vii) SEQ ID No. 20, (viii) SEQ ID No. 22, (ix) s SEQ ID No. 24, (x) SEQ ID No. 26, (xi) SEQ ID No. 28, (xii) SEQ ID No. 30, (xiii) SEQ ID No. 32, (xiv) SEQ ID No. 34, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 and SEQ ID No. 34.

23. The method according to claim 14, wherein the lipid acyltransferase has an initial percentage acyltransferase activity measured after 10% consumption of the donor molecule of at least 5% relative transferase activity.

24. The method according to claim 14, wherein the lipid acyltransferase has an initial percentage acyltransferase activity measured after 10% consumption of the donor molecule of at least 10% relative transferase activity.

25. The method according to claim 14, wherein the lipid acyltransferase when tested using the Transferase Assay in a Low Water Environment has a relative transferase activity of at least 1%.

26. The method according to claim 14, wherein the lipid acyltransferase when tested using a Transferase Assay in Buffered Substrate has a relative transferase activity of at least 5%.

\* \* \* \* \*

SEQUENCE LISTING

<160> NUMBER OF SEQ ID NOS: 74

<210> SEQ ID NO 1
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ile Val Ala Phe Gly Asp Ser Leu Thr Asp Gly Glu Ala Tyr Tyr Gly
1               5                   10                  15

Asp Ser Asp Gly Gly Gly Trp Gly Ala Gly Leu Ala Asp Arg Leu Thr
            20                  25                  30

Ala Leu Leu Arg Leu Arg Ala Arg Pro Arg Gly Val Asp Val Phe Asn
        35                  40                  45

Arg Gly Ile Ser Gly Arg Thr Ser Asp Gly Arg Leu Ile Val Asp Ala
    50                  55                  60

Leu Val Ala Leu Leu Phe Leu Ala Gln Ser Leu Gly Leu Pro Asn Leu
65                  70                  75                  80

Pro Pro Tyr Leu Ser Gly Asp Phe Leu Arg Gly Ala Asn Phe Ala Ser
                85                  90                  95

Ala Gly Ala Thr Ile Leu Pro Thr Ser Gly Pro Phe Leu Ile Gln Val
            100                 105                 110

Gln Phe Lys Asp Phe Lys Ser Gln Val Leu Glu Leu Arg Gln Ala Leu
        115                 120                 125

Gly Leu Leu Gln Glu Leu Leu Arg Leu Pro Val Leu Asp Ala Lys
    130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
                165                 170                 175

Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
        195                 200                 205

Asn Leu Gly Pro Leu Gly Cys Leu Pro Leu Lys Leu Ala Leu Ala Leu
    210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
            260                 265                 270

Ala Asp Val Pro Tyr Val Asp Leu Tyr Ser Ile Phe Gln Asp Leu Asp
        275                 280                 285

Gly Ile Gln Asn Pro Ser Ala Tyr Val Tyr Gly Phe Glu Thr Thr Lys
    290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
            340                 345                 350

Gly Tyr Lys Ala Val Ala Glu Ala Leu
        355                 360

<210> SEQ ID NO 2
<211> LENGTH: 335
<212> TYPE: PRT
<213> ORGANISM: Aeromonas hydrophila

<400> SEQUENCE: 2

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
        275                 280                 285

Met Ala Ala Arg Ser Ala Ser Thr Leu Asn Cys Glu Gly Lys Met Phe
    290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 3
<211> LENGTH: 336
<212> TYPE: PRT
<213> ORGANISM: Aeromonas salmonicida

<400> SEQUENCE: 3

```
Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Tyr Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335
```

<210> SEQ ID NO 4
<211> LENGTH: 295
<212> TYPE: PRT
<213> ORGANISM: Streptomyces coelicolor

<400> SEQUENCE: 4

```
Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
            20                  25                  30
```

```
Pro Ala Gln Ala Thr Pro Thr Leu Asp Tyr Val Ala Leu Gly Asp Ser
                35                  40                  45

Tyr Ser Ala Gly Ser Gly Val Leu Pro Val Asp Pro Ala Asn Leu Leu
 50                  55                  60

Cys Leu Arg Ser Thr Ala Asn Tyr Pro His Val Ile Ala Asp Thr Thr
 65                  70                  75                  80

Gly Ala Arg Leu Thr Asp Val Thr Cys Gly Ala Ala Gln Thr Ala Asp
                 85                  90                  95

Phe Thr Arg Ala Gln Tyr Pro Gly Val Ala Pro Gln Leu Asp Ala Leu
                100                 105                 110

Gly Thr Gly Thr Asp Leu Val Thr Leu Thr Ile Gly Asn Asp Asn
                115                 120                 125

Ser Thr Phe Ile Asn Ala Ile Thr Ala Cys Gly Thr Ala Gly Val Leu
                130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
                180                 185                 190

Tyr Pro Trp Ile Thr Pro Ala Thr Ala Asp Pro Ser Cys Phe Leu Lys
                195                 200                 205

Leu Pro Leu Ala Ala Gly Asp Val Pro Tyr Leu Arg Ala Ile Gln Ala
210                 215                 220

His Leu Asn Asp Ala Val Arg Arg Ala Ala Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
                260                 265                 270

Pro Val His Pro Asn Ala Leu Gly Glu Arg Arg Met Ala Glu His Thr
                275                 280                 285

Met Asp Val Leu Gly Leu Asp
                290                 295

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
 1               5                  10                  15

Val Gly Thr Leu Ala Leu Gly Leu Thr Asp Ala Thr Ala His Ala Ala
                 20                  25                  30

Pro Ala Gln Ala Thr Pro Thr Leu Asp Tyr Val Ala Leu Gly Asp Ser
                 35                  40                  45

Tyr Ser Ala Gly Ser Gly Val Leu Pro Val Asp Pro Ala Asn Leu Leu
 50                  55                  60

Cys Leu Arg Ser Thr Ala Asn Tyr Pro His Val Ile Ala Asp Thr Thr
 65                  70                  75                  80

Gly Ala Arg Leu Thr Asp Val Thr Cys Gly Ala Ala Gln Thr Ala Asp
                 85                  90                  95

Phe Thr Arg Ala Gln Tyr Pro Gly Val Ala Pro Gln Leu Asp Ala Leu
                100                 105                 110
```

```
Gly Thr Gly Thr Asp Leu Val Thr Leu Thr Ile Gly Gly Asn Asp Asn
            115                 120                 125

Ser Thr Phe Ile Asn Ala Ile Thr Ala Cys Gly Thr Ala Gly Val Leu
130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
                180                 185                 190

Tyr Pro Trp Ile Thr Pro Ala Thr Ala Asp Pro Ser Cys Phe Leu Lys
                195                 200                 205

Leu Pro Leu Ala Ala Gly Asp Val Pro Tyr Leu Arg Ala Ile Gln Ala
210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
                260                 265                 270

Pro Val His Pro Asn Ala Leu Gly Glu Arg Arg Met Ala Glu His Thr
                275                 280                 285

Met Asp Val Leu Gly Leu Asp
290                 295

<210> SEQ ID NO 6
<211> LENGTH: 238
<212> TYPE: PRT
<213> ORGANISM: Saccharomyces cerevisiae

<400> SEQUENCE: 6

Met Asp Tyr Glu Lys Phe Leu Leu Phe Gly Asp Ser Ile Thr Glu Phe
1               5                   10                  15

Ala Phe Asn Thr Arg Pro Ile Glu Asp Gly Lys Asp Gln Tyr Ala Leu
                20                  25                  30

Gly Ala Ala Leu Val Asn Glu Tyr Thr Arg Lys Met Asp Ile Leu Gln
            35                  40                  45

Arg Gly Phe Lys Gly Tyr Thr Ser Arg Trp Ala Leu Lys Ile Leu Pro
50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
                100                 105                 110

His Ile Arg Pro Ile Ile Ile Gly Pro Gly Leu Val Asp Arg Glu Lys
            115                 120                 125

Trp Glu Lys Glu Lys Ser Glu Glu Ile Ala Leu Gly Tyr Phe Arg Thr
130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190
```

```
Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
        210                 215                 220

Asp Trp Arg Asp Val Leu Asp Asp Gly Ser Asn Ile Met Ser
225                 230                 235

<210> SEQ ID NO 7
<211> LENGTH: 1005
<212> TYPE: DNA
<213> ORGANISM: Aeromonas hydrophila

<400> SEQUENCE: 7
atgaaaaaat ggtttgtgtg tttattggga ttggtcgcgc tgacagttca ggcagccgac      60
agccgtcccg ccttctcccg gatcgtgatg tttggcgaca gcctctccga taccggcaag     120
atgtacagca agatgcgcgg ttacctcccc tccagccccc cctactatga gggccgcttc     180
tccaacgggc ccgtctggct ggagcagctg accaacgagt cccgggcct gaccatagcc      240 aacgaggcgg aaggcggacc gaccgccgtg gcttacaaca agatctcctg gaatcccaag     300
tatcaggtca tcaacaacct ggactacgag gtcacccagt cctgcaaaa agacagcttc      360 aagccggacg atctggtgat cctctgggtc ggcgccaacg actatctggc ctatggctgg     420
aacacagagc aggatgccaa gcgggtgcgc gacgccatca gcgatgcggc caaccgcatg     480
gtgctgaacg gcgccaagga gatactgctg ttcaacctgc cggatctggg ccagaacccc     540
tcggcccgca gccagaaggt ggtcgaggcg ccagccatg tctccgccta ccacaaccag      600
ctgctgctga acctggcacg ccagctggct cccaccggca tggtgaagct gttcgagatc     660
gacaagcagt tgccgagat gctgcgtgat ccgcagaact tcggcctgag cgaccagagg      720
aacgcctgct acggtggcag ctatgtatgg aagccgtttg cctcccgcag cgccagcacc     780
gacagccagc tctccgcctt caacccgcag gagcgcctcg ccatcgccgg caacccgctg     840
ctggcccagg ccgtcgccag ccccatggct gcccgcagcg ccagcaccct caactgtgag     900
ggcaagatgt tctgggatca ggtccacccc accactgtcg tgcacgccgc cctgagcgag     960
cccgccgcca ccttcatcga gagccagtac gagttcctcg cccac                    1005

<210> SEQ ID NO 8
<211> LENGTH: 1011
<212> TYPE: DNA
<213> ORGANISM: Aeromonas salmonicida

<400> SEQUENCE: 8
atgaaaaaat ggtttgtttg tttattgggg ttgatcgcgc tgacagttca ggcagccgac      60
actcgccccg ccttctcccg gatcgtgatg ttcggcgaca gcctctccga taccggcaaa     120
atgtacagca agatgcgcgg ttacctcccc tccagcccgc cctactatga gggccgtttc     180
tccaacggac ccgtctggct ggagcagctg accaagcagt cccgggtct gaccatcgcc      240 aacgaagcgg aaggcggtgc cactgccgtg gcttacaaca agatctcctg gaatcccaag     300
tatcaggtct acaacaacct ggactacgag gtcacccagt tcttgcagaa agacagcttc     360
aagccggacg atctggtgat cctctgggtc ggtgccaatg actatctggc atatggctgg     420
aatacggagc aggatgccaa gcgagttcgc gatgccatca gcgatgcggc caaccgcatg     480
gtactgaacg gtgccaagca gatactgctg ttcaacctgc cggatctggg ccagaacccg     540
tcagcccgca gtcagaaggt ggtcgaggcg gtcagccatg tctccgccta tcacaacaag     600
ctgctgctga acctggcacg ccagctggcc cccaccggca tggtaaagct gttcgagatc     660
```

```
gacaagcaat tgccgagat gctgcgtgat ccgcagaact tcggcctgag cgacgtcgag    720
aacccctgct acgacggcgg ctatgtgtgg aagccgtttg ccacccgcag cgtcagcacc    780
gaccgccagc tctccgcctt cagtccgcag gaacgcctcg ccatcgccgg caacccgctg    840
ctggcacagg ccgttgccag tcctatggcc cgccgcagcg ccagccccct caactgtgag    900
ggcaagatgt tctgggatca ggtacacccg accactgtcg tgcacgcagc cctgagcgag    960
cgcgccgcca ccttcatcga gacccagtac gagttcctcg cccacggatg a           1011

<210> SEQ ID NO 9
<211> LENGTH: 888
<212> TYPE: DNA
<213> ORGANISM: Streptomyces coelicolor

<400> SEQUENCE: 9
atgccgaagc ctgcccttcg ccgtgtcatg accgcgacag tcgccgccgt cggcacgctc     60
gccctcggcc tcaccgacgc caccgcccac gccgcgcccg cccaggccac tccgaccctg    120
gactacgtcg ccctcggcga cagctacagc gccggctccg gcgtcctgcc cgtcgacccc    180
gccaacctgc tctgtctgcg ctcgacggcc aactacccccacgtcatcgc ggacacgacg    240 ggcgcccgcc tcacggacgt cacctgcggc gccgcgcaga ccgccgactt cacgcgggcc    300
cagtacccgg gcgtcgcacc ccagttggac gcgctcggca ccggcacgga cctggtcacg    360
ctcaccatcg gcggcaacga caacagcacc ttcatcaacg ccatcacggc ctgcggcacg    420
gcgggtgtcc tcagcggcgg caagggcagc ccctgcaagg acaggcacgg cacctccttc    480
gacgacgaga tcgaggccaa cacgtacccc gcgctcaagg aggcgctgct cggcgtccgc    540
gccagggctc cccacgccag ggtggcggct ctcggctacc cgtggatcac ccggccacc     600 gccgacccgt cctgcttcct gaagctcccc ctcgccgccg gtgacgtgcc ctacctgcgg    660
gccatccagg cacacctcaa cgacgcgtc cggcgggccg ccgaggagac cggagccacc    720
tacgtggact tctccggggt gtccgacggc cacgacgcct gcgaggcccc cggcacccgc    780
tggatcgaac cgctgctctt cgggcacagc ctcgttcccg tccacccca cgccctgggc    840 gagcggcgca tggccgagca cacgatggac gtcctcggcc tggactga               888

<210> SEQ ID NO 10
<211> LENGTH: 888
<212> TYPE: DNA
<213> ORGANISM: Streptomyces coelicolor

<400> SEQUENCE: 10
tcagtccagg ccgaggacgt ccatcgtgtg ctcggccatg cgccgctcgc ccagggcgtt     60
ggggtggacg ggaacgaggc tgtgcccgaa gagcagcggt tcgatccagc gggtgccggg    120
ggcctcgcag gcgtcgtggc cgtcggacac cccggagaag tccacgtagg tggctccggt    180
ctcctcggcg gcccgccgga ccgcgtcgtt gaggtgtgcc tggatggccc gcaggtaggg    240
cacgtcaccg gcggcgaggg ggagcttcag gaagcaggac gggtcggcgg tggccggggt    300
gatccacggg tagccgagag ccgccaccct ggcgtgggga gccctggcgc ggacgccgag    360
cagcgcctcc ttgagcgcgg ggtacgtgtt ggcctcgatc tcgtcgtcga aggaggtgcc    420
gtgcctgtcc ttgcagggc tgcccttgcc gccgctgagg acacccgccg tgccgcaggc    480
cgtgatggcg ttgatgaagg tgctgttgtc gttgccgccg atggtgagcg tgaccaggtc    540
cgtgccggtg ccgagcgcgt ccaactgggg tgcgacgccc gggtactggg cccgcgtgaa    600
gtcggcggtc tgcgcggcgc cgcaggtgac gtccgtgagg cgggcgcccg tcgtgtccgc    660
```
gatgacgtgg gggtagttgg ccgtcgagcg cagacagagc aggttggcgg ggtcgacggg 720
caggacgccg gagccggcgc tgtagctgtc gccgagggcg acgtagtcca gggtcggagt 780
ggcctgggcg ggcgcggcgt gggcggtggc gtcggtgagg ccgagggcga gcgtgccgac 840
ggcggcgact gtcgcggtca tgacacggcg aagggcaggc ttcggcat 888

<210> SEQ ID NO 11
<211> LENGTH: 717
<212> TYPE: DNA
<213> ORGANISM: Saccharomyces cerevisiae

<400> SEQUENCE: 11
atggattacg agaagtttct gttatttggg gattccatta ctgaatttgc ttttaatact 60
aggcccattg aagatggcaa agatcagtat gctcttggag ccgcattagt caacgaatat 120
acgagaaaaa tggatattct tcaaagaggg ttcaaagggt acacttctag atgggcgttg 180
aaaatacttc ctgagatttt aaagcatgaa tccaatattg tcatggccac aatatttttg 240
ggtgccaacg atgcatgctc agcaggtccc caaagtgtcc ccctccccga atttatcgat 300
aatattcgtc aaatggtatc tttgatgaag tcttaccata tccgtcctat tataatagga 360
ccggggctag tagatagaga gaagtgggaa aaagaaaaat ctgaagaaat agctctcgga 420
tacttccgta ccaacgagaa ctttgccatt tattccgatg ccttagcaaa actagccaat 480
gaggaaaaag ttcccttcgt ggctttgaat aaggcgtttc aacaggaagg tggtgatgct 540
tggcaacaac tgctaacaga tggactgcac ttttccggaa aagggtacaa aatttttcat 600
gacgaattat tgaaggtcat tgagacattc taccccccaat atcatcccaa aaacatgcag 660
tacaaactga aagattggag agatgtgcta gatgatggat ctaacataat gtcttga 717

<210> SEQ ID NO 12
<211> LENGTH: 347
<212> TYPE: PRT
<213> ORGANISM: Ralstonia solanacearum

<400> SEQUENCE: 12

Met Asn Leu Arg Gln Trp Met Gly Ala Ala Thr Ala Ala Leu Ala Leu
1 5 10 15

Gly Leu Ala Ala Cys Gly Gly Gly Gly Thr Asp Gln Ser Gly Asn Pro
20 25 30

Asn Val Ala Lys Val Gln Arg Met Val Val Phe Gly Asp Ser Leu Ser
35 40 45

Asp Ile Gly Thr Tyr Thr Pro Val Ala Gln Ala Val Gly Gly Gly Lys
50 55 60

Phe Thr Thr Asn Pro Gly Pro Ile Trp Ala Glu Thr Val Ala Ala Gln
65 70 75 80

Leu Gly Val Thr Leu Thr Pro Ala Val Met Gly Tyr Ala Thr Ser Val
85 90 95

Gln Asn Cys Pro Lys Ala Gly Cys Phe Asp Tyr Ala Gln Gly Gly Ser
100 105 110

Arg Val Thr Asp Pro Asn Gly Ile Gly His Asn Gly Gly Ala Gly Ala
115 120 125

Leu Thr Tyr Pro Val Gln Gln Gln Leu Ala Asn Phe Tyr Ala Ala Ser
130 135 140

Asn Asn Thr Phe Asn Gly Asn Asn Asp Val Val Phe Val Leu Ala Gly
145 150 155 160

Ser Asn Asp Ile Phe Phe Trp Thr Thr Ala Ala Ala Thr Ser Gly Ser

```
                165                 170                 175

Gly Val Thr Pro Ala Ile Ala Thr Ala Gln Val Gln Gln Ala Ala Thr
            180                 185                 190

Asp Leu Val Gly Tyr Val Lys Asp Met Ile Ala Lys Gly Ala Thr Gln
        195                 200                 205

Val Tyr Val Phe Asn Leu Pro Asp Ser Ser Leu Thr Pro Asp Gly Val
    210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
            260                 265                 270

Phe Gly Phe Ala Asn Thr Ser Ala Arg Ala Cys Asp Ala Thr Lys Ile
        275                 280                 285

Asn Ala Leu Val Pro Ser Ala Gly Gly Ser Ser Leu Phe Cys Ser Ala
    290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
            340                 345
```

<210> SEQ ID NO 13
<211> LENGTH: 1044
<212> TYPE: DNA
<213> ORGANISM: Ralstonia solanacearum

<400> SEQUENCE: 13

```
atgaacctgc gtcaatggat gggcgccgcc acggctgccc ttgccttggg cttggccgcg      60
tgcgggggcg gtgggaccga ccagagcggc aatcccaatg tcgccaaggt gcagcgcatg     120
gtggtgttcg gcgacagcct gagcgatatc ggcacctaca cccccgtcgc gcaggcggtg     180
ggcggcggca agttcaccac caacccgggc ccgatctggg ccgagaccgt ggccgcgcaa     240
ctgggcgtga cgctcacgcc ggcggtgatg ggctacgcca cctccgtgca gaattgcccc     300
aaggccggct gcttcgacta tgcgcagggc ggctcgcgcg tgaccgatcc gaacggcatc     360
ggccacaacg gcggcgcggg ggcgctgacc tacccggttc agcagcagct cgccaacttc     420
tacgcggcca gcaacaacac attcaacggc aataacgatg tcgtcttcgt gctggccggc     480
agcaacgaca ttttcttctg gaccactgcg gcggccacca gcggctccgg cgtgacgccc     540
gccattgcca cggcccaggt gcagcaggcc gcgacggacc tggtcggcta tgtcaaggac     600
atgatcgcca agggtgcgac gcaggtctac gtgttcaacc tgcccgacag cagcctgacg     660
ccggacggcg tggcaagcgg cacgaccggc caggcgctgc tgcacgcgct ggtgggcacg     720
ttcaacacga cgctgcaaag cgggctggcc ggcacctcgg cgcgcatcat cgacttcaac     780
gcacaactga ccgcggcgat ccagaatggc gcctcgttcg gcttcgccaa caccagcgcc     840
cgggcctgcg acgccaccaa gatcaatgcc ctggtgccga gcgccggcgg cagctcgctg     900
ttctgctcgg ccaacacgct ggtggcttcc ggtgcggacc agagctacct gttcgccgac     960
ggcgtgcacc cgaccacggc cggccatcgc ctgatcgcca gcaacgtgct ggcgcgcctg    1020
ctggcggata acgtcgcgca ctga                                           1044
```

```
<210> SEQ ID NO 14
<211> LENGTH: 295
<212> TYPE: PRT
<213> ORGANISM: Aeromonas salmonicida

<400> SEQUENCE: 14
```

| | | | | | | | | | | | | | | |
|---|---|---|---|---|---|---|---|---|---|---|---|---|---|---|
| Ile | Val | Met | Phe | Gly | Asp | Ser | Leu | Ser | Asp | Thr | Gly | Lys | Met | Tyr | Ser |
| 1 | | | | 5 | | | | | 10 | | | | | 15 |

| Lys | Met | Arg | Gly | Tyr | Leu | Pro | Ser | Ser | Pro | Tyr | Tyr | Glu | Gly | Arg |
|---|---|---|---|---|---|---|---|---|---|---|---|---|---|---|
| | | | 20 | | | | | 25 | | | | | 30 | |

| Phe | Ser | Asn | Gly | Pro | Val | Trp | Leu | Glu | Gln | Leu | Thr | Lys | Gln | Phe | Pro |
|---|---|---|---|---|---|---|---|---|---|---|---|---|---|---|---|
| | | | 35 | | | | | 40 | | | | | 45 | | |

| Gly | Leu | Thr | Ile | Ala | Asn | Glu | Ala | Glu | Gly | Ala | Thr | Ala | Val | Ala |
|---|---|---|---|---|---|---|---|---|---|---|---|---|---|---|
| | 50 | | | | | 55 | | | | | 60 | | | |

| Tyr | Asn | Lys | Ile | Ser | Trp | Asn | Pro | Lys | Tyr | Gln | Val | Tyr | Asn | Asn | Leu |
|---|---|---|---|---|---|---|---|---|---|---|---|---|---|---|---|
| 65 | | | | | 70 | | | | | 75 | | | | | 80 |

| Asp | Tyr | Glu | Val | Thr | Gln | Phe | Leu | Gln | Lys | Asp | Ser | Phe | Lys | Pro | Asp |
|---|---|---|---|---|---|---|---|---|---|---|---|---|---|---|---|
| | | | | 85 | | | | | 90 | | | | | 95 | |

| Asp | Leu | Val | Ile | Leu | Trp | Val | Gly | Ala | Asn | Asp | Tyr | Leu | Ala | Tyr | Gly |
|---|---|---|---|---|---|---|---|---|---|---|---|---|---|---|---|
| | | | 100 | | | | | 105 | | | | | 110 | | |

| Trp | Asn | Thr | Glu | Gln | Asp | Ala | Lys | Arg | Val | Arg | Asp | Ala | Ile | Ser | Asp |
|---|---|---|---|---|---|---|---|---|---|---|---|---|---|---|---|
| | | | 115 | | | | | 120 | | | | | 125 | | |

| Ala | Ala | Asn | Arg | Met | Val | Leu | Asn | Gly | Ala | Lys | Gln | Ile | Leu | Leu | Phe |
|---|---|---|---|---|---|---|---|---|---|---|---|---|---|---|---|
| 130 | | | | | 135 | | | | | 140 | | | | | |

| Asn | Leu | Pro | Asp | Leu | Gly | Gln | Asn | Pro | Ser | Ala | Arg | Ser | Gln | Lys | Val |
|---|---|---|---|---|---|---|---|---|---|---|---|---|---|---|---|
| 145 | | | | | 150 | | | | | 155 | | | | | 160 |

| Val | Glu | Ala | Val | Ser | His | Val | Ser | Ala | Tyr | His | Asn | Lys | Leu | Leu | Leu |
|---|---|---|---|---|---|---|---|---|---|---|---|---|---|---|---|
| | | | | 165 | | | | | 170 | | | | | 175 | |

| Asn | Leu | Ala | Arg | Gln | Leu | Ala | Pro | Thr | Gly | Met | Val | Lys | Leu | Phe | Glu |
|---|---|---|---|---|---|---|---|---|---|---|---|---|---|---|---|
| | | | 180 | | | | | 185 | | | | | 190 | | |

| Ile | Asp | Lys | Gln | Phe | Ala | Glu | Met | Leu | Arg | Asp | Pro | Gln | Asn | Phe | Gly |
|---|---|---|---|---|---|---|---|---|---|---|---|---|---|---|---|
| | | | 195 | | | | | 200 | | | | | 205 | | |

| Leu | Ser | Asp | Val | Glu | Asn | Pro | Cys | Tyr | Asp | Gly | Gly | Tyr | Val | Trp | Lys |
|---|---|---|---|---|---|---|---|---|---|---|---|---|---|---|---|
| | 210 | | | | | 215 | | | | | 220 | | | | |

| Pro | Phe | Ala | Thr | Arg | Ser | Val | Ser | Thr | Asp | Arg | Gln | Leu | Ser | Ala | Phe |
|---|---|---|---|---|---|---|---|---|---|---|---|---|---|---|---|
| 225 | | | | | 230 | | | | | 235 | | | | | 240 |

| Ser | Pro | Gln | Glu | Arg | Leu | Ala | Ile | Ala | Gly | Asn | Pro | Leu | Leu | Ala | Gln |
|---|---|---|---|---|---|---|---|---|---|---|---|---|---|---|---|
| | | | | 245 | | | | | 250 | | | | | 255 | |

| Ala | Val | Ala | Ser | Pro | Met | Ala | Arg | Arg | Ser | Ala | Ser | Pro | Leu | Asn | Cys |
|---|---|---|---|---|---|---|---|---|---|---|---|---|---|---|---|
| | | | 260 | | | | | 265 | | | | | 270 | | |

| Glu | Gly | Lys | Met | Phe | Trp | Asp | Gln | Val | His | Pro | Thr | Val | Val | His |
|---|---|---|---|---|---|---|---|---|---|---|---|---|---|---|
| | | 275 | | | | | 280 | | | | | 285 | | |

| Ala | Ala | Leu | Ser | Glu | Arg | Ala |
|---|---|---|---|---|---|---|
| | 290 | | | | | 295 |

```
<210> SEQ ID NO 15
<211> LENGTH: 295
<212> TYPE: PRT
<213> ORGANISM: Aeromonas hydrophila

<400> SEQUENCE: 15
```

| | | | | | | | | | | | | | | | |
|---|---|---|---|---|---|---|---|---|---|---|---|---|---|---|---|
| Ile | Val | Met | Phe | Gly | Asp | Ser | Leu | Ser | Asp | Thr | Gly | Lys | Met | Tyr | Ser |
| 1 | | | | 5 | | | | | 10 | | | | | 15 | |

| Lys | Met | Arg | Gly | Tyr | Leu | Pro | Ser | Ser | Pro | Tyr | Tyr | Glu | Gly | Arg |
|---|---|---|---|---|---|---|---|---|---|---|---|---|---|---|
| | | | 20 | | | | | 25 | | | | | 30 | |

| Phe | Ser | Asn | Gly | Pro | Val | Trp | Leu | Glu | Gln | Leu | Thr | Lys | Gln | Phe | Pro |
|---|---|---|---|---|---|---|---|---|---|---|---|---|---|---|---|
| | | | 35 | | | | | 40 | | | | | 45 | | |

```
Gly Leu Thr Ile Ala Asn Glu Ala Glu Gly Gly Ala Thr Ala Val Ala
     50                  55                  60

Tyr Asn Lys Ile Ser Trp Asn Pro Lys Tyr Gln Val Ile Asn Asn Leu
 65                  70                  75                  80

Asp Tyr Glu Val Thr Gln Phe Leu Gln Lys Asp Ser Phe Lys Pro Asp
                 85                  90                  95

Asp Leu Val Ile Leu Trp Val Gly Ala Asn Asp Tyr Leu Ala Tyr Gly
                100                 105                 110

Trp Asn Thr Glu Gln Asp Ala Lys Arg Val Arg Asp Ala Ile Ser Asp
            115                 120                 125

Ala Ala Asn Arg Met Val Leu Asn Gly Ala Lys Gln Ile Leu Leu Phe
        130                 135                 140

Asn Leu Pro Asp Leu Gly Gln Asn Pro Ser Ala Arg Ser Gln Lys Val
145                 150                 155                 160

Val Glu Ala Val Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Val Glu Asn Pro Cys Tyr Asp Gly Gly Tyr Val Trp Lys
210                 215                 220

Pro Phe Ala Thr Arg Ser Val Ser Thr Asp Arg Gln Leu Ser Ala Phe
225                 230                 235                 240

Ser Pro Gln Glu Arg Leu Ala Ile Ala Gly Asn Pro Leu Leu Ala Gln
                245                 250                 255

Ala Val Ala Ser Pro Met Ala Arg Arg Ser Ala Ser Pro Leu Asn Cys
            260                 265                 270

Glu Gly Lys Met Phe Trp Asp Gln Val His Pro Thr Thr Val Val His
        275                 280                 285

Ala Ala Leu Ser Glu Arg Ala
        290                 295

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Asp Ser Leu
1

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
1               5

<210> SEQ ID NO 18
<211> LENGTH: 18
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taatacgact cactatag                                                     18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctagttattg ctcagcgg                                                     18

<210> SEQ ID NO 20
<211> LENGTH: 261
<212> TYPE: PRT
<213> ORGANISM: Streptomyces coelicolor

<400> SEQUENCE: 20
```

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Pro Leu Pro Pro Arg
        195                 200                 205

Gly Thr Leu Asp Val Arg Arg Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260

<210> SEQ ID NO 21
<211> LENGTH: 786
<212> TYPE: DNA
<213> ORGANISM: Streptomyces coelicolor

<400> SEQUENCE: 21

```
gtgatcgggt cgtacgtggc ggtgggggac agcttcaccg agggcgtcgg cgaccccggc    60
cccgacgggg cgttcgtcgg ctgggccgac cggctcgccg tactgctcgc ggaccggcgc   120
cccgagggcg acttcacgta cacgaacctc gccgtgcgcg gcaggctcct cgaccagatc   180
gtggcggaac aggtcccgcg ggtcgtcgga ctcgcgcccg acctcgtctc gttcgcggcg   240
ggcggcaacg acatcatccg gcccggcacc gatcccgacg aggtcgccga gcggttcgag   300
ctggcggtgg ccgcgctgac cgccgcggcc ggaaccgtcc tggtgaccac cggggttcgac   360
acccgggggg tgcccgtcct caagcacctg cgcggcaaga tcgccacgta caacgggcac   420
gtccgcgcca tcgccgaccg ctacggctgc ccggtgctcg acctgtggtc gctgcggagc   480
gtccaggacc gcagggcgtg ggacgccgac cggctgcacc tgtcgccgga ggggcacacc   540
cgggtggcgc tgcgcgcggg gcaggccctg gcctgcgcg tcccggccga ccctgaccag   600
ccctggccgc cctgccgcc gcgcggcacg ctcgacgtcc ggcgcgacga cgtgcactgg   660
gcgcgcgagt acctggtgcc gtggatcggg cgccggctgc ggggcgagtc gtcgggcgac   720
cacgtgacgg ccaaggggac gctgtcgccg gacgccatca agacgcggat cgccgcggtg   780
gcctga                                                              786
```

<210> SEQ ID NO 22
<211> LENGTH: 260
<212> TYPE: PRT
<213> ORGANISM: Streptomyces coelicolor

<400> SEQUENCE: 22

```
Met Gln Thr Asn Pro Ala Tyr Thr Ser Leu Val Ala Val Gly Asp Ser
1               5                   10                  15

Phe Thr Glu Gly Met Ser Asp Leu Leu Pro Asp Gly Ser Tyr Arg Gly
                20                  25                  30

Trp Ala Asp Leu Leu Ala Thr Arg Met Ala Ala Arg Ser Pro Gly Phe
            35                  40                  45

Arg Tyr Ala Asn Leu Ala Val Arg Gly Lys Leu Ile Gly Gln Ile Val
        50                  55                  60

Asp Glu Gln Val Asp Val Ala Ala Met Gly Ala Asp Val Ile Thr
65                  70                  75                  80

Leu Val Gly Gly Leu Asn Asp Thr Leu Arg Pro Lys Cys Asp Met Ala
                85                  90                  95

Arg Val Arg Asp Leu Leu Thr Gln Ala Val Glu Arg Leu Ala Pro His
            100                 105                 110

Cys Glu Gln Leu Val Leu Met Arg Ser Pro Gly Arg Gln Gly Pro Val
        115                 120                 125

Leu Glu Arg Phe Arg Pro Arg Met Glu Ala Leu Phe Ala Val Ile Asp
    130                 135                 140

Asp Leu Ala Gly Arg His Gly Ala Val Val Asp Leu Tyr Gly Ala
145                 150                 155                 160

Gln Ser Leu Ala Asp Pro Arg Met Trp Asp Val Asp Arg Leu His Leu
                165                 170                 175

Thr Ala Glu Gly His Arg Arg Val Ala Glu Ala Val Trp Gln Ser Leu
```

```
                    180                 185                 190
Gly His Glu Pro Glu Asp Pro Glu Trp His Ala Pro Ile Pro Ala Thr
                195                 200                 205

Pro Pro Pro Gly Trp Val Thr Arg Arg Thr Ala Asp Val Arg Phe Ala
            210                 215                 220

Arg Gln His Leu Leu Pro Trp Ile Gly Arg Arg Leu Thr Gly Arg Ser
225                 230                 235                 240

Ser Gly Asp Gly Leu Pro Ala Lys Arg Pro Asp Leu Leu Pro Tyr Glu
                245                 250                 255

Asp Pro Ala Arg
            260

<210> SEQ ID NO 23
<211> LENGTH: 783
<212> TYPE: DNA
<213> ORGANISM: Streptomyces coelicolor

<400> SEQUENCE: 23
atgcagacga accccgcgta caccagtctc gtcgccgtcg gcgactcctt caccgagggc      60
atgtcggacc tgctgcccga cggctcctac cgtggctggg ccgacctcct cgccacccgg     120
atggcggccc gctcccccgg cttccggtac gccaacctgg cggtgcgcgg aagctgatc      180 ggacagatcg tcgacgagca ggtggacgtg ccgccgcca tgggagccga cgtgatcacg      240
ctggtcggcg ggctcaacga cacgctgcgg cccaagtgcg acatggcccg ggtgcgggac     300
ctgctgaccc aggccgtgga acggctcgcc ccgcactgcg agcagctggt gctgatgcgc     360
agtcccggtc gccagggtcc ggtgctggag cgcttccggc cccgcatgga ggccctgttc     420
gccgtgatcg cgaccctggc cgggcggcac ggcgccgtgg tcgtcgacct gtacggggcc     480
cagtcgctgg ccgacccctcg gatgtgggac gtggaccggc tgcacctgac cgccgagggc     540
caccgccggg tcgcggaggc ggtgtggcag tcgctcggcc acgagcccga ggaccccgag     600
tggcacgcgc cgatcccggc gacgccgccg ccggggtggg tgacgcgcag gaccgcggac     660
gtccggttcg cccggcagca cctgctgccc tggataggcc gcaggctgac cgggcgctcg     720
tccggggacg gcctgccggc caagcgcccg gacctgctgc cctacgagga ccccgcacgg     780
tga                                                                    783

<210> SEQ ID NO 24
<211> LENGTH: 454
<212> TYPE: PRT
<213> ORGANISM: Streptomyces coelicolor

<400> SEQUENCE: 24

Met Thr Arg Gly Arg Asp Gly Gly Ala Gly Ala Pro Pro Thr Lys His
1               5                   10                  15

Arg Ala Leu Leu Ala Ala Ile Val Thr Leu Ile Val Ala Ile Ser Ala
            20                  25                  30

Ala Ile Tyr Ala Gly Ala Ser Ala Asp Asp Gly Ser Arg Asp His Ala
        35                  40                  45

Leu Gln Ala Gly Gly Arg Leu Pro Arg Gly Asp Ala Ala Pro Ala Ser
    50                  55                  60

Thr Gly Ala Trp Val Gly Ala Trp Ala Thr Ala Pro Ala Ala Ala Glu
65                  70                  75                  80

Pro Gly Thr Glu Thr Thr Gly Leu Ala Gly Arg Ser Val Arg Asn Val
                85                  90                  95

Val His Thr Ser Val Gly Gly Thr Gly Ala Arg Ile Thr Leu Ser Asn
```

```
            100                 105                 110
Leu Tyr Gly Gln Ser Pro Leu Thr Val Thr His Ala Ser Ile Ala Leu
            115                 120                 125

Ala Ala Gly Pro Asp Thr Ala Ala Ile Ala Asp Thr Met Arg Arg
130                 135                 140

Leu Thr Phe Gly Gly Ser Ala Arg Val Ile Ile Pro Ala Gly Gly Gln
145                 150                 155                 160

Val Met Ser Asp Thr Ala Arg Leu Ala Ile Pro Tyr Gly Ala Asn Val
            165                 170                 175

Leu Val Thr Thr Tyr Ser Pro Ile Pro Ser Gly Pro Val Thr Tyr His
            180                 185                 190

Pro Gln Ala Arg Gln Thr Ser Tyr Leu Ala Asp Gly Asp Arg Thr Ala
            195                 200                 205

Asp Val Thr Ala Val Ala Tyr Thr Thr Pro Thr Pro Tyr Trp Arg Tyr
            210                 215                 220

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
            245                 250                 255

Asn His Arg Trp Thr Asp Val Leu Ala Ala Arg Leu His Glu Ala Ala
            260                 265                 270

Gly Asp Gly Arg Asp Thr Pro Arg Tyr Ser Val Val Asn Glu Gly Ile
            275                 280                 285

Ser Gly Asn Arg Leu Leu Thr Ser Arg Pro Gly Arg Pro Ala Asp Asn
            290                 295                 300

Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
            325                 330                 335

Pro Glu Leu Ala Asp Arg Asp Ala Ile Leu Thr Gly Leu Arg Thr Leu
            340                 345                 350

Val Asp Arg Ala His Ala Arg Gly Leu Arg Val Val Gly Ala Thr Ile
            355                 360                 365

Thr Pro Phe Gly Gly Tyr Gly Gly Tyr Thr Glu Ala Arg Glu Thr Met
370                 375                 380

Arg Gln Glu Val Asn Glu Ile Arg Ser Gly Arg Val Phe Asp Thr
385                 390                 395                 400

Val Val Asp Phe Asp Lys Ala Leu Arg Asp Pro Tyr Asp Pro Arg Arg
            405                 410                 415

Met Arg Ser Asp Tyr Asp Ser Gly Asp His Leu His Pro Gly Asp Lys
            420                 425                 430

Gly Tyr Ala Arg Met Gly Ala Val Ile Asp Leu Ala Ala Leu Lys Gly
            435                 440                 445

Ala Ala Pro Val Lys Ala
            450

<210> SEQ ID NO 25
<211> LENGTH: 1365
<212> TYPE: DNA
<213> ORGANISM: Streptomyces coelicolor

<400> SEQUENCE: 25
atgacccggg gtcgtgacgg gggtgcgggg gcgccccccca ccaagcaccg tgccctgctc      60
gcggcgatcg tcaccctgat agtggcgatc tccgcggcca tatacgccgg agcgtccgcg     120
```

-continued

```
gacgacggca gcagggacca cgcgctgcag gccggaggcc gtctcccacg aggagacgcc    180
gcccccgcgt ccaccggtgc ctgggtgggc gcctgggcca ccgcaccggc cgcggccgag    240
ccgggcaccg agacgaccgg cctggcgggc cgctccgtgc gcaacgtcgt gcacacctcg    300
gtcggcggca ccggcgcgcg gatcaccctc tcgaacctgt acgggcagtc gccgctgacc    360
gtcacacacg cctcgatcgc cctggccgcc gggcccgaca ccgccgccgc gatcgccgac    420
accatgcgcc ggctcacctt cggcggcagc gcccgggtga tcatcccggc gggcggccag    480
gtgatgagcg acaccgcccg cctcgccatc ccctacgggg cgaacgtcct ggtcaccacg    540
tactccccca tcccgtccgg gccggtgacc taccatccgc aggcccggca gaccagctac    600
ctggccgacg gcgaccgcac ggcggacgtc accgccgtcg cgtacaccac ccccacgccc    660
tactggcgct acctgaccgc cctcgacgtg ctgagccacg aggccgacgg cacggtcgtg    720
gcgttcggcg actccatcac cgacggcgcc cgctcgcaga gcgacgccaa ccaccgctgg    780
accgacgtcc tcgccgcacg cctgcacgag gcggcgggcg acggccggga cacgccccgc    840
tacagcgtcg tcaacgaggg catcagcggc aaccggctcc tgaccagcag gccggggcgg    900
ccggccgaca cccgagcgg actgagccgg ttccagcggg acgtgctgga acgcaccaac    960
gtcaaggccg tcgtcgtcgt cctcggcgtc aacgacgtcc tgaacagccc ggaactcgcc   1020
gaccgcgacg ccatcctgac cggcctgcgc accctcgtcg accgggcgca cgcccgggga   1080
ctgcgggtcg tcggcgccac gatcacgccg ttcggcggct acggcggcta caccgaggcc   1140
cgcgagacga tgcggcagga ggtcaacgag gagatccgct ccggccgggt cttcgacacg   1200
gtcgtcgact tcgacaaggc cctgcgcgac ccgtacgacc gcgccggat gcgctccgac   1260 tacgacagcg cgaccacct gcaccccggc gacaaggggt acgcgcgcat gggcgcggtc   1320
atcgacctgg ccgcgctgaa gggcgcggcg ccggtcaagg cgtag                   1365
```

<210> SEQ ID NO 26
<211> LENGTH: 340
<212> TYPE: PRT
<213> ORGANISM: Streptomyces coelicolor

<400> SEQUENCE: 26

```
Met Thr Ser Met Ser Arg Ala Arg Val Ala Arg Arg Ile Ala Ala Gly
1               5                   10                  15

Ala Ala Tyr Gly Gly Gly Ile Gly Leu Ala Gly Ala Ala Ala Val
            20                  25                  30

Gly Leu Val Val Ala Glu Val Gln Leu Ala Arg Arg Val Gly Val
        35                  40                  45

Gly Thr Pro Thr Arg Val Pro Asn Ala Gln Gly Leu Tyr Gly Gly Thr
    50                  55                  60

Leu Pro Thr Ala Gly Asp Pro Pro Leu Arg Leu Met Met Leu Gly Asp
65                  70                  75                  80

Ser Thr Ala Ala Gly Gln Gly Val His Arg Ala Gly Gln Thr Pro Gly
                85                  90                  95

Ala Leu Leu Ala Ser Gly Leu Ala Ala Val Ala Glu Arg Pro Val Arg
            100                 105                 110

Leu Gly Ser Val Ala Gln Pro Gly Ala Cys Ser Asp Asp Leu Asp Arg
        115                 120                 125

Gln Val Ala Leu Val Leu Ala Glu Pro Asp Arg Val Pro Asp Ile Cys
    130                 135                 140

Val Ile Met Val Gly Ala Asn Asp Val Thr His Arg Met Pro Ala Thr
145                 150                 155                 160
```

```
Arg Ser Val Arg His Leu Ser Ser Ala Val Arg Arg Leu Arg Thr Ala
            165                 170                 175
Gly Ala Glu Val Val Gly Thr Cys Pro Asp Leu Gly Thr Ile Glu
        180                 185                 190
Arg Val Arg Gln Pro Leu Arg Trp Leu Ala Arg Ala Ser Arg Gln
        195                 200                 205
Leu Ala Ala Ala Gln Thr Ile Gly Ala Val Glu Gln Gly Gly Arg Thr
    210                 215                 220
Val Ser Leu Gly Asp Leu Leu Gly Pro Glu Phe Ala Gln Asn Pro Arg
225                 230                 235                 240
Glu Leu Phe Gly Pro Asp Asn Tyr His Pro Ser Ala Glu Gly Tyr Ala
                245                 250                 255
Thr Ala Ala Met Ala Val Leu Pro Ser Val Cys Ala Ala Leu Gly Leu
            260                 265                 270
Trp Pro Ala Asp Glu Glu His Pro Asp Ala Leu Arg Arg Glu Gly Phe
        275                 280                 285
Leu Pro Val Ala Arg Ala Ala Glu Ala Ala Ser Glu Ala Gly Thr
    290                 295                 300
Glu Val Ala Ala Ala Met Pro Thr Gly Pro Arg Gly Pro Trp Ala Leu
305                 310                 315                 320
Leu Lys Arg Arg Arg Arg Arg Val Ser Glu Ala Glu Pro Ser Ser
                325                 330                 335
Pro Ser Gly Val
        340

<210> SEQ ID NO 27
<211> LENGTH: 1023
<212> TYPE: DNA
<213> ORGANISM: Streptomyces coelicolor

<400> SEQUENCE: 27
atgacgagca tgtcgagggc gagggtggcg cggcggatcg cggccggcgc ggcgtacggc      60
ggcggcggca tcggcctggc gggagcggcg gcggtcggtc tggtggtggc cgaggtgcag     120
ctggccagac gcagggtggg ggtgggcacg ccgacccggg tgccgaacgc gcagggactg     180
tacggcggca ccctgcccac ggccggcgac ccgccgctgc ggctgatgat gctgggcgac     240
tccacggccg ccgggcaggg cgtgcaccgg gccgggcaga cgccgggcgc gctgctggcg     300
tccgggctcg cggcggtggc ggagcggccg gtgcggctgg ggtcggtcgc ccagccgggg     360
gcgtgctcgg acgacctgga ccggcaggtg gcgctggtgc tcgccgagcc ggaccgggtg     420
cccgacatct gcgtgatcat ggtcggcgcc aacgacgtca cccaccggat gccggcgacc     480
cgctcggtgc ggcaccctgtc ctcggcggta cggcggctgc gcacggccgg tgcggaggtg     540
gtggtcggca cctgtccgga cctgggcacg atcgagcggg tgcggcagcc gctgcgctgg     600
ctggcccggc gggcctcacg gcagctcgcg gcggcacaga ccatcggcgc cgtcgagcag     660
ggcgggcgca cggtgtcgct gggcgacctg ctgggtccgg agttcgcgca gaacccgcgg     720
gagctcttcg gccccgacaa ctaccacccc tccgccgagg gtacgccac ggccgcgatg     780 gcggtactgc cctcggtgtg cgccgcgctc ggcctgtggc cggccgacga ggagcacccg     840
gacgcgctgc gccgcgaggg cttcctgccg gtgcgcgcg cggcggcgga ggcggcgtcc     900
gaggcgggta cggaggtcgc cgccgccatg cctacggggc tcgggggcc ctgggcgctg     960 ctgaagcgcc ggagacggcg tcgggtgtcg gaggcggaac cgtccagccc gtccggcgtt    1020
tga                                                                  1023
```

<210> SEQ ID NO 28
<211> LENGTH: 305
<212> TYPE: PRT
<213> ORGANISM: Streptomyces coelicolor

<400> SEQUENCE: 28

```
Met Gly Arg Gly Thr Asp Gln Arg Thr Arg Tyr Gly Arg Arg Arg Ala
1               5                   10                  15
Arg Val Ala Leu Ala Ala Leu Thr Ala Val Leu Gly Val Gly Val
            20                  25                  30
Ala Gly Cys Asp Ser Val Gly Gly Asp Ser Pro Ala Pro Ser Gly Ser
            35                  40                  45
Pro Ser Lys Arg Thr Arg Thr Ala Pro Ala Trp Asp Thr Ser Pro Ala
    50                  55                  60
Ser Val Ala Ala Val Gly Asp Ser Ile Thr Arg Gly Phe Asp Ala Cys
65                  70                  75                  80
Ala Val Leu Ser Asp Cys Pro Glu Val Ser Trp Ala Thr Gly Ser Ser
                85                  90                  95
Ala Lys Val Asp Ser Leu Ala Val Arg Leu Leu Gly Lys Ala Asp Ala
            100                 105                 110
Ala Glu His Ser Trp Asn Tyr Ala Val Thr Gly Ala Arg Met Ala Asp
            115                 120                 125
Leu Thr Ala Gln Val Thr Arg Ala Ala Gln Arg Glu Pro Glu Leu Val
    130                 135                 140
Ala Val Met Ala Gly Ala Asn Asp Ala Cys Arg Ser Thr Thr Ser Ala
145                 150                 155                 160
Met Thr Pro Val Ala Asp Phe Arg Ala Gln Phe Glu Glu Ala Met Ala
                165                 170                 175
Thr Leu Arg Lys Lys Leu Pro Lys Ala Gln Val Tyr Val Ser Ser Ile
            180                 185                 190
Pro Asp Leu Lys Arg Leu Trp Ser Gln Gly Arg Thr Asn Pro Leu Gly
            195                 200                 205
Lys Gln Val Trp Lys Leu Gly Leu Cys Pro Ser Met Leu Gly Asp Ala
    210                 215                 220
Asp Ser Leu Asp Ser Ala Ala Thr Leu Arg Arg Asn Thr Val Arg Asp
225                 230                 235                 240
Arg Val Ala Asp Tyr Asn Glu Val Leu Arg Glu Val Cys Ala Lys Asp
                245                 250                 255
Arg Arg Cys Arg Ser Asp Asp Gly Ala Val His Glu Phe Arg Phe Gly
            260                 265                 270
Thr Asp Gln Leu Ser His Trp Asp Trp Phe His Pro Ser Val Asp Gly
    275                 280                 285
Gln Ala Arg Leu Ala Glu Ile Ala Tyr Arg Ala Val Thr Ala Lys Asn
    290                 295                 300
Pro
305
```

<210> SEQ ID NO 29
<211> LENGTH: 918
<212> TYPE: DNA
<213> ORGANISM: Streptomyces coelicolor

<400> SEQUENCE: 29

```
atgggtcgag ggacggacca gcggacgcgg tacggccgtc gccgggcgcg tgtcgcgctc      60
gccgccctga ccgccgccgt cctgggcgtg ggcgtggcgg gctgcgactc cgtgggcggc     120
```

-continued

```
gactcacccg ctccttccgg cagcccgtcg aagcggacga ggacggcgcc cgcctgggac    180
accagcccgg cgtccgtcgc cgccgtgggc gactccatca cgcgcggctt cgacgcctgt    240
gcggtgctgt cggactgccc ggaggtgtcg tgggcgaccg gcagcagcgc gaaggtcgac    300
tcgctggccg tacggctgct ggggaaggcg gacgcggccg agcacagctg gaactacgcg    360
gtcaccgggg cccggatggc ggacctgacc gctcaggtga cgcgggcggc gcagcgcgag    420
ccggagctgt ggcggtgat ggccggggcg aacgacgcgt gccggtccac gacctcggcg    480
atgacgccgg tggcggactt ccgggcgcag ttcgaggagg cgatggccac cctgcgcaag    540
aagctcccca aggcgcaggt gtacgtgtcg agcatcccgg acctcaagcg gctctggtcc    600
cagggccgca ccaacccgct gggcaagcag gtgtggaagc tcggcctgtg cccgtcgatg    660
ctgggcgacg cggactccct ggactcggcg gcgaccctgc ggcgcaacac ggtgcgcgac    720
cgggtggcgg actacaacga ggtgctgcgg gaggtctgcg cgaaggaccg gcggtgccgc    780
agcgacgacg cgcgggtgca cgagttccgg ttcggcacgg accagttgag ccactgggac    840
tggttccacc cgagtgtgga cggccaggcc cggctggcgg agatcgccta ccgcgcggtc    900
accgcgaaga atccctga                                                  918
```

<210> SEQ ID NO 30
<211> LENGTH: 268
<212> TYPE: PRT
<213> ORGANISM: Streptomyces rimosus

<400> SEQUENCE: 30

```
Met Arg Leu Ser Arg Arg Ala Ala Thr Ala Ser Ala Leu Leu Leu Thr
1               5                   10                  15

Pro Ala Leu Ala Leu Phe Gly Ala Ser Ala Ala Val Ser Ala Pro Arg
            20                  25                  30

Ile Gln Ala Thr Asp Tyr Val Ala Leu Gly Asp Ser Tyr Ser Ser Gly
        35                  40                  45

Val Gly Ala Gly Ser Tyr Asp Ser Ser Gly Ser Cys Lys Arg Ser
    50                  55                  60

Thr Lys Ser Tyr Pro Ala Leu Trp Ala Ala Ser His Thr Gly Thr Arg
65                  70                  75                  80

Phe Asn Phe Thr Ala Cys Ser Gly Ala Arg Thr Gly Asp Val Leu Ala
                85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
        115                 120                 125

Leu Gln Gly Glu Ser Ala Cys Leu Ala Arg Ile Ala Lys Ala Arg Ala
    130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Leu Gly Tyr Pro
                165                 170                 175

Arg Phe Tyr Lys Leu Gly Gly Ser Cys Ala Val Gly Leu Ser Glu Lys
            180                 185                 190

Ser Arg Ala Ala Ile Asn Ala Ala Ala Asp Asp Ile Asn Ala Val Thr
        195                 200                 205

Ala Lys Arg Ala Ala Asp His Gly Phe Ala Phe Gly Asp Val Asn Thr
    210                 215                 220

Thr Phe Ala Gly His Glu Leu Cys Ser Gly Ala Pro Trp Leu His Ser
225                 230                 235                 240
```

Val Thr Leu Pro Val Glu Asn Ser Tyr His Pro Thr Ala Asn Gly Gln
            245                 250                 255

Ser Lys Gly Tyr Leu Pro Val Leu Asn Ser Ala Thr
            260                 265

<210> SEQ ID NO 31
<211> LENGTH: 1068
<212> TYPE: DNA
<213> ORGANISM: Streptomyces rimosus

<400> SEQUENCE: 31
ttcatcacaa cgatgtcaca acaccggcca tccgggtcat ccctgatcgt gggaatgggt        60
gacaagcctt cccgtgacga aagggtcctg ctacatcaga atgacagaa atcctgctca       120 gggaggttcc atgagactgt cccgacgcgc ggccacggct tccgcgctcc tcctcacccc      180
ggcgctcgcg ctcttcggcg cgagcgccgc cgtgtccgcg ccgcgaatcc aggccaccga      240
ctacgtggcc ctcggcgact cctactcctc ggggtcggc gcgggcagct acgacagcag       300
cagtggctcc tgtaagcgca gcaccaagtc ctacccggcc ctgtgggccg cctcgcacac      360
cggtacgcgg ttcaacttca ccgcctgttc gggcgcccgc acaggagacg tgctggccaa      420
gcagctgacc ccggtcaact ccggcaccga cctggtcagc attaccatcg gcggcaacga      480
cgcgggcttc gccgacacca tgaccacctg caacctccag ggcgagagcg cgtgcctggc      540
gcggatcgcc aaggcgcgcg cctacatcca gcagacgctg cccgcccagc tggaccaggt      600
ctacgacgcc atcgacagcc gggccccgc agcccaggtc gtcgtcctgg gctacccgcg       660
cttctacaag ctgggcggca gctgcgccgt cggtctctcg gagaagtccc gcgcggccat      720
caacgccgcc gccgacgaca tcaacgccgt caccgccaag cgcgccgccg accacggctt      780
cgccttcggg gacgtcaaca cgaccttcgc cgggcacgag ctgtgctccg cgcccctg      840 gctgcacagc gtcacccttc ccgtggagaa ctcctaccac cccacggcca acggacagtc      900
caagggctac ctgcccgtcc tgaactccgc cacctgatct cgcggctact ccgcccctga      960
cgaagtcccg cccccgggcg gggcttcgcc gtaggtgcgc gtaccgccgt cgcccgtcgc     1020
gccggtggcc ccgccgtacg tgccgccgcc cccggacgcg gtcggttc                  1068

<210> SEQ ID NO 32
<211> LENGTH: 335
<212> TYPE: PRT
<213> ORGANISM: Aeromonas hydrophila

<400> SEQUENCE: 32

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
            85                  90                  95

Trp Asn Pro Lys Tyr Gln Val Ile Asn Asn Leu Asp Tyr Glu Val Thr
            100                 105                 110

```
Gln Phe Leu Gln Lys Asp Ser Phe Lys Pro Asp Asp Leu Val Ile Leu
            115                 120                 125
Trp Val Gly Ala Asn Asp Tyr Leu Ala Tyr Gly Trp Asn Thr Glu Gln
        130                 135                 140
Asp Ala Lys Arg Val Arg Asp Ala Ile Ser Asp Ala Ala Asn Arg Met
145                 150                 155                 160
Val Leu Asn Gly Ala Lys Gln Ile Leu Leu Phe Asn Leu Pro Asp Leu
                165                 170                 175
Gly Gln Asn Pro Ser Ala Arg Ser Gln Lys Val Val Glu Ala Val Ser
            180                 185                 190
His Val Ser Ala Tyr His Asn Gln Leu Leu Asn Leu Ala Arg Gln
        195                 200                 205
Leu Ala Pro Thr Gly Met Val Lys Leu Phe Glu Ile Asp Lys Gln Phe
    210                 215                 220
Ala Glu Met Leu Arg Asp Pro Gln Asn Phe Gly Leu Ser Asp Val Glu
225                 230                 235                 240
Asn Pro Cys Tyr Asp Gly Gly Tyr Val Trp Lys Pro Phe Ala Thr Arg
                245                 250                 255
Ser Val Ser Thr Asp Arg Gln Leu Ser Ala Phe Ser Pro Gln Glu Arg
            260                 265                 270
Leu Ala Ile Ala Gly Asn Pro Leu Leu Ala Gln Ala Val Ala Ser Pro
        275                 280                 285
Met Ala Arg Arg Ser Ala Ser Pro Leu Asn Cys Glu Gly Lys Met Phe
    290                 295                 300
Trp Asp Gln Val His Pro Thr Thr Val Val His Ala Ala Leu Ser Glu
305                 310                 315                 320
Arg Ala Ala Thr Phe Ile Ala Asn Gln Tyr Glu Phe Leu Ala His
                325                 330                 335

<210> SEQ ID NO 33
<211> LENGTH: 1008
<212> TYPE: DNA
<213> ORGANISM: Aeromonas hydrophila

<400> SEQUENCE: 33
atgaaaaaat ggtttgtgtg tttattggga ttggtcgcgc tgacagttca ggcagccgac    60
agtcgccccg ccttttcccg gatcgtgatg ttcggcgaca gcctctccga taccggcaaa   120
atgtacagca agatgcgcgg ttacctcccc tccagcccgc cctactatga gggccgtttc   180
tccaacggac ccgtctggct ggagcagctg accaaacagt tcccgggtct gaccatcgcc   240
aacgaagcgg aaggcggtgc cactgccgtg gcttacaaca agatctcctg gaatcccaag   300
tatcaggtca tcaacaacct ggactacgag gtcacccagt tcttgcagaa agacagcttc   360
aagccggacg atctggtgat cctctggggtc ggtgccaatg actatctggc ctatggctgg   420
aacacggagc aggatgccaa gcgggttcgc gatgccatca gcgatgcggc caaccgcatg   480
gtactgaacg gtgccaagca gatactgctg ttcaacctgc cggatctggg ccagaacccg   540
tcagctcgca gtcagaaggt ggtcgaggcg gtcagccatg tctccgccta tcacaaccag   600
ctgctgctga acctggcacg ccagctggcc cccaccggca tggtaaagct gttcgagatc   660
gacaagcaat tgccgagat gctgcgtgat ccgcagaact tcggcctgag cgacgtcgag   720
aaccccctgct acgacggcgg ctatgtgtgg aagccgtttg ccaccgcag cgtcagcacc   780
gaccgccagc tctccgcctt cagtccgcag gaacgcctcg ccatcgccgg caacccgctg   840
ctggcacagg ccgttgccag tcctatggcc cgccgcagcg ccagcccct caactgtgag   900
```

```
ggcaagatgt tctgggatca ggtacacccg accactgtcg tgcacgcagc cctgagcgag    960
cgcgccgcca ccttcatcgc gaaccagtac gagttcctcg cccactga                1008
```

<210> SEQ ID NO 34
<211> LENGTH: 336
<212> TYPE: PRT
<213> ORGANISM: Aeromonas salmonicida

<400> SEQUENCE: 34

```
Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335
```

<210> SEQ ID NO 35
<211> LENGTH: 1011
<212> TYPE: DNA
<213> ORGANISM: Aeromonas salmonicida

<400> SEQUENCE: 35

```
atgaaaaaat ggtttgtttg tttattgggg ttgatcgcgc tgacagttca ggcagccgac      60
actcgccccg ccttctcccg gatcgtgatg ttcggcgaca gcctctccga taccggcaaa     120
atgtacagca agatgcgcgg ttacctcccc tccagcccgc cctactatga gggccgtttc     180
tccaacggac ccgtctggct ggagcagctg accaagcagt tcccgggtct gaccatcgcc     240
aacgaagcgg aaggcggtgc cactgccgtg gcttacaaca agatctcctg gaatcccaag     300
tatcaggtca tcaacaacct ggactacgag gtcacccagt tcttgcagaa agacagcttc     360
aagccggacg atctggtgat cctctgggtc ggtgccaatg actatctggc atatggctgg     420
aatacggagc aggatgccaa gcgagttcgc gatgccatca gcgatgcggc caaccgcatg     480
gtactgaacg gtgccaagca gatactgctg ttcaacctgc cggatctggg ccagaacccg     540
tcagcccgca gtcagaaggt ggtcgaggcg gtcagccatg tctccgccta tcacaacaag     600
ctgctgctga acctggcacg ccagctgcc cccaccggca tggtaaagct gttcgagatc      660
gacaagcaat tgccgagat gctgcgtgat ccgcagaact tcggcctgag cgacgtcgag      720
aaccctgct acgacggcgg ctatgtgtgg aagccgtttg ccacccgcag cgtcagcacc      780
gaccgccagc tctccgcctt cagtccgcag gaacgcctcg ccatcgccgg caacccgctg     840
ctggcacagg ccgttgccag tcctatggcc cgccgcagcg ccagcccct caactgtgag      900
ggcaagatgt tctgggatca ggtacacccg accactgtcg tgcacgcagc cctgagcgag     960
cgcgccgcca ccttcatcga gacccagtac gagttcctcg cccacggatg a            1011
```

<210> SEQ ID NO 36
<211> LENGTH: 347
<212> TYPE: PRT
<213> ORGANISM: Aeromonas hydrophila

<400> SEQUENCE: 36

```
Met Phe Lys Phe Lys Lys Asn Phe Leu Val Gly Leu Ser Ala Ala Leu
1               5                   10                  15
Met Ser Ile Ser Leu Phe Ser Ala Thr Ala Ser Ala Ala Ser Ala Asp
            20                  25                  30
Ser Arg Pro Ala Phe Ser Arg Ile Val Met Phe Gly Asp Ser Leu Ser
        35                  40                  45
Asp Thr Gly Lys Met Tyr Ser Lys Met Arg Gly Tyr Leu Pro Ser Ser
    50                  55                  60
Pro Pro Tyr Tyr Glu Gly Arg Phe Ser Asn Gly Pro Val Trp Leu Glu
65                  70                  75                  80
Gln Leu Thr Lys Gln Phe Pro Gly Leu Thr Ile Ala Asn Glu Ala Glu
                85                  90                  95
Gly Gly Ala Thr Ala Val Ala Tyr Asn Lys Ile Ser Trp Asn Pro Lys
            100                 105                 110
Tyr Gln Val Ile Asn Asn Leu Asp Tyr Glu Val Thr Gln Phe Leu Gln
        115                 120                 125
Lys Asp Ser Phe Lys Pro Asp Asp Leu Val Ile Leu Trp Val Gly Ala
    130                 135                 140
Asn Asp Tyr Leu Ala Tyr Gly Trp Asn Thr Glu Gln Asp Ala Lys Arg
145                 150                 155                 160
Val Arg Asp Ala Ile Ser Asp Ala Ala Asn Arg Met Val Leu Asn Gly
                165                 170                 175
Ala Lys Gln Ile Leu Leu Phe Asn Leu Pro Asp Leu Gly Gln Asn Pro
            180                 185                 190
```

```
Ser Ala Arg Ser Gln Lys Val Val Glu Ala Val Ser His Val Ser Ala
        195                 200                 205
Tyr His Asn Gln Leu Leu Leu Asn Leu Ala Arg Gln Leu Ala Pro Thr
    210                 215                 220
Gly Met Val Lys Leu Phe Glu Ile Asp Lys Gln Phe Ala Glu Met Leu
225                 230                 235                 240
Arg Asp Pro Gln Asn Phe Gly Leu Ser Asp Val Glu Asn Pro Cys Tyr
                245                 250                 255
Asp Gly Gly Tyr Val Trp Lys Pro Phe Ala Thr Arg Ser Val Ser Thr
            260                 265                 270
Asp Arg Gln Leu Ser Ala Phe Ser Pro Gln Glu Arg Leu Ala Ile Ala
        275                 280                 285
Gly Asn Pro Leu Leu Ala Gln Ala Val Ala Ser Pro Met Ala Arg Arg
    290                 295                 300
Ser Ala Ser Pro Leu Asn Cys Glu Gly Lys Met Phe Trp Asp Gln Val
305                 310                 315                 320
His Pro Thr Thr Val Val His Ala Ala Leu Ser Glu Arg Ala Ala Thr
                325                 330                 335
Phe Ile Ala Asn Gln Tyr Glu Phe Leu Ala His
                340                 345
```

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtgatggtgg gcgaggaact cgtactg                                      27

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agcatatgaa aaatggttt gtttgtttat tgggg                              35

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttggatccga attcatcaat ggtgatggtg atggtgggc                         39

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
taatacgact cactatag                                                   18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctagttattg ctcagcgg                                                   18

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtcatatgaa aaatggtttt gtgtgtttat tgggattggt c                         41

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atggtgatgg tgggcgagga actcgtactg                                      30

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gtcatatgaa aaatggtttt gtgtgtttat tgggattggt c                         41

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttggatccga attcatcaat ggtgatggtg atggtgggc                            39

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atgccatggc cgacagccgt cccgcc                                          26
```

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttggatccga attcatcaat ggtgatg                                         27

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttgctagcgc cgacagccgt cccgcc                                          26

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttggatccga attcatcaat ggtgatg                                         27

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttgccatggc cgacactcgc cccgcc                                          26

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttggatccga attcatcaat ggtgatg                                         27

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttgctagcgc cgacactcgc cccgcc                                          26

```
<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ttggatccga attcatcaat ggtgatg                                          27

<210> SEQ ID NO 54
<211> LENGTH: 1047
<212> TYPE: DNA
<213> ORGANISM: Aeromonas hydrophila

<400> SEQUENCE: 54
atgtttaagt ttaaaaagaa tttcttagtt ggattatcgg cagctttaat gagtattagc      60 ttgtttcgg  caaccgcctc tgcagctagc gccgacagcc gtcccgcctt ttcccggatc     120
gtgatgttcg gcgacagcct ctccgatacc ggcaaaatgt acagcaagat gcgcggttac    180
ctcccctcca gcccgcccta ctatgagggc cgtttctcca acggacccgt ctggctggag    240
cagctgacca aacagttccc gggtctgacc atcgccaacg aagcggaagg cggtgccact    300
gccgtggctt acaacaagat ctcctggaat cccaagtatc aggtcatcaa caacctggac    360
tacgaggtca cccagttctt gcagaaagac agcttcaagc cggacgatct ggtgatcctc    420
tgggtcggtg ccaatgacta tctggcctat ggctggaaca cggagcagga tgccaagcgg    480
gttcgcgatg ccatcagcga tgcggccaac cgcatggtac tgaacggtgc caagcagata    540
ctgctgttca acctgccgga tctgggccag aacccgtcag ctcgcagtca gaaggtggtc    600
gaggcggtca gccatgtctc cgcctatcac aaccagctgc tgctgaacct ggcacgccag    660 ctggcccca ccggcatggt aaagctgttc gagatcgaca gcaatttgc cgagatgctg    720 cgtgatccgc agaacttcgg cctgagcgac gtcgagaacc cctgctacga cggcggctat    780
gtgtggaagc cgtttgccac ccgcagcgtc agcaccgacc gccagctctc cgccttcagt    840
ccgcaggaac gcctcgccat cgccggcaac ccgctgctgg cacaggccgt tgccagtcct    900
atggcccgcc gcagcgccag cccctcaac tgtgagggca agatgttctg ggatcaggta    960
cacccgacca ctgtcgtgca cgcagccctg agcgagcgcg ccgccacctt catcgcgaac   1020
cagtacgagt tcctcgccca ctgatga                                      1047

<210> SEQ ID NO 55
<211> LENGTH: 295
<212> TYPE: PRT
<213> ORGANISM: Aeromonas hydrophila

<400> SEQUENCE: 55

Ile Val Met Phe Gly Asp Ser Leu Ser Asp Thr Gly Lys Met Tyr Ser
1               5                   10                  15

Lys Met Arg Gly Tyr Leu Pro Ser Ser Pro Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Glu Gly Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
```

```
                85                  90                  95
Asp Leu Val Ile Leu Trp Val Gly Ala Asn Asp Tyr Leu Ala Tyr Gly
            100                 105                 110
Trp Asn Thr Glu Gln Asp Ala Lys Arg Val Arg Asp Ala Ile Ser Asp
            115                 120                 125
Ala Ala Asn Arg Met Val Leu Asn Gly Ala Lys Glu Ile Leu Leu Phe
            130                 135                 140
Asn Leu Pro Asp Leu Gly Gln Asn Pro Ser Ala Arg Ser Gln Lys Val
145                 150                 155                 160
Val Glu Ala Ala Ser His Val Ser Ala Tyr His Asn Gln Leu Leu Leu
                165                 170                 175
Asn Leu Ala Arg Gln Leu Ala Pro Thr Gly Met Val Lys Leu Phe Glu
                180                 185                 190
Ile Asp Lys Gln Phe Ala Glu Met Leu Arg Asp Pro Gln Asn Phe Gly
                195                 200                 205
Leu Ser Asp Gln Arg Asn Ala Cys Tyr Gly Gly Ser Tyr Val Trp Lys
            210                 215                 220
Pro Phe Ala Ser Arg Ser Ala Ser Thr Asp Ser Gln Leu Ser Ala Phe
225                 230                 235                 240
Asn Pro Gln Glu Arg Leu Ala Ile Ala Gly Asn Pro Leu Leu Ala Gln
                245                 250                 255
Ala Val Ala Ser Pro Met Ala Ala Arg Ser Ala Ser Thr Leu Asn Cys
                260                 265                 270
Glu Gly Lys Met Phe Trp Asp Gln Val His Pro Thr Thr Val Val His
                275                 280                 285
Ala Ala Leu Ser Glu Pro Ala
            290                 295

<210> SEQ ID NO 56
<211> LENGTH: 295
<212> TYPE: PRT
<213> ORGANISM: Aeromonas salmonicida

<400> SEQUENCE: 56

Ile Val Met Phe Gly Asp Ser Leu Ser Asp Thr Gly Lys Met Tyr Ser
1               5                   10                  15
Lys Met Arg Gly Tyr Leu Pro Ser Ser Pro Tyr Tyr Glu Gly Arg
            20                  25                  30
Phe Ser Asn Gly Pro Val Trp Leu Glu Gln Leu Thr Lys Gln Phe Pro
            35                  40                  45
Gly Leu Thr Ile Ala Asn Glu Ala Glu Gly Gly Ala Thr Ala Val Ala
        50                  55                  60
Tyr Asn Lys Ile Ser Trp Asn Pro Lys Tyr Gln Val Tyr Asn Asn Leu
65                  70                  75                  80
Asp Tyr Glu Val Thr Gln Phe Leu Gln Lys Asp Ser Phe Lys Pro Asp
                85                  90                  95
Asp Leu Val Ile Leu Trp Val Gly Ala Asn Asp Tyr Leu Ala Tyr Gly
            100                 105                 110
Trp Asn Thr Glu Gln Asp Ala Lys Arg Val Arg Asp Ala Ile Ser Asp
            115                 120                 125
Ala Ala Asn Arg Met Val Leu Asn Gly Ala Lys Gln Ile Leu Leu Phe
            130                 135                 140
Asn Leu Pro Asp Leu Gly Gln Asn Pro Ser Ala Arg Ser Gln Lys Val
145                 150                 155                 160
Val Glu Ala Val Ser His Val Ser Ala Tyr His Asn Lys Leu Leu Leu
```

```
                    165                 170                 175
Asn Leu Ala Arg Gln Leu Ala Pro Thr Gly Met Val Lys Leu Phe Glu
                180                 185                 190

Ile Asp Lys Gln Phe Ala Glu Met Leu Arg Asp Pro Gln Asn Phe Gly
            195                 200                 205

Leu Ser Asp Val Glu Asn Pro Cys Tyr Asp Gly Gly Tyr Val Trp Lys
        210                 215                 220

Pro Phe Ala Thr Arg Ser Val Ser Thr Asp Arg Gln Leu Ser Ala Phe
225                 230                 235                 240

Ser Pro Gln Glu Arg Leu Ala Ile Ala Gly Asn Pro Leu Leu Ala Gln
                245                 250                 255

Ala Val Ala Ser Pro Met Ala Arg Arg Ser Ala Ser Pro Leu Asn Cys
            260                 265                 270

Glu Gly Lys Met Phe Trp Asp Gln Val His Pro Thr Val Val His
        275                 280                 285

Ala Ala Leu Ser Glu Arg Ala
    290                 295

<210> SEQ ID NO 57
<211> LENGTH: 247
<212> TYPE: PRT
<213> ORGANISM: Streptomyces coelicolor

<400> SEQUENCE: 57

Tyr Val Ala Leu Gly Asp Ser Tyr Ser Ala Gly Ser Gly Val Leu Pro
1               5                   10                  15

Val Asp Pro Ala Asn Leu Leu Cys Leu Arg Ser Thr Ala Asn Tyr Pro
            20                  25                  30

His Val Ile Ala Asp Thr Thr Gly Ala Arg Leu Thr Asp Val Thr Cys
        35                  40                  45

Gly Ala Ala Gln Thr Ala Asp Phe Thr Arg Ala Gln Tyr Pro Gly Val
    50                  55                  60

Ala Pro Gln Leu Asp Ala Leu Gly Thr Gly Thr Asp Leu Val Thr Leu
65                  70                  75                  80

Thr Ile Gly Gly Asn Asp Asn Ser Thr Phe Ile Asn Ala Ile Thr Ala
                85                  90                  95

Cys Gly Thr Ala Gly Val Leu Ser Gly Gly Lys Gly Ser Pro Cys Lys
            100                 105                 110

Asp Arg His Gly Thr Ser Phe Asp Asp Glu Ile Glu Ala Asn Thr Tyr
        115                 120                 125

Pro Ala Leu Lys Glu Ala Leu Leu Gly Val Arg Ala Arg Ala Pro His
    130                 135                 140

Ala Arg Val Ala Ala Leu Gly Tyr Pro Trp Ile Thr Pro Ala Thr Ala
145                 150                 155                 160

Asp Pro Ser Cys Phe Leu Lys Leu Pro Leu Ala Ala Gly Asp Val Pro
                165                 170                 175

Tyr Leu Arg Ala Ile Gln Ala His Leu Asn Asp Ala Val Arg Arg Ala
            180                 185                 190

Ala Glu Glu Thr Gly Ala Thr Tyr Val Asp Phe Ser Gly Val Ser Asp
        195                 200                 205

Gly His Asp Ala Cys Glu Ala Pro Gly Thr Arg Trp Ile Glu Pro Leu
    210                 215                 220

Leu Phe Gly His Ser Leu Val Pro Val His Pro Asn Ala Leu Gly Glu
225                 230                 235                 240

Arg Arg Met Ala Glu His Thr
```

<210> SEQ ID NO 58
<211> LENGTH: 247
<212> TYPE: PRT
<213> ORGANISM: Streptomyces coelicolor

<400> SEQUENCE: 58

Tyr Val Ala Leu Gly Asp Ser Tyr Ser Ala Gly Ser Gly Val Leu Pro
1               5                   10                  15

Val Asp Pro Ala Asn Leu Leu Cys Leu Arg Ser Thr Ala Asn Tyr Pro
            20                  25                  30

His Val Ile Ala Asp Thr Thr Gly Ala Arg Leu Thr Asp Val Thr Cys
        35                  40                  45

Gly Ala Ala Gln Thr Ala Asp Phe Thr Arg Ala Gln Tyr Pro Gly Val
    50                  55                  60

Ala Pro Gln Leu Asp Ala Leu Gly Thr Gly Thr Asp Leu Val Thr Leu
65                  70                  75                  80

Thr Ile Gly Gly Asn Asp Asn Ser Thr Phe Ile Asn Ala Ile Thr Ala
                85                  90                  95

Cys Gly Thr Ala Gly Val Leu Ser Gly Lys Gly Ser Pro Cys Lys
            100                 105                 110

Asp Arg His Gly Thr Ser Phe Asp Asp Glu Ile Glu Ala Asn Thr Tyr
        115                 120                 125

Pro Ala Leu Lys Glu Ala Leu Leu Gly Val Arg Ala Arg Ala Pro His
    130                 135                 140

Ala Arg Val Ala Ala Leu Gly Tyr Pro Trp Ile Thr Pro Ala Thr Ala
145                 150                 155                 160

Asp Pro Ser Cys Phe Leu Lys Leu Pro Leu Ala Ala Gly Asp Val Pro
                165                 170                 175

Tyr Leu Arg Ala Ile Gln Ala His Leu Asn Asp Ala Val Arg Arg Ala
            180                 185                 190

Ala Glu Glu Thr Gly Ala Thr Tyr Val Asp Phe Ser Gly Val Ser Asp
        195                 200                 205

Gly His Asp Ala Cys Glu Ala Pro Gly Thr Arg Trp Ile Glu Pro Leu
    210                 215                 220

Leu Phe Gly His Ser Leu Val Pro Val His Pro Asn Ala Leu Gly Glu
225                 230                 235                 240

Arg Arg Met Ala Glu His Thr
                245

<210> SEQ ID NO 59
<211> LENGTH: 198
<212> TYPE: PRT
<213> ORGANISM: Saccharomyces cerevisiae

<400> SEQUENCE: 59

Phe Leu Leu Phe Gly Asp Ser Ile Thr Glu Phe Ala Phe Asn Thr Arg
1               5                   10                  15

Pro Ile Glu Asp Gly Lys Asp Gln Tyr Ala Leu Gly Ala Ala Leu Val
            20                  25                  30

Asn Glu Tyr Thr Arg Lys Met Asp Ile Leu Gln Arg Gly Phe Lys Gly
        35                  40                  45

Tyr Thr Ser Arg Trp Ala Leu Lys Ile Leu Pro Glu Ile Leu Lys His
    50                  55                  60

Glu Ser Asn Ile Val Met Ala Thr Ile Phe Leu Gly Ala Asn Asp Ala
65                  70                  75                  80

```
Cys Ser Ala Gly Pro Gln Ser Val Pro Leu Pro Glu Phe Ile Asp Asn
                85                  90                  95

Ile Arg Gln Met Val Ser Leu Met Lys Ser Tyr His Ile Arg Pro Ile
            100                 105                 110

Ile Ile Gly Pro Gly Leu Val Asp Arg Glu Lys Trp Glu Lys Glu Lys
            115                 120                 125

Ser Glu Glu Ile Ala Leu Gly Tyr Phe Arg Thr Asn Glu Asn Phe Ala
    130                 135                 140

Ile Tyr Ser Asp Ala Leu Ala Lys Leu Ala Asn Glu Glu Lys Val Pro
145                 150                 155                 160

Phe Val Ala Leu Asn Lys Ala Phe Gln Gln Glu Gly Gly Asp Ala Trp
                165                 170                 175

Gln Gln Leu Leu Thr Asp Gly Leu His Phe Ser Gly Lys Gly Tyr Lys
            180                 185                 190

Ile Phe His Asp Glu Leu
            195

<210> SEQ ID NO 60
<211> LENGTH: 317
<212> TYPE: PRT
<213> ORGANISM: Aeromonas salmonicida

<400> SEQUENCE: 60

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255
```

```
Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His
305                 310                 315

<210> SEQ ID NO 61
<211> LENGTH: 320
<212> TYPE: PRT
<213> ORGANISM: Ralstonia solanacearum

<400> SEQUENCE: 61

Gln Ser Gly Asn Pro Asn Val Ala Lys Val Gln Arg Met Val Val Phe
1               5                   10                  15

Gly Asp Ser Leu Ser Asp Ile Gly Thr Tyr Thr Pro Val Ala Gln Ala
            20                  25                  30

Val Gly Gly Gly Lys Phe Thr Thr Asn Pro Gly Pro Ile Trp Ala Glu
        35                  40                  45

Thr Val Ala Ala Gln Leu Gly Val Thr Leu Thr Pro Ala Val Met Gly
    50                  55                  60

Tyr Ala Thr Ser Val Gln Asn Cys Pro Lys Ala Gly Cys Phe Asp Tyr
65                  70                  75                  80

Ala Gln Gly Gly Ser Arg Val Thr Asp Pro Asn Gly Ile Gly His Asn
                85                  90                  95

Gly Gly Ala Gly Ala Leu Thr Tyr Pro Val Gln Gln Gln Leu Ala Asn
            100                 105                 110

Phe Tyr Ala Ala Ser Asn Asn Thr Phe Asn Gly Asn Asn Asp Val Val
        115                 120                 125

Phe Val Leu Ala Gly Ser Asn Asp Ile Phe Phe Trp Thr Thr Ala Ala
    130                 135                 140

Ala Thr Ser Gly Ser Gly Val Thr Pro Ala Ile Ala Thr Ala Gln Val
145                 150                 155                 160

Gln Gln Ala Ala Thr Asp Leu Val Gly Tyr Val Lys Asp Met Ile Ala
                165                 170                 175

Lys Gly Ala Thr Gln Val Tyr Val Phe Asn Leu Pro Asp Ser Ser Leu
            180                 185                 190

Thr Pro Asp Gly Val Ala Ser Gly Thr Thr Gly Gln Ala Leu Leu His
        195                 200                 205

Ala Leu Val Gly Thr Phe Asn Thr Thr Leu Gln Ser Gly Leu Ala Gly
    210                 215                 220

Thr Ser Ala Arg Ile Ile Asp Phe Asn Ala Gln Leu Thr Ala Ala Ile
225                 230                 235                 240

Gln Asn Gly Ala Ser Phe Gly Phe Ala Asn Thr Ser Ala Arg Ala Cys
                245                 250                 255

Asp Ala Thr Lys Ile Asn Ala Leu Val Pro Ser Ala Gly Gly Ser Ser
            260                 265                 270

Leu Phe Cys Ser Ala Asn Thr Leu Val Ala Ser Gly Ala Asp Gln Ser
        275                 280                 285

Tyr Leu Phe Ala Asp Gly Val His Pro Thr Thr Ala Gly His Arg Leu
    290                 295                 300

Ile Ala Ser Asn Val Leu Ala Arg Leu Leu Ala Asp Asn Val Ala His
305                 310                 315                 320
```

<210> SEQ ID NO 62
<211> LENGTH: 226
<212> TYPE: PRT
<213> ORGANISM: Streptomyces rimosus

<400> SEQUENCE: 62

```
Tyr Val Ala Leu Gly Asp Ser Tyr Ser Gly Val Gly Ala Gly Ser
1               5                   10                  15

Tyr Asp Ser Ser Gly Ser Cys Lys Arg Ser Thr Lys Ser Tyr Pro
            20                  25                  30

Ala Leu Trp Ala Ala Ser His Thr Gly Thr Arg Phe Asn Phe Thr Ala
        35                  40                  45

Cys Ser Gly Ala Arg Thr Gly Asp Val Leu Ala Lys Gln Leu Thr Pro
50                  55                  60

Val Asn Ser Gly Thr Asp Leu Val Ser Ile Thr Ile Gly Gly Asn Asp
65                  70                  75                  80

Ala Gly Phe Ala Asp Thr Met Thr Thr Cys Asn Leu Gln Gly Glu Ser
                85                  90                  95

Ala Cys Leu Ala Arg Ile Ala Lys Ala Arg Ala Tyr Ile Gln Gln Thr
            100                 105                 110

Leu Pro Ala Gln Leu Asp Gln Val Tyr Asp Ala Ile Asp Ser Arg Ala
        115                 120                 125

Pro Ala Ala Gln Val Val Leu Gly Tyr Pro Arg Phe Tyr Lys Leu
130                 135                 140

Gly Gly Ser Cys Ala Val Gly Leu Ser Glu Lys Ser Arg Ala Ala Ile
145                 150                 155                 160

Asn Ala Ala Ala Asp Asp Ile Asn Ala Val Thr Ala Lys Arg Ala Ala
                165                 170                 175

Asp His Gly Phe Ala Phe Gly Asp Val Asn Thr Thr Phe Ala Gly His
            180                 185                 190

Glu Leu Cys Ser Gly Ala Pro Trp Leu His Ser Val Thr Leu Pro Val
        195                 200                 205

Glu Asn Ser Tyr His Pro Thr Ala Asn Gly Gln Ser Lys Gly Tyr Leu
    210                 215                 220

Pro Val
225
```

<210> SEQ ID NO 63
<211> LENGTH: 182
<212> TYPE: PRT
<213> ORGANISM: Streptomyces coelicolor

<400> SEQUENCE: 63

```
Tyr Val Ala Val Gly Asp Ser Phe Thr Glu Gly Val Gly Asp Pro Gly
1               5                   10                  15

Pro Asp Gly Ala Phe Val Gly Trp Ala Asp Arg Leu Ala Val Leu Leu
            20                  25                  30

Ala Asp Arg Arg Pro Glu Gly Asp Phe Thr Tyr Thr Asn Leu Ala Val
        35                  40                  45

Arg Gly Arg Leu Leu Asp Gln Ile Val Ala Glu Gln Val Pro Arg Val
    50                  55                  60

Val Gly Leu Ala Pro Asp Leu Val Ser Phe Ala Ala Gly Gly Asn Asp
65                  70                  75                  80

Ile Ile Arg Pro Gly Thr Asp Pro Asp Glu Val Ala Glu Arg Phe Glu
                85                  90                  95
```

```
Leu Ala Val Ala Ala Leu Thr Ala Ala Gly Thr Val Leu Val Thr
            100                 105                 110

Thr Gly Phe Asp Thr Arg Gly Val Pro Val Leu Lys His Leu Arg Gly
        115                 120                 125

Lys Ile Ala Thr Tyr Asn Gly His Val Arg Ala Ile Ala Asp Arg Tyr
130                 135                 140

Gly Cys Pro Val Leu Asp Leu Trp Ser Leu Arg Ser Val Gln Asp Arg
145                 150                 155                 160

Arg Ala Trp Asp Ala Asp Arg Leu His Leu Ser Pro Glu Gly His Thr
                165                 170                 175

Arg Val Ala Leu Arg Ala
            180
```

<210> SEQ ID NO 64
<211> LENGTH: 179
<212> TYPE: PRT
<213> ORGANISM: Streptomyces coelicolor

<400> SEQUENCE: 64

```
Leu Val Ala Val Gly Asp Ser Phe Thr Glu Gly Met Ser Asp Leu Leu
1               5                   10                  15

Pro Asp Gly Ser Tyr Arg Gly Trp Ala Asp Leu Leu Ala Thr Arg Met
            20                  25                  30

Ala Ala Arg Ser Pro Gly Phe Arg Tyr Ala Asn Leu Ala Val Arg Gly
        35                  40                  45

Lys Leu Ile Gly Gln Ile Val Asp Glu Gln Val Asp Val Ala Ala Ala
    50                  55                  60

Met Gly Ala Asp Val Ile Thr Leu Val Gly Gly Leu Asn Asp Thr Leu
65                  70                  75                  80

Arg Pro Lys Cys Asp Met Ala Arg Val Arg Asp Leu Leu Thr Gln Ala
                85                  90                  95

Val Glu Arg Leu Ala Pro His Cys Glu Gln Leu Val Leu Met Arg Ser
            100                 105                 110

Pro Gly Arg Gln Gly Pro Val Leu Glu Arg Phe Arg Pro Arg Met Glu
        115                 120                 125

Ala Leu Phe Ala Val Ile Asp Asp Leu Ala Gly Arg His Gly Ala Val
    130                 135                 140

Val Val Asp Leu Tyr Gly Ala Gln Ser Leu Ala Asp Pro Arg Met Trp
145                 150                 155                 160

Asp Val Asp Arg Leu His Leu Thr Ala Glu Gly His Arg Arg Val Ala
                165                 170                 175

Glu Ala Val
```

<210> SEQ ID NO 65
<211> LENGTH: 203
<212> TYPE: PRT
<213> ORGANISM: Streptomyces coelicolor

<400> SEQUENCE: 65

```
Val Val Ala Phe Gly Asp Ser Ile Thr Asp Gly Ala Arg Ser Gln Ser
1               5                   10                  15

Asp Ala Asn His Arg Trp Thr Asp Val Leu Ala Ala Arg Leu His Glu
            20                  25                  30

Ala Ala Gly Asp Gly Arg Asp Thr Pro Arg Tyr Ser Val Val Asn Glu
        35                  40                  45

Gly Ile Ser Gly Asn Arg Leu Leu Thr Ser Arg Pro Gly Arg Pro Ala
    50                  55                  60
```

```
Asp Asn Pro Ser Gly Leu Ser Arg Phe Gln Arg Asp Val Leu Glu Arg
 65                  70                  75                  80

Thr Asn Val Lys Ala Val Val Val Leu Gly Val Asn Asp Val Leu
             85                  90                  95

Asn Ser Pro Glu Leu Ala Asp Arg Asp Ala Ile Leu Thr Gly Leu Arg
            100                 105                 110

Thr Leu Val Asp Arg Ala His Ala Arg Gly Leu Arg Val Val Gly Ala
                115                 120                 125

Thr Ile Thr Pro Phe Gly Gly Tyr Gly Gly Tyr Thr Glu Ala Arg Glu
            130                 135                 140

Thr Met Arg Gln Glu Val Asn Glu Glu Ile Arg Ser Gly Arg Val Phe
145                 150                 155                 160

Asp Thr Val Val Asp Phe Asp Lys Ala Leu Arg Asp Pro Tyr Asp Pro
                165                 170                 175

Arg Arg Met Arg Ser Asp Tyr Asp Ser Gly Asp His Leu His Pro Gly
            180                 185                 190

Asp Lys Gly Tyr Ala Arg Met Gly Ala Val Ile
            195                 200

<210> SEQ ID NO 66
<211> LENGTH: 188
<212> TYPE: PRT
<213> ORGANISM: Streptomyces coelicolor

<400> SEQUENCE: 66

Leu Met Met Leu Gly Asp Ser Thr Ala Ala Gly Gln Gly Val His Arg
  1               5                  10                  15

Ala Gly Gln Thr Pro Gly Ala Leu Leu Ala Ser Gly Leu Ala Ala Val
             20                  25                  30

Ala Glu Arg Pro Val Arg Leu Gly Ser Val Ala Gln Pro Gly Ala Cys
         35                  40                  45

Ser Asp Asp Leu Asp Arg Gln Val Ala Leu Val Leu Ala Glu Pro Asp
 50                  55                  60

Arg Val Pro Asp Ile Cys Val Ile Met Val Gly Ala Asn Asp Val Thr
 65                  70                  75                  80

His Arg Met Pro Ala Thr Arg Ser Val Arg His Leu Ser Ser Ala Val
             85                  90                  95

Arg Arg Leu Arg Thr Ala Gly Ala Glu Val Val Val Gly Thr Cys Pro
            100                 105                 110

Asp Leu Gly Thr Ile Glu Arg Val Arg Gln Pro Leu Arg Trp Leu Ala
            115                 120                 125

Arg Arg Ala Ser Arg Gln Leu Ala Ala Ala Gln Thr Ile Gly Ala Val
            130                 135                 140

Glu Gln Gly Gly Arg Thr Val Ser Leu Gly Asp Leu Leu Gly Pro Glu
145                 150                 155                 160

Phe Ala Gln Asn Pro Arg Glu Leu Phe Gly Pro Asp Asn Tyr His Pro
                165                 170                 175

Ser Ala Glu Gly Tyr Ala Thr Ala Ala Met Ala Val
            180                 185

<210> SEQ ID NO 67
<211> LENGTH: 231
<212> TYPE: PRT
<213> ORGANISM: Streptomyces coelicolor

<400> SEQUENCE: 67
```

```
Val Ala Ala Val Gly Asp Ser Ile Thr Arg Gly Phe Asp Ala Cys Ala
1               5                   10                  15

Val Leu Ser Asp Cys Pro Glu Val Ser Trp Ala Thr Gly Ser Ser Ala
            20                  25                  30

Lys Val Asp Ser Leu Ala Val Arg Leu Leu Gly Lys Ala Asp Ala Ala
        35                  40                  45

Glu His Ser Trp Asn Tyr Ala Val Thr Gly Ala Arg Met Ala Asp Leu
    50                  55                  60

Thr Ala Gln Val Thr Arg Ala Ala Gln Arg Glu Pro Glu Leu Val Ala
65                  70                  75                  80

Val Met Ala Gly Ala Asn Asp Ala Cys Arg Ser Thr Thr Ser Ala Met
                85                  90                  95

Thr Pro Val Ala Asp Phe Arg Ala Gln Phe Glu Glu Ala Met Ala Thr
            100                 105                 110

Leu Arg Lys Lys Leu Pro Lys Ala Gln Val Tyr Val Ser Ser Ile Pro
        115                 120                 125

Asp Leu Lys Arg Leu Trp Ser Gln Gly Arg Thr Asn Pro Leu Gly Lys
    130                 135                 140

Gln Val Trp Lys Leu Gly Leu Cys Pro Ser Met Leu Gly Asp Ala Asp
145                 150                 155                 160

Ser Leu Asp Ser Ala Ala Thr Leu Arg Arg Asn Thr Val Arg Asp Arg
                165                 170                 175

Val Ala Asp Tyr Asn Glu Val Leu Arg Glu Val Cys Ala Lys Asp Arg
            180                 185                 190

Arg Cys Arg Ser Asp Asp Gly Ala Val His Glu Phe Arg Phe Gly Thr
        195                 200                 205

Asp Gln Leu Ser His Trp Asp Trp Phe His Pro Ser Val Asp Gly Gln
    210                 215                 220

Ala Arg Leu Ala Glu Ile Ala
225                 230

<210> SEQ ID NO 68
<211> LENGTH: 295
<212> TYPE: PRT
<213> ORGANISM: Aeromonas hydrophila

<400> SEQUENCE: 68

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Gly Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140
```

```
Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
    290                 295

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agcatatgaa aaaatggttt gtttgtttat tgggg                              35

<210> SEQ ID NO 70
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ile Val Ala Phe Gly Asp Ser Leu Thr Asp Gly Gly Ala Tyr Tyr
1               5                   10                  15

Gly Asp Ser Asp Gly Gly Gly Trp Gly Ala Gly Leu Ala Asp Arg Leu
            20                  25                  30

Thr Ser Leu Ala Arg Leu Arg Ala Arg Gly Arg Gly Val Asp Val Phe
        35                  40                  45

Asn Arg Gly Ile Ser Gly Arg Thr Ser Asp Gly Arg Leu Val Val Asp
    50                  55                  60

Ala Arg Leu Val Ala Thr Leu Leu Phe Leu Ala Gln Phe Leu Gly Leu
65                  70                  75                  80

Asn Leu Pro Pro Tyr Leu Ser Gly Asp Phe Leu Arg Gly Ala Asn Phe
                85                  90                  95

Ala Ser Ala Gly Ala Thr Ile Leu Gly Thr Ser Leu Ile Pro Phe Leu
            100                 105                 110

Asn Ile Gln Val Gln Phe Lys Asp Phe Lys Ser Lys Val Leu Glu Leu
        115                 120                 125

Arg Gln Ala Leu Gly Leu Leu Gln Glu Leu Leu Arg Leu Val Pro Val
    130                 135                 140
```

```
Leu Asp Ala Lys Ser Pro Asp Leu Val Thr Ile Met Ile Gly Thr Asn
145                 150                 155                 160

Asp Leu Ile Thr Val Ala Lys Phe Gly Pro Lys Ser Thr Lys Ser Asp
                165                 170                 175

Arg Asn Val Ser Val Pro Glu Phe Arg Asp Asn Leu Arg Lys Leu Ile
            180                 185                 190

Lys Arg Leu Arg Ser Ala Asn Gly Ala Arg Ile Ile Ile Leu Ile Thr
        195                 200                 205

Leu Val Leu Leu Asn Leu Pro Leu Pro Leu Gly Cys Leu Pro Gln Lys
    210                 215                 220

Leu Ala Leu Ala Leu Ala Ser Ser Lys Asn Val Asp Ala Thr Gly Cys
225                 230                 235                 240

Leu Glu Arg Leu Asn Glu Ala Val Ala Asp Tyr Asn Glu Ala Leu Arg
                245                 250                 255

Glu Leu Ala Glu Ile Glu Lys Leu Gln Ala Gln Leu Arg Lys Asp Gly
            260                 265                 270

Leu Pro Asp Leu Lys Glu Ala Asn Val Pro Tyr Val Asp Leu Tyr Ser
        275                 280                 285

Ile Phe Gln Asp Leu Asp Gly Ile Gln Asn Pro Ser Ala Tyr Val Tyr
    290                 295                 300

Gly Phe Glu Glu Thr Lys Ala Cys Cys Gly Tyr Gly Gly Arg Tyr Asn
305                 310                 315                 320

Tyr Asn Arg Val Cys Gly Asn Ala Gly Leu Cys Lys Val Thr Ala Lys
                325                 330                 335

Ala Cys Asp Ala Ser Ser Tyr Leu Leu Ala Thr Leu Phe Trp Asp Gly
            340                 345                 350

Phe His Pro Ser Glu Lys Gly Tyr Lys Ala Val Ala Glu Ala Leu
        355                 360                 365

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Leu, Ala, Val, Ile, Phe, Tyr, His, Gln, Thr,
      Asn, Met or Ser

<400> SEQUENCE: 71

Gly Asp Ser Xaa
1

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Met, Ile, Leu, Val, Ala, Gly, Cys, His, Lys,
      Trp, Tyr or Phe
<220> FEATURE:
<221> NAME/KEY: MOD_RES
<222> LOCATION: (8)..(8)
<223> OTHER INFORMATION: Met, Ile, Leu, Val, Ala, Gly, Cys, His, Lys,
      Trp, Tyr or Phe
```

```
<400> SEQUENCE: 72

Xaa Xaa Xaa Xaa Gly Asp Ser Xaa
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ala Asn Asp Tyr
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Ile, Leu, Val, Ala, Gly, Cys, His, Lys,
      Trp, Tyr or Phe
<220> FEATURE:
<221> NAME/KEY: MOD_RES
<222> LOCATION: (3)..(3)
<223> OTHER INFORMATION: Met, Ile, Leu, Val, Ala, Gly, Cys, His, Lys,
      Trp, Tyr or Phe
<220> FEATURE:
<221> NAME/KEY: MOD_RES
<222> LOCATION: (6)..(6)
<223> OTHER INFORMATION: Met, Ile, Leu, Val, Ala, Gly, Cys, His, Lys,
      Trp, Tyr or Phe

<400> SEQUENCE: 74

Xaa Gly Xaa Asn Asp Xaa
1               5
```